US011008313B2

United States Patent
Imbriglio et al.

(10) Patent No.: US 11,008,313 B2
(45) Date of Patent: May 18, 2021

(54) SUBSTITUTED 1-METHYL-1,2,3,4-TETRAHYDROISOQUINOLINE MOLECULES AS PCSK9 ALLOSTERIC BINDERS

(71) Applicant: Merck Sharp & Dohme Corp., Rahway, NJ (US)

(72) Inventors: Jason Eugene Imbriglio, Piscataway, NJ (US); Whitney Lane Petrilli, Summit, NJ (US); Yusheng Xiong, Plainsboro, NJ (US); Zhe Feng, Hillsborough, NJ (US); Hyewon Youm, Berkeley Heights, NJ (US); Wonsuk Chang, Princeton, NJ (US); Rui Liang, East Brunswick, NJ (US); Zhijian Lu, Plainfield, IN (US); Jerry Andrew Taylor, Trenton, NJ (US); Scott B. Hoyt, Arlington, VA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 239 days.

(21) Appl. No.: 16/334,605

(22) PCT Filed: Sep. 15, 2017

(86) PCT No.: PCT/US2017/051690
§ 371 (c)(1),
(2) Date: Mar. 19, 2019

(87) PCT Pub. No.: WO2018/057409
PCT Pub. Date: Mar. 29, 2018

(65) Prior Publication Data
US 2020/0369657 A1 Nov. 26, 2020

Related U.S. Application Data

(60) Provisional application No. 62/397,116, filed on Sep. 20, 2016.

(51) Int. Cl.
*C07D 417/12* (2006.01)
*G01N 33/58* (2006.01)

(52) U.S. Cl.
CPC ......... *C07D 417/12* (2013.01); *G01N 33/582* (2013.01)

(58) Field of Classification Search
CPC .................. C07D 417/12; G01N 33/582
See application file for complete search history.

(56) References Cited

FOREIGN PATENT DOCUMENTS

| CN | 105777633 | 7/2016 |
|---|---|---|
| WO | 2016036633 | 3/2016 |
| WO | 2016036636 | 3/2016 |

OTHER PUBLICATIONS

"Substance Record for SID 75920391" to PubChem, Deposit Date Jun. 11, 2009. Retrieved from the Internet [retrieved on Oct. 20, 2017] URL:HTTPS://pubchem.ncbi.nlm.nih.gov/substance/75920391#section=Top entire document.
Schneekloth, John S., Chemical Genetic Control of Protein Levels; Selective in Vivo Targeted Degradation, J. Am Chem Soc, 2004, 3748-3754, 126.
Schreiber, S., A chemical biology view of bioactive small molecules and a binder-based approach to connect biology to precision medicines, BioRxiv, 2018, 386904, 1, US.
Scott, D. E., Small Molecules, Big Targets: drug discovery faces the protein-protein interaction challenge, Nat. Rev. Drug Discov, 2016, 533-550, 15, US.

(Continued)

*Primary Examiner* — Alicia L Otton
(74) *Attorney, Agent, or Firm* — Dianne Pecoraro; John C. Todaro

(57) ABSTRACT

The present invention relates to PCSK9 allosteric binding compounds of Formula I: (Formula (I)) and pharmaceutically acceptable salts thereof, wherein $X_1$, $X_2$, Y, $R^1$, $R^2$, $R^A$, $R^B$ and n are as defined herein. The present invention also relates to compositions which comprise an allosteric binding compound of the invention or a pharmaceutically acceptable salt thereof and a pharmaceutically acceptable carrier. The invention further relates, inter alia, to methods for inducing PCSK9 protein degradation in a subject, and methods for treating atherosclerosis, hypercholesterolemia, coronary heart disease, metabolic syndrome, acute coronary syndrome, or related cardiovascular disease and cardiometabolic conditions, comprising administering to a subject an effective amount of a compound or a pharmaceutically acceptable salt of the invention. The invention also provides a means for the in vitro labeling, detection and/or quantification of PCSK9 in biological samples.

(I)

14 Claims, No Drawings

(56) References Cited

OTHER PUBLICATIONS

Seidah, N.G., PCSK9: A Key Modulator of cardiovascular health, Circ Res, 2014, 1022-1036, 114, US.
Shi, Y., Boc3Arg-Linked Ligands induce Degradation by Localizing Target Proteins . . . , ACS Chem Biol, 2016, 3328-3337, 11, US.
Thirumurugan, P., Click chemistry for drug development and diverse chemical-biology applications, Chem Rev, 2013, 4905-4979, 113, US.
Unver, M.Y., Druggability Assessment of Target Used in Kinetic Target-Guided Synthesis, J. Med Chem, 2018, 9395-9409, 61, US.
Watkins, A.M., Antaomy of β-strands at protein-protein interfaces, ACS Chemical Biology, 2014, 1747-1754, 9, US.
Xiong, Yusheng, Exploration of a PCSK9 allosteric binding site for cholesterol reduction, 14th Annual Discovery on Target, Sep. 19-22, 2016.
Xu, W., c-IAP1 binds and processes PCSK9 protein: linking the c-IAP1 in a TNF-alpha pathway to PCSK9-mediated LDLR degradation pathway, Molecules, 2012, 12086-12101, 17, US.

SUBSTITUTED 1-METHYL-1,2,3,4-TETRAHYDROISOQUINOLINE MOLECULES AS PCSK9 ALLOSTERIC BINDERS

CROSS REFERENCE TO RELATED APPLICATIONS

This application is a U.S. National Phase application under 35 U.S.C. § 371 of PCT Application No. PCT/US2017/051690, filed Sep. 15, 2017, which claims the priority of U.S. provisional Application No. 62/397,116, filed Sep. 20, 2016.

FIELD OF THE INVENTION

This invention relates to novel PCSK9 allosteric binding molecules having high affinity for PCSK9 at a unique site that does not interfere with the binding of PCSK9 to the low-density lipoprotein (LDL) receptor. The PCSK9 binding molecules can be used, inter alia, in the detection, quantitation, imaging, and/or degradation of PCSK9. Select molecules disclosed herein may further be of import in the treatment of conditions associated with or impacted by PCSK9 function, including, but not limited to atherosclerosis, hypercholesterolemia, coronary heart disease, metabolic syndrome, acute coronary syndrome, and related cardiovascular disease and cardiometabolic conditions.

BACKGROUND OF THE INVENTION

Proprotein convertase subtilisin-like/kexin type 9 (PCSK9) is a major regulator of plasma low-density lipoprotein (LDL) cholesterol (LDL-C) and consequently an important therapeutic target for treating coronary heart disease; see Seidah et al., 2014 *Circ. Res.* 14:1022-1036. PCSK9 binds to the LDL receptor (LDLR) on the cell surface of hepatocytes and directs the receptor to intracellular lysosomes for degradation. Abundant genetic data confirm that the level of PCSK9 function affects the level of LDL-C; Horton et al., 2007 *Trends Biochem. Sci.* 32:71-77; see, e.g., Horton et al., 2009 *J. Lipid Res.* 50(Suppl):S172-S177. Gain-of-function mutations in PCSK9, which increase its affinity for LDLR, result in decreased LDLR on the cell surface, increased serum LDL-C, and negative consequences for cardiovascular health. Conversely, loss-of-function mutations in PCSK9 lead to higher LDLR levels and lower LDL-C, which is associated with positive clinical outcomes. Therapeutic strategies that have demonstrated clinical efficacy in reducing LDL-C accomplish the loss of PCSK9 function by either blocking PCSK9's LDLR binding activity with a monoclonal antibody or reducing the PCSK9 protein level with RNA interference (RNAi); see, e.g., Dias et al., 2012 *J. Am. Coll. Cardiol.* 60:1888-1898; Fitzgerald et al., 2014 *Lancet* 383:60-68; Stein et al., 2012 *N. Engl. J. Med.* 366:1108-1118.

PCSK9 belongs to the mammalian proprotein convertase family of serine proteases and contains an N-terminal signal sequence, prodomain, catalytic domain, and C-terminal domain; see Seidah et al., 2012 *Nat. Rev. Drug Discov.* 11:367-383. While in the endoplasmic reticulum, PCSK9 performs its only catalytic activity, an autocleavage between residues Gln-152 and Ser-153; see Naureckiene et al., 2003 *Arch. Biochem. Biophys.* 420:55-67; Seidah et al., 2003 *Proc. Natl. Acad. Sci. U.S.A.* 100:928-933. The prodomain remains tightly associated with the catalytic domain during subsequent trafficking through the trans-Golgi network. The maturation via autocleavage has been demonstrated to be critical for PCSK9 secretion and subsequent extracellular function (see Benjannet et al., 2012 *J. Biol. Chem.* 287:33745-33755).

The identification of compounds and/or agents effective in the treatment of cardiovascular affliction is highly desirable. In clinical trials, reductions in LDL cholesterol levels have been directly related to the rate of coronary events; Law et al., 2003 *BMJ* 326:1423-1427. The moderate lifelong reduction in plasma LDL cholesterol levels was found to correlate with a substantial reduction in the incidence of coronary events; Cohen et al., 2006 *N. Engl. J. Med.* 354:1264-1272. This was the case even in populations with a high prevalence of non-lipid-related cardiovascular risk factors: supra. Accordingly, there is great benefit to be reaped from the managed control of LDL cholesterol levels.

The present invention advances these interests by providing compounds that specifically bind PCSK9 at a unique site that does not interfere with the binding of PCSK9 with the LDL receptor. PCSK9 binding molecules can be used, inter alia, in the detection, quantitation, promoting or inhibiting intracellular transport imaging, and/or degradation of PCSK9; see, e.g., Ehrhardt et al., 2012 *Current Chemical Genomics* 6:38-47; and WO2016085820A1.

Agents capable of decreasing PCSK9 levels may increase the cell surface expression of the low density lipoprotein (LDL) receptor and accordingly reduce LDL cholesterol. Such agents may prove useful for the treatment and correction of the various dyslipidemias observed to be associated with the development and incidence of atherosclerosis and cardiovascular disease.

SUMMARY OF THE INVENTION

The present invention is directed to substituted 1-methyl-1,2,3,4-tetrahydroisoquinoline PCSK9 allosteric binding molecules having high affinity for PCSK9 at a unique site that does not interfere with the binding of PCSK9 to the low-density lipoprotein (LDL) receptor. The compounds, and their pharmaceutically acceptable salts, are useful, for example, in the detection, quantitation, imaging, and/or degradation of PCSK9. More particularly, the present invention includes compounds of Formula I:

(I)

or a pharmaceutically acceptable salt thereof,
wherein:
$R^A$ is —$C_1$-$C_6$alkyl, —[$OCH_2CH_2$]$_m$$NR^a$C(O)$R^C$, —($CH_2$)$_n$-AryA1, —($CH_2$)$_n$-HetA1 or —$C_1$-$C_3$alkyl$N_3$;
wherein the —$C_1$-$C_6$alkyl or —$C_1$-$C_3$alkyl$N_3$ is optionally substituted with 1, 2, or 3 substituents independently selected from the group consisting of halogen, —$C_1$-$C_6$alkoxy, —$C_1$-$C_6$haloalkoxy, —C(O)$OR^a$, —$NR^aR^b$ and —OH;

AryA1 is a 5-6 membered aromatic monocyclic ring with 0, 1, 2 or 3 heteroatom ring atoms independently selected from the group consisting of N and O, optionally substituted with 1, 2, or 3 substituents independently selected from the group consisting of halogen, —$C_1$-$C_6$alkyl, —$C_1$-$C_6$haloalkyl, —$C_1$-$C_6$alkoxy, —$C_1$-$C_6$haloalkoxy, —CN, —$CH_2$OH, —C(O)NR$^a$R$^b$, —S$C_1$-$C_6$alkyl, —$SO_2$R$^a$, —$SO_2$NR$^a$R$^b$, —C(O)OR$^a$, —CH(OH)C(NH$_2$)C(O)OR$^a$, —$CH_2$O$CH_2$$CH_2$CH, AryA2, —(CH$_2$)$_n$-HetA1, —NR$^a$ and —OH; wherein the —$C_1$-$C_6$alkyl is optionally substituted with 1 or 2 substituents independently selected from the group consisting of —OR$^a$, —NR$^a$R$^b$, —COOR$^a$, —$C_3$-$C_6$cycloalkyl, —$C_1$-$C_4$alkylCOOR$^a$, —NR$^a$C(O)R$^b$, —NR$^a$S(O)$_2$R$^b$, —(CH$_2$)$_n$-AryA2, —OAryA2 and —NR$^a$C(O)-AryA2, each occurrence of AryA2 is individually a 5-6 membered aromatic monocyclic ring with 0, 1, 2 or 3 heteroatom ring atoms independently selected from the group consisting of N and O, optionally substituted with 1, 2, or 3 substituents independently selected from the group consisting of halogen, —$C_1$-$C_6$alkyl, —$C_1$-$C_6$haloalkyl-$C_1$-$C_6$alkoxy, —$C_1$-$C_6$haloalkoxy, —COOR$^a$, —CN, —$CH_2$OH, —C(O)NR$^a$R$^b$, —S$C_1$-$C_6$alkyl, —$SO_2$R$^a$, —$SO_2$NR$^a$R$^b$, —OR$^a$, —NR$^a$R$^b$, AryA3 and oxo;

HetA1 is a 5-6-membered saturated monocyclic ring with 1 or 2 heteroatom ring atoms independently selected from the group consisting of N and O, wherein the ring is optionally substituted with 1 or 2 substituents independently selected from the group consisting of —$C_1$-$C_6$alkyl, —$CH_2$OH, —C(O)NR$^a$R$^b$, —S$C_1$-$C_6$alkyl, —$SO_2$R$^a$, —$SO_2$NR$^a$R$^b$, —OR$^a$, —NR$^a$R$^b$, —CN and oxo;

$X_1$ and $X_2$ are independently selected from the group consisting of N and CH;

wherein if $X_1$ is CH, $X_1$ is optionally linked to R$^B$ through an —O$C_6$-$C_7$alkylene or an —O$C_6$-$C_7$alkenylene, wherein the O of the —O$C_6$-$C_7$alkylene or —O$C_6$-$C_7$alkenylene is bound at the $X_1$ position;

or alternatively $X_1$ and $X_2$ together with the ring atoms to which they are attached form a 5-6 membered aromatic monocyclic ring with 0, 1 or 2 heteroatom ring atoms independently selected from the group consisting of N and O, wherein said monocyclic ring is fused to the ring having $X_1$ and $X_2$, further wherein said monocyclic ring is optionally substituted with 1, 2, or 3 substituents independently selected from the group consisting of halogen, —$C_1$-$C_6$alkyl and —$C_1$-$C_6$haloalkyl;

Y is O or a bond;

R$^1$ is:
 1) hydrogen,
 2) halogen,
 3) —$C_1$-$C_6$alkyl,
 4) —$C_1$-$C_6$haloalkyl,
 5) —$C_1$-$C_6$alkoxy,
 6) —$C_1$-$C_6$haloalkoxy,
 7) —C(O)OR$^a$,
 8) —C(O)NR$^a$R$^b$,
 9) —CN,
 10) —$CH_2$OH,
 11) —S$C_1$-$C_6$alkyl.
 12) —$SO_2$R$^a$,
 13) —$SO_2$NR$^a$R$^b$,
 14) —OR$^a$,
 15) —NR$^a$R$^b$,
 16) —C(O)NR$^a$AryA3, or
 17) -AryA3;

AryA3 is an aromatic 5-6 membered monocyclic ring or an 8-10 membered bicyclic ring with 0, 1, 2, or 3 heteroatom ring atoms independently selected from the group consisting of N and O, wherein the 5-6 membered monocyclic ring or the 8-10 membered bicyclic ring are optionally substituted with 1, 2 or 3 substituents independently selected from the group consisting of halogen, —$C_1$-$C_6$alkyl, —$C_1$-$C_6$alkenyl, —$C_1$-$C_6$haloalkyl, —$C_1$-$C_6$alkoxy, —$C_1$-$C_6$haloalkoxy, —CN, —$CH_2$OH, —S$C_1$-$C_6$alkyl, —$SO_2$R$^a$, —$SO_2$NR$^a$R$^b$, —OR$^a$, —C(O)OR$^a$, —C(O)NR$^a$R$^b$, —C(O)NR$^a$AryA4, —NR$^a$C(O)AryA4, AryA4, —NR$^a$R$^b$, oxo and —OH wherein the —$C_1$-$C_6$alkyl or the —$C_1$-$C_6$alkenyl are optionally substituted with 1 or 2 substituents independently selected from the group consisting of —$C_1$-$C_6$cycloalkyl, —C(O)OR$^a$ and —C(O)NR$^a$R$^b$;

AryA4 is a 5-6 membered aromatic monocyclic ring with 0, 1, 2 or 3 heteroatom ring atoms independently selected from the group consisting of N and O, optionally substituted with 1, 2, or 3 substituents independently selected from the group consisting of halogen, —$C_1$-$C_6$alkyl, —$C_1$-$C_6$haloalkyl, —$C_1$-$C_6$alkoxy, —$C_1$-$C_6$haloalkoxy, —CN, —$CH_2$OH, —C(O)NR$^a$R$^b$, —S$C_1$-$C_6$alkyl, —$SO_2$R$^a$, —$SO_2$NR$^a$R$^b$, —OR$^a$ and —NR$^a$R$^b$;

each R$^2$ is independently halogen. —$C_1$-$C_6$alkyl, —$C_1$-$C_6$haloalkyl, —$C_1$-$C_6$alkoxy, —$C_1$-$C_6$haloalkoxy, —CN, —$CH_2$OH, —C(O)NR$^a$R$^b$, —S$C_1$-$C_6$alkyl, —$SO_2$R$^a$, —$SO_2$NR$^a$R$^b$, —OR$^a$ or —NR$^a$R$^b$;

R$^B$ is -AryA5; wherein if $X_1$ is CH, R$^B$ is optionally linked to $X_1$ through an —O$C_6$-$C_7$alkylene or an —O$C_6$-$C_7$alkenylene, wherein the O of the —O$C_6$-$C_7$alkylene or —O$C_6$-$C_7$alkenylene is bound at the $X_1$ position;

AryA5 is an aromatic 5-6 membered monocyclic ring or an 8-10 membered bicyclic ring with 0, 1, 2, or 3 heteroatom ring atoms independently selected from the group consisting of N, O and S, optionally substituted with 1, 2 or 3 substituents independently selected from the group consisting of halogen, —$C_1$-$C_6$alkyl, —$C_1$-$C_6$haloalkyl, —$C_1$-$C_6$alkoxy, —$C_1$-$C_6$haloalkoxy, —NR$^a$R$^b$, —CN, —$CH_2$OH, —C(O)NR$^a$R$^b$, —S$C_1$-$C_6$alkyl, —$SO_2$R$^a$, —$SO_2$NR$^a$R$^b$, and —OR$^a$;

R$^C$ is —(CH$_2$)$_p$-adamantane, —(CH$_2$)$_m$-5,5-difluoro-1,3-dimethyl-5H-5$\lambda^4$,6$\lambda^4$-dipyrrolo[1,2-c:2',1'-f][1,3,2]diazaborinine, —(CH$_2$)$_m$-(3aR,6aS)-tetrahydro-1H-thieno[3,4-d]imidazol-2(3H)-one, —$C_1$-$C_6$alkyl and —$C_1$-$C_2$alkylene[O$C_1$-$C_2$alkylene]$_o$C(O)NR$^a$$C_1$-$C_6$alkyl;

wherein the —$C_1$-$C_6$alkyl is optionally substituted with 1 or 2 substituents independently selected from the group consisting of —NR$^a$C(O)$C_1$-$C_6$alkyl, —NR$^a$C(O)O$C_1$-$C_6$alkyl, —NR$^a$C(=NC(O)OR$^b$)(NR$^a$C(O)OR$^b$), —[O$C_1$-$C_2$alkylene]$_o$C(O)NR$^a$$C_1$-$C_6$alkyl and AryB1;

wherein the —NR$^a$C(O)$C_1$-$C_6$alkyl is optionally substituted with 1, 2 or 3 substituents independently selected from the group consisting of —OR$^a$, —NR$^a$R$^b$ and AryB1;

wherein the —$C_1$-$C_2$alkylene[O$C_1$-$C_2$alkylene]$_o$C(O)NR$^a$$C_1$-$C_6$alkyl is optionally substituted with a substituent selected from the group consisting of -HetB1 and —C(O)HetB1;

HetB1 is a 5-membered saturated monocyclic ring with 1 N atom, optionally substituted with 1 or 2 substituents independently selected from the group consisting of —C(O)NR$^a$(CH$_2$)$_n$-AryB1 and —OR$^a$;

AryB1 is a 5-6 membered aromatic monocyclic ring with 0 or 1 N ring atoms, optionally substituted with 1, 2, or 3 substituents independently selected from the group consisting of AryB2, halogen, —$C_1$-$C_6$alkyl, —$C_1$-$C_6$haloalkyl, —$C_1$-$C_6$alkoxy, —$C_1$-$C_6$haloalkoxy, —C(O)OR$^a$, —NR$^a$R$^b$ and —OH;

AryB2 is a 5-6 membered aromatic monocyclic ring with 0, 1, 2 or 3 heteroatom ring atoms independently selected from the group consisting of N, O and S, optionally substituted with 1, 2, or 3 substituents independently selected from the group consisting of halogen, —$C_1$-$C_6$alkyl, —$C_1$-$C_6$haloalkyl, —$C_1$-$C_6$alkoxy, —$C_1$-$C_6$haloalkoxy, and —$OR^a$;

$R^a$ and $R^b$ are independently H or $C_1$-$C_6$ alkyl;

or alternatively $R^a$ and $R^b$, if bound to the same atom, can together with the atom to which they are both attached form a —$C_1$-$C_6$cycloalkyl;

each n is independently 0, 1 or 2;
each m is independently 1, 2, 3 or 4;
each o is independently 1, 2 or 3; and
each p is independently 1, 2, 3 or 4.

Compounds of Formula I and their pharmaceutically acceptable salts are allosteric binders of PCSK9 with the potential to affect the activity of PCSK9. The compounds and their respective salts are characterized by high nanomolar affinity for PCSK9 and offer unique functionality in that the site of interaction does not interfere with PCSK9's binding to the LDL receptor. As such, while the compounds do not inhibit PCSK9 functioning in the traditional sense by blocking the interaction of PCSK9 with the LDL receptor, the compounds of Formula I have utility in the detection, quantitation and imaging of PCSK9 whether or not the protein is bound to the LDL receptor. Coupled with or comprising a detectable marker (e.g., a fluorescence probe), compounds of Formula I may be used for the in vitro labeling, detection and/or quantification of PCSK9 in a sample. Furthermore, select compounds of Formula I offer utility in the degradation of PCSK9 by, for example, the ubiquitin-proteosome pathway (J Am Chem Soc. 2004 Mar. 31; 126(12):3748-54). Compounds disclosed herein when administered to cells expressing PCSK9 exhibited reduced cellular levels of PCSK9 both pro-protein and mature. Such molecules are, therefore, of import in the treatment of conditions associated with or impacted by PCSK9 function, including, but not limited to atherosclerosis, hypercholesterolemia, coronary heart disease, metabolic syndrome, acute coronary syndrome, and related cardiovascular disease and cardiometabolic conditions. The invention further includes compositions comprising a compound of Formula I or a pharmaceutically acceptable salt thereof, and a pharmaceutically acceptable carrier. The invention also provides methods for treating atherosclerosis, hypercholesterolemia, coronary heart disease, metabolic syndrome, acute coronary syndrome, or related cardiovascular disease and cardiometabolic conditions by administration of select compounds of Formula I, or a pharmaceutically acceptable salt thereof, to a subject in need thereof, or by administration of a pharmaceutical composition comprising a compound of Formula I or its salt and a pharmaceutically acceptable carrier.

Embodiments, sub-embodiments, aspects and features of the present invention are either further described in or will be apparent from the ensuing description, examples and appended claims.

DETAILED DESCRIPTION OF THE INVENTION

As noted above, the present invention includes compounds of Formula I wherein the compounds are PCSK9 allosteric binding molecules.

The invention is based in part on the high nanomolar affinity for PCSK9 exhibited by compounds of Formula I and pharmaceutically acceptable salts thereof and the unique functionality such compounds offer in that the site of interaction does not interfere with PCSK9's interaction with the LDL receptor.

In each of the various embodiments of the compounds of the invention described herein, each variable of Formula I and the various embodiments thereof, are selected independently of the other variables unless otherwise indicated.

The present invention encompasses for each of the various embodiments of the compounds of the invention described herein, including those of Formula I and the various embodiments thereof and the compounds of the examples, all forms of the compounds such as, for example, any solvates, hydrates, stereoisomers, and tautomers of said compounds and of any pharmaceutically acceptable salts thereof, unless otherwise indicated. Additionally, in the examples described herein, the compounds of the invention may be depicted in the salt form. In such cases, it is to be understood that the compounds of the invention include the free acid or free base forms of such salts, and any pharmaceutically acceptable salt of said free acid or free base forms.

The Compounds of Formula (I):

In one aspect, the present invention includes compounds of Formula I:

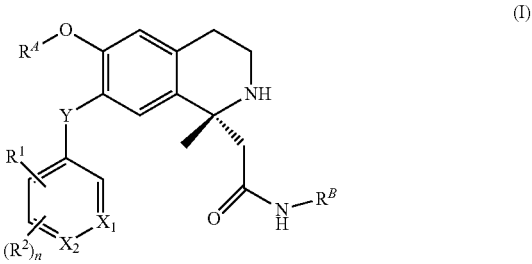

(I)

or a pharmaceutically acceptable salt thereof, wherein $X_1$, $X_2$, Y, $R^1$, $R^2$, $R^A$, $R^B$ and n, are as defined herein for the Compounds of Formula (I) (i.e. as defined in the Summary of the Invention).

A first embodiment of the invention (Embodiment E1) is a compound of Formula I, or a pharmaceutically acceptable salt thereof, wherein $X_1$, $X_2$, Y, $R^1$, $R^2$, $R^A$, $R^B$ and n are as defined in Formula (I) in the Summary of the Invention.

A second embodiment (Embodiment E2) is a compound of Formula I, or a pharmaceutically acceptable salt thereof, wherein $X_1$ is N, and all other variables are as defined in Embodiment E1.

A third embodiment (Embodiment E3) is a compound of Formula I, or a pharmaceutically acceptable salt thereof, wherein $X_1$ is CH, and all other variables are as defined in Embodiment E1.

A fourth embodiment (Embodiment E4) is a compound of Formula I, or a pharmaceutically acceptable salt thereof wherein $X_1$ is defined in Embodiment E2 or E3, $X_2$ is N, and all other variables are as defined in Embodiment E1.

A fifth embodiment (Embodiment E5) is a compound of Formula I, or a pharmaceutically acceptable salt thereof, wherein $X_1$ is defined in Embodiment E2 or E3. $X_2$ is CH, and all other variables are as defined in Embodiment E1.

A sixth embodiment (Embodiment E6) is a compound of Formula I, or a pharmaceutically acceptable salt thereof, wherein $X_1$ and $X_2$ together with the ring atoms to which they are attached form a 5-6 membered aromatic monocyclic ring with 0, 1 or 2 heteroatom ring atoms independently selected from the group consisting of N and O, wherein said monocyclic ring is fused to the ring having $X_1$ and $X_2$ further wherein said monocyclic ring is optionally substituted with 1, 2, or 3 substituents independently selected from the group consisting of halogen, —$C_1$-$C_6$alkyl and —$C_1$-$C_6$haloalkyl, and all other variables are as defined in Embodiment E1;

In one sub-embodiment of Embodiment E6, the monocyclic ring has 0 heteroatom ring atoms. In another sub-embodiment of Embodiment E6, the monocyclic ring has 1 heteroatom ring atom. In particular instances of this sub-embodiment, the heteroatom ring atom is N. In another sub-embodiment of Embodiment E6, the monocyclic ring has 2 heteroatom ring atoms.

A seventh embodiment (Embodiment E7) is a compound of Formula I, or a pharmaceutically acceptable salt thereof wherein $X_1$ is defined in any of Embodiments E2, E3 and E6, $X_2$ is defined in any of Embodiments E4-E6, Y is O and all other variables are as defined in Embodiment E1.

An eighth embodiment (Embodiment E8) is a compound of Formula I, or a pharmaceutically acceptable salt thereof, wherein $X_1$ is defined in any of Embodiments E2, E3 and E6, $X_2$ is defined in any of Embodiments E4-E6, Y is a bond and all other variables are as defined in Embodiment E1.

A ninth embodiment (Embodiment E9) is a compound of Formula I, or a pharmaceutically acceptable salt thereof, wherein $X_1$ is defined in any of Embodiments E2, E3 and E6, $X_2$ is defined in any of Embodiments E4-E6, Y is defined in Embodiment E7 or E8, $R^1$ is hydrogen and all other variables are as defined in Embodiment E1.

A tenth embodiment (Embodiment E10) is a compound of Formula I, or a pharmaceutically acceptable salt thereof, wherein $X_1$ is defined in any of Embodiments E2, E3 and E6, $X_2$ is defined in any of Embodiments E4-E6, Y is defined in Embodiment E7 or E8, $R^1$ is halogen and all other variables are as defined in Embodiment E1. In specific instances of this embodiment, halogen is selected from F or Br.

An eleventh embodiment (Embodiment E11) is a compound of Formula I, or a pharmaceutically acceptable salt thereof, wherein $X_1$ is defined in any of Embodiments E2, E3 and E6, $X_2$ is defined in any of Embodiments E4-E6, Y is defined in Embodiment E7 or E8, $R^1$ is —$C_1$-$C_6$alkyl and all other variables areas defined in Embodiment E1. In specific instances of this embodiment, —$C_1$-$C_6$alkyl is —$CH_3$.

A twelfth embodiment (Embodiment E12) is a compound of Formula I. or a pharmaceutically acceptable salt thereof, wherein $X_1$ is defined in any of Embodiments E2, E3 and E6, $X_2$ is defined in any of Embodiments E4-E6, Y is defined in Embodiment E7 or E8, $R^1$ is —$C_1$-$C_6$haloalkyl and all other variables are as defined in Embodiment E1.

A thirteenth embodiment (Embodiment E13) is a compound of Formula I, or a pharmaceutically acceptable salt thereof, wherein $X_1$ is defined in any of Embodiments E2, E3 and E6, $X_2$ is defined in any of Embodiments E4-E6, Y is defined in Embodiment E7 or E8, $R^1$ is —$C_1$-$C_6$alkoxy and all other variables areas defined in Embodiment E1. In specific instances of this embodiment, —$C_1$-$C_6$alkoxy is —$OCH_3$.

A fourteenth embodiment (Embodiment E14) is a compound of Formula I, or a pharmaceutically acceptable salt thereof, wherein $X_1$ is defined in any of Embodiments E2, E3 and E6, $X_2$ is defined in any of Embodiments E4-E6, Y is defined in Embodiment E7 or E8, $R^1$ is —$C_1$-$C_6$haloalkoxy and all other variables are as defined in Embodiment E1.

A fifteenth embodiment (Embodiment E15) is a compound of Formula I, or a pharmaceutically acceptable salt thereof, wherein $X_1$ is defined in any of Embodiments E2, E3 and E6, $X_2$ is defined in any of Embodiments E4-E6, Y is defined in Embodiment E7 or E8, $R^1$ is —C(O)$OR^a$ and all other variables are as defined in Embodiment E1.

A sixteenth embodiment (Embodiment E16) is a compound of Formula I, or a pharmaceutically acceptable salt thereof, wherein $X_1$ is defined in any of Embodiments E2, E3 and E6, $X_2$ is defined in any of Embodiments E4-E6, Y is defined in Embodiment E7 or E8, $R^1$ is —C(O)$NR^aR^b$ and all other variables are as defined in Embodiment E1.

A seventeenth embodiment (Embodiment E17) is a compound of Formula I, or a pharmaceutically acceptable salt thereof, wherein $X_1$ is defined in any of Embodiments E2, E3 and E6, $X_2$ is defined in any of Embodiments E4-E6, Y is defined in Embodiment E7 or E8, $R^1$ is —CN and all other variables are as defined in Embodiment E1.

An eighteenth embodiment (Embodiment E18) is a compound of Formula I, or a pharmaceutically acceptable salt thereof, wherein $X_1$ is defined in any of Embodiments E2, E3 and E6. $X_2$ is defined in any of Embodiments E4-E6, Y is defined in Embodiment E7 or E8, $R^1$ is —$CH_2OH$ and all other variables are as defined in Embodiment E1.

A nineteenth embodiment (Embodiment E19) is a compound of Formula I, or a pharmaceutically acceptable salt thereof, wherein $X_1$ is defined in any of Embodiments E2, E3 and E6, $X_2$ is defined in any of Embodiments E4-E6, Y is defined in Embodiment E7 or E8, $R^1$ is —S$C_1$-$C_6$alkyl and all other variables are as defined in Embodiment E1.

A twentieth embodiment (Embodiment E20) is a compound of Formula I, or a pharmaceutically acceptable salt thereof, wherein $X_1$ is defined in any of Embodiments E2, E3 and E6, $X_2$ is defined in any of Embodiments E4-E6, Y is defined in Embodiment E7 or E8, $R^1$ is —$SO_2R^a$ and all other variables are as defined in Embodiment E1.

A twenty-first embodiment (Embodiment E21) is a compound of Formula I, or a pharmaceutically acceptable salt thereof, wherein $X_1$ is defined in any of Embodiments E2, E3 and E6. $X_2$ is defined in any of Embodiments E4-E6, Y is defined in Embodiment E7 or E8, $R^1$ is —$SO_2NR^aR^b$ and all other variables are as defined in Embodiment E1.

A twenty-second embodiment (Embodiment E22) is a compound of Formula I, or a pharmaceutically acceptable salt thereof, wherein $X_1$ is defined in any of Embodiments E2, E3 and E6, $X_2$ is defined in any of Embodiments E4-E6, Y is defined in Embodiment E7 or E8, $R^1$ is —$OR^a$ and all other variables are as defined in Embodiment E1.

A twenty-third embodiment (Embodiment E23) is a compound of Formula I, or a pharmaceutically acceptable salt thereof, wherein $X_1$ is defined in any of Embodiments E2, E3 and E6, $X_2$ is defined in any of Embodiments E4-E6, Y is defined in Embodiment E7 or E8, $R^1$ is —$NR^aR^b$ and all other variables are as defined in Embodiment E1.

A twenty-fourth embodiment (Embodiment E24) is a compound of Formula I, or a pharmaceutically acceptable salt thereof, wherein $X_1$ is defined in any of Embodiments E2, E3 and E6, $X_2$ is defined in any of Embodiments E4-E6, Y is defined in Embodiment E7 or E8, $R^1$ is —C(O)$NR^a$AryA3 and all other variables are as defined in Embodiment E1. In specific instances of this embodiment, AryA3 is pyrazolyl, imidazolyl, pyrrolyl, phenyl, pyrazolo[5,4-b]pyridinyl, 3,4-dihydro-H-isoquinolinyl, or indolyl, optionally substituted with 1, 2 or 3 substituents independently selected from the group consisting of halogen, —$C_1$-$C_6$alkyl, —$C_1$-$C_6$alkenyl, —$C_1$-$C_6$haloalkyl, —$C_1$-$C_6$alkoxy, —$C_1$-$C_6$haloalkoxy, —CN, —$CH_2OH$, —S$C_1$-$C_6$alkyl, —$SO_2R^a$, —$SO_2NR^aR^b$, —$OR^a$, —C(O)$OR^a$, —C(O)$NR^aR^b$, —C(O)$NR^a$AryA4, —$NR^a$C(O)AryA4, AryA4, —$NR^aR^b$, oxo and —OH; wherein the —$C_1$-

$C_6$alkyl or the —$C_1$-$C_6$alkenyl are optionally substituted with 1 or 2 substituents independently selected from the group consisting of —$C_3$-$C_6$cycloalkyl, —C(O)OR$^a$ and —C(O)NR$^a$R$^b$. AryA4, in specific instances of the foregoing is pyridyl or pyrazolyl, optionally substituted with 1, 2, or 3 substituents independently selected from the group consisting of halogen, —$C_1$-$C_6$alkyl, —$C_1$-$C_6$haloalkyl, —$C_1$-$C_6$alkoxy, —$C_1$-$C_6$haloalkoxy, —CN, —CH$_2$OH, —C(O)NR$^a$R$^b$, —SC$_1$-$C_6$alkyl, —SO$_2$R$^a$, —SO$_2$NR$^a$R$^b$, —OR$^a$ and —NR$^a$R$^b$.

A twenty-fifth embodiment (Embodiment E25) is a compound of Formula I, or a pharmaceutically acceptable salt thereof, wherein $X_1$ is defined in any of Embodiments E2, E3 and E6, $X_2$ is defined in any of Embodiments E4-E6, Y is defined in Embodiment E7 or E8, $R^1$ is -AryA3 and all other variables areas defined in Embodiment E1. In specific instances of this embodiment, AryA3 is pyrazolyl, imidazolyl, pyrrolyl, phenyl, pyrazolo[5,4-b]pyridinyl, 3,4-dihydro-1H-isoquinolinyl, or indolyl, optionally substituted with 1, 2 or 3 substituents independently selected from the group consisting of halogen, —$C_1$-$C_6$alkyl, —$C_1$-$C_6$alkenyl, —$C_1$-$C_6$haloalkyl, —$C_1$-$C_6$alkoxy, —$C_1$-$C_6$haloalkoxy, —CN, —CH$_2$OH, —SC$_1$-$C_6$alkyl, —SO$_2$R$^a$, —SO$_2$NR$^a$R$^b$, —OR$^a$, —C(O)OR$^a$, —C(O)NR$^a$R$^b$, —C(O)NR$^a$AryA4, AryA4, —NR$^a$R$^b$, oxo and —OH; wherein the —$C_1$-$C_6$alkyl or the —$C_1$-$C_6$alkenyl are optionally substituted with 1 or 2 substituents independently selected from the group consisting of —$C_1$-$C_6$cycloalkyl, —C(O)OR$^a$ and —C(O)NR$^a$R$^b$. AryA4, in specific instances of the foregoing is pyridyl or pyrazolyl, optionally substituted with 1, 2, or 3 substituents independently selected from the group consisting of halogen, —$C_1$-$C_6$alkyl, —$C_1$-$C_6$haloalkyl, —$C_1$-$C_6$alkoxy, —$C_1$-$C_6$haloalkoxy, —CN, —CH$_2$OH, —C(O)NR$^a$R$^b$, —SC$_1$-$C_6$alkyl, —SO$_2$R$^a$, —SO$_2$NR$^a$R$^b$, —OR$^a$ and —NR$^a$R$^b$.

A twenty-sixth embodiment (Embodiment E26) is a compound of Formula I, or a pharmaceutically acceptable salt thereof, wherein $X_1$ is defined in any of Embodiments E2, E3 and E6, $X_2$ is defined in any of Embodiments E4-E6, Y is defined in Embodiment E7 or E8, $R^1$ is defined in any of Embodiments E9-E25, each $R^2$ is independently halogen, —$C_1$-$C_6$alkyl, —$C_1$-$C_6$haloalkyl, —$C_1$-$C_6$alkoxy, —$C_1$-$C_6$haloalkoxy, —CN, —CH$_2$OH, —C(O)NR$^a$R$^b$, —SC$_1$-$C_6$alkyl, —SO$_2$R$^a$, —SO$_2$NR$^a$R$^b$, —OR$^a$ or —NR$^a$R$^b$ and all other variables are as defined in Embodiment E1. In specific instances of this Embodiment, each $R^2$ is selected from halogen and —$C_1$-$C_6$alkyl. In particular instances of this embodiment, halogen is F or Br.

A twenty-seventh embodiment (Embodiment E27) is a compound of Formula I, or a pharmaceutically acceptable salt thereof, wherein $X_1$ is defined in any of Embodiments E2, E3 and E6, $X_2$ is defined in any of Embodiments E4-E6, Y is defined in Embodiment E7 or E8, $R^1$ is defined in any of Embodiments E9-E25, $R^2$ is defined in Embodiment E26, $R^A$ is-$C_1$-$C_6$alkyl wherein the —$C_1$-$C_6$alkyl is optionally substituted with 1, 2, or 3 substituents independently selected from the group consisting of halogen, —$C_1$-$C_6$alkoxy, —$C_1$-$C_6$haloalkoxy, —C(O)OR$^a$, —NR$^a$R$^b$ and —OH, and all other variables are as defined in Embodiment E1. In particular instances of this embodiment, —$C_1$-$C_6$alkyl is unsubstituted. In other instances of this embodiment, —$C_1$-$C_6$alkyl is substituted with —$C_1$-$C_6$alkoxy. In other instances of this embodiment, —$C_1$-$C_6$alkyl is substituted with —C(O)OR$^a$.

A twenty-eighth embodiment (Embodiment E28) is a compound of Formula I, or a pharmaceutically acceptable salt thereof, wherein $X_1$ is defined in any of Embodiments E2, E3 and E6, $X_2$ is defined in any of Embodiments E4-E6, Y is defined in Embodiment E7 or E8, $R^1$ is defined in any of Embodiments E9-E25, $R^2$ is defined in Embodiment E26, $R^A$ is —[OCH$_2$CH$_2$]$_m$NR$^a$C(O)R$^C$ and all other variables areas defined in Embodiment E1. In specific instances of this embodiment, R$^C$ is —(CH$_2$)$_p$-adamantane. In other instances of this embodiment, R$^C$ is (CH$_2$)$_m$-5,5-difluoro-1,3-dimethyl-5H-5λ$^4$,6λ$^4$-dipyrrolo[1,2-c:2',1'-f][1,3,2]diazaborinine. In other instances of this embodiment, R$^C$ is —(CH$_2$)$_m$-(3aR,6aS)-tetrahydro-1H-thieno[3,4-d]imidazol-2(3H)-one. In other instances of this embodiment, R$^C$ is —$C_1$-$C_6$alkyl, wherein the —$C_1$-$C_6$alkyl is optionally substituted with 1 or 2 substituents independently selected from the group consisting of —NR$^a$C(O)C$_1$-$C_6$alkyl —NR$^a$C(O)OC$_1$-$C_6$alkyl, —NR$^a$C(=NC(O)OR$^b$)(NR$^a$C(O)OR$^b$), —[OC$_1$-$C_6$alkylene]$_o$C(O)NR$^a$C$_1$-$C_6$alkyl and AryB1, wherein the —NR$^a$C(O)C$_1$-$C_6$alkyl is optionally substituted with 1, 2 or 3 substituents independently selected from the group consisting of —OR$^a$, —NR$^a$R$^b$ and AryB1. AryB1, in specific instances of the foregoing, is phenyl, optionally substituted with 1, 2, or 3 substituents independently selected from the group consisting of AryB2, halogen, —$C_1$-$C_6$alkyl, —$C_1$-$C_6$haloalkyl, —$C_1$-$C_6$alkoxy, —$C_1$-$C_6$haloalkoxy, —C(O)OR$^a$, —NR$^a$R$^b$ and —OH. AryB2, in specific instances of the foregoing, is thiazolyl, optionally substituted with 1, 2, or 3 substituents independently selected from the group consisting of halogen, —$C_1$-$C_6$alkyl, —$C_1$-$C_6$haloalkyl, —$C_1$-$C_6$alkoxy, —$C_1$-$C_6$haloalkoxy, and —OR$^a$. In other instances of this embodiment. R$^C$ is —$C_1$-$C_2$alkylene[OC$_1$-$C_2$alkylene]$_o$C(O)NR$^a$C$_1$-$C_6$alkyl, wherein the —$C_1$-$C_2$alkylene[OC$_1$-$C_2$alkylene]$_o$C(O)NR$^a$C$_1$-$C_6$alkyl is optionally substituted with -HetB1 or —C(O)HetB1. HetB1, in specific instances of the foregoing, is pyrrolidinyl, optionally substituted with 1 or 2 substituents independently selected from the group consisting of —C(O)NR$^a$(CH$_2$)$_n$-AryB1 and —OR$^a$. AryB1, in specific instances of the foregoing, is phenyl, optionally substituted with 1, 2, or 3 substituents independently selected from the group consisting of AryB2, halogen, —$C_1$-$C_6$alkyl, —$C_1$-$C_6$haloalkyl, —$C_1$-$C_6$alkoxy, —$C_1$-$C_6$haloalkoxy, —C(O)OR$^a$, —NR$^a$R$^b$ and —OH. AryB2, in specific instances of the foregoing, is thiazolyl, optionally substituted with 1, 2, or 3 substituents independently selected from the group consisting of halogen, —$C_1$-$C_6$alkyl, —$C_1$-$C_6$haloalkyl, —$C_1$-$C_6$alkoxy, —$C_1$-$C_6$haloalkoxy, and —OR$^a$.

In one sub-embodiment of Embodiment E28 is a compound of Formula I wherein $R^A$ is —[OCH$_2$CH$_2$]$_m$NR$^a$C(O)R$^C$; each m is 2, 3 or 4, and R$^C$ is selected from the group consisting of:

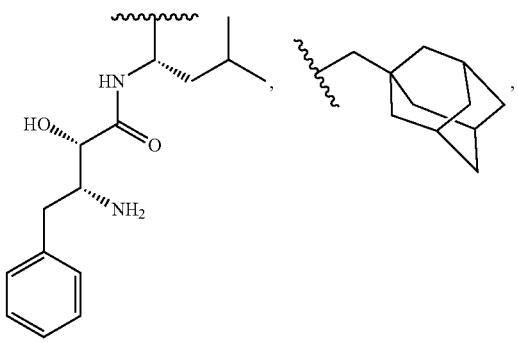

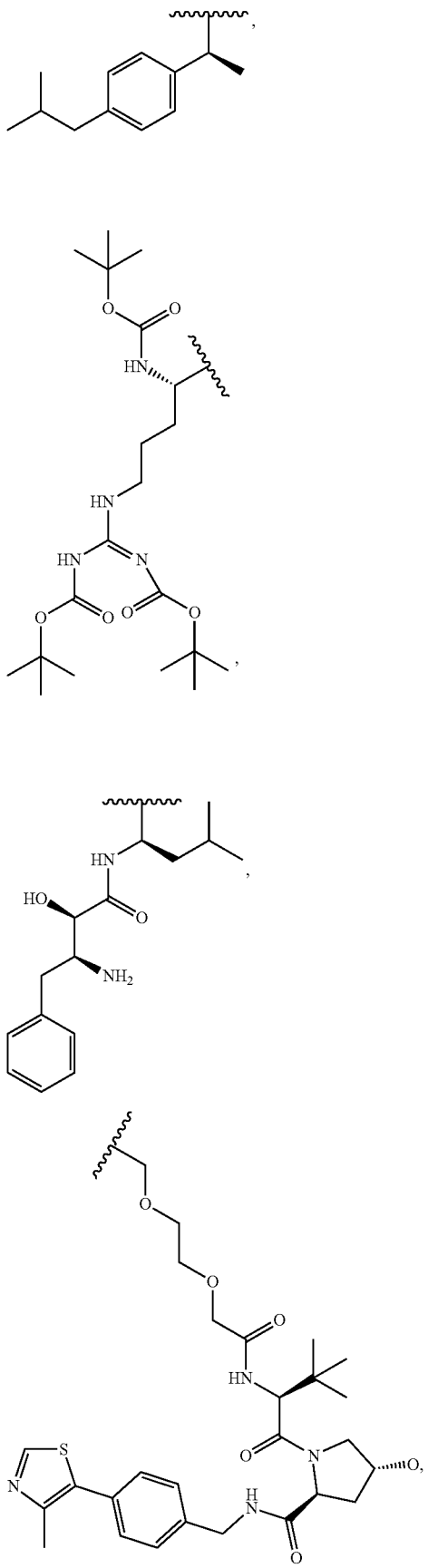
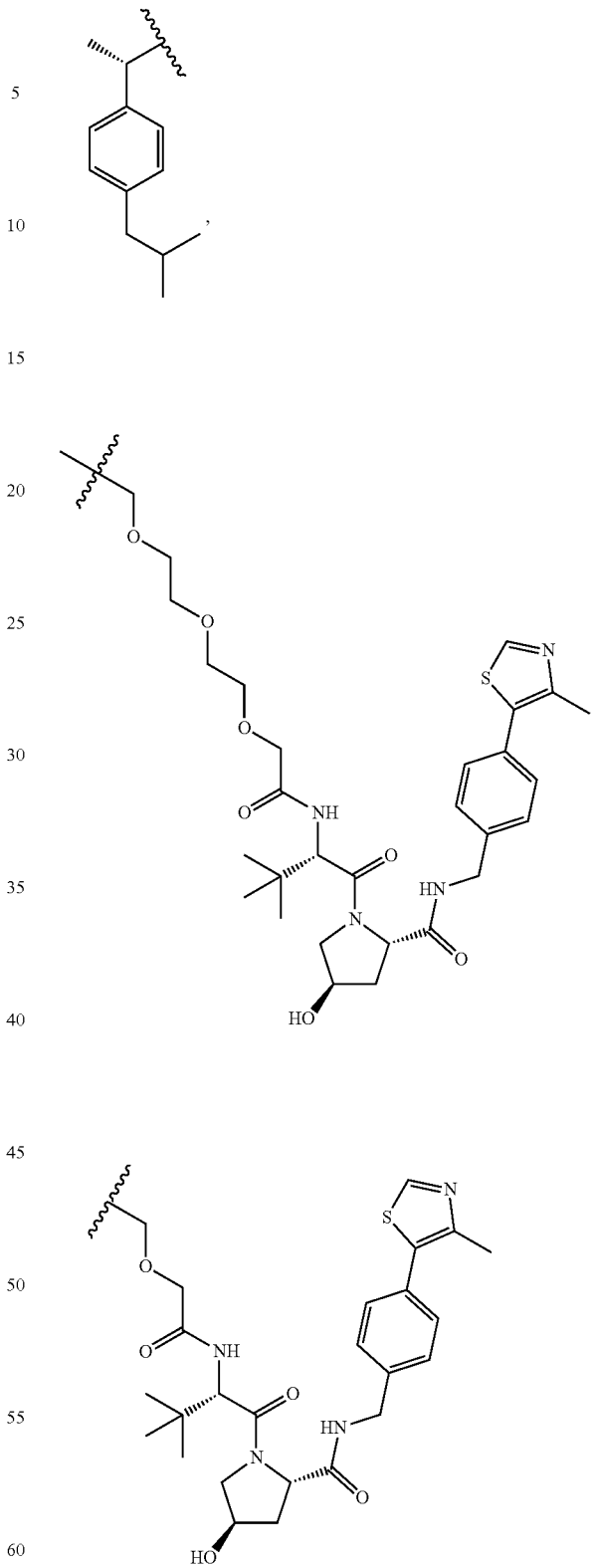
or a pharmaceutically acceptable salt thereof and all other variables are as defined in Embodiment E1. In particular instances of this sub-Embodiment, the compound is selected from the group consisting of:

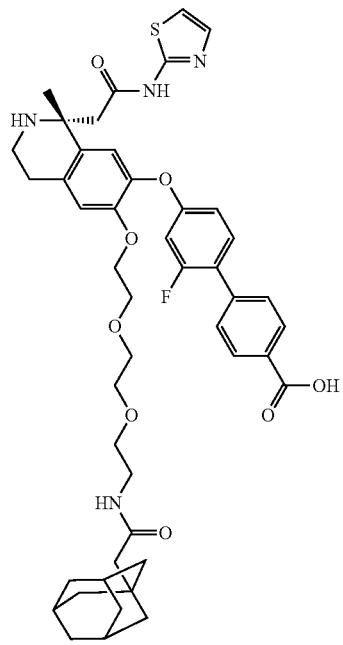
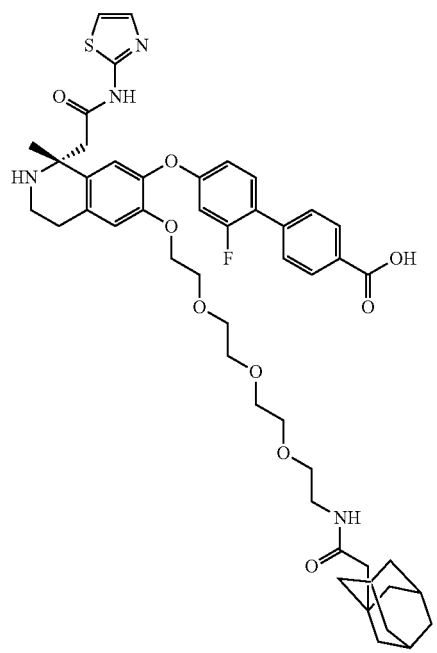
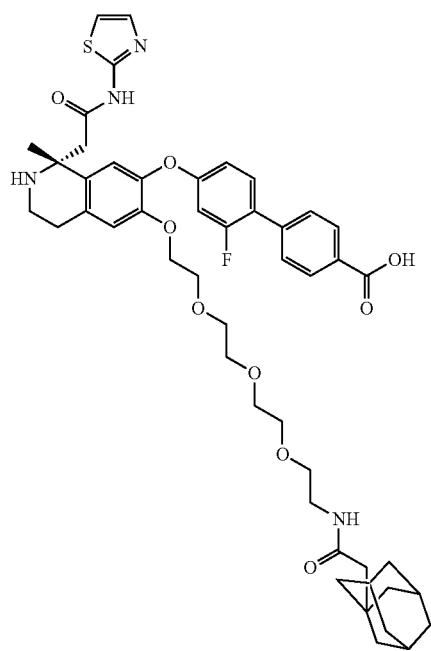
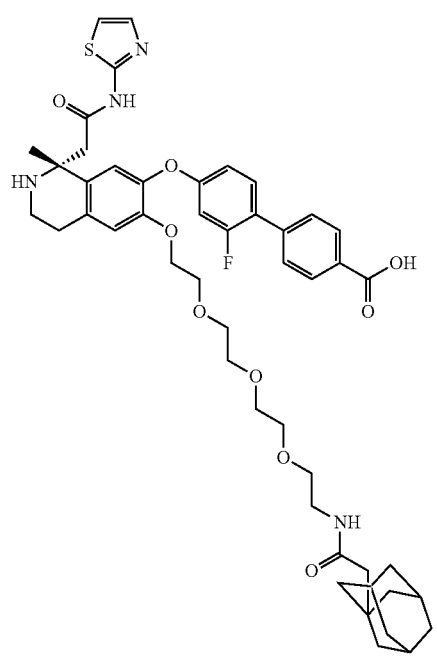

-continued

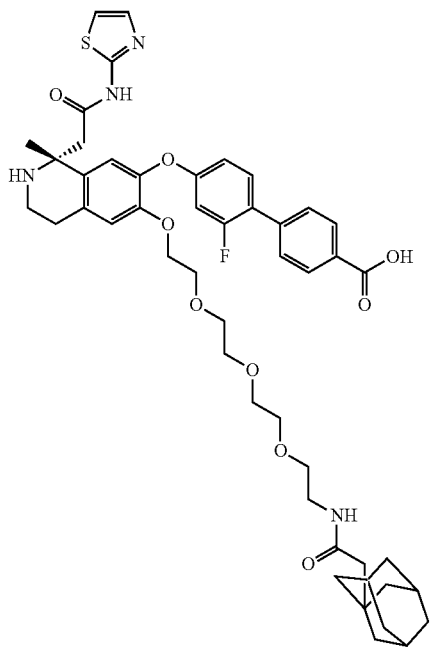 [SMILES: C[C@]1(CC(=O)Nc2nccs2)NCCc2cc(OCCOCCOCCOCCNC(=O)CC34CC5CC(CC(C5)C3)C4)c(Oc3ccc(-c4ccc(C(=O)O)cc4)c(F)c3)cc21]

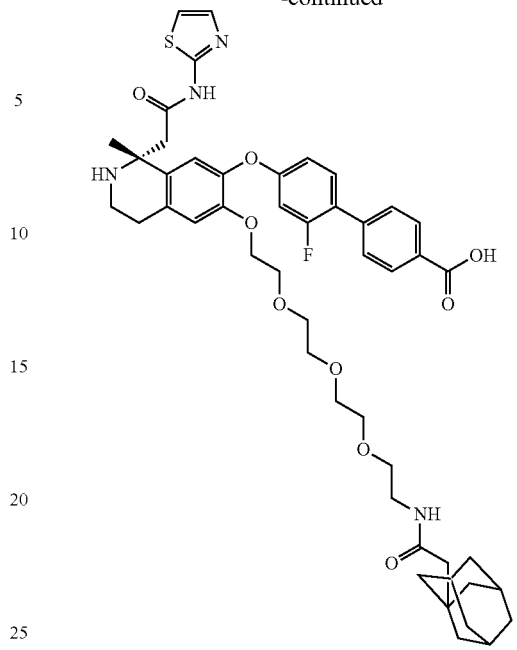

or a pharmaceutically acceptable salt thereof.

In another sub-embodiment of Embodiment E28 is a compound of Formula I wherein $R^A$ is —[OCH$_2$CH$_2$]$_m$N-R$^a$C(O)R$^C$; each m is 2, 3 or 4, and R$^C$ is selected from the group consisting of biotin, fluorescein, AlexaFluor® dyes, BODIPY®, Cascade Blue®, coumarins, Oregon Green®, Pacific Blue™, Pacific Green™, Pacific Orange™, Rhodamine Green™, Rhodamine Red™, and Texas Red® or a pharmaceutically acceptable salt thereof and all other variables are as defined in Embodiment E1.

In another sub-embodiment of Embodiment E28 is a compound of Formula I wherein $R^A$ is —[OCH$_2$CH$_2$]$_m$N-R$^a$C(O)R$^C$: each m is 2, 3 or 4, and R$^C$ is a BODIPY group which is:

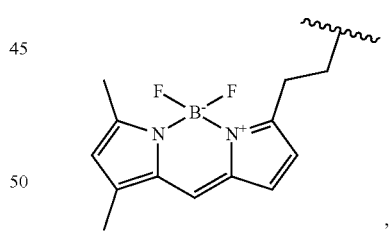

or a pharmaceutically acceptable salt thereof and all other variables are as defined in Embodiment E1.

A twenty-ninth embodiment (Embodiment E29) is a compound of Formula I, or a pharmaceutically acceptable salt thereof, wherein X$_1$ is defined in any of Embodiments E2, E3 and E6, X$_2$ is defined in any of Embodiments E4-E6, Y is defined in Embodiment E7 or E8, R$^1$ is defined in any of Embodiments E9-E25, R$^2$ is defined in Embodiment E26, R$^A$ is —(CH$_2$)$_n$-AryA1. In specific instances of this embodiment. AryA1 is pyridyl, pyrimidinyl, oxadiazolyl or triazolyl, optionally substituted with 1, 2, or 3 substituents independently selected from the group consisting of halogen, —C$_1$-C$_6$alkyl, —C$_1$-C$_6$haloalkyl, —C$_1$-C$_6$alkoxy, —C$_1$-C$_6$haloalkoxy, —CN, —CH$_2$OH, —C(O)NR$^a$R$^b$,

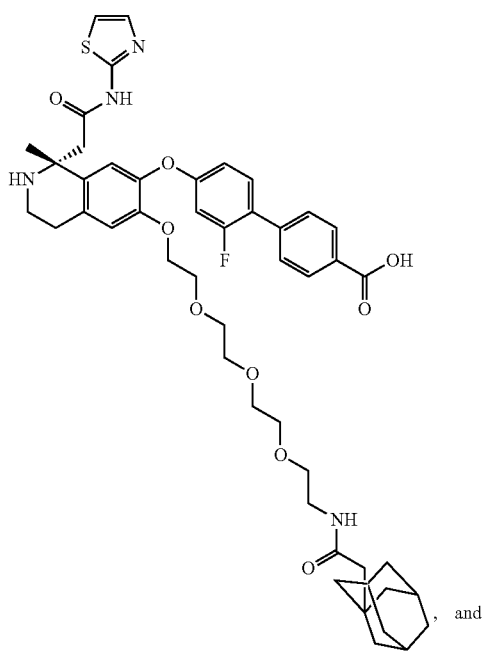

, and

—$SC_1$-$C_6$alkyl, —$SO_2R^a$, —$SO_2NR^aR^b$, —$C(O)OR^a$, —$CH(OH)C(NH_2)C(O)OR^a$, —$CH_2OCH_2CH_2OCH_3$, AryA2, —$(CH_2)_n$-HetA1, —$NR^aR^b$ and —OH; wherein the —$C_1$-$C_6$alkyl is optionally substituted with 1 or 2 substituents independently selected from the group consisting of —$OR^a$, —$NR^aR^b$, —$COOR^a$, —$C_1$-$C_6$cycloalkyl, —$C_1$-$C_4$akylCOOR$^a$, —$NR^aC(O)R^b$, —$NR^aS(O)_2R^b$, —$(CH_2)_n$-AryA2, —OAryA2 and —$NR^aC(O)$-AryA2, AryA2, in specific instances of the foregoing, is phenyl, pyrazinyl, oxadiazolyl or imidazolyl, optionally substituted with 1, 2, or 3 substituents independently selected from the group consisting of halogen, —$C_1$-$C_6$alkyl, —$C_1$-$C_6$haloalkyl-$C_1$-$C_6$alkoxy, —$C_1$-$C_6$haloalkoxy, —$COOR^a$, —CN, —$CH_2OH$, —$C(O)NR^aR^b$, —$SC_1$-$C_6$alkyl, —$SO_2R^a$, —$SO_2NR^aR^b$, —$OR^a$, —$NR^aR^b$, AryA3 and oxo. AryA3, in specific instances of the foregoing, is pyrazolyl, imidazolyl, pyrrolyl, phenyl, pyrazolo[5,4-b]pyridinyl, 3,4-dihydro-1H-isoquinolinyl, or indolyl, optionally substituted with 1, 2 or 3 substituents independently selected from the group consisting of halogen, —$C_1$-$C_6$alkyl. —$C_1$-$C_6$alkenyl, —$C_1$-$C_6$haloalkyl. —$C_1$-$C_6$alkoxy, —$C_1$-$C_6$haloalkoxy, —CN, —$CH_2OH$, —$SC_1$-$C_6$alkyl, —$SO_2R^a$, —$SO_2NR^aR^b$, —$OR^a$, —$C(O)OR^a$, —$C(O)NR^aR^b$, —$C(O)NR^a$AryA4, —$NR^aC(O)$AryA4, AryA4, —$NR^aR^b$, oxo and —OH; wherein the —$C_1$-$C_6$alkyl or the —$C_1$-$C_6$alkenyl are optionally substituted with 1 or 2 substituents independently selected from the group consisting of —$C_3$-$C_6$cycloalkyl, —$C(O)OR^a$ and —$C(O)NR^aR^b$, AryA4, in specific instances of the foregoing is pyridyl or pyrazolyl, optionally substituted with 1, 2, or 3 substituents independently selected from the group consisting of halogen, —$C_1$-$C_6$alkyl, —$C_1$-$C_6$haloalkyl, —$C_1$-$C_6$alkoxy, —$C_1$-$C_6$haloalkoxy, —CN, —$CH_2OH$, —$C(O)NR^aR^b$, —$SC_1$-$C_6$alkyl, —$SO_2R^a$, —$SO_2NR^aR^b$, —$OR^a$ and —$NR^aR^b$. HetA1, in specific instances of the foregoing, is tetrahydrofuranyl, tetrahydropyranyl, or imidazolidinyl, optionally substituted with 1 or 2 substituents independently selected from the group consisting of —$C_1$-$C_6$alkyl, —$CH_2OH$, —$C(O)NR^aR^b$, —$SC_1$-$C_6$alkyl, —$SO_2R^a$, —$SO_2NR^aR^b$, —$OR^a$, —$NR^aR^b$, —CN and oxo.

A thirtieth embodiment (Embodiment E30) is a compound of Formula I, or a pharmaceutically acceptable salt thereof, wherein $X_1$ is defined in any of Embodiments E2, E3 and E6, $X_2$ is defined in any of Embodiments E4-E6, Y is defined in Embodiment E7 or E8, $R^1$ is defined in any of Embodiments E9-E25, $R^2$ is defined in Embodiment E26, $R^A$ is —$(CH_2)_n$-HetA1. In specific instances of this embodiment, HetA1 is tetrahydrofuranyl, tetrahydropyranyl, or imidazolidinyl, optionally substituted with 1 or 2 substituents independently selected from the group consisting of —$C_1$-$C_6$alkyl, —$CH_2OH$, —$C(O)NR^aR^b$, —$SC_1$-$C_6$alkyl, —$SO_2R^a$, —$SO_2NR^aR^b$, —$OR^a$, —$NR^aR^b$, —CN and oxo.

A thirty-first embodiment (Embodiment E31) is a compound of Formula I, or a pharmaceutically acceptable salt thereof, wherein $X_1$ is defined in any of Embodiments E2, E3 and E6, $X_2$ is defined in any of Embodiments E4-E6, Y is defined in Embodiment E7 or E8, $R^1$ is defined in any of Embodiments E9-E25, $R^2$ is defined in Embodiment E26, $R^A$ is —$C_1$-$C_3$alkylN$_3$ wherein the —$C_1$-$C_3$alkylN$_3$ is optionally substituted with 1, 2, or 3 substituents independently selected from the group consisting of halogen, —$C_1$-$C_6$alkoxy, —$C_1$-$C_6$haloalkoxy, —$C(O)OR^a$, —$NR^aR^b$ and —OH, and all other variables are as defined in Embodiment E1. In particular instances of this embodiment. —$C_1$-$C_3$alkylN$_3$ is unsubstituted.

A thirty-second embodiment (Embodiment E32) is a compound of Formula I, or a pharmaceutically acceptable salt thereof, wherein $X_1$ is defined in any of Embodiments E2, E3 and E6. $X_2$ is defined in any of Embodiments E4-E6, Y is defined in Embodiment E7 or E8, $R^1$ is defined in any of Embodiments E9-E25, $R^2$ is defined in Embodiment E26, $R^A$ is defined in any of Embodiments E27-E31, $R^B$ is -AryA5 and all other variables are as defined in Embodiment E1. In specific instances of this embodiment, AryA5 is thiazolyl, phenyl, pyridyl, pyridazinyl or indolyl, optionally substituted with 1, 2 or 3 substituents independently selected from the group consisting of halogen, —$C_1$-$C_6$alkyl, —$C_1$-$C_6$haloalkoxy, —$C_1$-$C_6$haloalkoxy, —$NR^aR^b$, —CN, —$CH_2OH$, —$C(O)NR^aR^b$, —$SC_1$-$C_6$alkyl, —$SO_2R^a$, —$SO_2NR^aR^b$, and —$OR^a$.

A thirty-third embodiment (Embodiment E33) is a compound of Formula I, or a pharmaceutically acceptable salt thereof, wherein $X_1$ is defined in Embodiment E3, $X_2$ is defined in Embodiment E4 or E5, Y is defined in Embodiment E7 or E8, $R^1$ is defined in any of Embodiments E9-E25, $R^2$ is defined in Embodiment E26, $R^A$ is defined in any of Embodiments E27-E31, $R^B$ is -AryA5 linked to $X_1$ through an —$OC_1$-$C_6$alkylene or an —$OC_6$-$C_7$alkenylene, wherein the O of the —$OC_6$-$C_7$alkylene or —$OC_6$-$C_7$alkenylene is bound at the $X_1$ position and all other variables are as defined in Embodiment E1. In specific instances of this embodiment, AryA5 is thiazolyl.

A thirty-fourth embodiment (Embodiment E34) is a compound of Formula I, or a pharmaceutically acceptable salt thereof, wherein $X_1$ is defined in any of Embodiments E2, E3 and E6, $X_2$ is defined in any of Embodiments E4, E5 and E6, Y is defined in Embodiment E7 or E8, $R^1$ is defined in any of Embodiments E9-E25, $R^2$ is defined in Embodiment E26, $R^A$ is defined in any of Embodiments E27-E31, $R^B$ is defined in Embodiment E32 or E33, each $R^a$ and $R^b$ is selected from the group consisting of H and —$C_1$-$C_6$alkyl and all other variables are as defined in Embodiment E1.

A thirty-fifth embodiment (Embodiment E35) is a compound of Formula I, or a pharmaceutically acceptable salt thereof, wherein $X_1$ is defined in any of Embodiments E2, E3 and E6, $X_2$ is defined in any of Embodiments E4, E5 and E6, Y is defined in Embodiment E7 or E8, $R^1$ is defined in any of Embodiments E9-E25, $R^2$ is defined in Embodiment E26, $R^A$ is defined in any of Embodiments E27-E31, $R^B$ is defined in Embodiment E32 or E33, each $R^a$ and $R^b$ is defined in Embodiment E1 or E34, each n is 0, 1 or 2 and all other variables are as defined in Embodiment E1. In particular instances of this Embodiment, each n is 0 or 1.

A thirty-sixth embodiment (Embodiment E36) is a compound of Formula I, or a pharmaceutically acceptable salt thereof, wherein $X_1$ is defined in any of Embodiments E2, E3 and E6, $X_2$ is defined in any of Embodiments E4, E5 and E6, Y is defined in Embodiment E7 or E8, $R^1$ is defined in any of Embodiments E9-E25, $R^2$ is defined in Embodiment E26, $R^A$ is defined in any of Embodiments E27-E31, $R^B$ is defined in Embodiment E32 or E33, each $R^a$ and $R^b$ is defined in Embodiment E1 or E34, each n is defined in Embodiment E35, each m is 1, 2, 3, or 4 and all other variables are as defined in Embodiment E1. In particular instances of this Embodiment, each m is 2, 3, or 4.

A thirty-seventh embodiment (Embodiment E37) is a compound of Formula I, or a pharmaceutically acceptable salt thereof, wherein $X_1$ is defined in any of Embodiments E2, E3 and E6, $X_2$ is defined in any of Embodiments E4, E5 and E6, Y is defined in Embodiment E7 or E8, $R^1$ is defined in any of Embodiments E9-E25, $R^2$ is defined in Embodiment E26, $R^A$ is defined in any of Embodiments E27-E31, $R^B$ is defined in Embodiment E32 or E33, each $R^a$ and $R^b$ is defined in Embodiment E1 or E34, each n is defined in Embodiment E35, each m is defined in Embodiment E36, each o is 1, 2 or 3 and all other variables are as defined in Embodiment E1. In particular instances of this Embodiment, each o is 3.

A thirty-eighth embodiment (Embodiment E38) is a compound of Formula I, or a pharmaceutically acceptable salt thereof, wherein $X_1$ is defined in any of Embodiments E2, E3 and E6, $X_2$ is defined in any of Embodiments E4, E5 and E6, Y is defined in Embodiment E7 or E8, $R^1$ is defined in any of Embodiments E9-E25, $R^2$ is defined in Embodiment E26, $R^A$ is defined in any of Embodiments E27-E31, $R^B$ is defined in Embodiment E32 or E33, each $R^a$ and $R^b$ is defined in Embodiment E34, each n is defined in Embodiment E35, each m is defined in Embodiment E36, each o is defined in Embodiment E37, each p is 1, 2, 3 or 4 and all other variables are as defined in Embodiment E1. In particular instances of this Embodiment, each p is 1 or 2.

A thirty-ninth embodiment of the invention (Embodiment E39) is: (1) a compound having a structure of any of the compounds numbered 1-112 in the Examples herein, (2) the free acid or free base base form of any compound numbered 1-112 herein that is depicted as a salt, (3) the zwitterionic form of any of compounds 1-112, or (4) a pharmaceutically acceptable salt of the compounds described in (1), (2), and/or (3).

A fortieth embodiment of the invention (Embodiment E40) is a compound having a structure selected from the group consisting of:

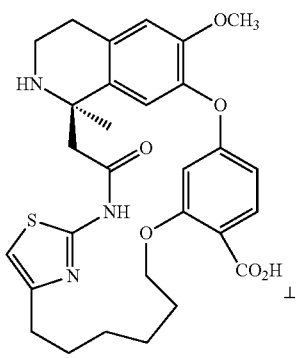

1

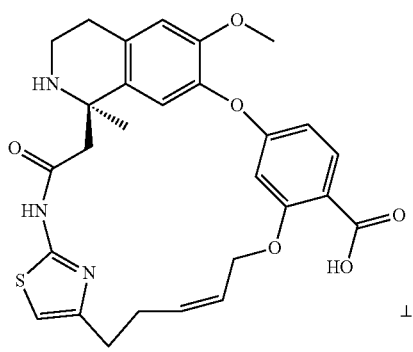

2

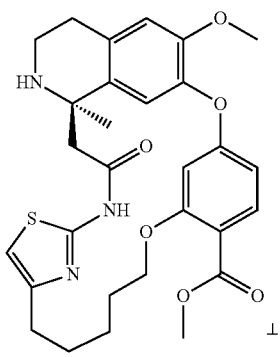

3

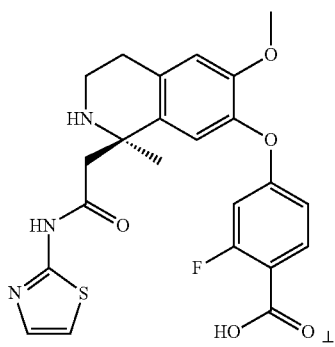

4

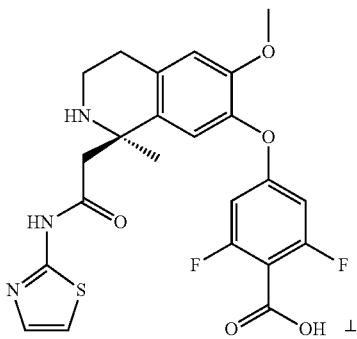

5

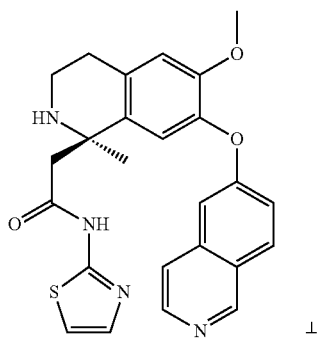

6

-continued
7
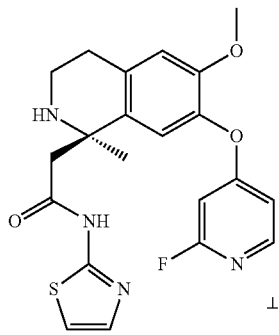
8
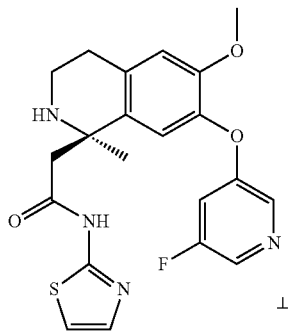
9
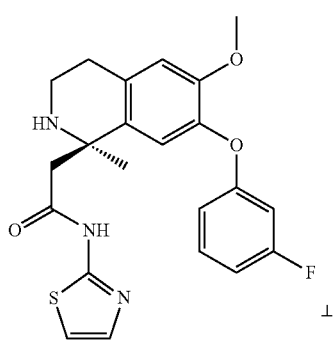
10
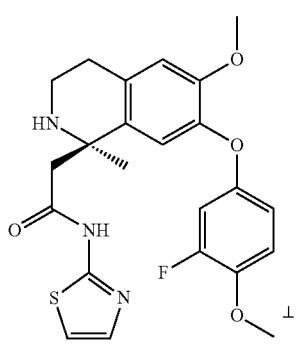
11
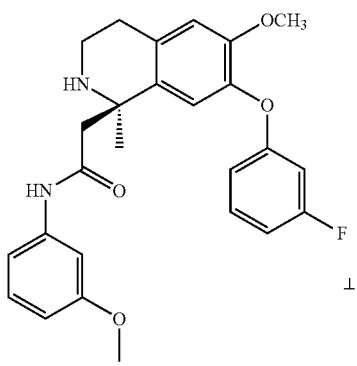
12
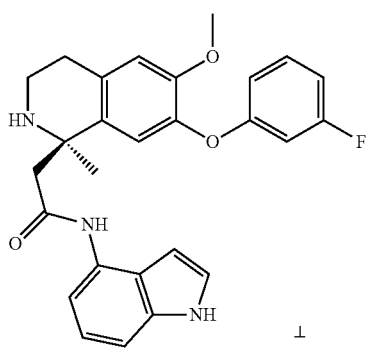
13
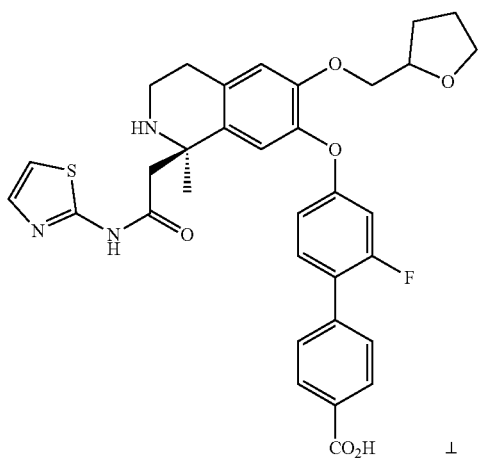
14
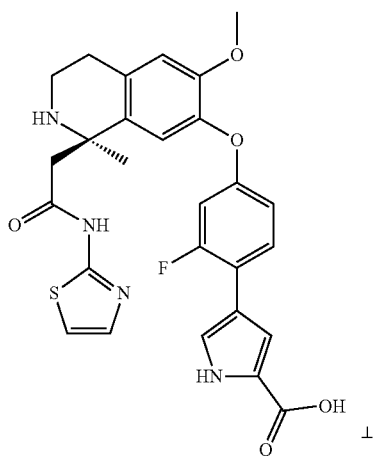

-continued
15
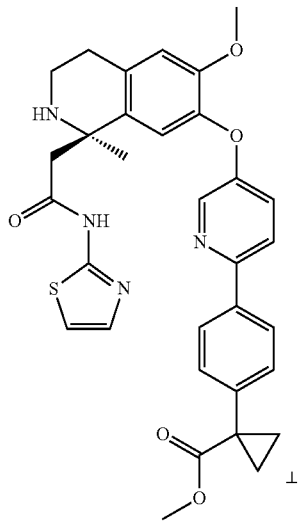
16
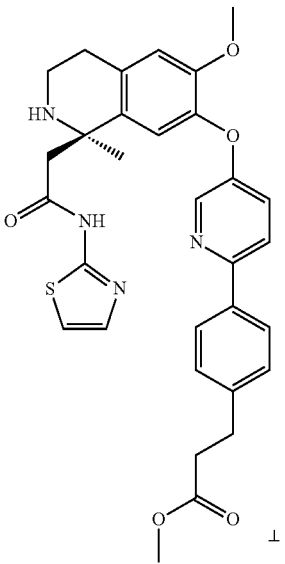
17
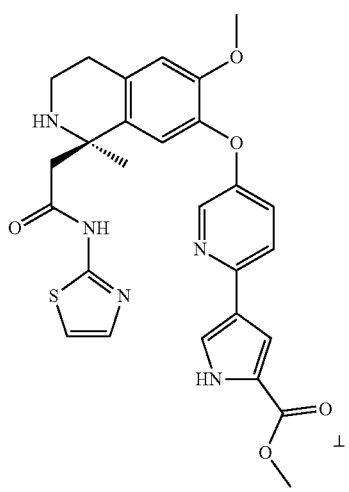
18
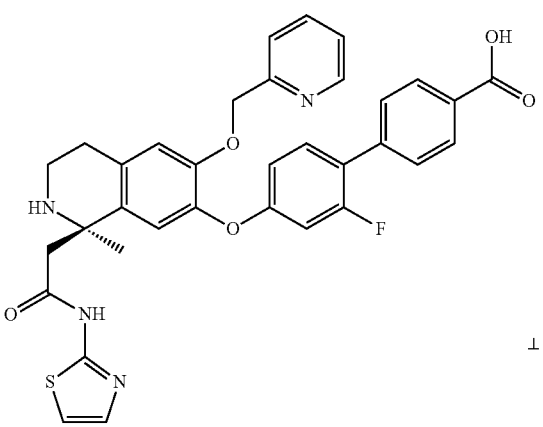
19
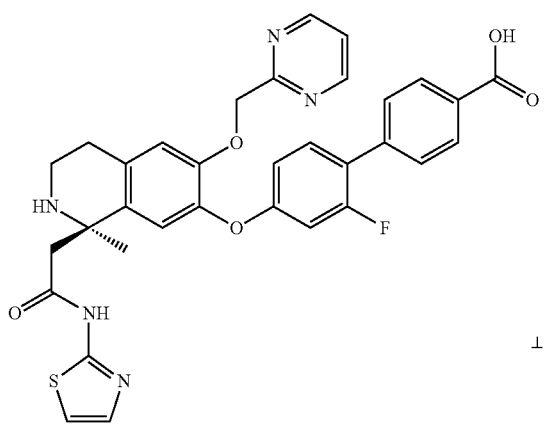
20
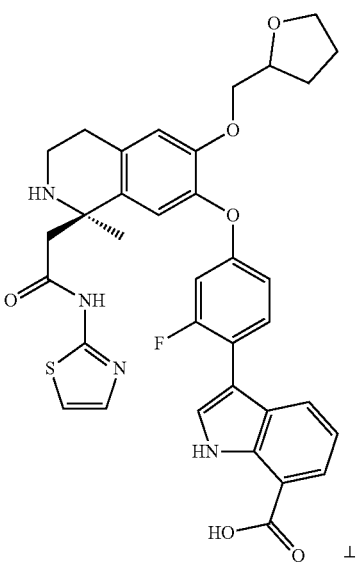

-continued
21
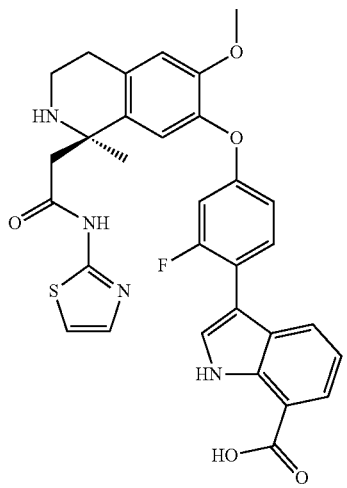
22
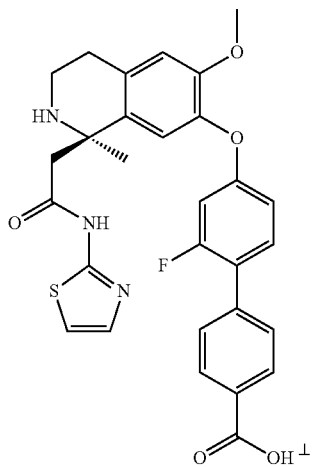
23
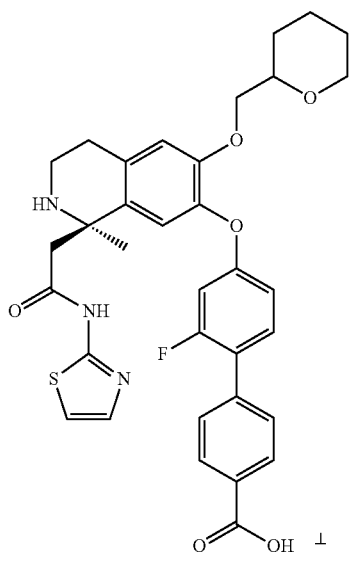
24
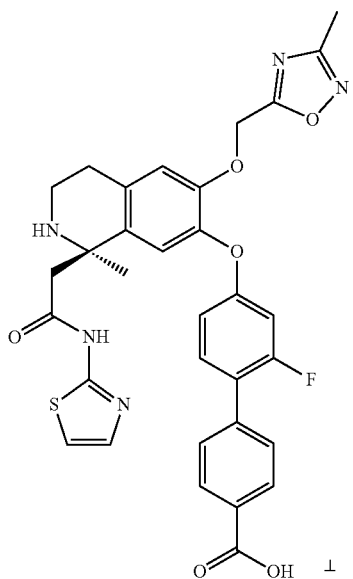
25
26
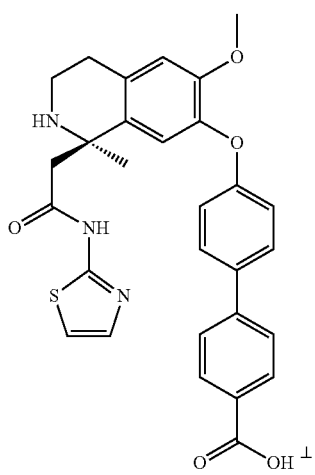

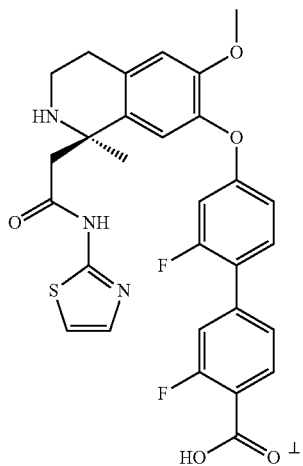
27
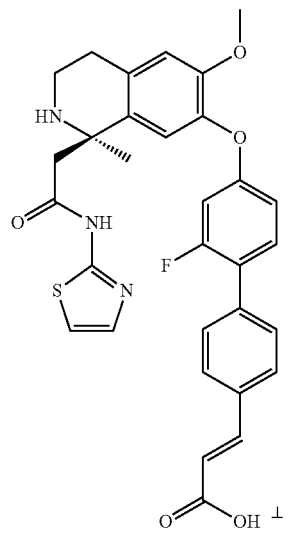
28
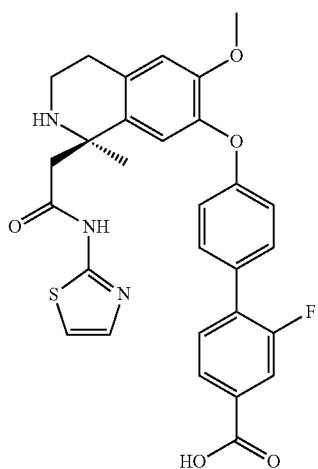
29
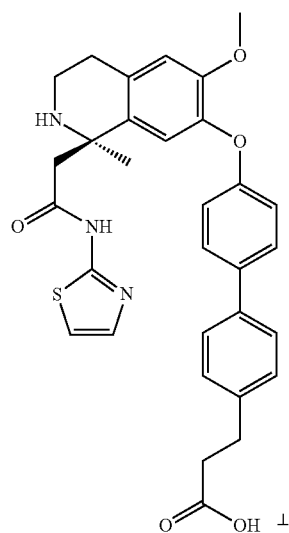
30
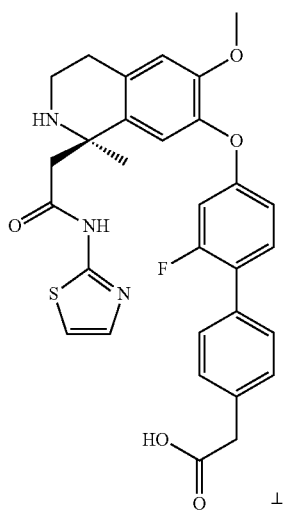
31
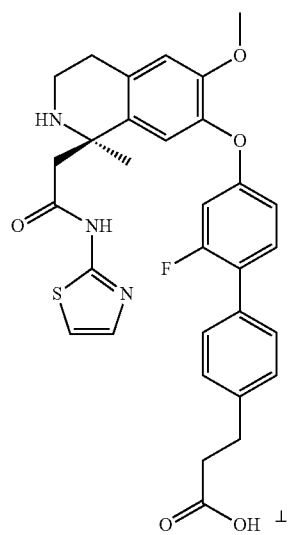
32

-continued
33
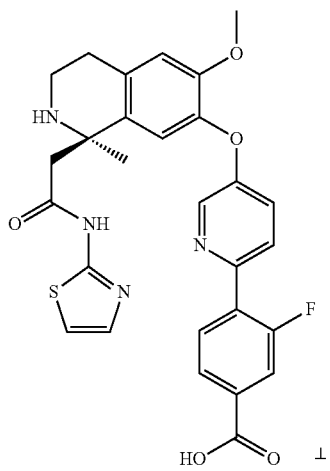
34
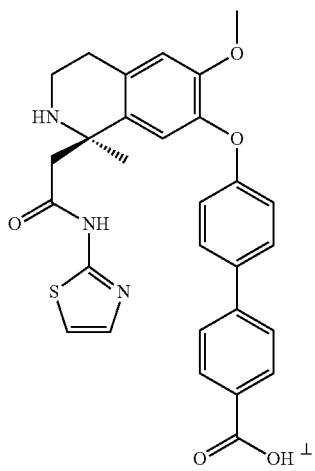
35
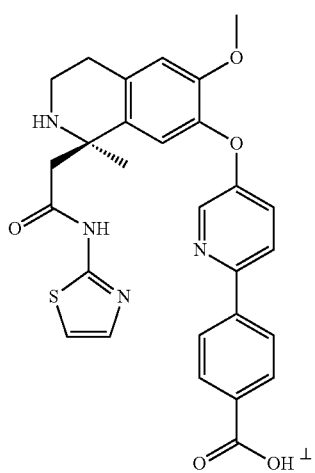
36
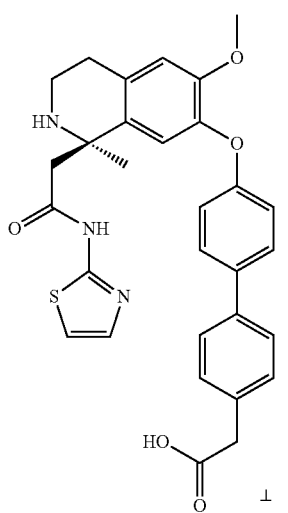
37
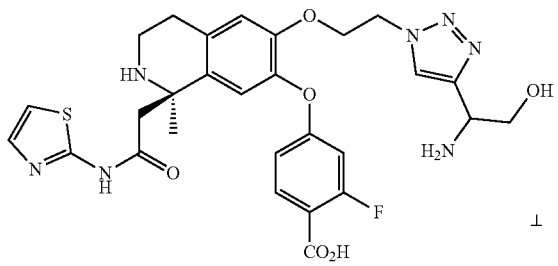
38
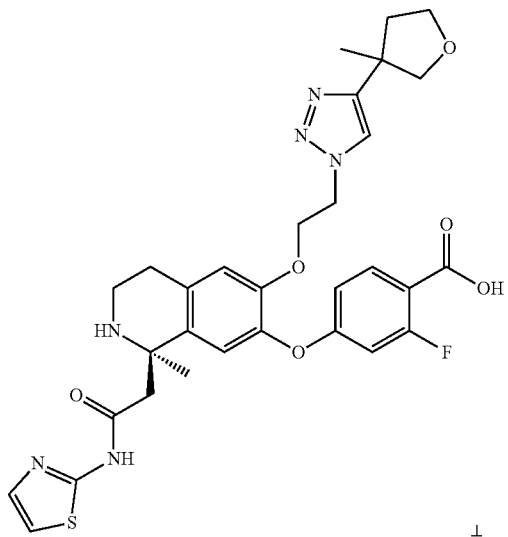

-continued
39
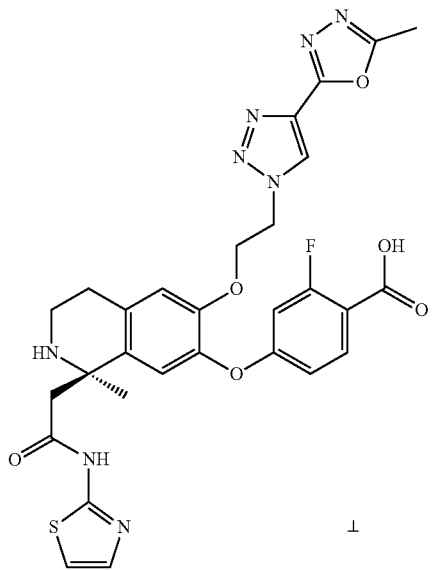
41
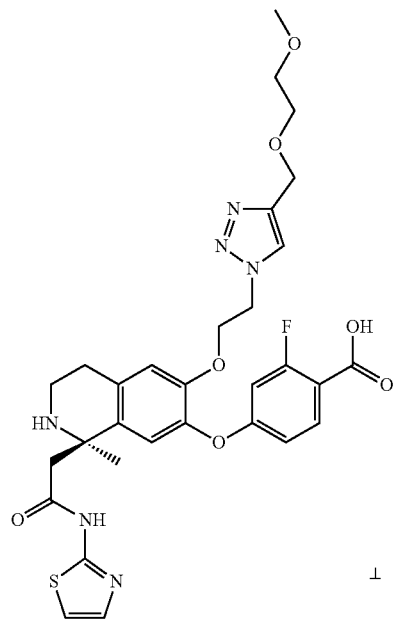
42
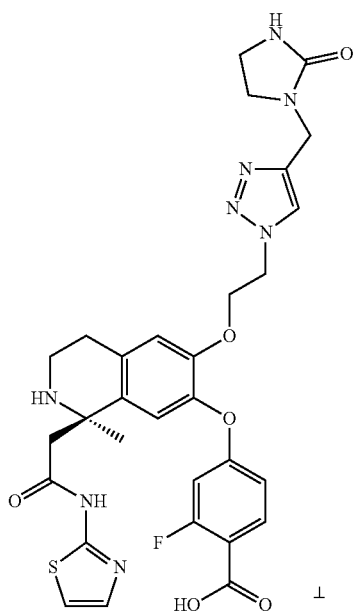
43
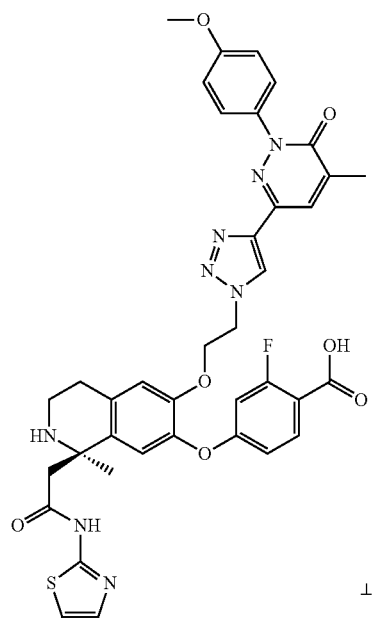

44
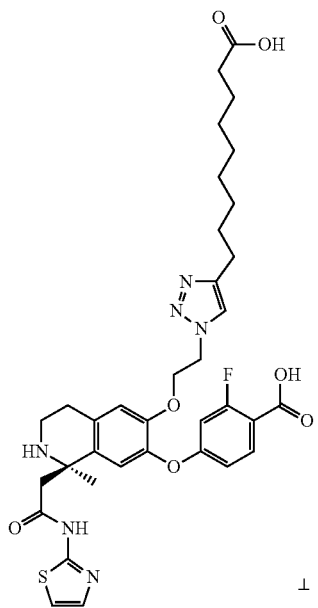
45
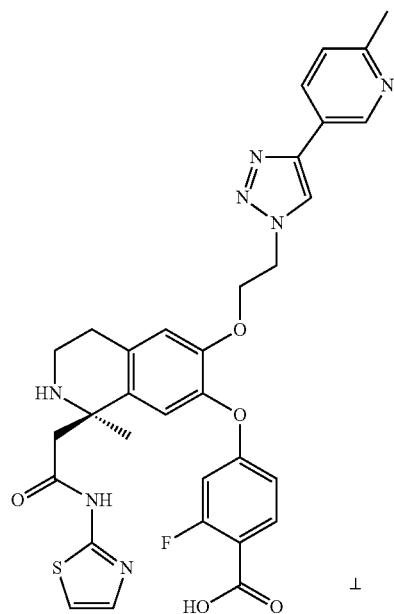
46
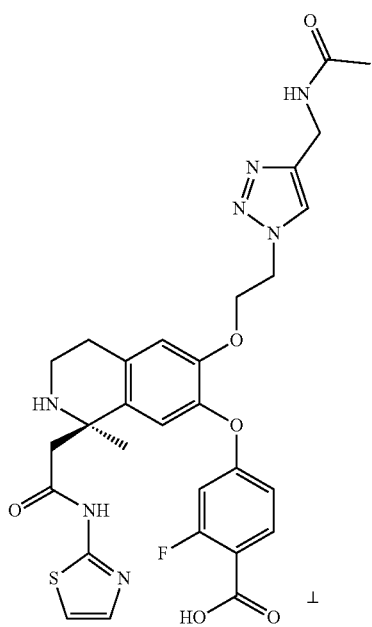
47
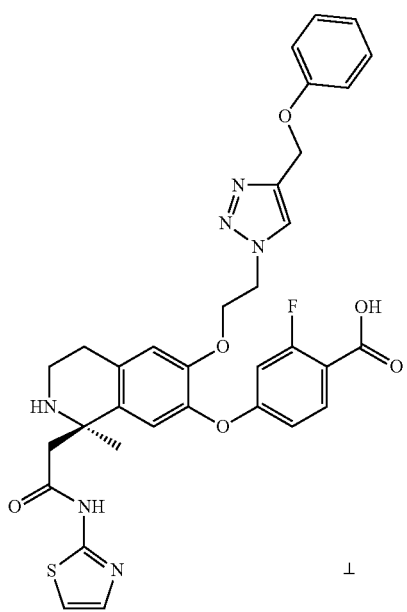

48
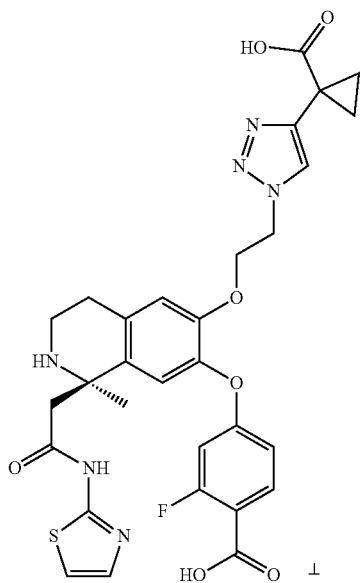
49
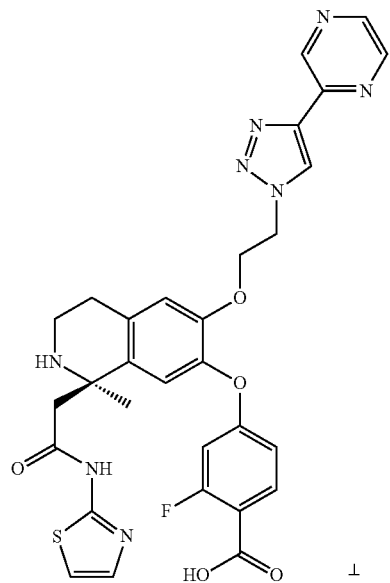
50
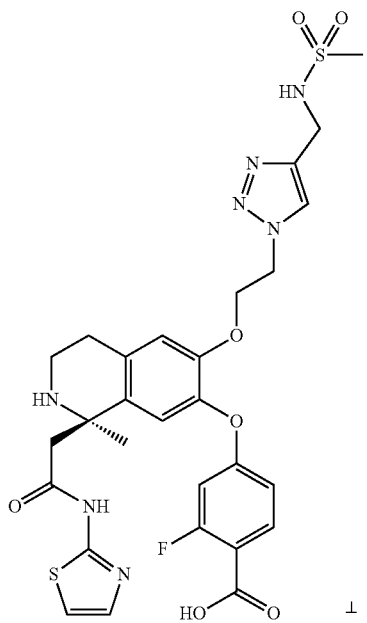
51
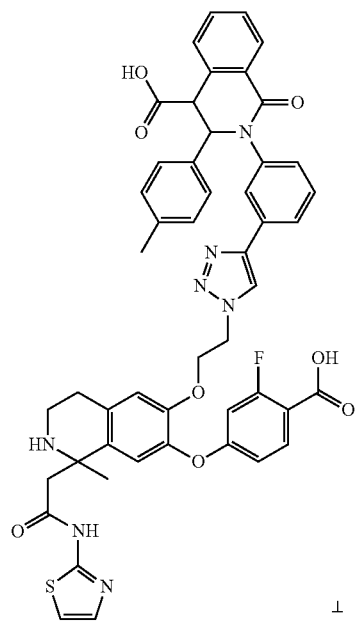

-continued
52
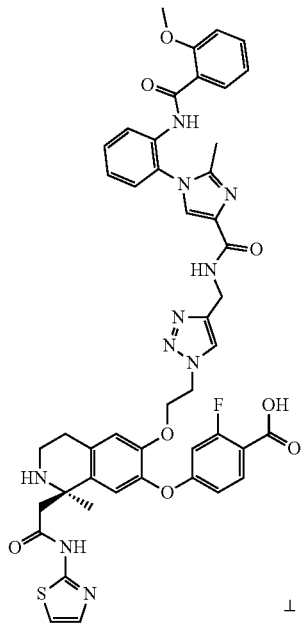
53
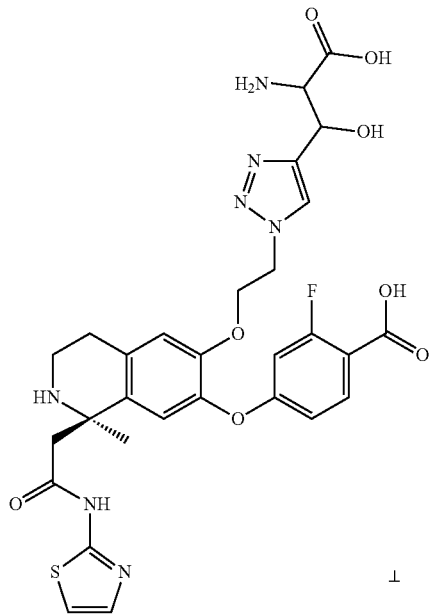
54
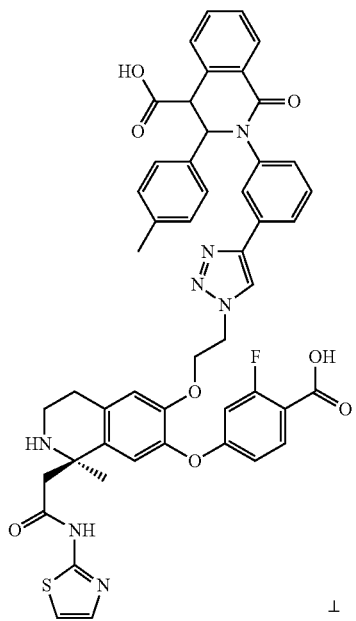
55
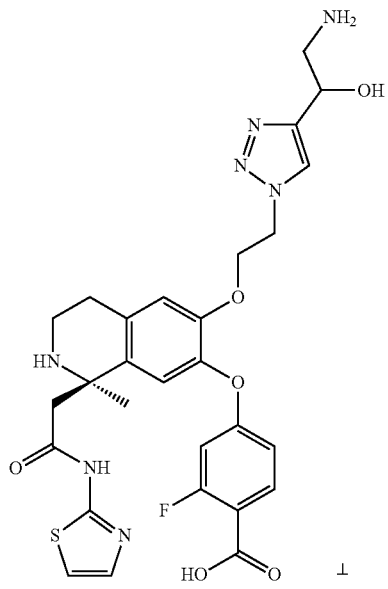

-continued
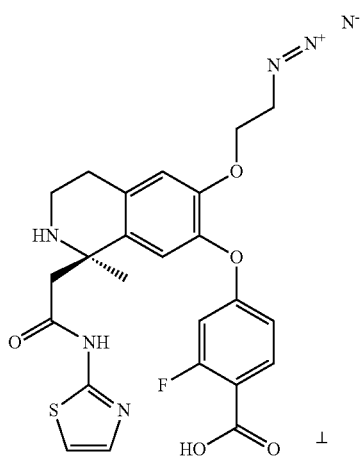
56
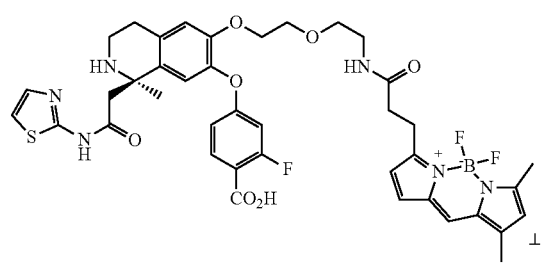
57
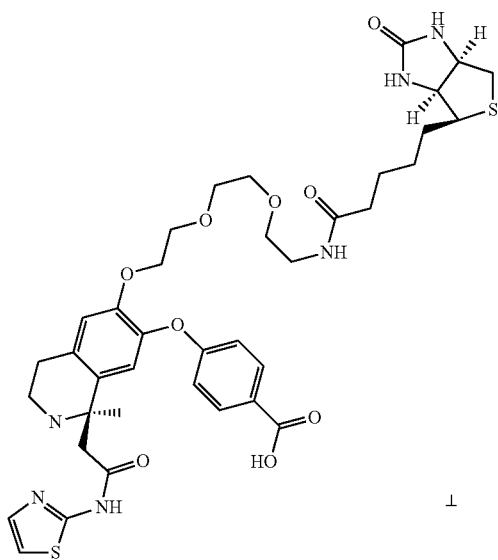
58
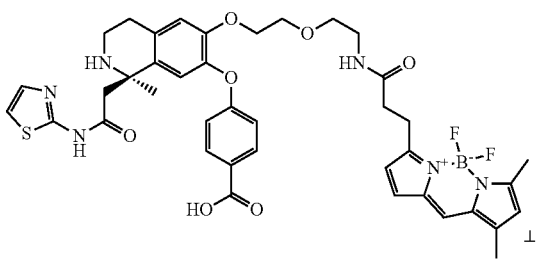
59
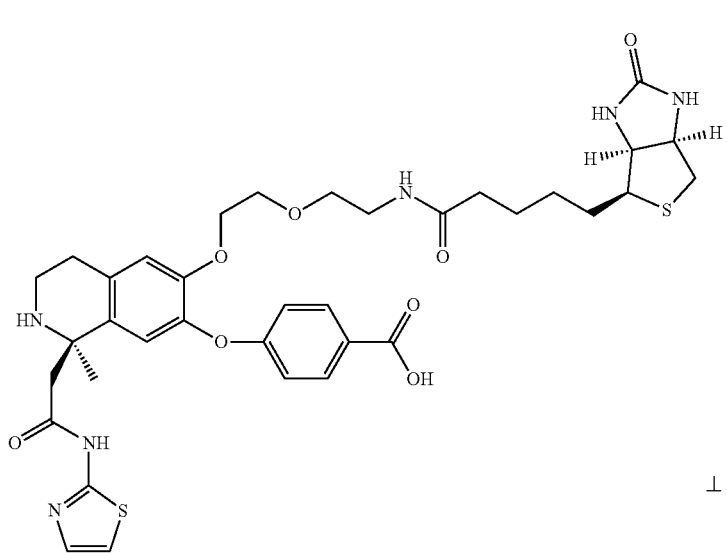
60

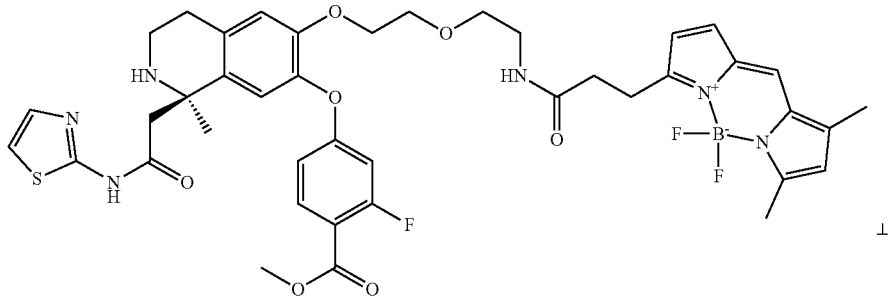
61
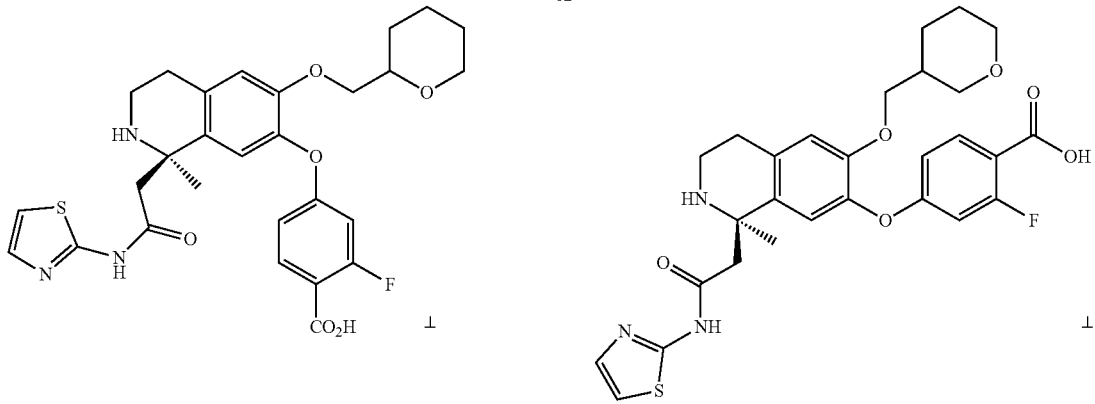
62
63
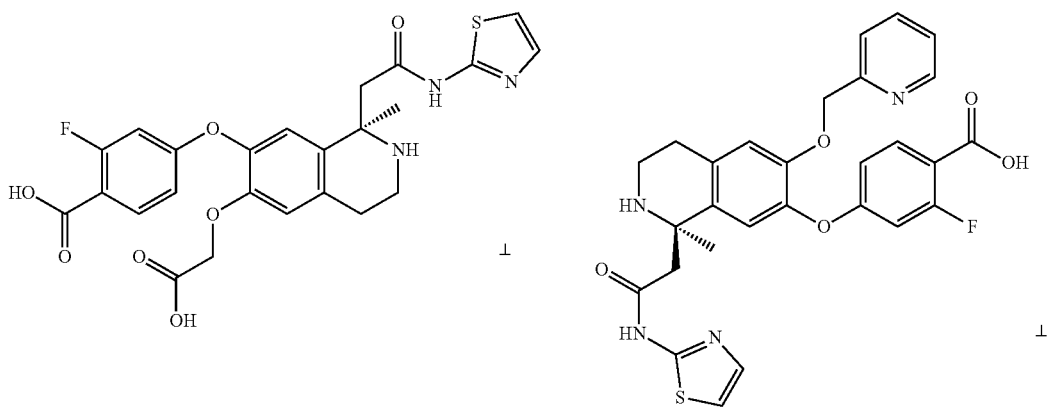
64
65
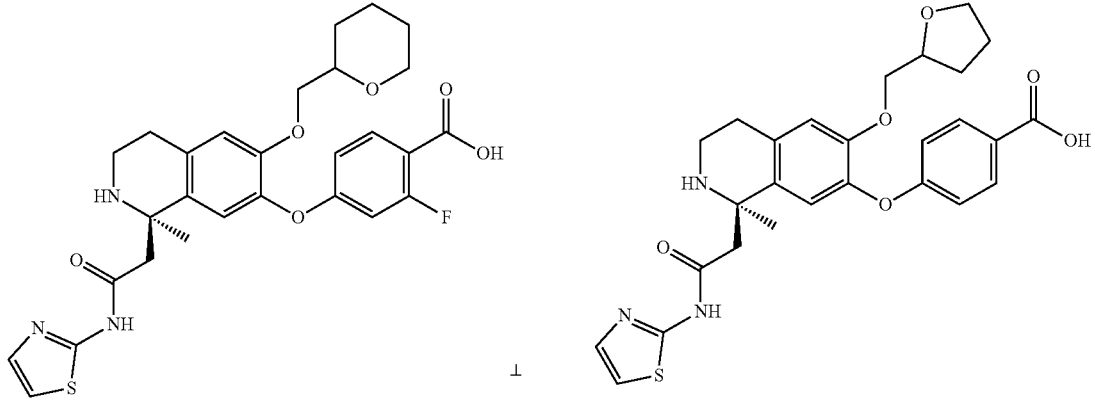
66
67

-continued
68
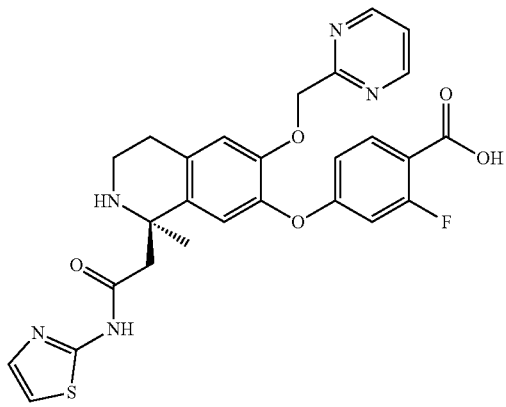
69
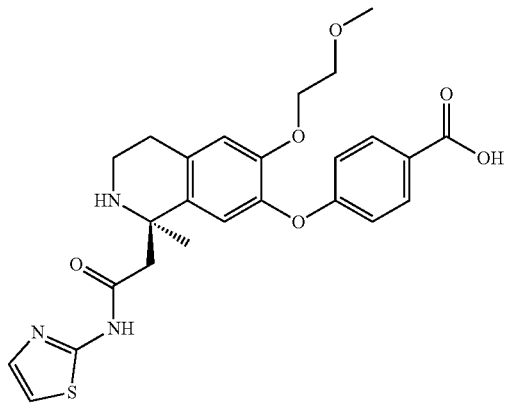
70
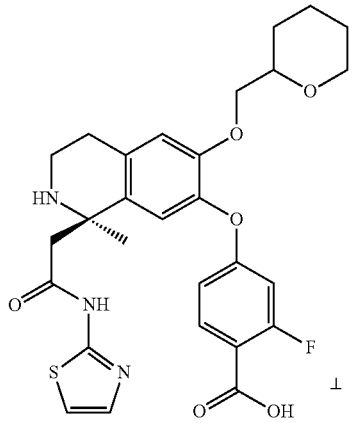
71
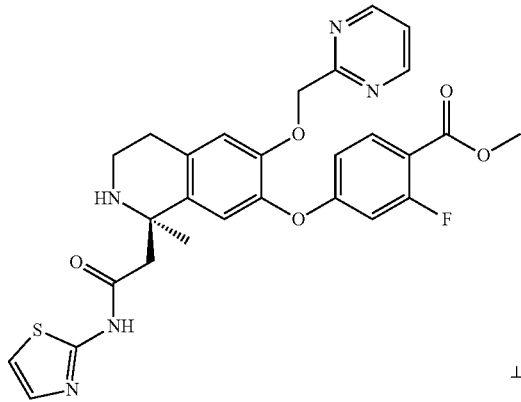
72
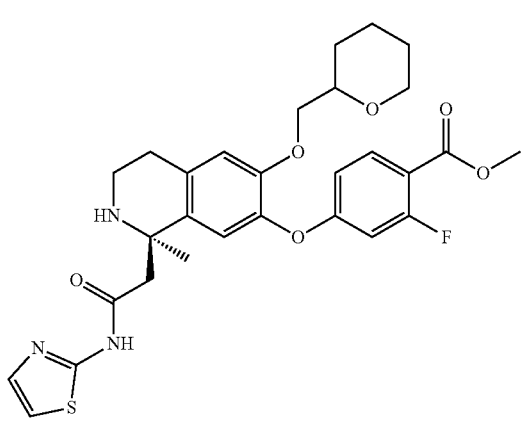
73
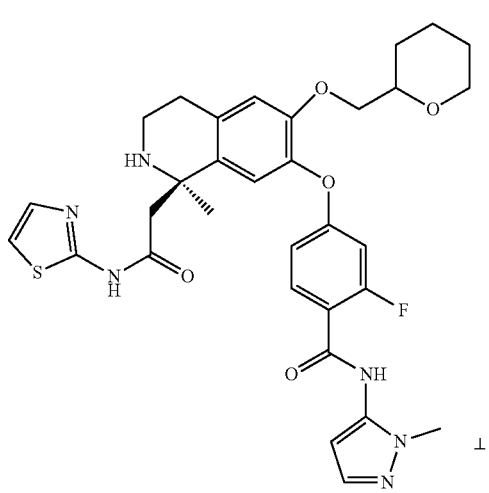

-continued
| 74 | 75 |
|---|---|
| 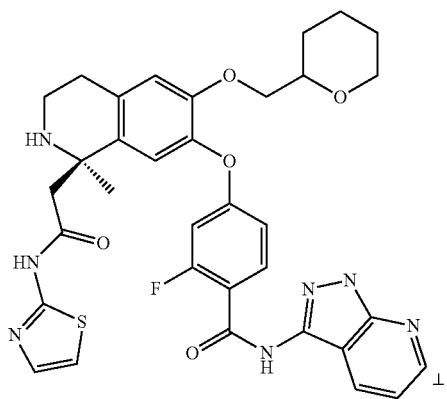 | 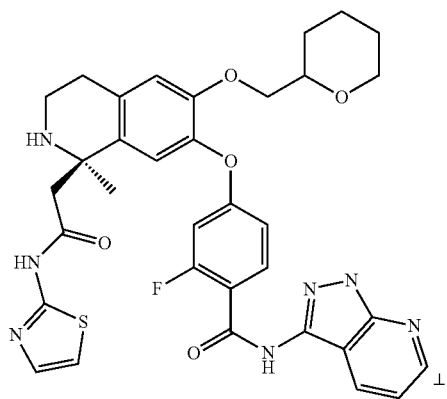 |
| 76 | 77 |
| 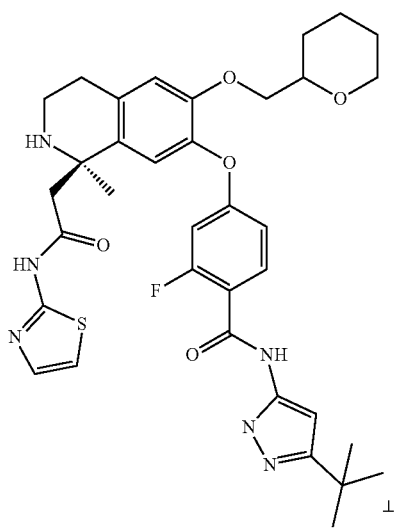 | 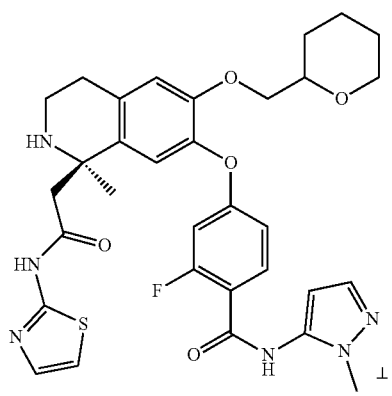 |
| 78 | 79 |
| 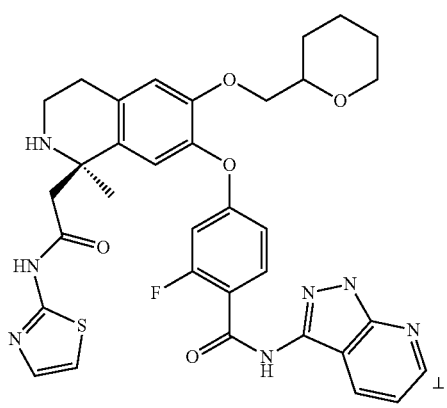 | 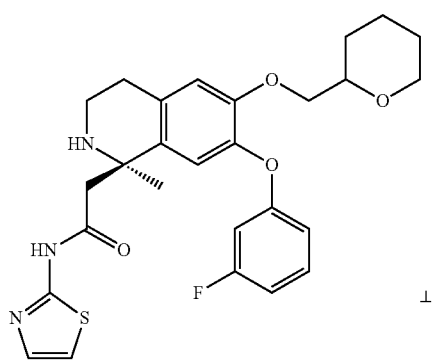 |

-continued
80 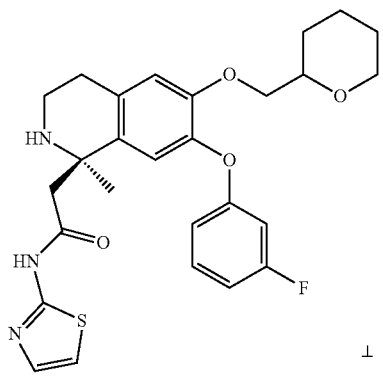 81 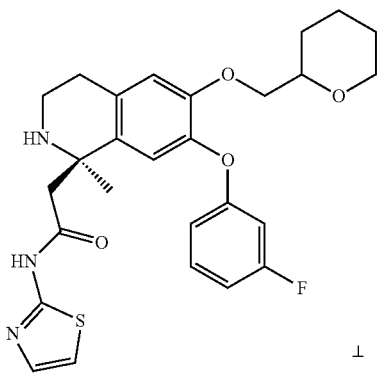
82 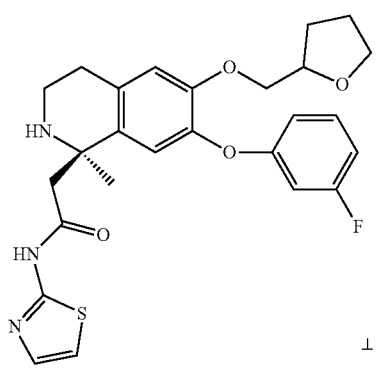 83 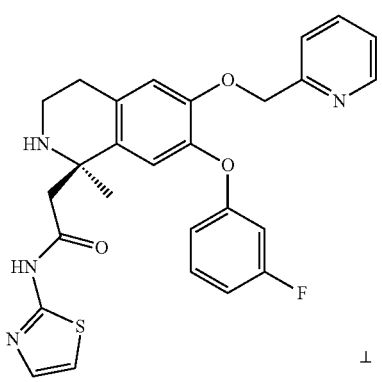
84 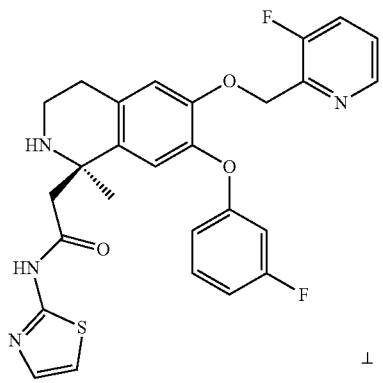 85 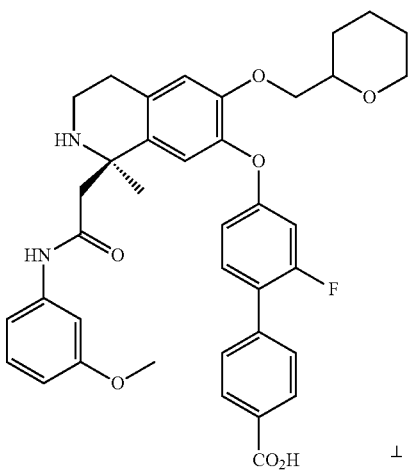

-continued
86
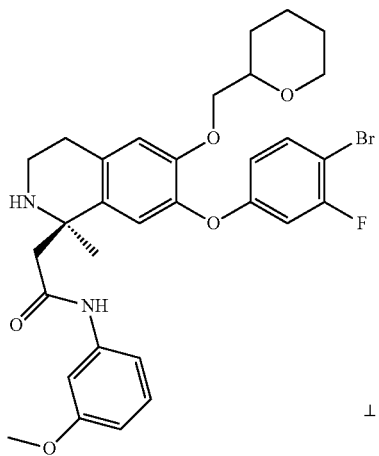
87
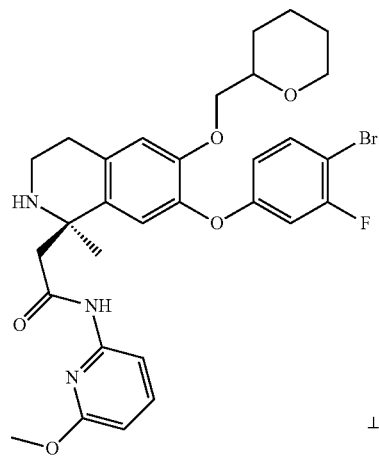
88
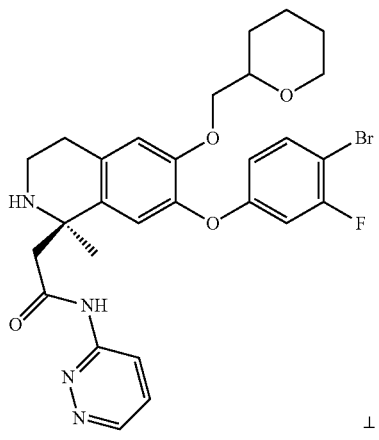
89
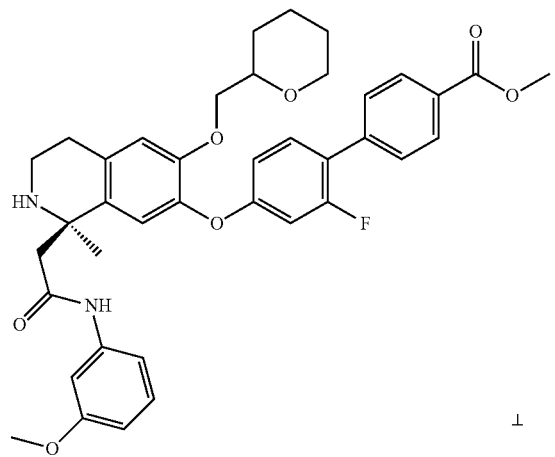
90
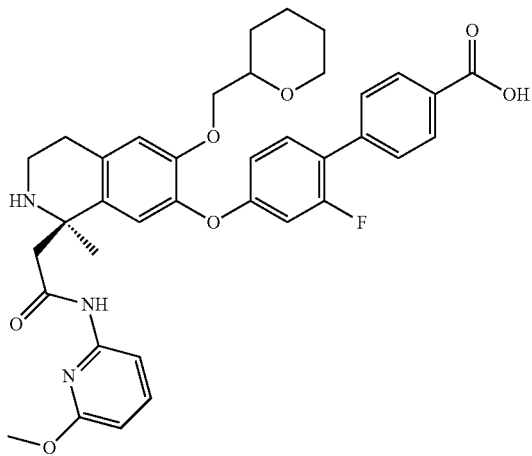
91
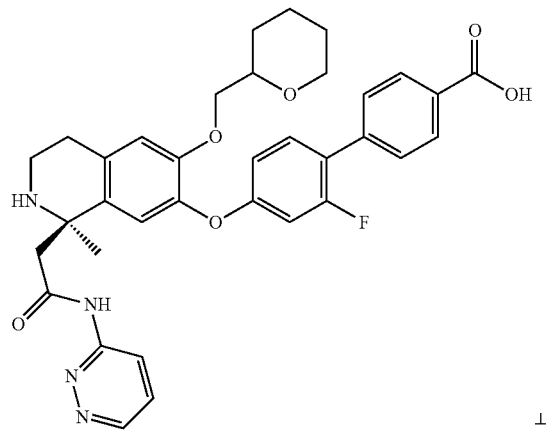

92
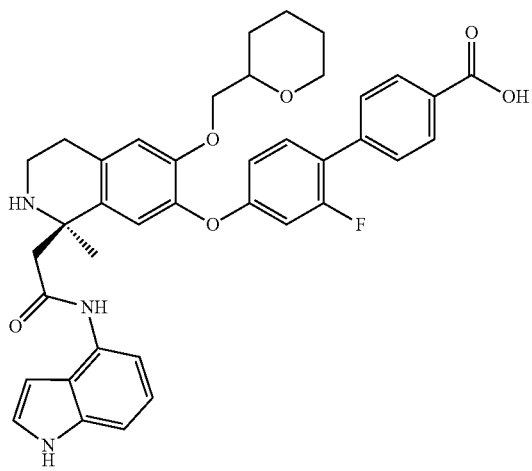
93
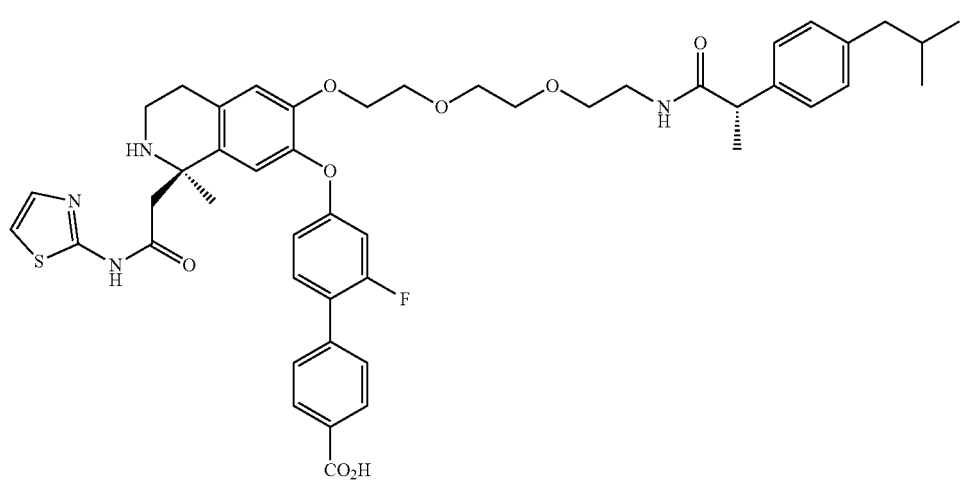
94
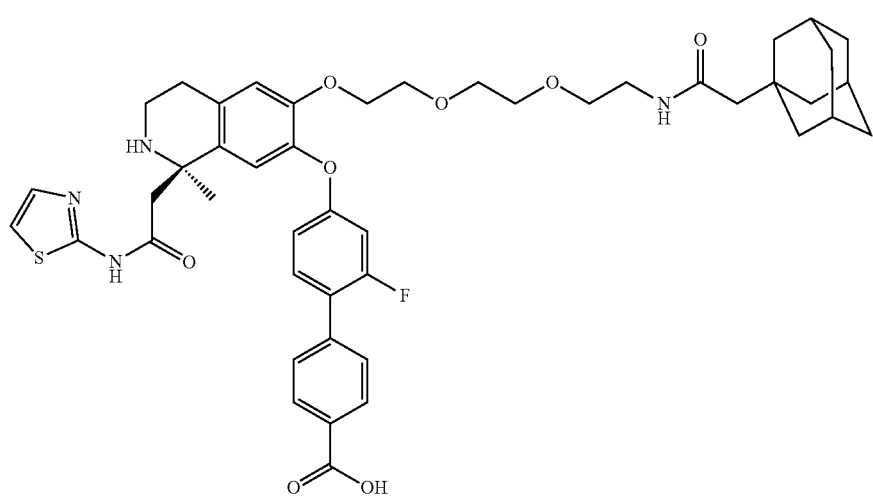

-continued
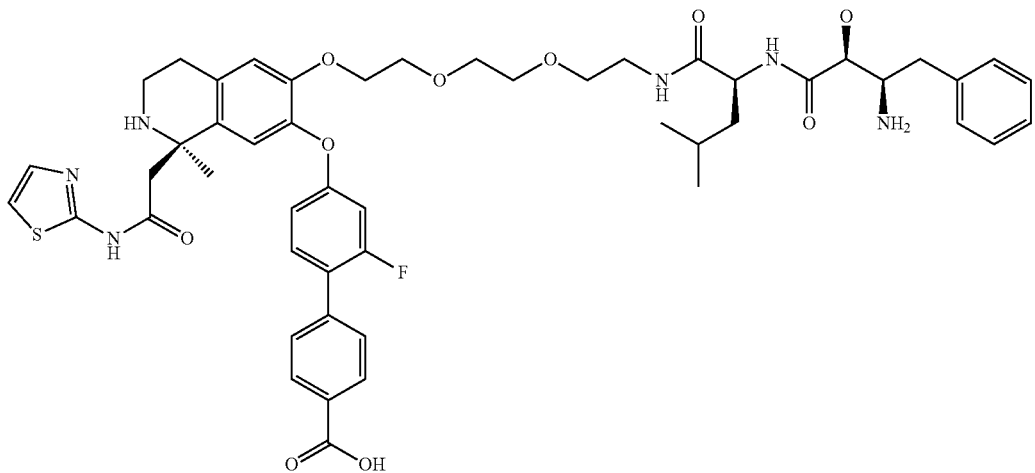
95
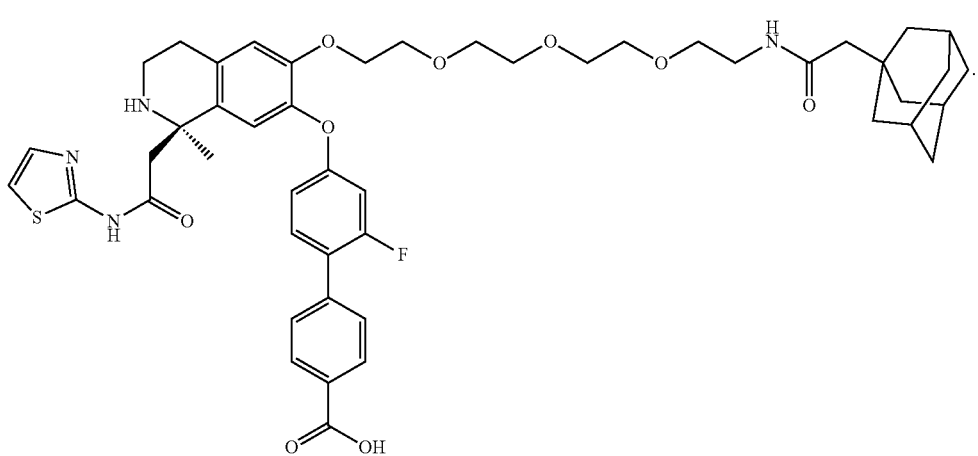
96
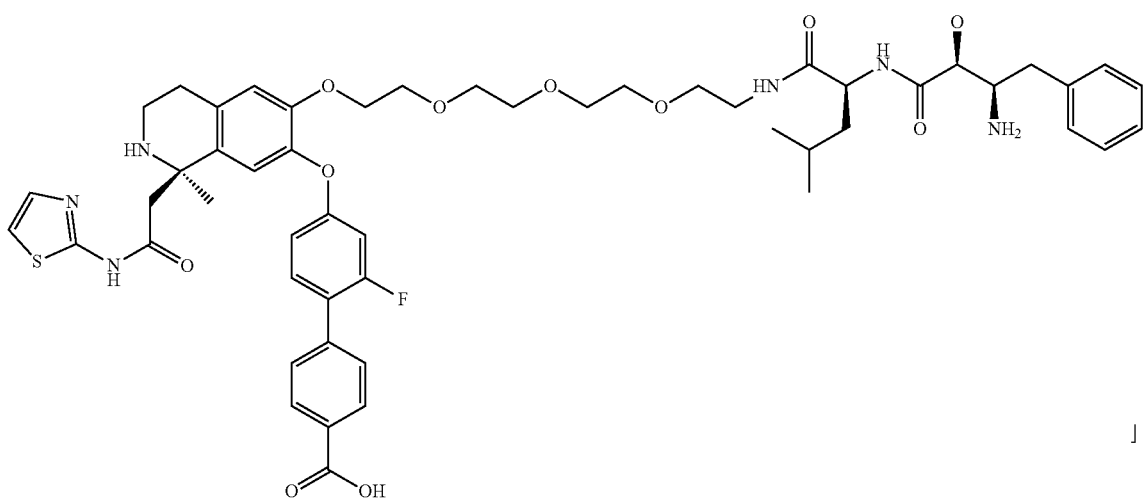
97

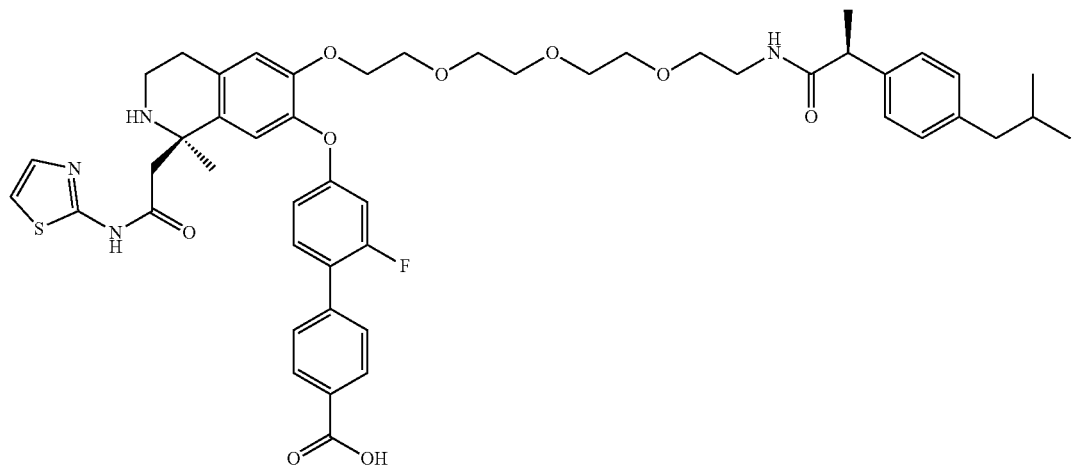
98
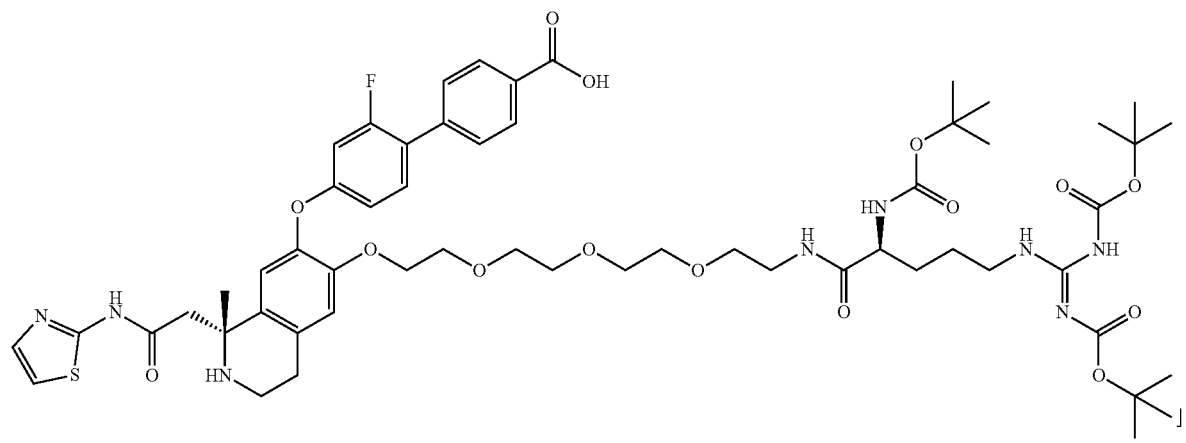
99
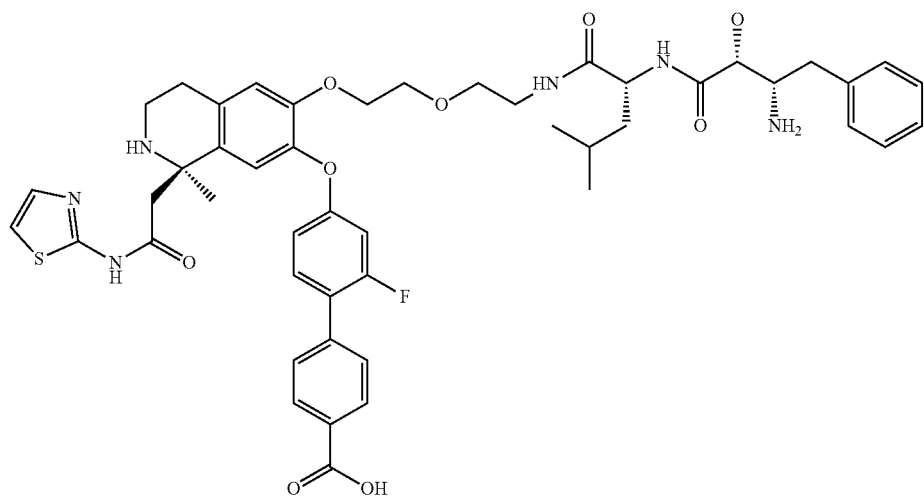
100

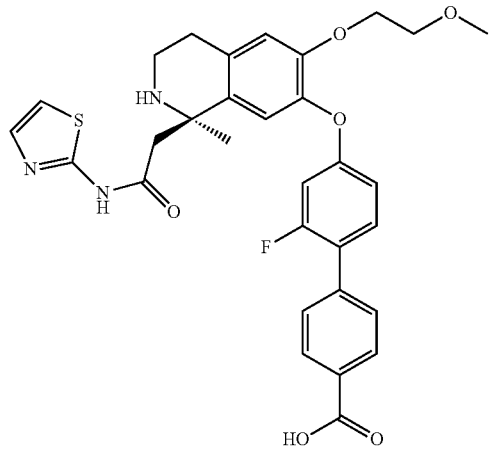
101
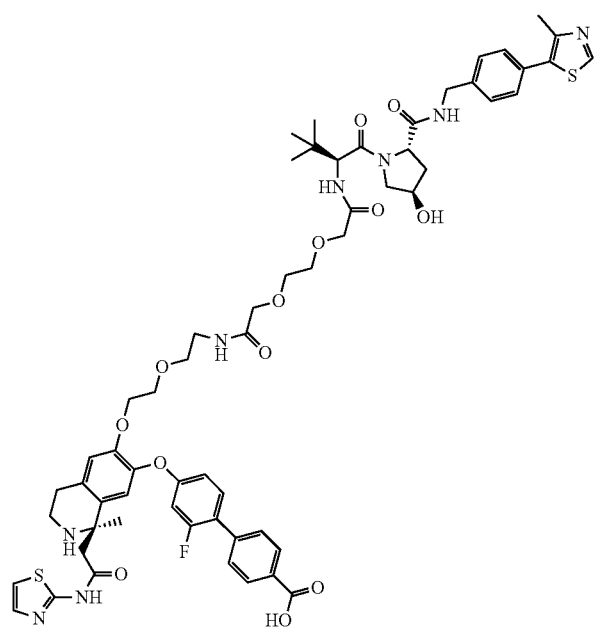
102

103
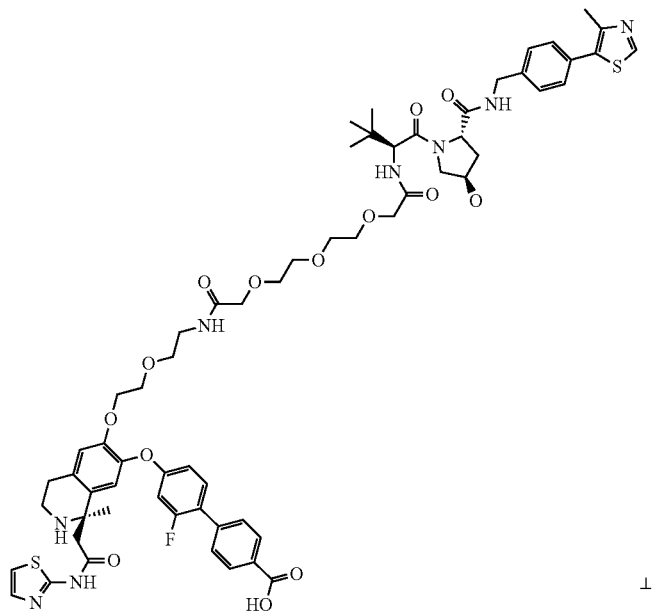
104
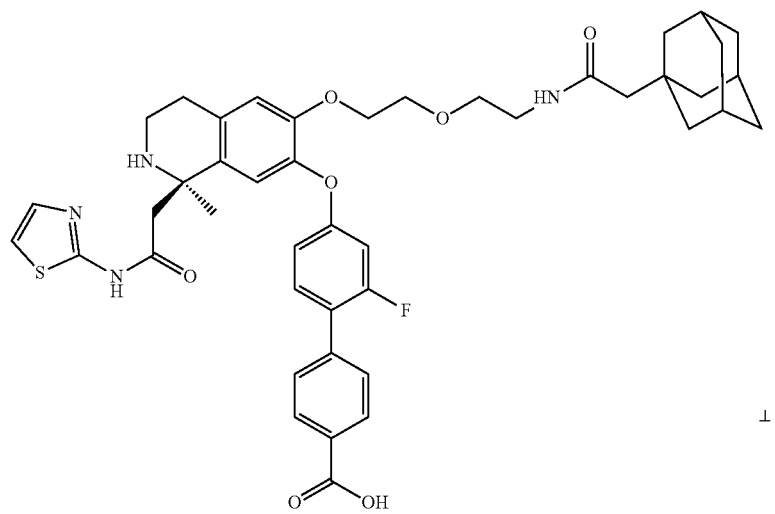

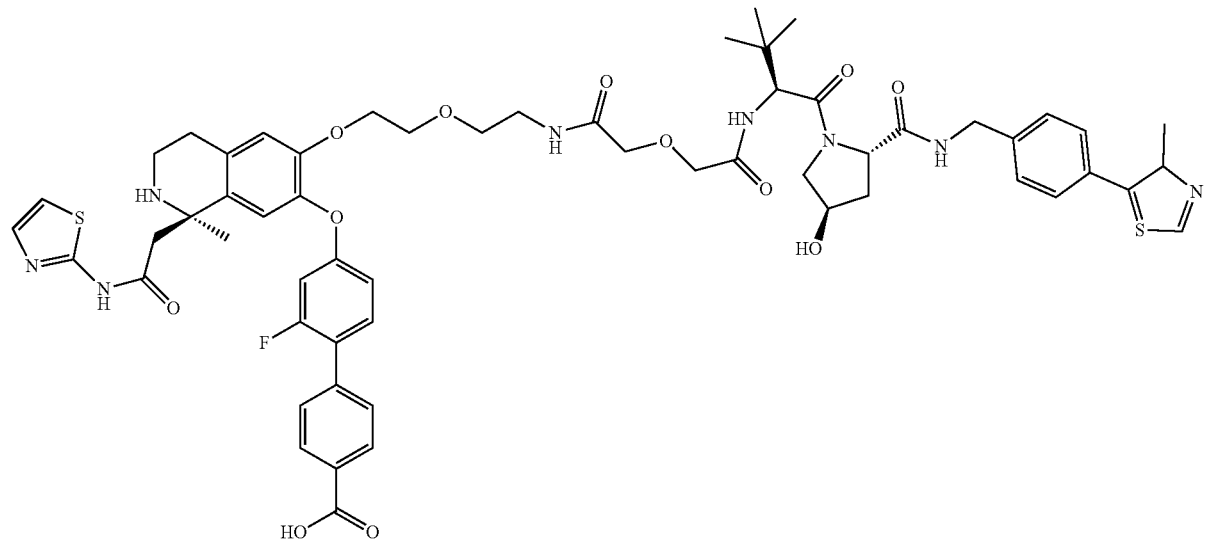
105
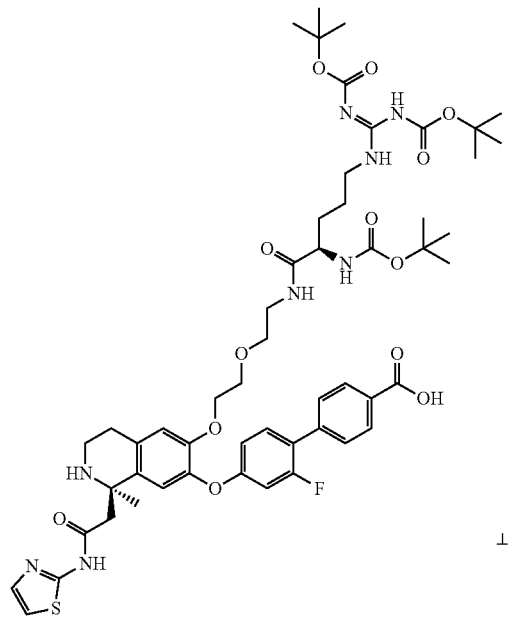
106

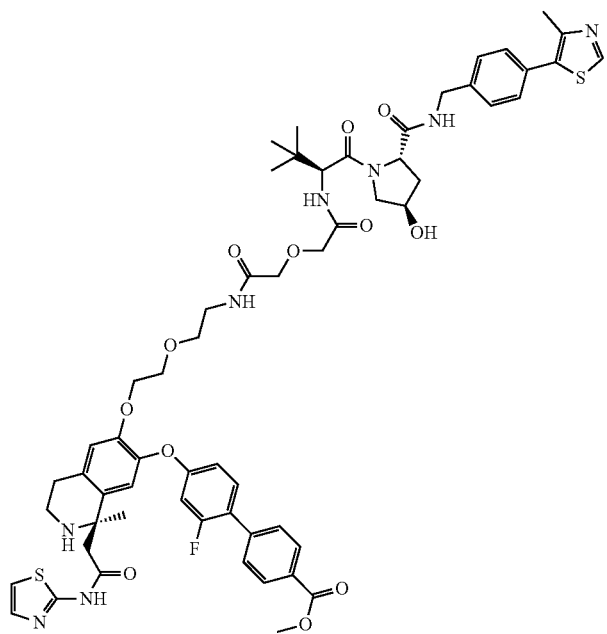
107
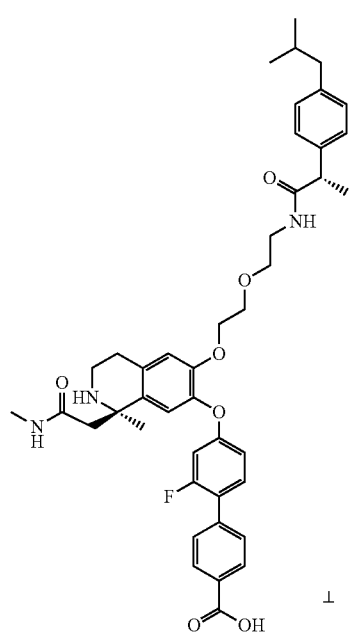
108
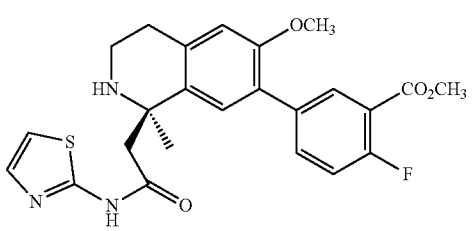
109

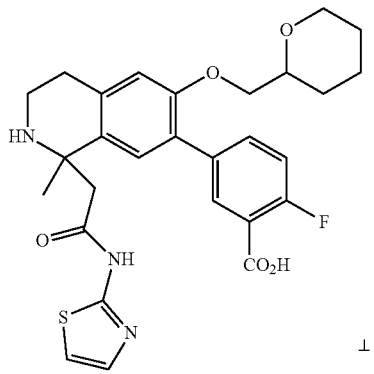

110

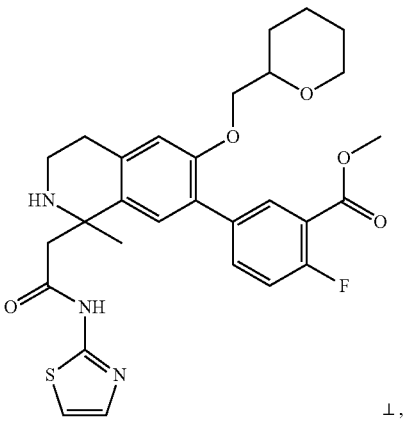

111

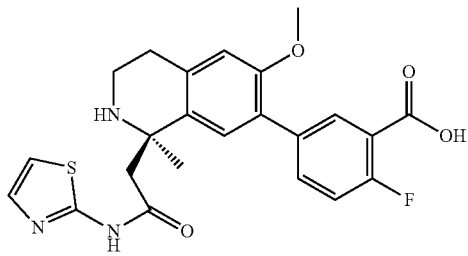

112 or a pharmaceutically acceptable salt thereof.

Other embodiments of the present invention include the following:

(a) A pharmaceutical composition comprising an effective amount of a compound of Formula I as defined above, or a pharmaceutically acceptable salt thereof, and a pharmaceutically acceptable carrier.

(b) A pharmaceutical composition comprising an effective amount of a compound of Formula I wherein $R^4$ is —[OCH$_2$CH$_2$]$_m$NR$^a$C(O)R$^C$, each m is 2, 3 or 4, and R$^C$ is selected from the group consisting of:

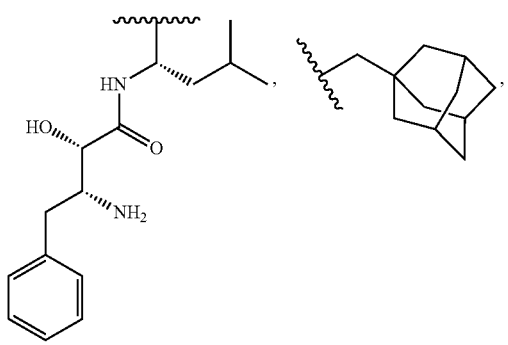

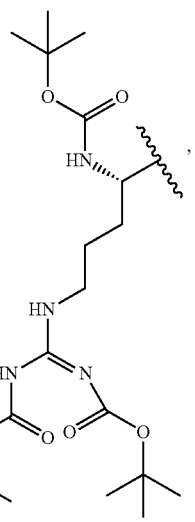

67
-continued
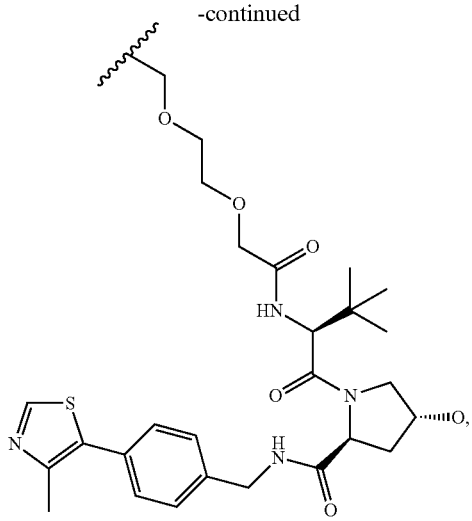
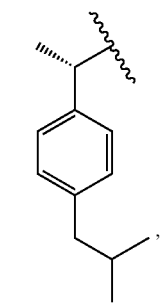
68
-continued
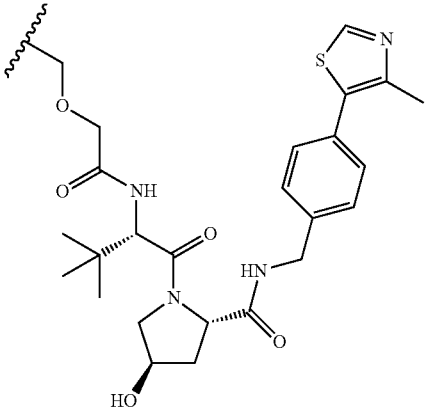
and all other variables are as defined in Embodiment E1 or a pharmaceutically acceptable salt thereof, and a pharmaceutically acceptable carrier.
(c) A pharmaceutical composition comprising an effective amount of a compound selected from the group consisting of:
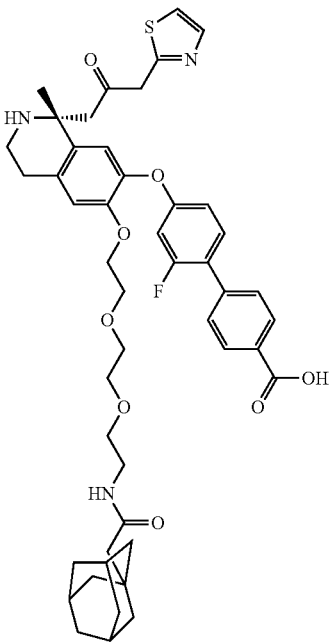

69
-continued
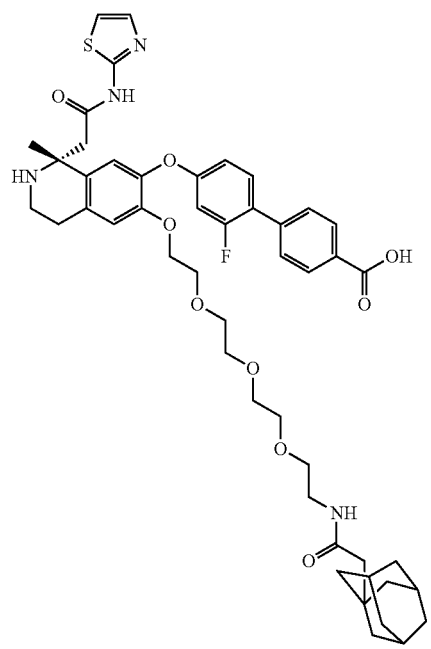
70
-continued
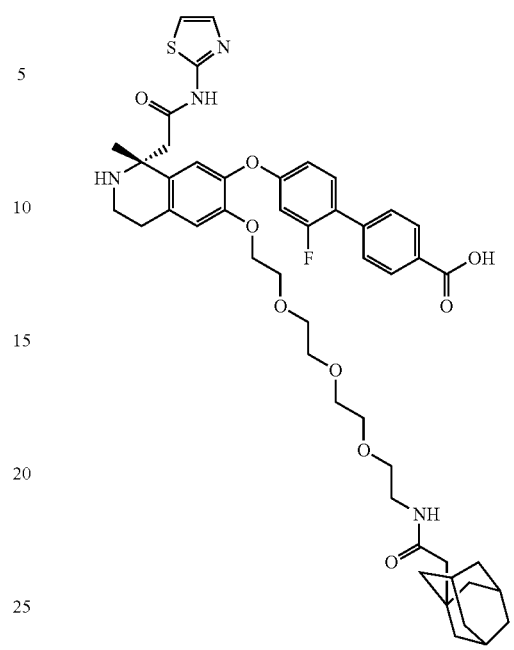
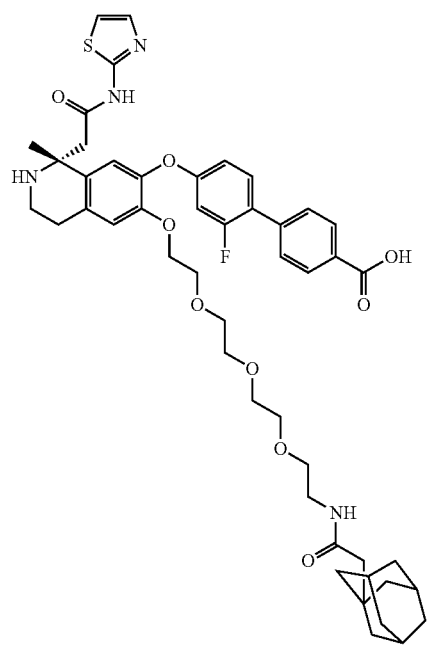 [SMILES: C[C@]1(CC(=O)Nc2nccs2)NCCc2cc(OCCOCCOCCOCCNC(=O)CC34CC5CC(CC(C5)C3)C4)c(Oc3ccc(-c4ccc(C(=O)O)cc4)c(F)c3)cc21]
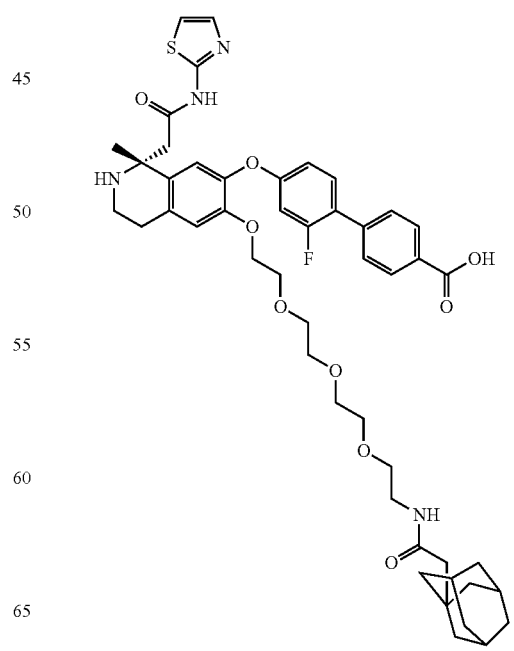

-continued

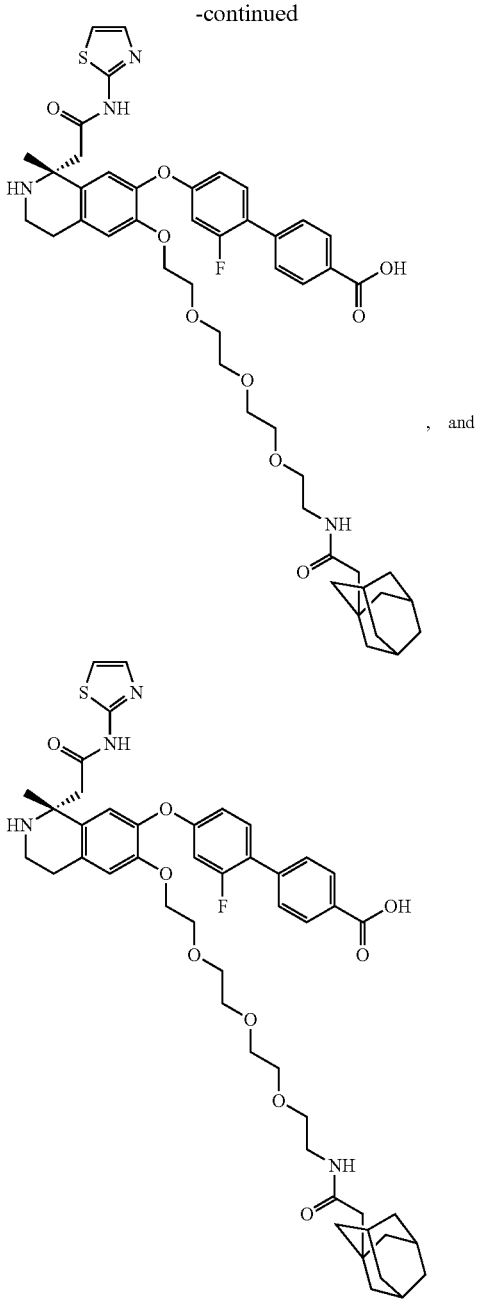

, and or a pharmaceutically acceptable salt thereof, and a pharmaceutically acceptable carrier.

(d) The pharmaceutical composition of (a), (b) or (c), further comprising an effective amount of an additional pharmacologically active agent.

(e) A method for treating atherosclerosis, hypercholesterolemia, coronary heart disease, metabolic syndrome, acute coronary syndrome, or related cardiovascular disease and cardiometabolic conditions which comprises administering to a subject in need of such treatment a therapeutically effective amount of a compound of Formula I (wherein such compound comprises or is conjugated to a signal marking it for destruction, e.g., by the ubiquitin-proteosome pathway (J Am Chem Soc. 2004 Mar. 31; 126(12):3748-54), the pharmaceutical composition of (b), or the pharmaceutical composition of (c).

(f) A method for the in vitro labeling, detection and/or quantification of PCSK9 in a biological sample, which comprises the steps of: (i) incubating the sample with a compound of Formula I or pharmaceutically acceptable salt thereof where the compound or salt comprises a detectable marker which confers a detectable signal, for a time sufficient for the compound or salt to bind to PCSK9 present in the sample, (ii) activating or irradiating the detectable marker of step (i), and (iii) visualizing the detectable signal of step (i).

(g) A method for the in vitro labeling, detection and/or quantification of PCSK9 in a biological sample, which comprises the steps of: (i) incubating the sample with a compound of Formula I or pharmaceutically acceptable salt thereof comprising the following BODIPY group:

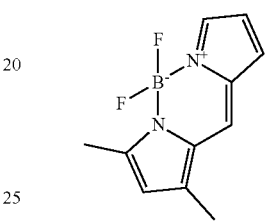

for a time sufficient for the compound or salt to bind to PCSK9 present in the sample, (ii) irradiating the BODIPY group of step (i), and (iii) visualizing a fluorescent signal conferred by the BODIPY group of step (i).

The present invention also includes a compound of Formula I or a pharmaceutically acceptable salt thereof, (i) for use in, (ii) for use as a medicament for, or (iii) for use in the preparation (or manufacture) of a medicament for, inducing the degradation of PCSK9 or treating atherosclerosis, hypercholesterolemia, coronary heart disease, metabolic syndrome, acute coronary syndrome, or related cardiovascular disease and cardiometabolic conditions. In these uses, the compounds of the present invention can optionally be employed in combination with one or more an additional pharmacologically active agents.

Additional embodiments of the invention include the pharmaceutical compositions, combinations and methods set forth in (a)-(g) above and the uses set forth in the preceding paragraph, wherein the compound of the present invention employed therein is a compound of one of the embodiments, sub-embodiments, classes or sub-classes described above. The compound may optionally be used in the form of a pharmaceutically acceptable salt in these embodiments. In addition, the compound may optionally be used in the form of a prodrug that releases the active parent compound after dosing by intravenous or oral administration.

In the embodiments of the compounds and salts provided above, it is to be understood that each embodiment may be combined with one or more other embodiments, to the extent that such a combination provides a stable compound or salt and is consistent with the description of the embodiments. It is further to be understood that the embodiments of compositions and methods provided as (a) through (g) above are understood to include all embodiments of the compounds and/or salts, including such embodiments as result from combinations of embodiments.

Additional embodiments of the present invention include each of the pharmaceutical compositions, combinations, methods and uses set forth in the preceding paragraphs, wherein the compound of the present invention or its salt employed therein is substantially pure. With respect to a pharmaceutical composition comprising a compound of Formula I or its salt and a pharmaceutically acceptable carrier and optionally one or more excipients, it is understood that the term "substantially pure" is in reference to a compound of Formula I or its salt per se; i.e., the purity of the active ingredient in the composition.

Definitions and Abbreviations

The term "about", when modifying the quantity (e.g., kg, L, or equivalents) of a substance or composition, or the value of a physical property, or the value of a parameter characterizing a process step (e.g., the temperature at which a process step is conducted), or the like refers to variation in the numerical quantity that can occur, for example, through typical measuring, handling and sampling procedures involved in the preparation, characterization and/or use of the substance or composition; through inadvertent error in these procedures; through differences in the manufacture, source, or purity of the ingredients employed to make or use the compositions or carry out the procedures; and the like. In certain embodiments, "about" can mean a variation of ±0.1, 0.2, 0.3, 0.4, 0.5, 1.0, 2.0, 3.0, 4.0, or 5.0 of the appropriate unit. In certain embodiments. "about" can mean a variation of ±1%, 2%, 3%, 4%, 5%, 10%, or 20%.

Another embodiment of the present invention is a compound of Formula I, or a pharmaceutically acceptable salt thereof, as originally defined or as defined in any of the foregoing embodiments, sub-embodiments, aspects, classes or sub-classes, wherein the compound or its salt is in a substantially pure form. As used herein "substantially pure" means suitably at least about 60 wt. %, typically at least about 70 wt. %, preferably at least about 80 wt. %, more preferably at least about 90 wt. % (e.g., from about 90 wt. % to about 99 wt. %), even more preferably at least about 95 wt. % (e.g., from about 95 wt. % to about 99 wt. %, or from about 98 wt. % to 100 wt. %), and most preferably at least about 99 wt. % (e.g., 100 wt. %) of a product containing a compound of Formula I or its salt (e.g., the product isolated from a reaction mixture affording the compound or salt) consists of the compound or salt. The level of purity of the compounds and salts can be determined using a standard method of analysis such as thin layer chromatography, gel electrophoresis, high performance liquid chromatography, and/or mass spectrometry. If more than one method of analysis is employed and the methods provide experimentally significant differences in the level of purity determined, then the method providing the highest level of purity governs. A compound or salt of 100% purity is one which is free of detectable impurities as determined by a standard method of analysis.

With respect to a compound of the invention which has one or more asymmetric centers and can occur as mixtures of stereoisomers, a substantially pure compound can be either a substantially pure mixture of the stereoisomers or a substantially pure individual diastereomer or enantiomer unless expressly depicted otherwise. The present invention encompasses all stereoisomeric forms of the compounds of Formula I. Unless a specific stereochemistry is indicated, the present invention is meant to comprehend all such isomeric forms of these compounds. Centers of asymmetry that are present in the compounds of Formula I can all independently of one another have (R) configuration or (S) configuration. When bonds to the chiral carbon are depicted as straight lines in the structural Formulas of the invention, it is understood that both the (R) and (S) configurations of the chiral carbon, and hence both enantiomers and mixtures thereof, are embraced within the Formula. Similarly, when a compound name is recited without a chiral designation for a chiral carbon, it is understood that both the (R) and (S) configurations of the chiral carbon, and hence individual enantiomers, diastereomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis.

Optionally a derivatization can be carried out before a separation of stereoisomers. The separation of a mixture of stereoisomers can be carried out at an intermediate step during the synthesis of a compound of Formula I or it can be done on a final racemic product. Absolute stereochemistry may be determined by X-ray crystallography of crystalline products or crystalline intermediates which are derivatized, if necessary, with a reagent containing a stereogenic center of known configuration. Unless a particular isomer, salt, solvate (including hydrates) or solvated salt of such racemate, enantiomer, or diastereomer is indicated, the present invention includes all such isomers, as well as salts, solvates (including hydrates) and solvated salts of such racemates, enantiomers, diastereomers and mixtures thereof.

"Alkyl" means saturated carbon chains which may be linear or branched or combinations thereof, unless the carbon chain is defined otherwise. Other groups having the prefix "alk", such as alkoxy and alkanoyl, also may be linear or branched, or combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like.

"Aminoalkyl" means saturated carbon chains which may be linear or branched or combinations thereof which are substituted with one amino group which may be terminal (—NH$_2$) or internal (—NH—).

"Alkenyl" means carbon chains which contain at least one carbon-carbon double bond, and which may be linear or branched, or combinations thereof, unless otherwise defined. Examples of alkenyl include vinyl, allyl, isopropenyl, pentenyl, hexenyl, heptenyl, 1-propenyl, 2-butenyl, 2-methyl-2-butenyl, and the like.

Reference to an "aromatic" ring means a monocyclic, bicyclic or tricyclic aromatic ring or ring system containing 5-14 ring atoms, wherein at least one of the rings is aromatic. The term may be used to describe a carbocyclic ring fused to an aryl group. For example, a 5-7-membered cycloalkyl can be fused through two adjacent ring atoms to a 5-6-membered heteroaryl containing 1, 2, or 3 heteroatom ring atoms selected from N, O, and S. In other example, a heteromonocyclic ring is fused through two ring atoms to a phenyl or 5-6-membered heteroaryl containing 1, 2, or 3 heteroatoms selected from N, O, and S. In the case of a heteromonocyclic ring containing one or more N atoms, the N can be in the form of quarternary amine. In certain embodiments, a N ring atom can be in the form of an N-oxide.

"Aryl" means a monocyclic, bicyclic or tricyclic carbocyclic aromatic ring or ring system containing 5-14 carbon atoms, wherein at least one of the rings is aromatic. Examples of aryl include phenyl and naphthyl. In one embodiment of the present invention, aryl is phenyl.

"Cycloalkyl" means a saturated monocyclic, bicyclic or bridged carbocyclic ring, having a specified number of carbon atoms. Examples of cycloalkyl include cyclopropyl, cyclobutyl, cyclopentyl, cyclohexyl, cycloheptyl, indanyl, 1,2,3,4-tetrahydronaphthyl and the like. In one embodiment of the present invention, cycloalkyl is selected from: cyclopropane, cyclobutane, cyclopentane and cyclohexane.

"Heteroaryl" means monocyclic, bicyclic or tricyclic ring or ring system containing 5-14 carbon atoms and containing at least one ring heteroatom selected from N, S (including SO and $SO_2$) and O, wherein at least one of the heteroatom containing rings is aromatic. In the case of a heteroaryl ring system where one or more of the rings are saturated and contain one or more N atoms, the N can be in the form of quarternary amine. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzisoxazolyl, benzoxazolyl, benzothiazolyl, benzimidazolyl, benzopyrazolyl, benzofuranyl, benzothiophenyl (including S-oxide and dioxide), benzotriazolyl, furo(2,3-b)pyridyl, quinolyl, indolyl, isoquinolyl, quinazolinyl, dibenzofuranyl, and the like.

"Halogen" includes fluorine, chlorine, bromine and iodine.

"Oxo" means an oxygen atom connected to another atom by a double bond and is can be represented "=O".

Where any amine is present in the compound, the N atom may be optionally in the form of a quaternary amine having one or more appropriate additional substitutions, as further described herein.

When any ring atom is specified as being optionally substituted with, or in a specified form, for example, S substituted with oxo groups, or N in the form of a N-oxide, this does not preclude the substitution of any ring atom with the other listed optional substituents when not substituted with oxo groups or in the form of a N-oxide.

When any variable (e.g., n, $R^a$, $R^b$, etc.) occurs more than one time in any constituent or in Formula I, its definition on each occurrence is independent of its definition at every other occurrence. Also, combinations of substituents and/or variables are permissible only if such combinations result in stable compounds.

A wavy line , as used herein, indicates a point of attachment to the rest of

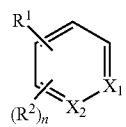

the compound. Lines drawn into a ring system, for example, indicate that the bond may be attached to any of the substitutable ring atoms.

Under standard nomenclature used throughout this disclosure, the terminal portion of the designated side chain is described last, preceded by the adjacent functionality toward the point of attachment.

In choosing compounds of the present invention, one of ordinary skill in the art will recognize that the various substituents, i.e. $R^1$, $R^4$, etc., are to be chosen in conformity with well-known principles of chemical structure connectivity and stability.

The term "substituted" shall be deemed to include multiple degrees of substitution by a named substituent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of Formula I. For example, different isotopic forms of hydrogen (H) include protium ($^1H$) and deuterium ($^2H$ or D). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within Formula I can be prepared without undue experimentation by conventional techniques well known to those skilled in the art or by processes analogous to those described in the Schemes and Examples herein using appropriate isotopically-enriched reagents and/or intermediates.

Unless expressly stated to the contrary in a particular context, any of the various cyclic ring and ring system variables or substituents described herein may be attached to the rest of the compound at any ring atom (i.e., any carbon atom or any heteroatom) provided that a stable compound results.

Unless expressly stated to the contrary, all ranges cited herein are inclusive. For example, a heteroaromatic ring described as containing from 1 to 4 or 1-4 heteroatoms means the ring can contain 1, 2, 3 or 4 heteroatoms. It is also to be understood that any range cited herein includes within its scope all of the sub-ranges within that range. Thus, for example, a heterocyclic ring described as containing from 1 to 4 heteroatoms is intended to include as aspects thereof, heterocyclic rings containing 2 to 4 heteroatoms, 3 or 4 heteroatoms, 1 to 3 heteroatoms, 2 or 3 heteroatoms, 1 or 2 heteroatoms, 1 heteroatom, 2 heteroatoms, 3 heteroatoms, and 4 heteroatoms. Similarly, $C_1$-$C_6$ when used with a chain, for example an alkyl chain, means that the chain can contain 1, 2, 3, 4, 5 or 6 carbon atoms. It also includes all ranges contained therein including $C_1$-$C_5$, $C_1$-$C_4$, $C_1$-$C_3$, $C_1$-$C_2$, $C_2$-$C_6$, $C_3$-$C_6$, $C_4$-$C_6$, $C_5$-$C_6$, and all other possible combinations within its scope and as express embodiments thereof.

A "stable" compound is a compound which can be prepared and isolated and whose structure and properties remain or can be caused to remain essentially unchanged for a period of time sufficient to allow use of the compound for the purposes described herein (e.g., therapeutic administration to a subject). The compounds of the present invention are limited to stable compounds embraced by Formula I.

The term "compound" refers to the compound and, in certain embodiments, to the extent they are stable, any hydrate or solvate thereof. A hydrate is the compound complexed with water, and a solvate is the compound complexed with an organic solvent.

As indicated above, the compounds of the present invention can be employed in the form of pharmaceutically acceptable salts. Those skilled in the art will recognize those instances in which the compounds of the invention may form salts. The term "pharmaceutically acceptable salt" refers to a salt (including an inner salt such as a zwitterion) which possesses effectiveness similar to the parent compound and which is not biologically or otherwise undesirable (e.g., is neither toxic nor otherwise deleterious to the recipient thereof). Thus, an embodiment of the invention provides pharmaceutically acceptable salts of the compounds of the invention. The term "salt(s)", as employed herein, denotes any of the following: acidic salts formed with inorganic and/or organic acids, as well as basic salts formed with inorganic and/or organic bases. Salts of compounds of the invention may be formed by methods known to those of ordinary skill in the art, for example, by reacting a compound of the invention with an amount of acid or base, such as an equivalent amount, in a medium such as one in which the salt precipitates or in aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates ("mesylates"), naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties. Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996). Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

In addition, when a compound of the invention contains both a basic moiety, such as, but not limited to an aliphatic primary, secondary, tertiary or cyclic amine, an aromatic or heteroaryl amine, pyridine or imidazole, and an acidic moiety, such as, but not limited to tetrazole or carboxylic acid, zwitterions ("inner salts") may be formed and are included within the terms "salt(s)" as used herein. It is understood that certain compounds of the invention may exist in zwitterionic form, having both anionic and cationic centers within the same compound and a net neutral charge. Such zwitterions are included within the invention.

It is understood that all possible tautomeric forms of the compounds of Formula I are contemplated as being within the scope of the instant invention, as well as mixtures thereof. It is further understood that while only one said tautomeric form of each example compound and embodiment of the invention may be depicted in the specification and appended claims, such depiction includes reference to all tautomeric forms of said compounds, which are included within the scope of the invention.

As set forth above, the present invention includes pharmaceutical compositions comprising a compound of Formula I of the present invention, and a pharmaceutically acceptable carrier. The characteristics of the carrier will depend on the route of administration. By "pharmaceutically acceptable" is meant that the ingredients of the pharmaceutical composition must be compatible with each other, do not interfere with the effectiveness of the active ingredient(s), and are not deleterious (e.g., toxic) to the recipient thereof. Thus, compositions according to the invention may, in addition to the inhibitor, contain diluents, fillers, salts, buffers, stabilizers, solubilizers, and other materials well known in the art.

Also as set forth above, the present invention includes a method for treating atherosclerosis, hypercholesterolemia, coronary heart disease, metabolic syndrome, acute coronary syndrome, or related cardiovascular disease and cardiometabolic conditions which comprises administering to a subject in need of such treatment a therapeutically effective amount of a compound of Formula I or a pharmaceutically acceptable salt thereof. The term "subject" (or, alternatively, "patient") as used herein refers to an animal, preferably a mammal, and in particular a human or a non-human animal including livestock animals and domestic animals including, but not limited to, cattle, horses, sheep, swine, goats, rabbits, cats, dogs, and other mammals in need of treatment. In select embodiment, the subject is a human. In select embodiments, the subject has been the object of treatment, observation or experiment. The term "administration" and variants thereof (e.g., "administering" a compound) in reference to a compound of Formula I mean providing the compound, or a pharmaceutically acceptable salt thereof, to the subject in need of treatment. The subject may be in need of, or desire, treatment for an existing disease or medical condition. As used herein, the subject "in need" of treatment of an existing condition encompasses both a determination of need by a medical professional as well as the desire of the subject for such treatment. When a compound or a salt thereof is provided in combination with one or more other active agents, "administration" and its variants are each understood to include provision of the compound or its salt and the other agents at the same time or at different times. When the agents of a combination are administered at the same time, they can be administered together in a single composition or they can be administered separately. It is understood that a "combination" of active agents can be a single composition containing all of the active agents or multiple compositions each containing one or more of the active agents. In the case of two active agents a combination can be either a single composition comprising both agents or two separate compositions each comprising one of the agents; in the case of three active agents a combination can be either a single composition comprising all three agents, three separate compositions each comprising one of the agents, or two compositions one of which comprises two of the agents and the other comprises the third agent; and so forth.

The compositions and combinations of the present invention are suitably administered in effective amounts. The term "effective amount" means the amount of active compound sufficient to induce the degradation of PCSK9 and thereby elicit the response being sought (i.e., degradation of PCSK9 in a cell, tissue or sample of interest, or the treatment of conditions associated with or impacted by PCSK9 function, including, but not limited to atherosclerosis, hypercholesterolemia, coronary heart disease, metabolic syndrome, acute coronary syndrome, and related cardiovascular disease and cardiometabolic conditions in an animal or human). In one embodiment, the effective amount is a "therapeutically effective amount" for the alleviation of the symptoms of the disease or condition being treated (e.g., the amelioration of symptoms associated with associated with PCSK9 function, including, but not limited to atherosclerosis, hypercholesterolemia, coronary heart disease, metabolic syndrome, acute coronary syndrome, and related cardiovascular disease and cardiometabolic conditions). When the active compound (i.e., active ingredient) is administered as the salt, references to the amount of active ingredient are to the free acid or free base form of the compound.

Compounds of Formula I or pharmaceutically acceptable salts thereof and pharmaceutical compositions comprising the compounds or salts can be administered orally, for example in the form of pills, tablets, lacquered tablets, sugar-coated tablets, granules, hard and soft gelatin capsules, aqueous, alcoholic or oily solutions, syrups, emulsions or suspensions, or rectally, for example in the form of suppositories. Administration can also be carried out parenterally, for example subcutaneously, intramuscularly or intravenously in the form of solutions for injection or infusion. Other suitable administration forms are, for example, percutaneous or topical administration, for example in the form of ointments, tinctures, sprays or transdermal therapeutic systems, or the inhalative administration in the form of nasal sprays or aerosol mixtures, or, for example, microcapsules, implants or rods. The preferred administration form depends, for example, on the disease to be treated and on its severity.

For the production of pills, tablets, sugar-coated tablets and hard gelatin capsules it is possible to use, for example, lactose, starch, for example maize starch, or starch derivatives, talc, stearic acid or its salts, etc. Carriers for soft gelatin capsules and suppositories are, for example, fats, waxes, semisolid and liquid polyols, natural or hardened oils, etc. Suitable carriers for the preparation of solutions, for example of solutions for injection, or of emulsions or syrups are, for example, water, physiologically sodium chloride solution, alcohols such as ethanol, glycerol, polyols, sucrose, invert sugar, glucose, mannitol, vegetable oils, etc. It is also possible to lyophilize the compounds of Formula I and their pharmaceutically acceptable salts and to use the resulting lyophilisates, for example, for preparing preparations for injection or infusion. Suitable carriers for microcapsules, implants or rods are, for example, copolymers of glycolic acid and lactic acid.

Besides the active compounds and carriers, the pharmaceutical preparations can also contain customary additives, for example fillers, disintegrants, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

The dosage of the active compound of Formula I and/or of a pharmaceutically acceptable salt thereof to be administered depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to compounds of Formula I or pharmaceutically acceptable salts thereof. In general, the daily dose range lies within the range of from about 0.001 mg to about 7 g per kg body weight, preferably about 0.01 mg to about 3.5 g per kg, and more preferably 0.1 to 10 mg per kg, in single or divided doses. It may be necessary to use dosages outside of these limits in some cases. Representative dosages of compounds disclosed herein, as well as the pharmaceutically acceptable salts and solvates thereof, for adults range from about 0.1 mg to about 1.0 g per day, preferably about 1 mg to about 500 mg, in single or divided doses. Examples of suitable dosages include 0.1 mg, 1 mg, 2 mg, 5 mg, 10 mg, 20 mg, 40 mg, 50 mg, 75 mg, 100 mg, 150 mg, 200 mg, 250 mg, 500 mg, 1000 mg and similar such doses. Representative dosages of compounds used in combination with the compounds disclosed herein are known, or the determination thereof is within the level of skill in the art, taking into account the description provided herein. One or more additional pharmacologically active agents may be administered in combination with a compound of Formula I. An additional active agent (or agents) is intended to mean a pharmaceutically active agent (or agents) that is active in the body, including pro-drugs that convert to pharmaceutically active form after administration, which are different from the compound of Formula I, and also includes free-acid, free-base and pharmaceutically acceptable salts of said additional active agents. Generally, any suitable additional active agent or agents, including but not limited to anti-hypertensive agents, anti-atherosclerotic agents such as a lipid modifying compound, anti-diabetic agents and/or anti-obesity agents may be used in any combination with the compound of Formula I in a single dosage formulation (a fixed dose drug combination), or may be administered to the subject in one or more separate dosage formulations which allows for concurrent or sequential administration of the active agents (co-administration of the separate active agents).

Examples of additional active agents which may be employed include but are not limited to angiotensin converting enzyme inhibitors (e.g., alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril), angiotensin II receptor antagonists (e.g., losartan i.e., COZAAR®, valsartan, candesartan, olmesartan, telmesartan and any of these drugs used in combination with hydrochlorothiazide such as HYZAAR®); neutral endopeptidase inhibitors (e.g., thiorphan and phosphoramidon), aldosterone antagonists, aldosterone synthase inhibitors, renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives, peptidyl amino diols and peptidyl beta-aminoacyl aminodiol carbamates, and small molecule renin inhibitors (including diol sulfonamides and sulfinyls), N-morpholino derivatives, N-heterocyclic alcohols and pyrolimidazolones; also, pepstatin derivatives and fluoro- and chloro-derivatives of statone-containing peptides, enalkrein, RO 42-5892, A 65317, CP 80794, ES 1005, ES 8891, SQ 34017, aliskiren (2(S),4(S),5(S),7(S)—N-(2-arbamoyl-2-methylpropyl)-5-amino-4-hydroxy-2,7-diisopropyl-8-[4-methoxy-3-(3-methoxypropoxy)-phenyl]-octanamid hemifimarate) SPP600, SPP630 and SPP635), endothelin receptor antagonists, phosphodiesterase-5 inhibitors (e.g. sildenafil, tadalfil and vardenafil), vasodilators, calcium channel blockers (e.g., amlodipine, nifedipine, veraparmil, diltiazem, gallopamil, niludipine, nimodipins, nicardipine), potassium channel activators (e.g., nicorandil, pinacidil, cromakalim, minoxidil, aprilkalim, loprazolam), diuretics (e.g., hydrochlorothiazide), sympatholitics, beta-adrenergic blocking drugs (e.g., propranolol, atenolol, bisoprolol, carvedilol, metoprolol, or metoprolol tartate), alpha adrenergic blocking drugs (e.g., doxazocin, prazocin or alpha methyldopa) central alpha adrenergic agonists, peripheral vasodilators (e.g. hydralazine); lipid lowering agents e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), fluvastatin (particularly the sodium salt sold in LESCOL®), crivastatin, and pitavastatin; a cholesterol absorption inhibitor such as ezetimibe (ZETIA®) and ezetimibe in combination with any other lipid lowering agents such as the HMG-CoA reductase inhibitors noted above and particularly with simvastatin (VYTORIN@) or with atorvastatin calcium; niacin in immediate-release or controlled release forms and/or with an HMG-CoA reductase inhibitor; niacin receptor agonists such as acipimox and acifran, as well as niacin receptor partial agonists; metabolic altering agents including insulin and insulin mimetics (e.g., insulin degludec, insulin glargine, insulin lispro), dipeptidyl peptidase-IV (DPP-4) inhibitors (e.g., sitagliptin, alogliptin, omarigliptin, linagliptin, vildagliptin); insulin sensitizers, including (i) PPARγ agonists, such as the glitazones (e.g. pioglitazone, AMG 131, MBX2044, mitoglitazone, lobeglitazone, IDR-105, rosiglitazone, and balaglitazone), and other PPAR ligands, including (1) PPARα/γ dual agonists (e.g., ZYH2, ZYH, GFT505, chiglitazar, muraglitazar, aleglitazar, sodelglitazar, and naveglitazar); (2) PPARα agonists such as fenofibric acid derivatives (e.g., gemfibrozil, clofibrate, ciprofibrate, fenofibrate, bezafibrate), (3) selective PPARγ modulators (SPPARγM's), (e.g., such as those disclosed in WO 02/060388, WO 02/08188, WO 2004/019869, WO 2004/020409, WO 2004/020408, and WO 2004/066963); and (4) PPARγ partial agonists; (ii) biguanides, such as metformin and its pharmaceutically acceptable salts, in particular, metformin hydrochloride, and extended-release formulations thereof, such as Glumetza™ Fortamet™, and GlucophageXR™; and (iii) protein tyrosine phosphatase-1B (PTP-1B) inhibitors (e.g., ISIS-113715 and TTP814); insulin or insulin analogs (e.g., insulin detemir, insulin glulisine, insulin degludec, insulin glargine, insulin lispro and inhalable formulations of each); leptin and leptin derivatives and agonists; amylin and amylin analogs (e.g., pramlintide); sulfonylurea and non-sulfonylurea insulin secretagogues (e.g., tolbutamide, glyburide, glipizide, glimepiride, mitiglinide, meglitinides, nateglinide and repaglinide); α-glucosidase inhibitors (e.g., acarbose, voglibose and miglitol); glucagon receptor antagonists (e.g., MK-3577, MK-0893, LY-2409021 and KT6-971); incretin mimetics, such as GLP-1, GLP-1 analogs, derivatives, and mimetics; and GLP-1 receptor agonists (e.g., dulaglutide, semaglutide, albiglutide, exenatide, liraglutide, lixisenatide, taspoglutide, CJC-1131, and BIM-51077, including intranasal, transdermal, and once-weekly formulations thereof); bile acid sequestering agents (e.g., colestilan, colestimide, colesevalam hydrochloride, colestipol, cholestyramine, and dialkylaminoalkyl derivatives of a cross-linked dextran), acyl CoA:cholesterol acyltransferase inhibitors, (e.g., avasimibe); antiobesity compounds; agents intended for use in inflammatory conditions, such as aspirin, non-steroidal anti-inflammatory drugs or NSAIDs, glucocorticoids, and selective cyclooxygenase-2 or COX-2 inhibitors; glucokinase activators (GKAs) (e.g., AZD6370); inhibitors of 11β-hydroxysteroid dehydrogenase type 1, (e.g., such as those disclosed in U.S. Pat. No. 6,730,690, and LY-2523199); CETP inhibitors (e.g., anacetrapib, torcetrapib, and evacetrapib); inhibitors of fructose 1,6-bisphosphatase, (e.g., such as those disclosed in U.S. Pat. Nos. 6,054,587; 6,110,903; 6,284,748; 6,399,782; and 6,489,476); inhibitors of acetyl CoA carboxylase-1 or 2 (ACC1 or ACC2); AMP-activated Protein Kinase (AMPK) activators; other agonists of the G-protein-coupled receptors: (i) GPR-109, (ii) GPR-119 (e.g., MBX2982 and PSN821), and (iii) GPR-40 (e.g., TAK875); SSTR3 antagonists (e.g., such as those disclosed in WO 2009/001836); neuromedin U receptor agonists (e.g., such as those disclosed in WO 2009/042053, including, but not limited to, neuromedin S (NMS)); SCD modulators; GPR-105 antagonists (e.g., such as those disclosed in WO 2009/000087); SGLT inhibitors (e.g., ASP1941, SGLT-3, empagliflozin, dapagliflozin, canagliflozin, BI-10773, ertugliflozin, remogloflozin, TS-071, tofogliflozin, ipragliflozin, and LX-4211); inhibitors of acyl coenzyme A:diacylglycerol acyltransferase 1 and 2 (DGAT-1 and DGAT-2); inhibitors of fatty acid synthase; inhibitors of acyl coenzyme A:monoacylglycerol acyltransferase 1 and 2 (MGAT-1 and MGAT-2); agonists of the TGR5 receptor (also known as GPBAR1, BG37, GPCR19, GPR131, and M-BAR); ileal bile acid transporter inhibitors; PACAP, PACAP mimetics, and PACAP receptor 3 agonists; PPAR agonists; protein tyrosine phosphatase-1B (PTP-1B) inhibitors; IL-1b antibodies, (e.g., XOMA052 and canakinumab); and bromocriptine mesylate and rapid-release formulations thereof; or with other drugs beneficial for the treatment of the above-mentioned conditions or disorders including the free-acid, free-base, and pharmaceutically acceptable salt forms of the above active agents where chemically possible.

In accordance with the present invention, there is further provided a method for the in vitro labeling, detection and/or quantification of PCSK9 in a biological sample, which comprises the steps of: (i) incubating the sample with a compound of Formula I or pharmaceutically acceptable salt thereof where the compound or salt comprises a detectable marker which confers a detectable signal for a time sufficient for the compound or salt to bind to PCSK9 present in the sample, (ii) activating or irradiating the detectable marker of step (i), and (iii) visualizing the detectable signal of step (i). The detectable marker conferring a detectable signal may comprise, without limitation, a dye, (chromophore or fluorophore), a fluorescent protein, a phosphorescent dye, a tandem dye (energy transfer pair), a microparticle, a hapten, an enzyme and a radioisotope. In specific embodiments, the detectable signal is a dye (e.g., chromophores and fluorophores), fluorescent protein, hapten, or enzyme.

In specific embodiments, the compounds of Formula I or pharmaceutically acceptable salt thereof have a fluorescence detectable marker including but not limited to a BODIPY group such as:

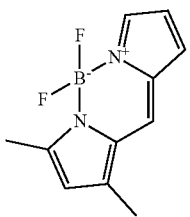 [SMILES: Cc1cc(C)n2c1C=C1C=CC=[N+]1[B-]2(F)F]

Visualization of the detectable signal is either direct or indirect. This may be carried out via any method available to the skilled artisan including the fluoresence polarization assay described herein; see, e.g. Lea & Simeonov, 2011 *Expert Opin Drug Discov.* 6(1): 17-32; Rossi & Taylor, 2011 *Nat Protoc.* 6(3): 365-387. Visualization of the detectable signal is typically through noting a change in fluorescence, such as a change in the intensity, excitation or emission wavelength, distribution of fluorescence, fluorescence lifetime, fluorescence polarization, or a combination thereof. The biological sample can be any of the following, cells expressing native and recombinant PCSK9, blood, blood plasma, serum and tissues or sections thereof.

A specific embodiment, therefore, of the foregoing method for the in vitro labeling, detection and/or quantification of PCSK9 in a biological sample, which comprises the steps of: (i) incubating the sample with a compound of Formula I or pharmaceutically acceptable salt thereof comprising the following BODIPY group:

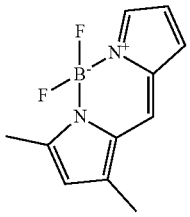 [SMILES: Cc1cc(C)n2c1C=C1C=CC=[N+]1[B-]2(F)F]

for a time sufficient for the compound or salt to bind to PCSK9 present in the sample, (ii) irradiating the BODIPY group of step (i), and (iii) visualizing a fluorescent signal conferred by the BODIPY group of step (i). Visualization of the fluorescent signal may be carried out via any method available to the skilled artisan including the fluoresence polarization assay described herein; see, e.g. Lea & Simeonov, 2011 *Expert Opin Drug Discov.* 6(1): 17-32; Rossi & Taylor, 2011 *Nat Protoc.* 6(3): 365-387.

The following examples are provided so that the invention might be more fully understood. Unless otherwise indicated, the starting materials are commercially available. They should not be construed as limiting the invention in any way.

Abbreviations employed herein include the following: Ac=acetyl=CH$_3$C(=O); ACN=MeCN=acetonitrile; aq=aqueous; BOC (or Boc)=tert-butyloxycarbonyl; CH$_3$CN=acetonitrile; conc.=concentrated; DC$_{50}$=concentration of compound to reduce protein levels to 50%; DCM=dichloromethane; DEAD=diethyl azodicarboxylate; DIAD=diisopropyl azodicarboxylate; DIEA=N,N-Diisopropylethylamine; DIPEA=diisopropylethylamine (or Hunig's base); DMEM=Dulbecco's Modified Eagle's medium; DMF=N,N-dimethylformamide; DMSO=dimethyl sulfoxide; EA=AcOEt=EtOAc=ethyl acetate; EDC=1-ethyl-3-(3-dimethylaminopropyl) carbodiimide; Et=ethyl; EtOH=ethanol; FP=fluorescence polarization; HATU=(1-[Bis(dimethylamino)methylene]-1H-1,2,3-triazolo[4,5-b]pyridinium 3-oxid hexafluorophosphate); HPLC=high-performance liquid chromatography; h or hr or hrs=hours; LCMS=LC-MS=liquid chromatography/mass spectrometry; Me=methyl; McCN=acetonitrile; MeOH=methanol; min or mins=minutes; MS=molecular sieves; NBS=N-bromosuccinimide; NMP=N-Methyl-2-pyrrolidone; NMR=nuclear magnetic resonance; PdCl$_2$(dppf)=[1,1'-Bis(diphenylphosphino)ferrocene]dichloropalladium(II); PE=Pet. ether=petroleum ether; Ph=phenyl; prep=preparative; prep-HPLC=preparative HPLC; RCM=ring closing metathesis; RPLC=reverse phase liquid chromatography; RT=room temp.=room temperature; SFC=supercritical fluid chromatography; TFA=trifluoroacetic acid; THF=tetrahydrofuran; and TLC=thin layer chromatography.

The compounds of the present invention can be readily prepared according to the following reaction schemes and examples, or modifications thereof, using readily available starting materials, reagents and conventional synthesis procedures. In these reactions, it is also possible to make use of known variants. Other methods for preparing compounds of the invention will be readily apparent to the person of ordinary skill in the art in light of the following reaction schemes and examples.

Scheme 1, Preparation of Intermediates I-V

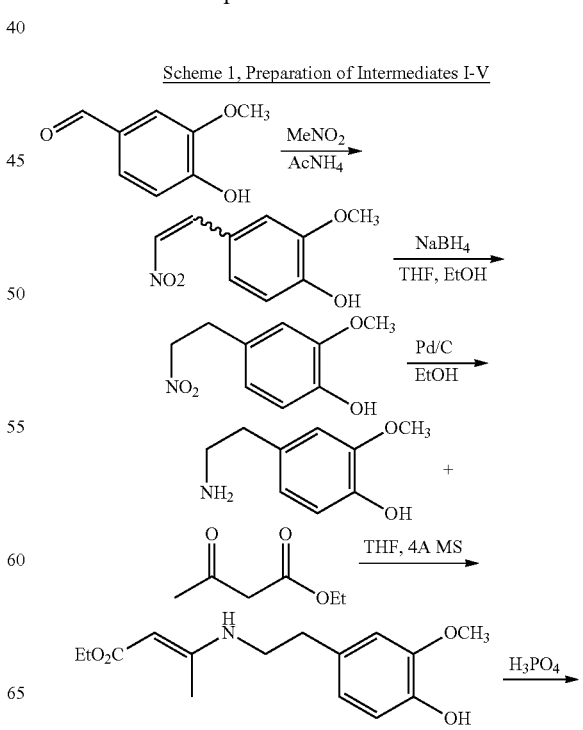

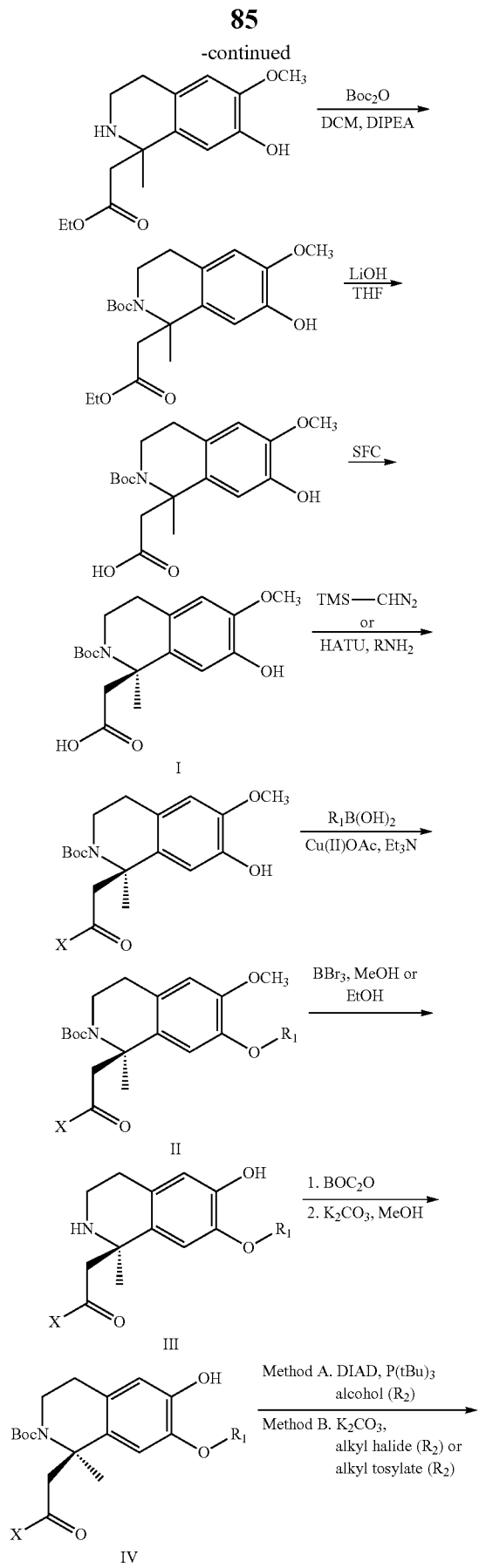

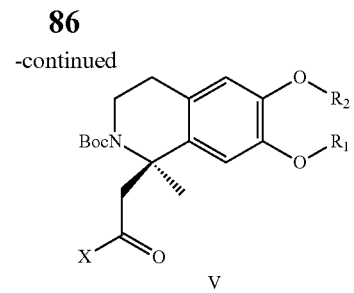

V

Step A: Preparation of 2-methoxy-4-(2-nitrovinyl)phenol

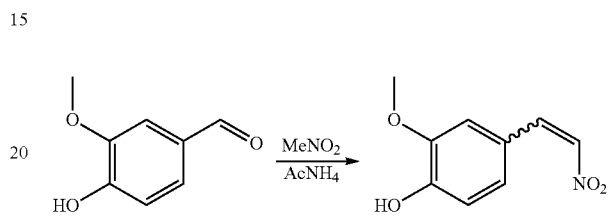

To a solution of 4-hydroxy-3-methoxybenzaldehyde (169 g, 1.11 mol) in nitromethane (1.50 L) was added ammonium acetate (23.1 g, 300 mmol) at 28° C. The reaction mixture was stirred at 118° C. for 16 hours. The starting material was completely consumed by TLC (petroleum ether/ethyl acetate=3:1). The reaction was cooled to room temperature and filtered. The product was washed with methanol (400 mL) and methyl tert-butyl ether (100 mL). Then the filtrate was concentrated. The product was washed with methanol (400 mL) and methyl tert-butyl ether (100 mL) to give the second batch of product. The batches were combined to give the title compound.

1H NMR: 400 MHz CDCl$_3$ δ 7.98-7.94 (d, J=13.6 Hz, 1H), 7.54-7.50 (d, 13.6 Hz, 1H), 7.15-7.13 (d, J=8 Hz, 7.01-6.97 (m, 2H), 6.06 (s, 1H), 3.96 (s, 3H).

Step B: Preparation of 2-methoxy-4-(2-nitroethyl)phenol

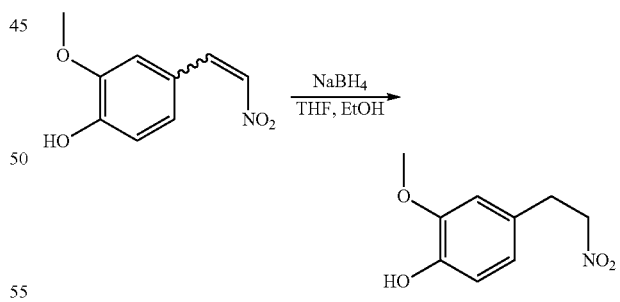

To a mixture of sodium borohydride (35.7 g, 943 mmol) in tetrahydofuran (600 mL) and ethanol (210 mL) a solution of 2-methoxy-4-(2-nitrovinyl)phenol (80.0 g, 410 mmol) in tetrahydrofuran (600 mL) was added drop wise at 0° C. After warming to room temperature over 45 min ice water (820 mL) was added to the reaction mixture. The resulting slurry was neutralized by addition of 1.0 N aqueous hydrochloric acid solution (1.0 N, 415 mL) and then concentrated. This mixture was extracted with dichloromethane, washed with brine, dried over Na$_2$SO$_4$ and evaporated to afford the title compound.

¹H NMR: 400 MHz CDCl₃ δ 6.88-6.86 (d, J=8.4 Hz, 1H), 6.73-6.70 (m, 2H), 5.66 (m, 2H), 4.61-4.57 (t, J=7.2, 2H), 3.89 (s, 3H), 3.28-3.24 (t, J 7.6 Hz, 2H)

Step C: Preparation of 4-(2-aminoethyl)-2-methoxyphenol

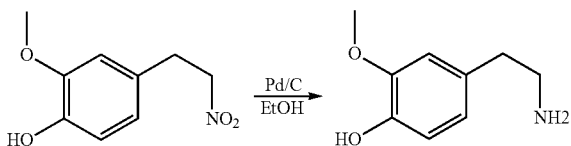

To a solution of 2-methoxy-4-(2-nitroethyl)phenol (100 g, 507 mmol) in ethanol (1.00 L) was added Pd—C(10%, 20 g) under N₂. The suspension was degassed under vacuum and purged with H₂ several times. The mixture was stirred under H₂ (45 psi) at 50° C. for 16 hours. TLC (petroleum ether/ethyl acetate=3:1) showed the starting material was consumed completely. The reaction mixture was filtered and the filter was concentrated to give the title compound.

1H NMR: 400 MHz CD₃OD δ 6.79 (s, 1H), 6.75-6.73 (d, J=8 Hz, 1H), 6.66-6.64 (dd, J=2 Hz, 8.4 Hz, 1H), 3.84 (s, 3H), 2.88-2.84 (t, J=6.8 Hz, 2H), 2.70-2.66 (t, J=7.2 Hz, 2H)

Step D: Preparation of ethyl (E)-3-((4-hydroxy-3-methoxyphenethyl)amino)but-2-enoate

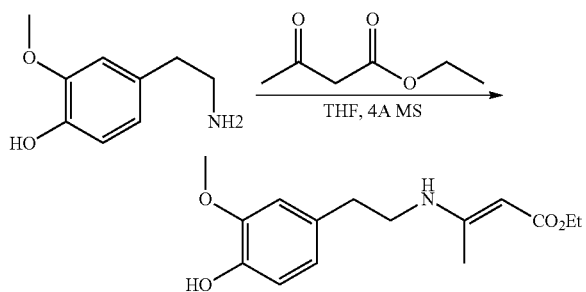

To a mixture of 4-(2-aminoethyl)-2-methoxyphenol (92.0 g, 550 mmol) and ethyl 3-oxobutanoate (68.0 g, 522 mmol) in tetrahydrofuran (1.20 L), was added 4 Å MS (37.0 g, 726 mmol) at 25° C. The reaction was stirred for 16 hours. The mixture was filtered and concentrated. The residue was purified by silica gel chromatography (petroleum ether/ethyl acetate=25/1, 5/1) to afford the title compound.

1H NMR: 300 MHz CDCl₃ δ 8.58 (m, 1H), 6.78-6.76 (d, J=7.8 Hz, 1H), 6.62-6.59 (m, 1H), 5.50 (s, 1H), 4.41234 (s, 1H) 4.04-3.96 (m, 2H), 3.80 (s, 3H), 3.37-3.29 (m, 2H), 2.71-2.66 (t, J=7.2 Hz, 2H), 1.71 (s, 3H), 1.21-1.14 (t, J=7.2 Hz, 3H).

Step E: Preparation of ethyl 2-(7-hydroxy-6-methoxy-1-methyl-1,2,3,4-tetrahydroisoquinolin-1-yl)acetate

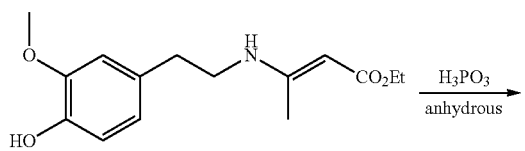

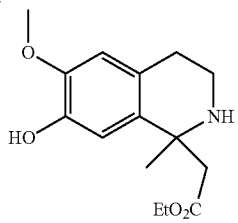

To a mixture of P₂O₅ (239 g, 1.68 mol) in H₃PO₄ (550 g, 2.99 mol), was added ethyl (E)-3-((4-hydroxy-3-methoxyphenethyl)amino)but-2-enoate (52 g, 186 mmol) at 30° C. The mixture was heated to 120° C. where it was stirred for 1 hour. TLC (petroleum ether:ethyl acetate=3:1) showed the reaction was completed. The mixture was cooled to 30° C. and ice water was added. The residue was adjusted to PH=9-10 with 25% NH₄OH and extracted with dichloromethane. The combined organic phase was washed with saturated brine, dried with anhydrous Na₂SO₄, filtered and concentrated to afford the title compound.

1H NMR: 400 MHz CDCl₃ δ 6.71 (s, 1H), 6.52 (s, 1H), 4.09-4.04 (m, 2H), 3.84 (s, 3H), 3.13-3.08 (m, 2H), 2.89-2.857 (d, J=14.8 Hz, 1H), 2.72-2.69 (t, J=6.0 Hz, 2H), 2.65-2.61 (d, J=15.2 Hz, 1H), 1.46 (s, 3H), 1.19-1.16 (t, J=15.2 Hz, 3H).

Step F: Preparation of tert-butyl 1-(2-ethoxy-2-oxoethyl)-7-hydroxy-6-methoxy-1-methyl-3,4-dihydroisoquinoline-2(1H)-carboxylate

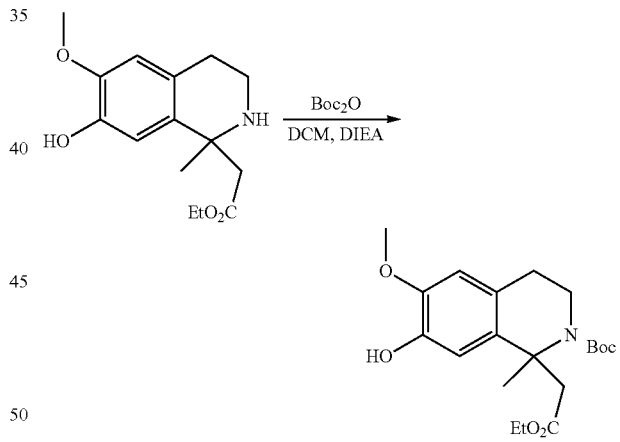

To a mixture of ethyl 2-(7-hydroxy-6-methoxy-1-methyl-1,2,3,4-tetrahydroisoquinolin-1-yl)acetate (26.0 g, 93.1 mmol) and di-tert-butyl dicarbonate (24.4 g, 112 mmol) in dichloromethane (400 mL), was added N,N-diisopropylethylamine (19.5 mL g, 112 mmol) at 30° C. The mixture was stirred at 30° C. for 16 hour, then additional di-tert-butyl dicarbonate (20.3 g, 93.1 mmol) and N,N-diisopropylethylamine (16.2 mL g, 93.0 mmol) were added. After stirring for 48 hours at 30° C. the reaction was complete by TLC (petroleum ether:ethyl acetate=3:1). The mixture was concentrated and then purified by silica gel chromatography (petroleum ether/ethyl acetate=20/1 to 8/1) to afford the title compound.

1H NMR: 300 MHz CDCl₃ δ 6.82 (s, 1H), 6.53 (s, 1H), 5.49 (s, 1H), 4.13-3.82 (m, 7H), 3.60-3.56 (m, 1H), 2.82-

2.75 (m, 2H), 2.67-2.66 (m, 1H), 1.70-1.67 (t, J=4.8 Hz, 3H), 1.54 (s, 9H), 1.11-1.06 (t, J=7.2 Hz, 3H).

Step G: Preparation of 2-(2-(tert-butoxycarbonyl)-7-hydroxy-6-methoxy-1-methyl-1,2,3,4-tetrahydroisoquinolin-1-yl)acetic acid

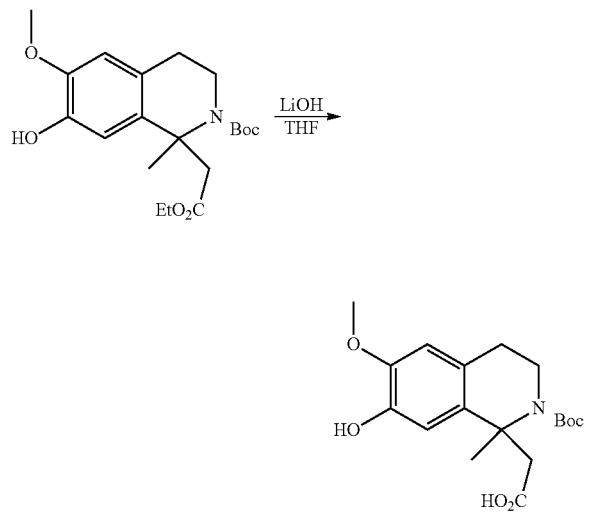

To a mixture of tert-butyl 1-(2-ethoxy-2-oxoethyl)-7-hydroxy-6-methoxy-1-methyl-3,4-dihydroisoquinoline-2(1H)-carboxylate (48 g, 127 mmol) in tetrahydrofuran (400 mL), was added a 1N aqueous lithium hydroxide solution (320 mL, 1N) at 30° C. After heating at 90° C. for 16 hours the reaction was complete by TLC (petroleum ether:ethyl acetate=3:1). The solvent was removed in vacuum and extracted with methyl tert-butyl ether. The aqueous layer was acidified to pH=5 with 1N aqueous hydrochloric acid solution and extracted with ethyl acetate. The organic layer was concentrated to afford the title compound.

$^1$H NMR: 300 MHz CDCl$_3$ δ 6.79 (s, 1H), 6.51 (s, 1H), 5.48 (m, 1H), 4.05-4.00 (d, J=15.6 Hz, 1H), 3.85-3.81 (m, 4H), 3.53-3.50 (m, 1H), 2.84-2.73 (m, 2H), 2.72-2.61 (m, 1H), 1.66 (s, 3H), 1.49 (s, 9H).

Step H: Preparation of Intermediate I, Exemplified by (R)-2-(2-(tert-butoxycarbonyl)-7-hydroxy-6-methoxy-1-methyl-1,2,3,4-tetrahydroisoquinolin-1-yl)acetic acid

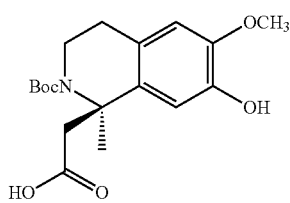

The racemic mixture from scheme 1, step G was resolved using supercritical fluid chromatography using a chiral OJ column eluting with 15% ethanol:CO$_2$. Isomer A eluted at 1.24 minutes, Isomer B at 1.79 minutes. Data for enantiomer A: LCMS m/z 352.1 [M+H]$^+$. Data for enantiomer B: LCMS m/z 352.3 [M+H]$^+$. Enantiomer A (shown) was found to be the (R)-enantiomer and was used in subsequent steps.

Step I: Preparation of tert-butyl (R)-7-hydroxy-6-methoxy-1-methyl-1-(2-oxo-2-(thiazol-2-ylamino)ethyl)-3,4-dihydroisoquinoline-2(1H)-carboxylate

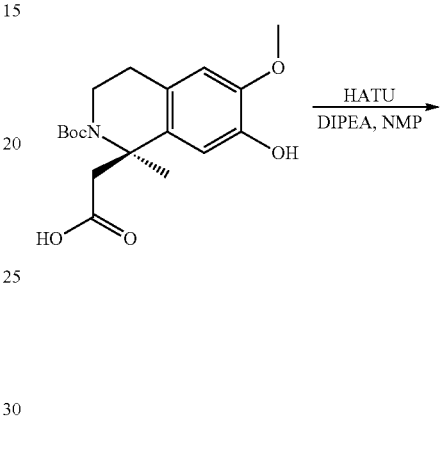

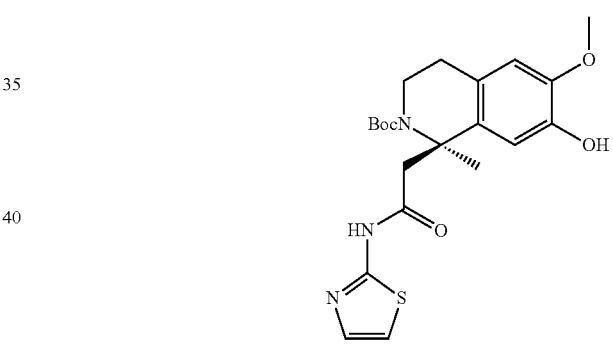

To the solution of enantiomer A, the title compound from scheme 1, step H (2.58 g, 7.34 mmol) and 1-[bis(dimethylamino)methylene]-1H-1,2,3-triazolo[4,5-b]pyridinium 3-oxid hexafluorophosphate (5.58 g, 14.7 mmol) in N-methyl-2-pyrrolidinone (24.5 mL) was added N,N-diisopropylethylamine (3.80 g, 29.4 mmol) at room temperature. After stirring for 1 hour 2-aminothiazole (2.94 g, 29.4 mmol) was added and the reaction was heated to 80° C. After stirring overnight the reaction was cooled to room temperature and the solution was washed with saturated aqueous ammonium chloride (4×10 mL). The organic layer was dried over sodium sulfate, filtered and the solvent was evaporated under reduced pressure. The residue was purified by column chromatography on silica gel, eluting with ethyl acetate/isohexane 70:30 to give the title compound: LCMS m/z 434.2 [M+H]$^+$.

Step J: Preparation of Intermediate IIa, tert-butyl (K)-7-(3-fluoro-4-(methoxycarbonyl)phenoxy)-6-methoxy-1-methyl-1-(2-oxo-2-(thiazol-2-ylamino)ethyl)-3,4-dihydroisoquinoline-2(1H)-carboxylate

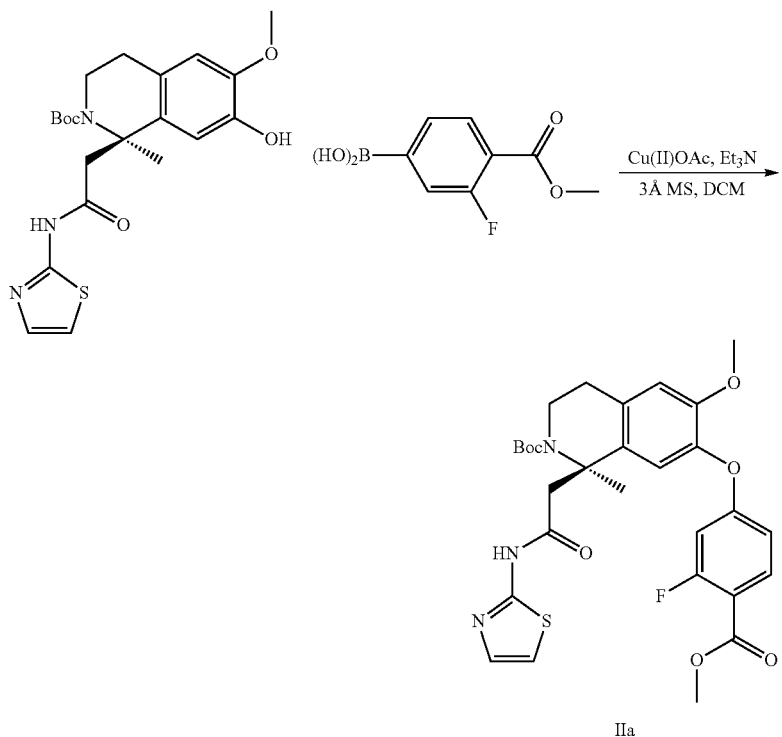

To the solution of the title compound from scheme 1, step I (200 mg, 0.461 mmol) in dichloromethane (9.23 was added (3-fluoro-4-(methoxycarbonyl)phenyl)boronic acid (274 mg, 1.38 mmol), copper (11) acetate (168 mg, 0.923 mmol) and triethylamine (193 μL, 1.384 mmol). To the solution was added 3 Å MS and the reaction was left to stir at room temperature for 72 h. The mixture was filtered, washing with ethyl acetate and the solution was removed in vacuo. The residue was purified by preparative HPLC on a C18 reverse-phase column, eluting with acetonitrile/water+0.1% trifluoroacetic acid, to give the title compound: LCMS m/z 586.19 [M+H]$^+$.

Intermediates II b-c in the table below were prepared in an analogous fashion as described for Intermediate IIa substituting; the appropriate reactants and reagents that are prepared as described herein or that are commercially available.

| No. | Structure | Name | LC/MS [M + H]$^+$ |
|---|---|---|---|
| IIb | 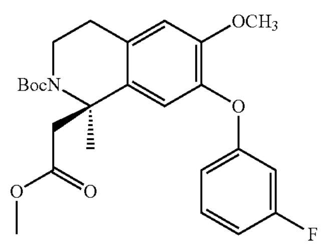 [SMILES: COC(=O)C[C@]1(C)c2cc(Oc3cccc(F)c3)c(OC)cc2CCN1C(=O)OC(C)(C)C] | tert-butyl (R)-7-(3-fluorophenoxy)-6-methoxy-1-(2-methoxy-2-oxoethyl)-1-methyl-3,4-dihydroisoquinoline-2(1H)-carboxylate | 482.14 [M + Na]$^+$ |
| IIc | 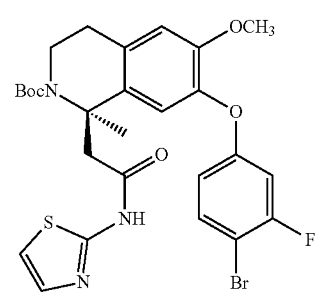 [SMILES: COc1cc2c(cc1Oc1ccc(Br)c(F)c1)[C@@](C)(CC(=O)Nc1nccs1)N(C(=O)OC(C)(C)C)CC2] | tert-butyl (R)-7-(4-bromo-3-fluorophenoxy)-6-methoxy-1-methyl-1-(2-oxo-2-thiazol-2-ylamino)ethyl)-3,4-dihydroisoquinoline-2(1H)-earboxylate | 608.16 [M + 3H (Br)]$^+$ |

Step K: Preparation of Intermediate III, Exemplified by tert-butyl (R)-7-(3-fluoro-4-(methoxycarbonyl)phenoxy)-6-hydroxy-1-methyl-1-(2-oxo-2-(thiazol-2-ylamino)ethyl)-3,4-dihydroisoquinoline-2(1H)-carboxylate Step L: Preparation of Intermediate IVa, Exemplified by tert-butyl (R)-7-(3-fluoro-4-(methoxycarbonyl)phenoxy)-6-hydroxy-1-methy-1-(2-oxo-2-(thiazol-2-ylamino)ethyl-3,4-dihydroquinoline-2(1H)-carboxylate

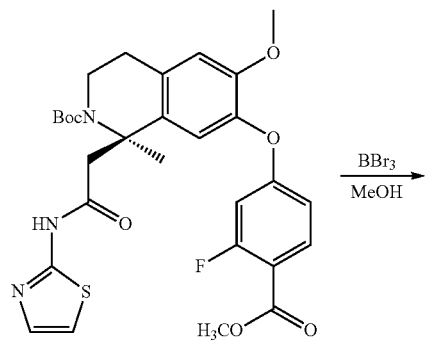

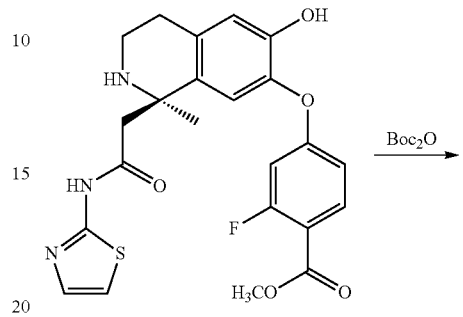

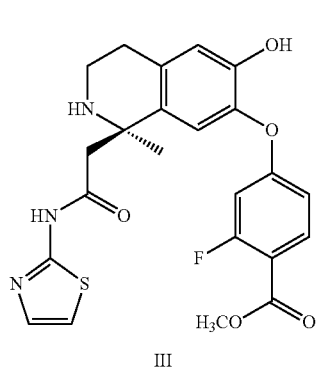

III

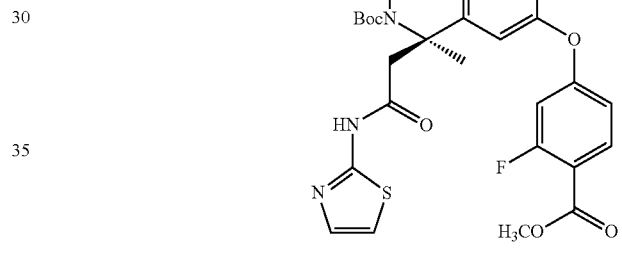

IVa

To a solution of tert-butyl (R)-7-(3-fluoro-4-(methoxycarbonyl)phenoxy)-6-methoxy-1-methyl-1-(2-oxo-2-(thiazol-2-ylamino)ethyl)-3,4-dihydroisoquinoline-2(1H)-carboxylate (Intermediate IIa, scheme 1, step J, 426 mg, 0.727 mmol) in dichloromethane (9.09 mL) at −78° C. was added boron tribromide, 1M solution in dichloromethane (2.91 mL, 2.91 mmol). The reaction was slowly warmed to room temperature where it stirred overnight. It was cooled back down to −78° C., methanol (9 mL) was added and the resulting solution was warmed to room temperature where it stirred until the methyl ester was regenerated. The reaction was quenched carefully with saturated aqueous sodium bicarbonate solution. The resulting mixture was concentrated to remove the methanol and then extracted three times with dichloromethane. The combined organics were dried over sodium sulfate, filtered and concentrated to afford the title compound: LCMS m/z 471.95 [M+H]+.

To a solution of tert-butyl (R)-7-(3-fluoro-4-(methoxycarbonyl)phenoxy)-6-hydroxy-1-methyl-1-(2-oxo-2-(thiazol-2-ylamino)ethyl)-3,4-dihydroisoquinoline-2(1H)-carboxylate (Intermediate III, scheme 1, step K, 480 mg, 1.02 mmol) and di-tert-butyl dicarbonate (0.945 mL, 4.07 mmol) in 1,4-dioxane (10.2 mL) was added triethylamine (0.570 mL, 4.07 mmol). The reaction was stirred at 85° C. for 16 hours overnight. The solution was cooled to room temperature, and saturated aqueous ammonium chloride solution was added followed by ethyl acetate. The layers were separated and the aqeuous was extracted twice more with ethyl acetate. The combined organics were dried over sodium sulfate, filtered and concentrated. The crude material was taken up in methanol (10.2 mL) and then potassium carbonate (141 mg, 1.018 mmol) was added. The resulting mixture was heated to 55° C. for 3 hours. The solution was cooled to room temperature and then concentrated. It was extracted with ethyl acetate, washed with brine, dried over sodium sulfate and concentrated. It was purified by column chromatography on silica gel (eluting with 10-70% ethyl acetate in hexanes) to afford the title compound: LCMS m/z 572.42 [M+H]+.

Intermediate IVb in the table below was prepared in an analogous fashion as described for Intermediate IVa substituting the appropriate reactants and reagents that are prepared as described herein or that are commercially available.

| No. | Structure | Name | LC/MS [M + H]+ |
|---|---|---|---|
| IVb | (structure shown) | tert-butyl (R)-7-(4-(ethoxycarbonyl)-3-fluorophenoxy)-6-hydroxy-1-methyl-1-(2-oxo-2-thiazol-2-ylamino)ethyl)-3,4-dihydroisoquinoline-2(1H)-carboxylate | 586.22 [M + H]+ |

Step M: Preparation of (tetrahydro-2H-pyran-2-yl)methyl trifluoromethanesulfonate

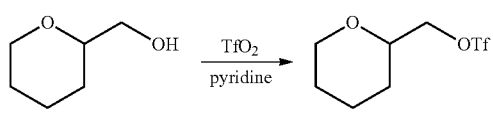 [SMILES: "TfO2" ; OCC1CCCCO1 ; O=S(=O)(OCC1CCCCO1)C(F)(F)F]

To a solution of (tetrahydro-2H-pyran-2-yl)methanol (0.20 g, 1.72 mmol) in dichloromethane (6.38 mL) at −5° C. was added pyridine (0.237 mL, 2.93 mmol) followed by trifluoromethanesulfonic anhydride (0.407 ml, 2.41 mmol). The reaction was stirred for 20 minutes at −5° C. and was then passed through a silica plug flushing with dichloromethane and then ethyl acetate. The solution was concentrated to afford the title compound.

1H NMR: 500 MHz CDCl$_3$ δ 4.47-4.41 (m, 2H), 3.92-3.89 (m, 1H), 3.83-3.79 (m, 1H), 3.52-3.47 (m, 1H), 3.39-3.35 (m, 1H), 2.18-2.10 (m, 1H), 1.71-1.60 (m, 2H), 1.49-1.42 (m, 1H).

Step N: Preparation of Intermediate Va. Exemplified by tert-butyl (1R)-7-(3-fluoro-4-(methoxycarbonyl)phenyl)-1-methyl-1-(2-oxo-2-(thiazol-2-ylamino)ethyl)-6-((tetrahydro-2H-pyran-2-yl)methoxy)-3,4-dihydroisoquinoline-2(1H)-carboxylate

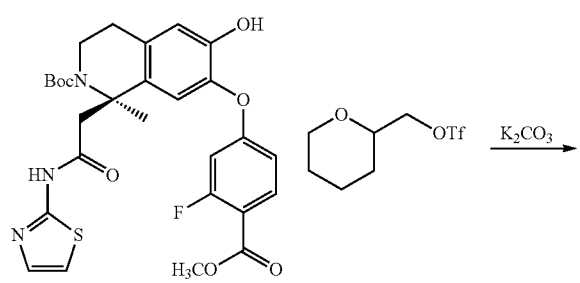

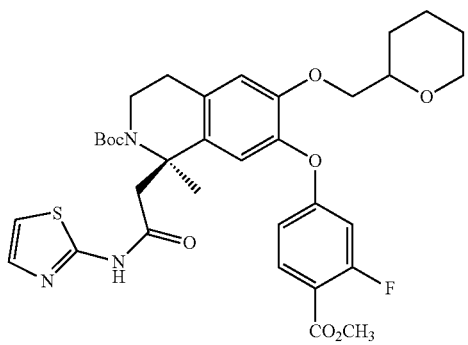

Va

To a vial with tert-butyl (R)-7-(3-fluoro-4-(methoxycarbonyl)phenoxy)-6-hydroxy-1-methyl-1-(2-oxo-2-(thiazol-2-ylamino)ethyl)-3,4-dihydroisoquinoline-2(1H)-carboxylate (Intermediate IVa, scheme 1, step L, 30.0 mg, 0.052 mmol) and the title compound from scheme 1, step M (14.0 mg, 0.055 mmol) in acetone (500 µL) was added potassium carbonate (8.70 mg, 0.063 mmol), The reaction was stirred at room temperature for 16 hours overnight. It was concentrated and then taken up in a solution of 1:1 acetonitrile:water. The solution was acidified with TFA and then passed through a syringe filter before being purified by HPLC on a C18 reverse-phase column eluting with 10-100% acetonitrile in water with 0.1% TFA. The fractions containing product were combined and concentrated to afford the title compound: LCMS m/z 670.33[M+H]+.

Intermediates Vb-c in the table below were prepared in an analogous fashion as described for Intermediate Va substituting the appropriate reactants and reagents that are prepared as described herein or that are commercially available.

| No. | Structure | Name | LC/MS [M + H]+ |
|---|---|---|---|
| Vb | 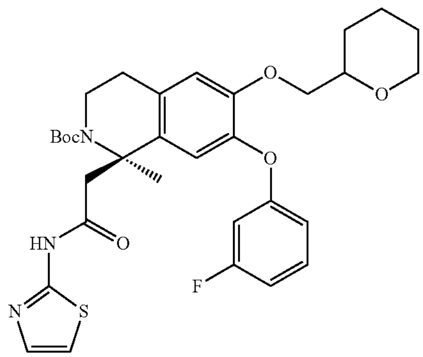 [SMILES: CC(C)(C)OC(=O)N1CCc2cc(OCC3CCCCO3)c(Oc3cccc(F)c3)cc2[C@@]1(C)CC(=O)Nc1nccs1] | tert-butyl (1R)-7-(3-fluorophenoxy)-1-methyl-1-(2-oxo-2-(thiazol-2-ylamino)ethyl)-6-((tetrahydro-2H-pyran-2-yl)methoxy)-3,4-dihydroisoquinoline-2(1H)-carboxylate | 612.24 [M + H]+ |
| Vc | 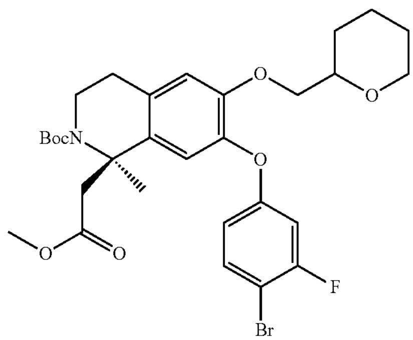 [SMILES: COC(=O)C[C@]1(C)c2cc(Oc3ccc(Br)c(F)c3)c(OCC3CCCCO3)cc2CCN1C(=O)OC(C)(C)C] | tert-butyl (1R)-7-(4-bromo-3-fluorophenoxy)-1-(2-methoxy-2-oxoethyl)-1-methyl-6-((tetrahydro-2H-pyran-2-yl)methoxy)-3,4-dihydroisoquinoline-2(1H)-carboxylate | 624.09 [M + 3H (Br)]+ |

Examples 1-3

Example 1: (Z)-36-methoxy-31-methyl-5-oxo-31,32,33,34-tetrahydro-2,14-dioxa-6-aza-7(2,4)-thiazola-3(7,1)-isoquinolina-1(1,3)-benzenacyclotetradecaphane-14-carboxylic acid

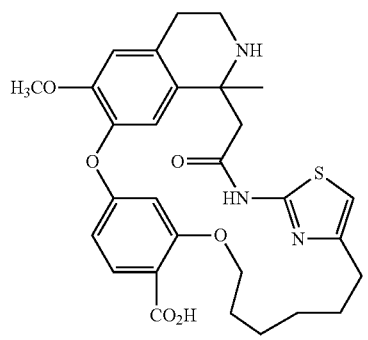 [SMILES: COc1cc2c3cc1Oc1ccc(C(=O)O)c(c1)OCCCCCCc1csc(n1)NC(=O)CC3(C)NCC2]

Example 1 was made according to general Scheme 2 below.

Scheme 2

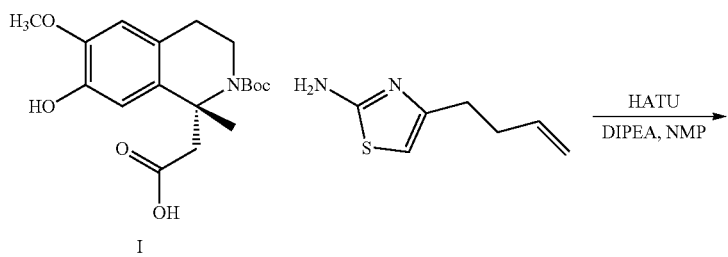

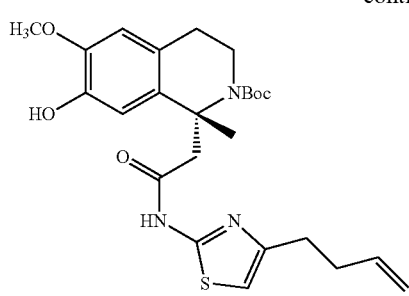
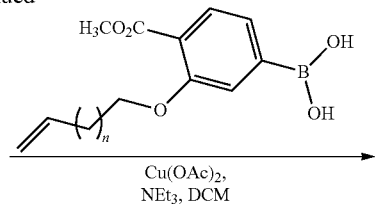

Cu(OAc)₂,
NEt₃, DCM

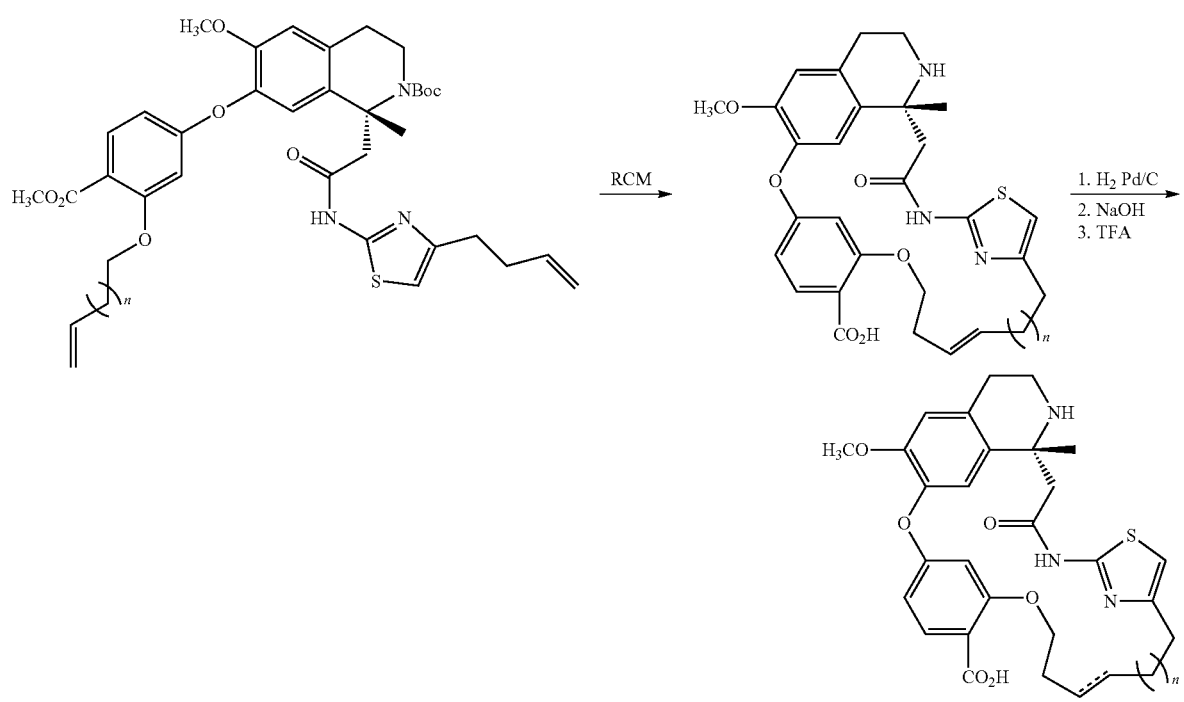

1. H₂ Pd/C
2. NaOH
3. TFA

RCM

Step A: tert-butyl (R)-1-(2-((4-(but-3-en-1-yl)thiazol-2-yl)amino)-2-oxoethyl)-7-hydroxy-6-methoxy-1-methyl-3,4-dihydroisoquinoline-2(1H)-carboxylate

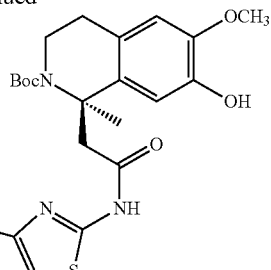

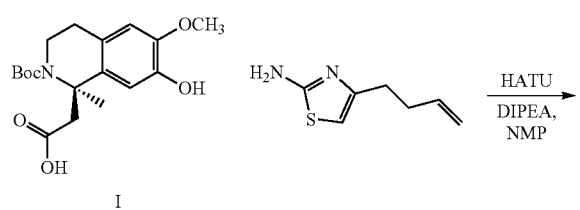

HATU
DIPEA,
NMP 2-(2-(tert-butoxycarbonyl)-7-hydroxy-6-methoxy-1-methyl-1,2,3,4-tetrahydroisoquinolin-1-yl)acetic acid (Int. 1, enantiomer A, 1.00 g, 2.85 mmol), 1-[Bis(dimethylamino)methylene]-1H-1,2,3-triazolo[4,5-b]pyridinium 3-oxid hexafluorophosphate (2.16 g, 5.69 mmol), and N,N-diisopropylethylamine (1.99 mL, 11.4 mmol) were mixed and stirred for 2 hr at room temperature. 4-(but-3-en-1-yl)thiazol-2-amine (0.878 g, 5.69 mmol) was added and the reaction was heated to 80° C. for 24 hrs. The reaction was cooled to room temperature, washed with 1M aq. HCl and brine. The organic was dried over sodium sulfate and purified by column chromatography on silica gel eluting with 0 to 100% ethyl acetate in hexanes to afford the title compound: LCMS m/z 488.09 [M+H]+.
Step B: tert-butyl (R)-1-(2-((4-(but-3-en-1-yl)thiazol-2-yl)amino)-2-oxoethyl)-7-(3-(but-3-en-1-yloxy)-4-(methoxycarbonyl)phenoxy-6-methoxy-1-methyl-3,4-dihydroisoquinoline-2(1H)-carboxylate
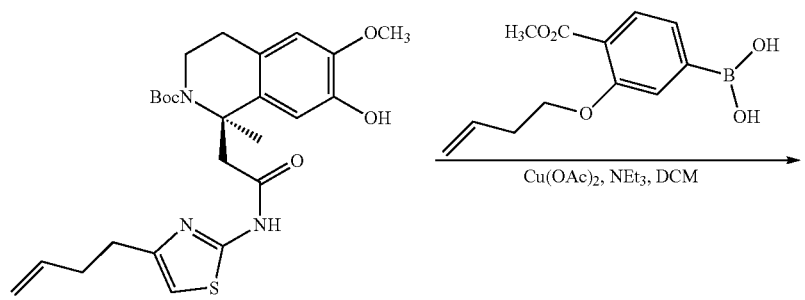
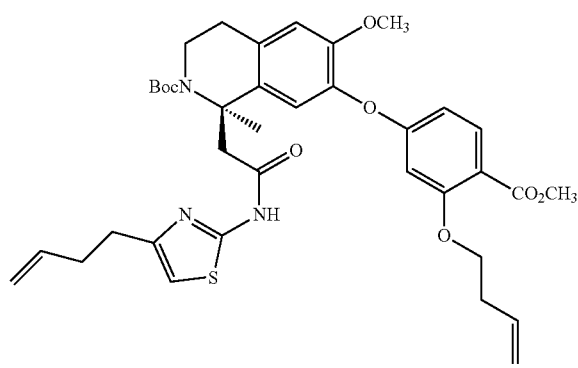

The title compound from scheme 2, step A (100 mg, 0.205 mmol), triethylamine (0.086 mL, 0.615 mmol), copper (II) acetate (37.2 mg, 0.205 mmol), and (3-(but-3-en-1-yloxy)-4-(methoxycarbonyl)phenyl)boronic acid (154 mg, 0.615 mmol) were stirred in dichloromethane (10.0 mL) in an atmosphere of oxygen for 48 hours. The reaction was washed with brine and the organics were dried with sodium sulfate then concentrated. The residue was purified by preparative HPLC on a C18 reverse-phase column eluting with 30-100% acetonitrile in water (with 0.05% trifluoroacetic acid) to afford the title compound: LCMS m/z 692.33 [M+H]$^+$.

Step C: 32-(tert-butyl) 14-methyl (R,7Z,10E)-36-methoxy-31-methyl-5-oxo-31,32,33,34-tetrahydro-2,14-dioxa-6-aza-7(2,4)-thiazola-3(7,1)-isoquinolina-1(1,3)-benzenacyclotetradecaphan-10-ene-14,32-dicarboxylate

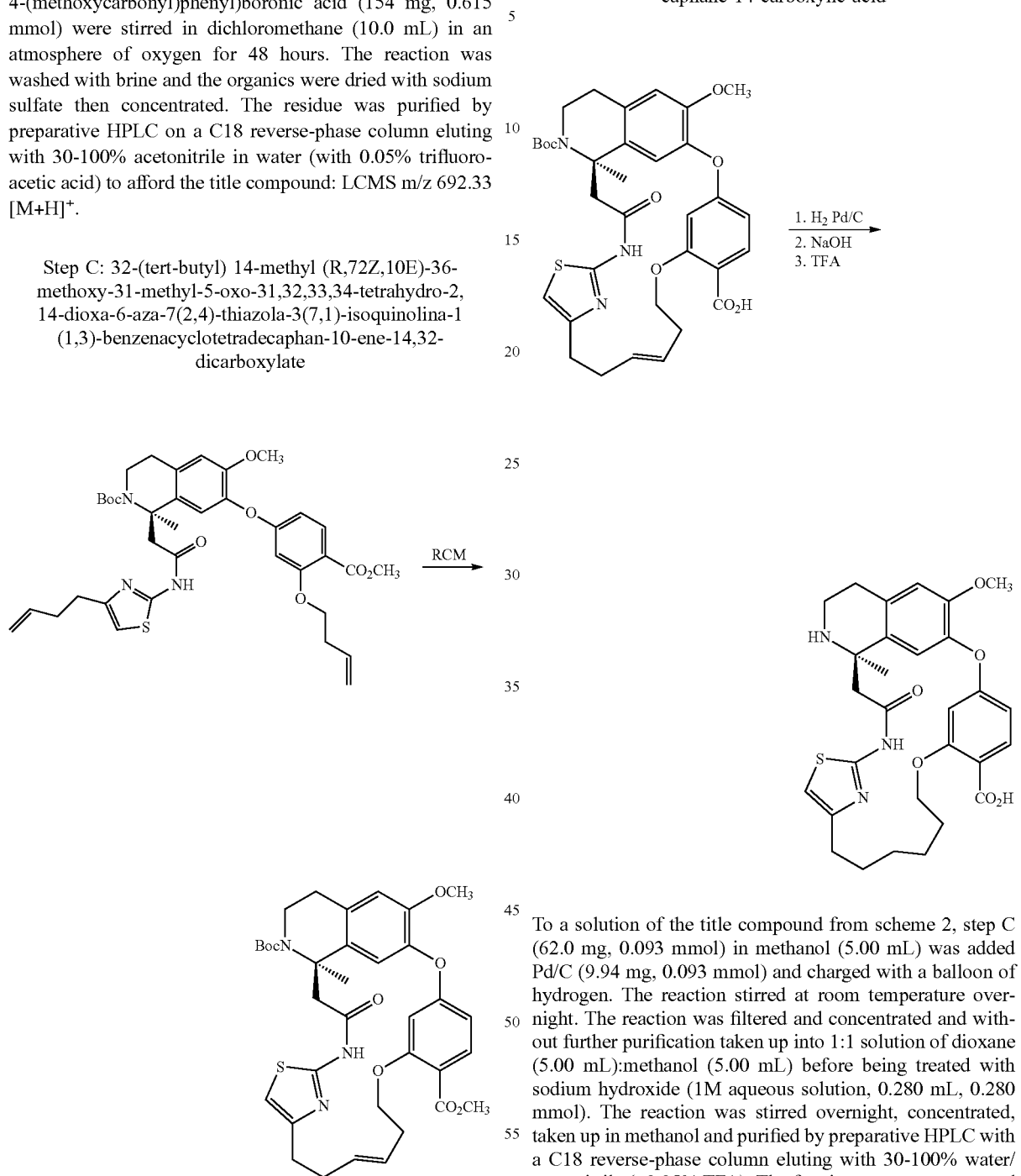

Step D: (R,Z)-36-methoxy-31-methyl-5-oxo-31,32,33,34-tetrahydro-2,14-dioxa-6-aza-7(2,4)-thiazola-3(7,1)-isoquinolina-1(1,3)-benzenacyclotetradecaphane-14-carboxylic acid To the title compound from scheme 2, step B (0.205 mmol) was added Hoveyda-Grubbs catalyst 2nd generation (6.43 mg, 10.3 µmol) and toluene (5.00 mL). The solution was degassed and heated to 60° C. After 1 hour the reaction was cooled to room temperature and concentrated to afford the title compound: LCMS m/z 664.69 [M+H]$^+$.

To a solution of the title compound from scheme 2, step C (62.0 mg, 0.093 mmol) in methanol (5.00 mL) was added Pd/C (9.94 mg, 0.093 mmol) and charged with a balloon of hydrogen. The reaction stirred at room temperature overnight. The reaction was filtered and concentrated and without further purification taken up into 1:1 solution of dioxane (5.00 mL):methanol (5.00 mL) before being treated with sodium hydroxide (1M aqueous solution, 0.280 mL, 0.280 mmol). The reaction was stirred overnight, concentrated, taken up in methanol and purified by preparative HPLC with a C18 reverse-phase column eluting with 30-100% water/acetonitrile (+0.05% TFA). The fractions were concentrated to dryness. To the solid was added dichloromethane (5.00 mL) and TFA (1.08 mL, 14.0 mmol). The reaction was stirred for 2 hr and then concentrated and lyophilized to afford the title compound: LCMS m/z 551.9 [M+H]$^+$.

EXAMPLES 2-3 in the table below were prepared in an analogous fashion as described for EXAMPLE 1 and generally shown in Scheme 2, substituting the appropriate reactants and reagents that are reared as described herein or that are commercially available.

| EX. No. | Structure | Name | LC/MS [M + H]+ |
|---|---|---|---|
| 2 | 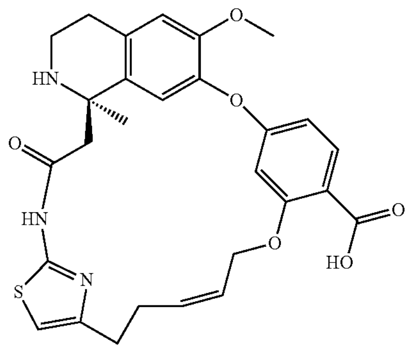 [SMILES: COc1cc2c3cc1Oc1ccc(C(=O)O)c(c1)OC/C=C\CCc1csc(n1)NC(=O)C[C@@]3(C)NCC2] | (R,7ZZ)-36-methoxy-31-methyl-5-oxo-31,32,33,34-tetrahydro-2,13-dioxa-6-aza-7(2,4)-thiazola-3(7,1)-isoquinolina-1(1,3)-benzenacyclotridecaphan-10-ene-14-carboxylic acid | 536.14 |
| 3 | 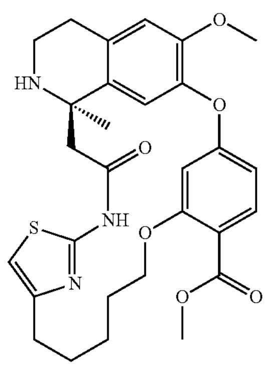 [SMILES: COC(=O)c1ccc2cc1OCCCCCc1csc(n1)NC(=O)C[C@@]1(C)NCCc3cc(OC)c(cc31)O2] | methyl (R,Z)-36-methoxy-31-methyl-5-oxo-31,32,33,34-tetrahydro-2,13-dioxa-6-aza-7(2,4)-thiazola-3(7,1)-isoquinolina-1(1,3)-benzenacyclotridecaphane-14-carboxylate | 552.18 |

Examples 4-10

Example 4: (R)-2-fluoro-4-((6-methoxy-1-methyl-1-(2-oxo-2-(thiazol-2-ylamino)ethyl)-1,2,3,4-tetrahydroisoquinolin-7-yl)oxy)benzoic acid

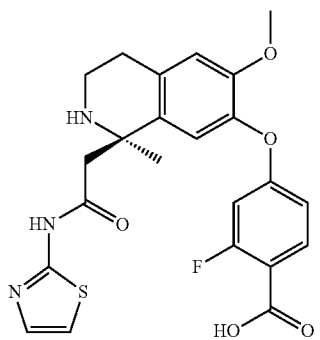 [SMILES: COc1cc2c(cc1Oc1ccc(C(=O)O)c(F)c1)[C@@](C)(CC(=O)Nc1nccs1)NCC2]

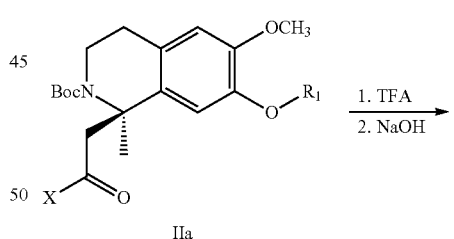

Scheme 3

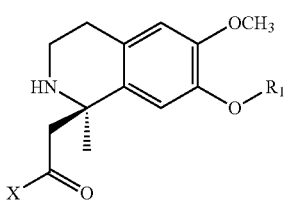

Example 4 was made according to general Scheme 3 below.

Step A: methyl (R)-2-fluoro-4-((6-methoxy-1-methyl-1-(2-oxo-2-(thiazol-2-ylamino)ethyl)-1,2,3,4-tetrahydroisoquinolin-7-yl)oxy)benzoate Step B: (R)-2-fluoro-4-((6-methoxy-1-methyl-1-(2-oxo-2-(thiazol-2-ylamino)ethyl)-1,2,3,4-tetrahydroisoquinolin-7-yl)oxy)benzoic acid

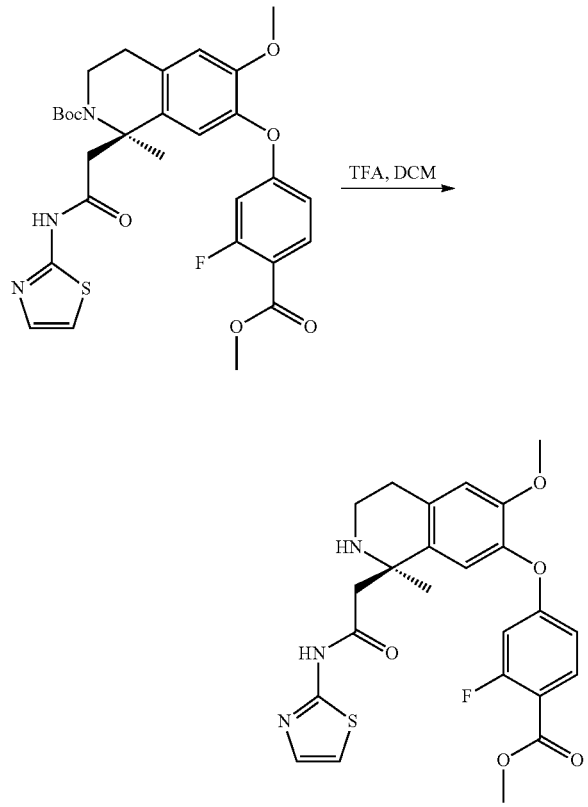

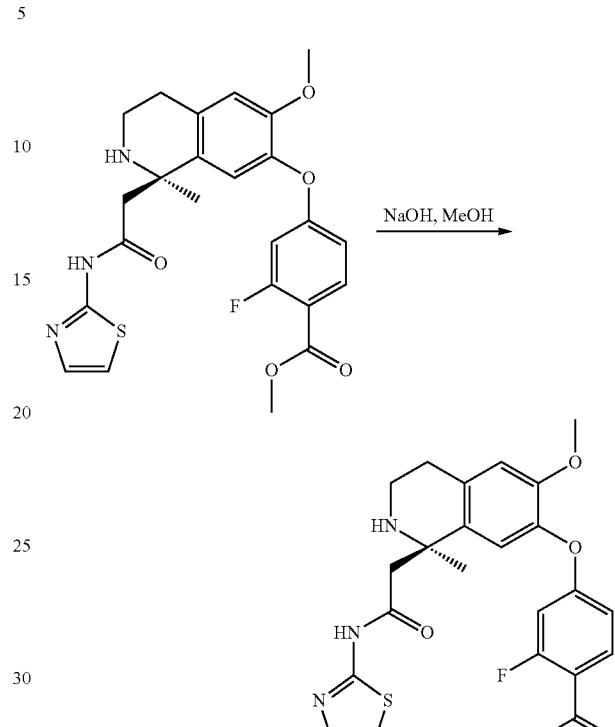

To a solution of tert-butyl (R)-7-(3-fluoro-4-(methoxycarbonyl)phenoxy)-6-methoxy-1-methyl-1-(2-oxo-2-(thiazol-2-ylamino)ethyl)-3,4-dihydroisoquinoline-2(1H)-carboxylate (Int. IIa, 15.0 mg, 0.03 mmol) in dichloromethane was added trifluoroacetic acid (0.50 mL, 6.5 mmol). After stirring at room temperature for 40 minutes the reaction was complete. The solvent was removed and the residue was used without further purification in scheme 3, step B.

To a solution of the title compound from scheme 3, step A in methanol was added a 4N aqueous solution of sodium hydroxide (1.0 mL, 4.0 mmol) at room temperature. After an hour the ester was completely hydrolyzed to the acid. It was neutralized with acetic acid (0.5 mL), then purified by preparative HPLC on a C18 reverse-phase column eluting with acetonitrile/water+0.1% trifluoroacetic acid, to give the title compound. LCMS m/z 471.52 [M+H]$^+$.

EXAMPLES 5-10 in the table below were prepared in an analogous fashion as described for EXAMPLE 4 and generally shown in Scheme 3, substituting the appropriate reactants and reagents that are reared as described herein or that are commercially available.

| EX. No. | Structure | Name | LC/MS [M + H]$^+$ |
|---|---|---|---|
| 5 | 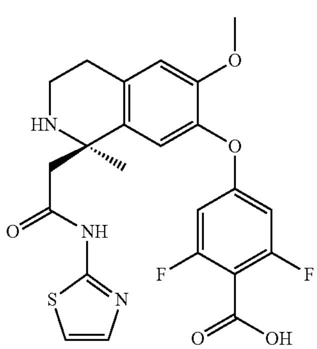 [SMILES: COc1cc2c(cc1Oc1cc(F)c(C(=O)O)c(F)c1)[C@@](C)(CC(=O)Nc1nccs1)NCC2] | (R)-2,6-difluoro-4-((6-methoxy-1-methyl-1-(2-oxo-2-(thiazol-2-ylamino)ethyl)-1,2,3,4-tetrahydroisoquinolin-7-yl)oxy)benzoic acid | 490.13 |

-continued

| EX. No. | Structure | Name | LC/MS [M + H]+ |
|---|---|---|---|
| 6 | 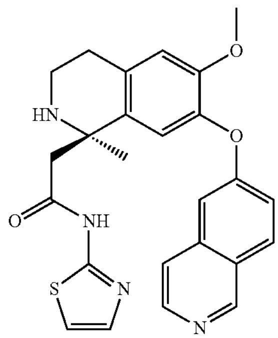 [SMILES: COc1cc2c(cc1Oc1ccc3cnccc3c1)[C@@](C)(CC(=O)Nc1nccs1)NCC2] | (R)-2-(7-(isoquinolin-6-yloxy)-6-methoxy-1-methyl-1,2,3,4-tetrahydroisoquinolin-1-yl)-N-(thiazol-2-yl)acetamide | 461.31 |
| 7 | 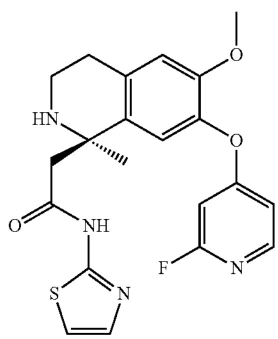 [SMILES: COc1cc2c(cc1Oc1ccnc(F)c1)[C@@](C)(CC(=O)Nc1nccs1)NCC2] | (R)-2-(7-((2-fluoropyridin-4-yl)oxy)-6-methoxy-1-methyl-1,2,3,4-tetrahydroisoquinolin-1-yl)-N-(thiazol-2-yl)acetamide | 429.12 |
| 8 | 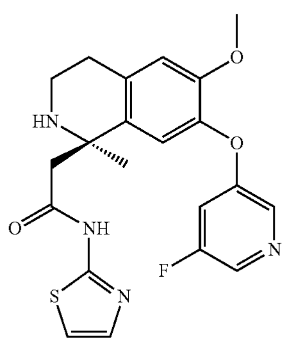 [SMILES: COc1cc2c(cc1Oc1cncc(F)c1)[C@@](C)(CC(=O)Nc1nccs1)NCC2] | (R)-2-(7-((5-fluoropyridin-3-yl)oxy)-6-methoxy-1-methyl-1,2,3,4-tetrahydroisoquinolin-1-yl)-N-(thiazol-2-yl)acetamide | 429.25 |
| 9 | 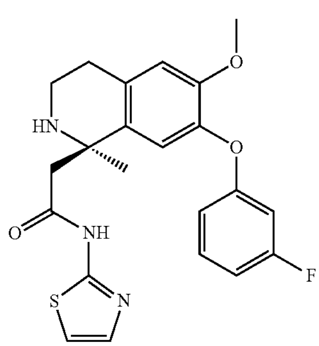 [SMILES: COc1cc2c(cc1Oc1cccc(F)c1)[C@@](C)(CC(=O)Nc1nccs1)NCC2] | (R)-2-(7-(3-fluorophenoxy)-6-methoxy-1-methyl-1,2,3,4-tetrahydroisoquinolin-1-yl)-N-(thiazol-2-yl)acetamide | 428 |

| EX. No. | Structure | Name | LC/MS [M + H]+ |
|---|---|---|---|
| 10 | 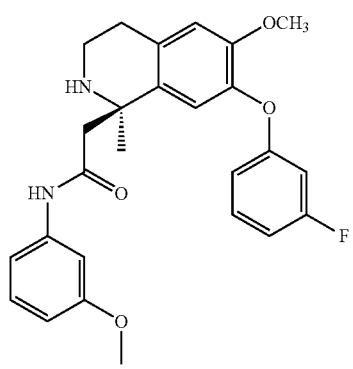 | (R)-2-(7-(3-fluoro-4-methoxyphenoxy)-6-methoxy-1-methyl-1,2,3,4-tetrahydroisoquinolin-1-yl)-N-(thiazol-2-yl)acetamide | 458.73 |

Examples 11-12

Example 11: (R)-2-(7-(3-fluorophenoxy)-6-methoxy-1-methyl-1,2,3,4-tetrahydroisoquinolin-1-yl)-N-(3-methoxyphenyl)acetamide

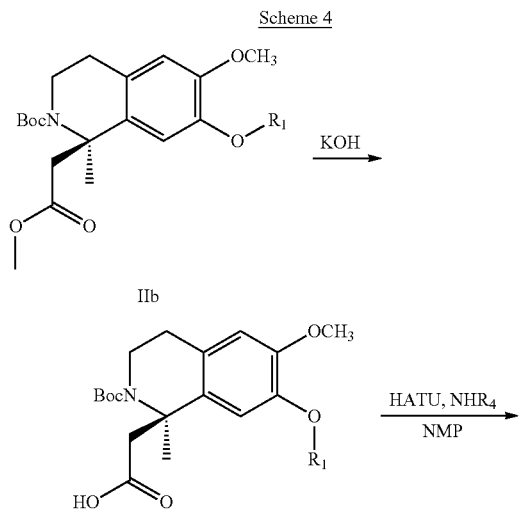

Example 11 was made according to general Scheme 4 below.

Scheme 4

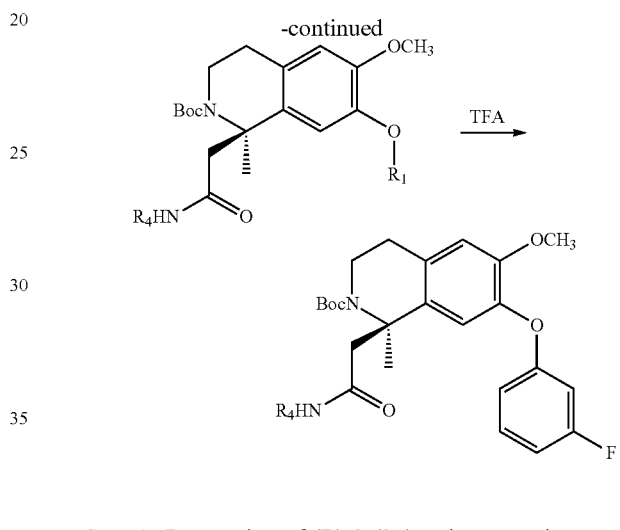

Step A: Preparation of (R)-2-(2-(tert-butoxycarbonyl)-7-(3-fluorophenoxy)-6-methoxy-1-methyl-1,2,3,4-tetrahydroisoquinolin-1-yl)acetic acid

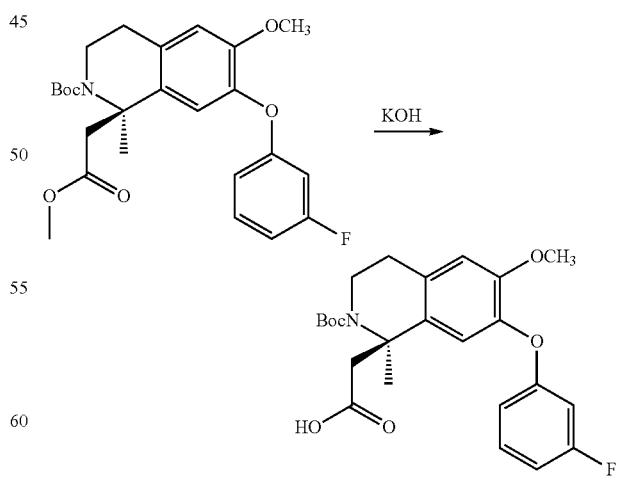

To a solution of tert-butyl (R)-7-(3-fluorophenoxy)-6-methoxy-1-(2-methoxy-2-oxoethyl)-1-methyl-3,4-dihydroisoquinoline-2(1H)-carboxylate (Int. IIb, 500 mg, 1.09 mmol) in methanol (5.00 mL), water (2.00 mL) was added.

Solid potassium hydroxide (1.10 g, 19.6 mmol) was added to the reaction mixture, followed by tetrahydrofuran (2.00 mL). The reaction mixture was heated to 80° C. for 1 hour. The mixture was acidified with 5N aqueous HCl and then ethyl acetate was added. The organic layer was separated and the aqueous layer was washed twice more with ethyl acetate. The combined organic layers were washed with a saturated solution of NaCl, dried over anhydrous sodium sulfate, filtered and concentrated to give the title compound: LCMS m/z 446.15 [M+H]$^+$.

Step B: Preparation of tert-butyl (R)-7-(3-fluoro-phenoxy)-6-methoxy-1-(2-((3-methoxyphenyl)amino)-2-oxoethyl)-1-methyl-3,4-dihydroisoquino-line-2(1H)-carboxylate

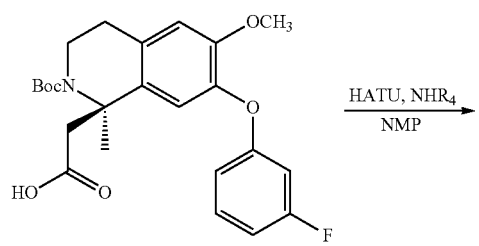

Step C: Preparation of (R)-2-(7-(3-fluorophenoxy)-6-methoxy-1-methyl-1,2,3,4-tetrahydroisoquinolin-1-yl)-N-(3-methoxyphenyl)acetamide

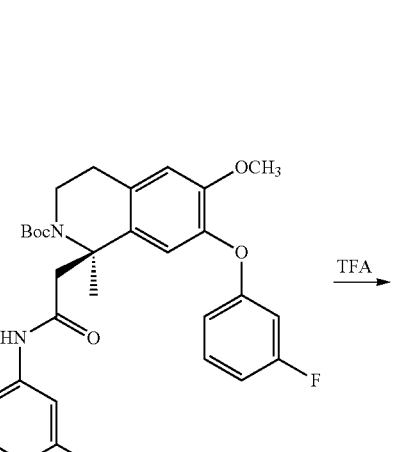

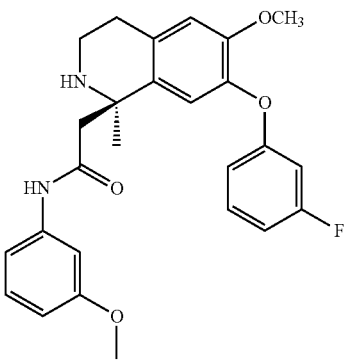 [SMILES: COc1cccc(NC(=O)C[C@@]2(C)NCCc3cc(OC)c(Oc4cccc(F)c4)cc32)c1]

To a solution of the title compound from scheme 4, step A (30 mg, 0.067 mmol) and 1-[Bis(dimethylamino)methyl-ene]-1H-1,2,3-triazolo[4,5-b]pyridinium 3-oxid hexafluorophosphate (33.3 mg, 0.088 mmol) in acetonitrile (1.0 mL) was added N-methylmorpholine (0.022 mL, 0.202 mmol) at room temperature. After one hour p-anisidine (49.8 mg, 0.404 mmol) was added and the reaction mixture was heated to 45° C. for 18 hours. The reaction mixture was filtered and purified by preparative HPLC on a C18 reverse-phase column, eluting with 15-100% acetonitrile/water (with 0.05% v/v trifluoroacetic acid) to give the title compound: LCMS m/z 551.21 [M+H]$^+$.

To a solution of the title compound from scheme 4, step B (37 mg, 0.067 mmol) in dichloromethane (1.0 mL) was added trifluoroacetic acid (0.05 mL, 0.67 mmol). The reaction mixture was stirred for 30 minutes at room temperature and was then concentrated to give the title compound: LCMS m/z 451.19 [M+H]$^+$.

EXAMPLE 12 in the table below was prepared in an analogous fashion as described for EXAMPLE 11 and generally shown in Scheme 4, substituting the appropriate reactants and reagents that are prepared as described herein or that are commercially available.

| EX. No. | Structure | Name | LC/MS [M + H]+ |
|---|---|---|---|
| 12 | 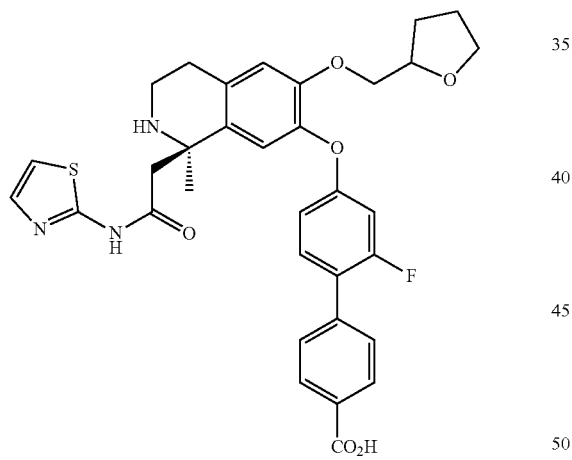 | (R)-2-(7-(3-fluorophenoxy)-6-methoxy-1-methyl-1,2,3,4-tetrahydroisoquinolin-1-yl)-N-(1H-indol-4-yl)acetamide | 459.99 |
Examples 13-36
Example 13: 2'-fluoro-4'-(((1R)-1-methyl-1-(2-oxo-2-(thiazol-2-ylamino)ethyl)-6-((tetrahydrofuran-2-ylmethoxy)-1,2,3,4-tetrahydroisoquinolin-7-yl)oxy)-[1,1'-biphenyl]-4-carboxylic acid
Example 13 was made according to general Scheme 5 below.
Scheme 5
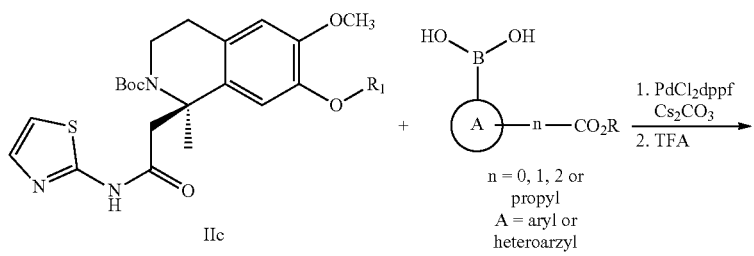

-continued

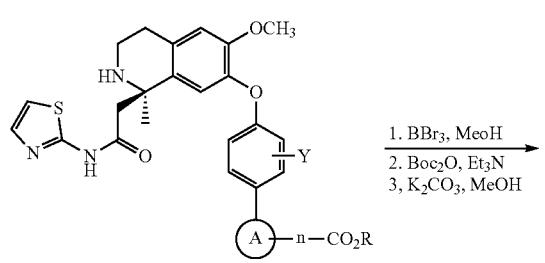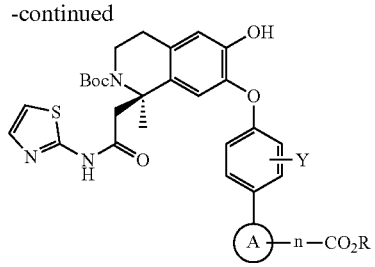

Method A. DEAD, PPh₃
alcohol (R₂)
Method B. K₂CO₃,
alkyl halide (R₂)
or alkyl tosylate (R₂)
2. TFA, DCM 1. BBr₃, MeOH
2. Boc₂O, Et₃N
3. K₂CO₃, MeOH

VI

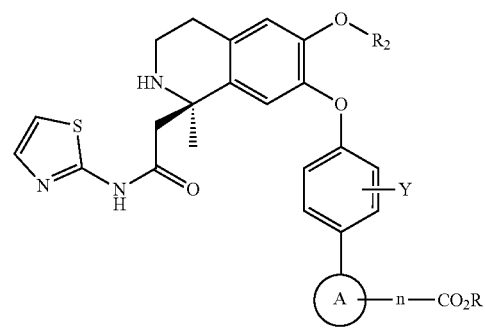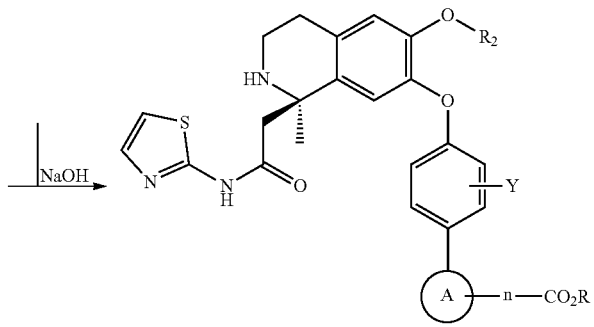

NaOH

Step A: tert-butyl (R)-7-((2-fluoro-4'-(methoxycarbonyl)-[1,1'-biphenyl]-4-yl)oxy)-6-methoxy-1-methyl-1-(2-oxo-2-(thiazol-2-ylamino)ethyl)-3,4-dihydroisoquinoline-2(1H)-carboxylate

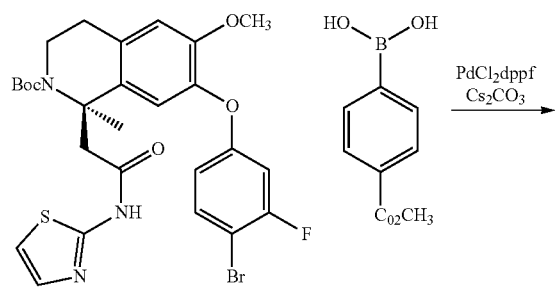

PdCl₂dppf
Cs₂CO₃

To a solution of the title compound from tert-butyl (R)-7-(4-bromo-3-fluorophenoxy)-6-methoxy-1-methyl-1-(2-oxo-2-(thiazol-2-ylamino)ethyl)-3,4-dihydroisoquinoline-2(1H)-carboxylate (Int. IIc, 212 mg, 0.350 mmol) in dioxane (3495 µl) was added (4-(methoxycarbonyl)phenyl)boronic acid (94 mg, 0.524 mmol), [1,1'-Bis(diphenylphosphino)ferrocene]dichloropalladium(i) complex with dichloromethane (28.5 mg, 0.035 mmol) and cesium carbonate (1.00 M aqueous solution, 699 µl, 0.699 mmol) at room temperature under nitrogen. The reaction mixture was heated in a microwave oven to 90° C. for 45 min. The mixture was filtered through Na₂SO₄ and the solvent was removed by reduced pressure. The residue was purified by column chromatography on silica gel, eluting with EtOAc/isohexane 7:3 to give the title compound: LCMS m/z 662.4 [M+H]⁺.

Step B: methyl (R)-2'-fluoro-4'-((6-hydroxy-1-methyl-1-(2-oxo-2-(thiazol-2-ylamino)ethyl)-1,2,3,4-tetrahydroisoquinolin-7-yl)oxy)-[1,1'-biphenyl]-4-carboxylate

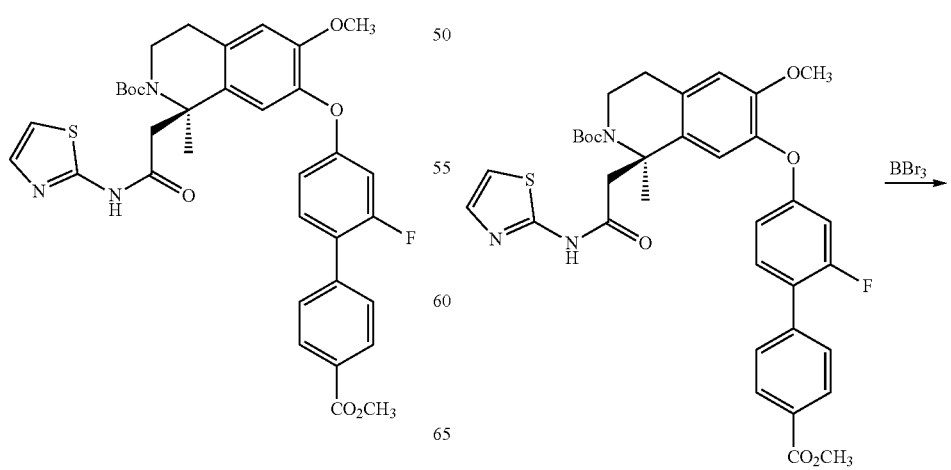

BBr₃

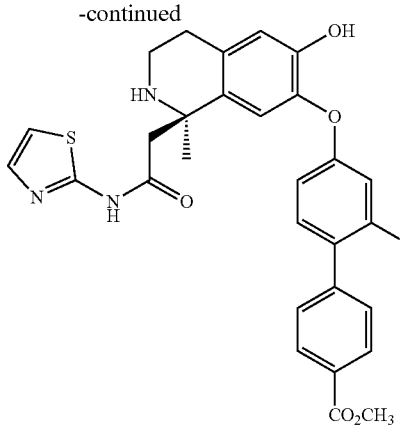

To a solution of the title compound from scheme 5, step A (218 mg, 0.329 mmol) in dichloromethane (3.3 mL) at 0° C. was added boron tribromide (1M solution in dichloromethane, 3.29 ml, 3.29 mmol) and the reaction was allowed to slowly warm to room temperature. After stirring at room temperature overnight the reaction mixture was quenched with methanol (10 mL) at 0° C. The solution warmed to room temperature and was concentrated under reduced pressure and used without purification.

Step C: Preparation of Intermediate VI, tert-butyl (R)-74(2-fluoro-4'-(methoxycarbonyl)-[1,1'-biphenyl]-4-yl)oxy)-6-hydroxy-1-methyl-1-(2-oxo-2-(thiazol-2-ylamino)ethyl)-3,4-dihydroisoquinoline-2(1H)-carboxylate

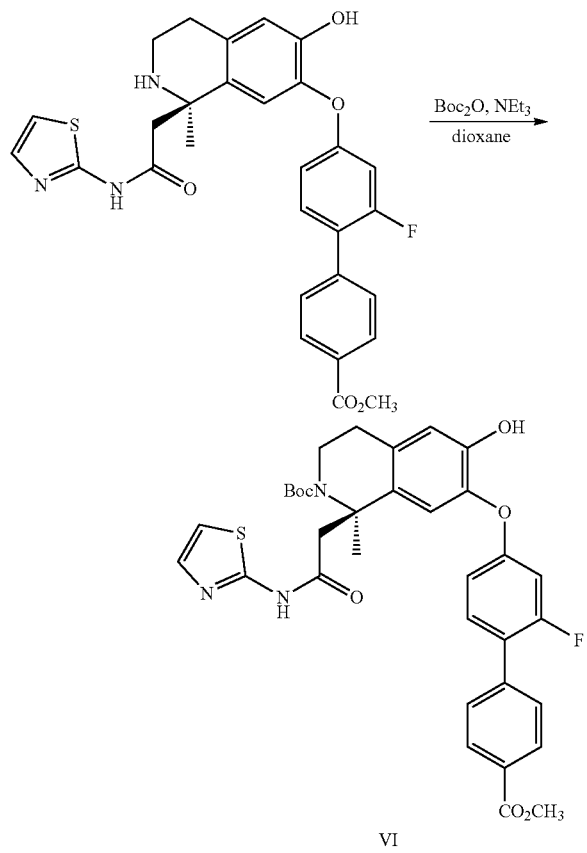

To a solution of the title compound in scheme 5, step B in dioxane (10 mL) was added triethylamine (0.046 ml, 0.329 mmol) and di-tert-butyl dicarbonate (0.076 ml, 0.329 mmol). The reaction mixture was heated to 90° C. for 4 h. The residue was concentrated and then purified by column chromatography on silica gel, eluting with EtOAc/isohexane 7:3 to give the title compound: LCMS m/z 662.4 [M+H]$^+$.

Step D: tert-butyl (1R)-7-((2-fluoro-4'-(methoxycarbonyl)-[1,1'-biphenyl]-4-yl)oxy)-1-methyl-1-(2-oxo-2-(thiazol-2-ylamino)ethyl)-6-((tetrahydrofuran-2-yl)methoxy)-3,4-dihydroisoquinoline-2(1H)-carboxylate

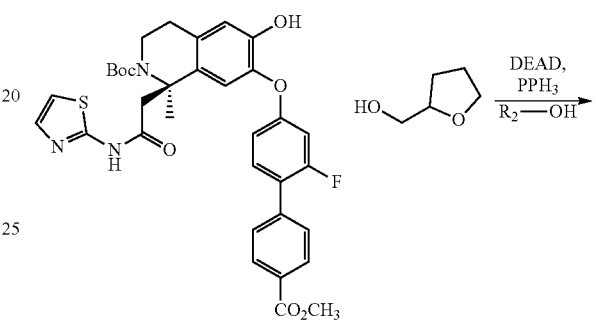

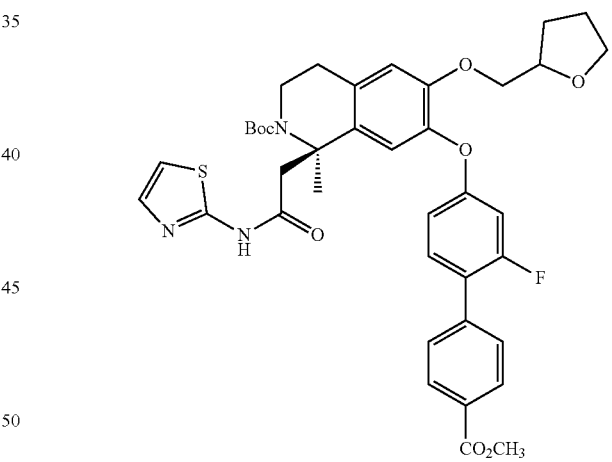

To a solution of the title compound from scheme 5, step C (89.1 mg, 0.135 mmol), triphenylphosphine (45.9 mg, 0.175 mmol) and tetrahydrofuran-2-yl)methanol (15.7 µL, 0.162 mmol) in dichloromethane (1.35 mL) at 0° C. was added diethyl azodicarboxylate (29.8 µl, 0.189 mmol) in dichloromethane 500 µL. The reaction mixture was slowly warmed to room temperature where it was stirred for 3 h. The reaction mixture was diluted with ethyl acetate (100 mL) and washed with aqueous ammonium chloride (3×50 mL). The organic phase was filtered over sodium sulfate and the solvents was removed by reduced pressure. The residue was purified by column chromatography on silica gel, eluting with EtOAc/isohexane 7:3 to give the title compound: LCMS m/z 746.5 [M+H]$^+$.

121

Step E: methyl 2'-fluoro-4'-(((1R)-1-methyl-1-(2-oxo-2-(thiazol-2-ylamino)ethyl)-6-((tetrahydrofuran-2-yl)methoxy)-1,2,3,4-tetrahydroisoquinolin-7-yl)oxy)-[1,1'-biphenyl]-4-carboxylate

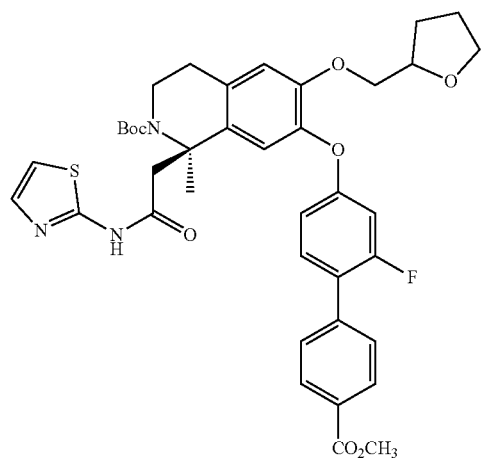 [SMILES: C[C@]1(CC(=O)Nc2nccs2)NCCc2cc(OCC3CCCO3)c(Oc3ccc(-c4ccc(C(=O)O)cc4)c(F)c3)cc21]

122

Step F: 2'-fluoro-4'-(((1R)-1-methyl-1-(2-oxo-2-(thiazol-2-ylamino)ethyl-6-((tetrahydrofuran-2-yl)methoxy)-1,2,3,4-tetrahydroisoquinolin-7-yl)oxy)-[1,1'-biphenyl]-4-carboxylic acid

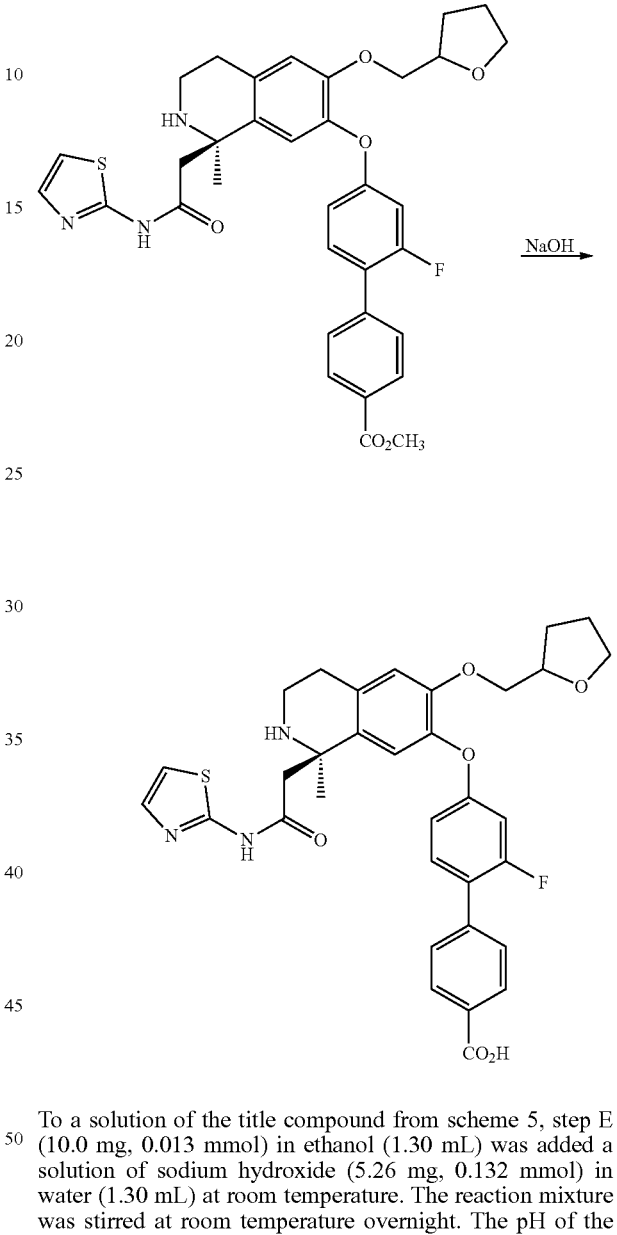

To a solution of the title compound from scheme 5, step D (27.1 mg, 0.036 mmol) in dichloromethane (727 μL) was added trifluoroacetic acid (560 μl, 7.27 mmol) at room temperature. After an hour the solvent was removed under reduced pressure. The residue was purified by preparative HPLC on a C18 reverse-phase column, eluting with acetonitrile/water+0.1% trifluoroacetic acid, to give the title compound: LCMS m/z 646.4 [M+H]$^+$.

To a solution of the title compound from scheme 5, step E (10.0 mg, 0.013 mmol) in ethanol (1.30 mL) was added a solution of sodium hydroxide (5.26 mg, 0.132 mmol) in water (1.30 mL) at room temperature. The reaction mixture was stirred at room temperature overnight. The pH of the reaction mixture was adjusted to a pH of 4 to 5 with aq. HCl solution. The resulting solution was purified by preparative HPLC on a C-18 reverse-phase column, eluting with acetonitrile/water+0.1% trifluoroacetic acid, to give the title compound: LCMS m/z 618.4 [M+H]$^+$.

$^1$H NMR 500 MHz CD$_3$OD δ 8.1 (d, 2H), 7.6 (d, 2H), 7.4 (d, 1H), 7.3-7.1 (m, 3H), 7.0 (s, 1H), 6.7-6.5 (m, 2H), 4.0-3.8 (m, 3H), 3.8-3.6 (m, 2H), 3.5-3.0 (m, 6H), 1.35-1.25 (m, 3H), 1.1-1.0 (m, H).

EXAMPLES 14-36 in the table below were prepared in an analogous fashion as described for EXAMPLE 13 and generally shown in Scheme 5, substituting the appropriate reactants and reagents that are reed as described herein or that are commercially available.

| EX. No. | Structure | Name | LC/MS [M + H]+ |
|---|---|---|---|
| 14 | 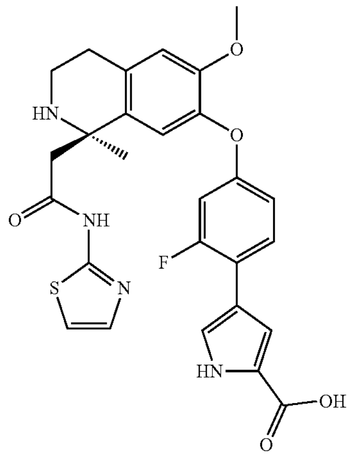 [SMILES: COc1cc2c(cc1Oc1ccc(-c3c[nH]c(C(=O)O)c3)c(F)c1)[C@@](C)(CC(=O)Nc1nccs1)NCC2] | (R)-4-(2-fluoro-4-((6-methoxy-1-methyl-1-(2-oxo-2-(thiazol-2-ylamino)ethyl)-1,2,3,4-tetrahydroisoquinolin-7-yl)oxy)phenyl)-1H-pyrrole-2-carboxylic acid | 537.29 |
| 15 | 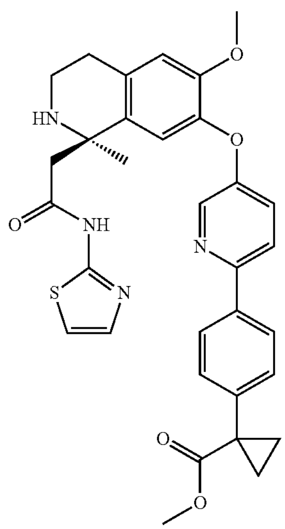 [SMILES: COC(=O)C1(c2ccc(-c3ccc(Oc4cc5c(cc4OC)CCN[C@]5(C)CC(=O)Nc4nccs4)cn3)cc2)CC1] | methyl (R)-1-(4-(5-((6-methoxy-1-methyl-1-(2-oxo-2-(thiazol-2-ylamino)ethyl)-1,2,3,4-tetrahydroisoquinolin-7-yl)oxy)pyridin-2-yl)phenyl)cyclopropane-1-carboxylate | 585.36 |
| 16 | 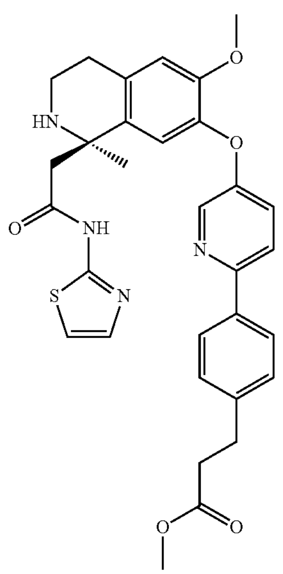 [SMILES: COC(=O)CCc1ccc(-c2ccc(Oc3cc4c(cc3OC)CCN[C@]4(C)CC(=O)Nc3nccs3)cn2)cc1] | methyl (R)-3-(4-(5-((6-methoxy-1-methyl-1-(2-oxo-2-(thiazol-2-ylamino)ethyl)-1,2,3,4-tetrahydroisoquinolin-7-yl)oxy)pyridin-2-yl)phenyl)propanoate | 573.36 |

| EX. No. | Structure | Name | LC/MS [M + H]+ |
|---|---|---|---|
| 17 | 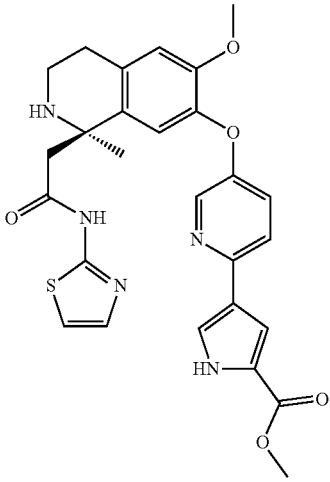 [SMILES: COC(=O)c1cc(-c2ccc(Oc3cc4c(cc3OC)CCN[C@]4(C)CC(=O)Nc3nccs3)cn2)c[nH]1] | methyl (R)-4-(5-((6-methoxy-1-methyl-1-(2-oxo-2-(thiazol-2-ylamino)ethyl)-1,2,3,4-tetrahydroisoquinolin-7-yl)oxy)pyridin-2-yl)-1H-pyrrole-2-carboxylate | 534.3 |
| 18 | 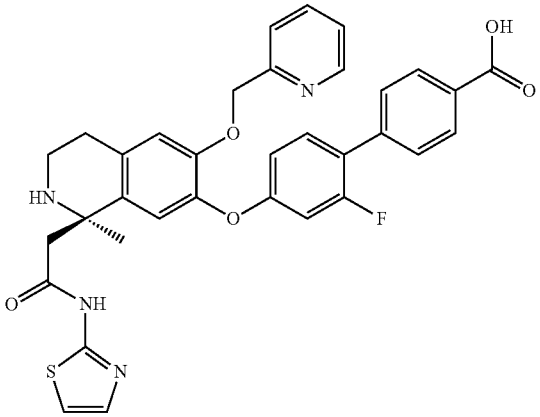 [SMILES: C[C@]1(CC(=O)Nc2nccs2)NCCc2cc(OCc3ccccn3)c(Oc3ccc(-c4ccc(C(=O)O)cc4)c(F)c3)cc21] | (R)-2'-fluoro-4'-((1-methyl-1-(2-oxo-2-(thiazol-2-ylamino)ethyl)-6-(pyridin-2-ylmethoxy)-1,2,3,4-tetrahydroisoquinolin-7-yl)oxy)-[1,1'-biphenyl]-4-carboxylic acid | 625.11 |
| 19 | 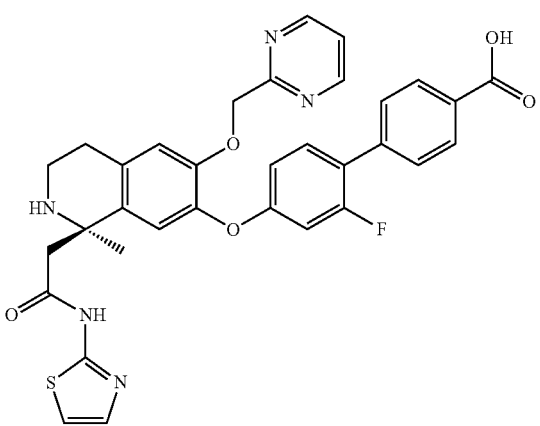 [SMILES: C[C@]1(CC(=O)Nc2nccs2)NCCc2cc(OCc3ncccn3)c(Oc3ccc(-c4ccc(C(=O)O)cc4)c(F)c3)cc21] | (R)-2'-fluoro-4'-((1-methyl-1-(2-oxo-2-(thiazol-2-ylamino)ethyl)-6-(pyrimidin-2-ylmethoxy)-1,2,3,4-tetrahydroisoquinolin-7-yl)oxy)-[1,1'-biphenyl]-4-carboxylic acid | 626.22 |

| EX. No. | Structure | Name | LC/MS [M + H]+ |
|---|---|---|---|
| 20 | 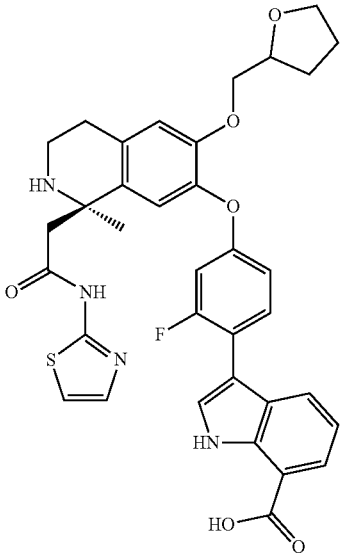 [SMILES: C[C@]1(CC(=O)Nc2nccs2)NCCc2cc(OCC3CCCO3)c(Oc3ccc(-c4c[nH]c5c(C(=O)O)cccc45)c(F)c3)cc21] | 3-(2-fluoro-4-(((1R)-1-methyl-1-(2-oxo-2-(thiazol-2-ylamino)ethyl)-6-((tetrahydrofuran-2-yl)methoxy)-1,2,3,4-tetrahydroisoquinolin-7-yl)oxy)phenyl)-1H-indole-7-carboxylic acid | 657.47 |
| 21 | 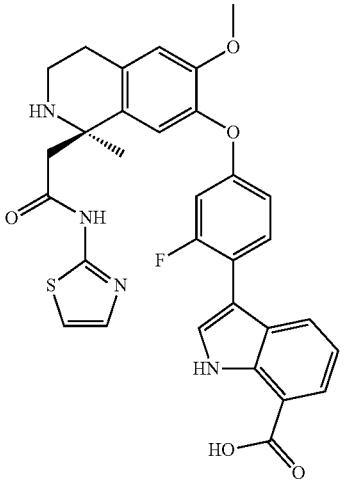 [SMILES: COc1cc2c(cc1Oc1ccc(-c3c[nH]c4c(C(=O)O)cccc34)c(F)c1)[C@@](C)(CC(=O)Nc1nccs1)NCC2] | (R)-3-(2-fluoro-4-((6-methoxy-1-methyl-1-(2-oxo-2-(thiazol-2-ylamino)ethyl)-1,2,3,4-tetrahydroisoquinolin-7-yl)oxy)phenyl)-1H-indole-7-carboxylic acid | 587.41 |
| 22 | 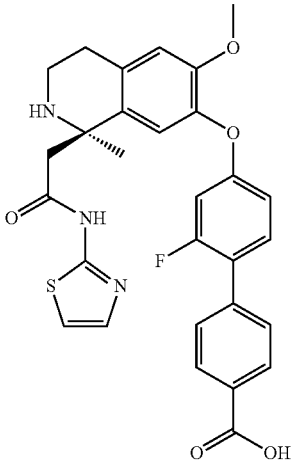 [SMILES: COc1cc2c(cc1Oc1ccc(-c3ccc(C(=O)O)cc3)c(F)c1)[C@@](C)(CC(=O)Nc1nccs1)NCC2] | (R)-2'-fluoro-4'-((6-methoxy-1-methyl-1-(2-oxo-2-(thiazol-2-ylamino)ethyl)-1,2,3,4-tetrahydroisoquinolin-7-yl)oxy)-[1,1'-biphenyl]-4-carboxylic acid | 548.28 |

| EX. No. | Structure | Name | LC/MS [M + H]+ |
|---|---|---|---|
| 23 | 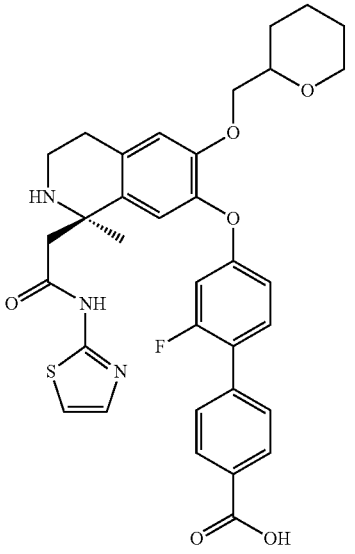 [SMILES: C[C@]1(CC(=O)Nc2nccs2)NCCc2cc(OCC3CCCCO3)c(Oc3ccc(-c4ccc(C(=O)O)cc4)c(F)c3)cc21] | 2'-fluoro-4'-(((1R)-1-methyl-1-(2-oxo-2-(thiazol-2-ylamino)ethyl)-6-((tetrahydro-2H-pyran-2-yl)methoxy)-1,2,3,4-tetrahydroisoquinolin-7-yl)oxy)-[1,1'-biphenyl]-4-carboxylic acid | 632.45 |
| 24 | 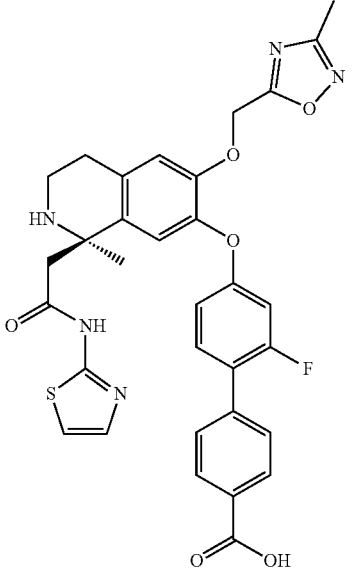 [SMILES: Cc1noc(COc2cc3c(cc2Oc2ccc(-c4ccc(C(=O)O)cc4)c(F)c2)[C@@](C)(CC(=O)Nc2nccs2)NCC3)n1] | (R)-2'-fluoro-4'-((1-methyl-6-((3-methyl-1,2,4-oxadiazol-5-yl)methoxy)-1-(2-oxo-2-(thiazol-2-ylamino)ethyl)-1,2,3,4-tetrahydroisoquinolin-7-yl)oxy)-[1,1'-biphenyl]-4-carboxylic acid | 630.09 |
| 25 | 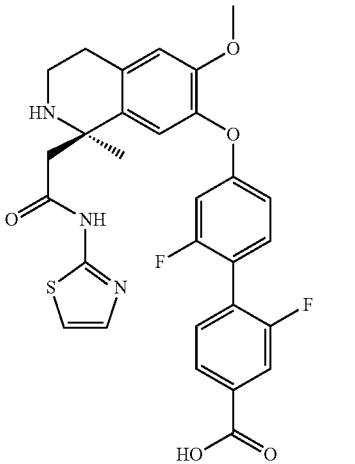 [SMILES: COc1cc2c(cc1Oc1ccc(-c3ccc(C(=O)O)cc3F)c(F)c1)[C@@](C)(CC(=O)Nc1nccs1)NCC2] | (R)-2,2'-difluoro-4'-((6-methoxy-1-methyl-1-(2-oxo-2-(thiazol-2-ylamino)ethyl)-1,2,3,4-tetrahydroisoquinolin-7-yl)oxy)-[1,1'-biphenyl]-4-carboxylic acid | 566.25 |

| EX. No. | Structure | Name | LC/MS [M + H]+ |
|---|---|---|---|
| 26 | 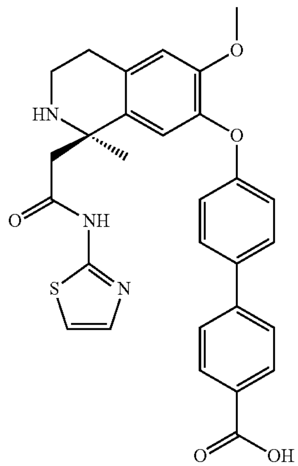 [SMILES: COc1cc2c(cc1Oc1ccc(-c3ccc(C(=O)O)cc3)cc1)[C@@](C)(CC(=O)Nc1nccs1)NCC2] | (R)-4'-((6-methoxy-1-methyl-1-(2-oxo-2-(thiazol-2-ylamino)ethyl)-1,2,3,4-tetrahydroisoquinolin-7-yl)oxy)-[1,1'-biphenyl]-4-carboxylic acid | 530.27 |
| 27 | 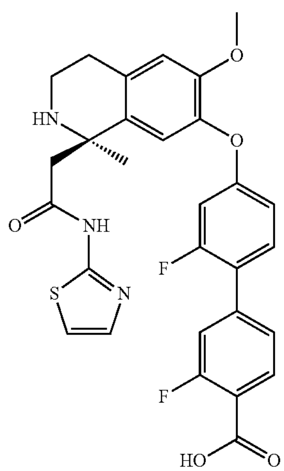 [SMILES: COc1cc2c(cc1Oc1ccc(-c3ccc(C(=O)O)c(F)c3)c(F)c1)[C@@](C)(CC(=O)Nc1nccs1)NCC2] | (R)-2',3-difluoro-4'-((6-methoxy-1-methyl-1-(2-oxo-2-(thiazol-2-ylamino)ethyl)-1,2,3,4-tetrahydroisoquinolin-7-yl)oxy)-[1,1'-biphenyl]-4-carboxylic acid | 566.24 |
| 28 | 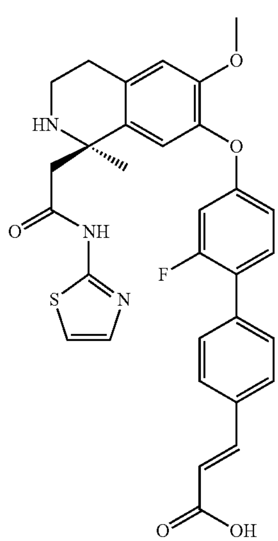 [SMILES: COc1cc2c(cc1Oc1ccc(-c3ccc(/C=C/C(=O)O)cc3)c(F)c1)[C@@](C)(CC(=O)Nc1nccs1)NCC2] | (RE)-3-(2'-fluoro-4'-((6-methoxy-1-methyl-1-(2-oxo-2-(thiazol-2-ylamino)ethyl)-1,2,3,4-tetrahydroisoquinolin-7-yl)oxy)-[1,1'-biphenyl]-4-yl)acrylic acid | 574.45 |

-continued

| EX. No. | Structure | Name | LC/MS [M + H]+ |
|---|---|---|---|
| 29 | 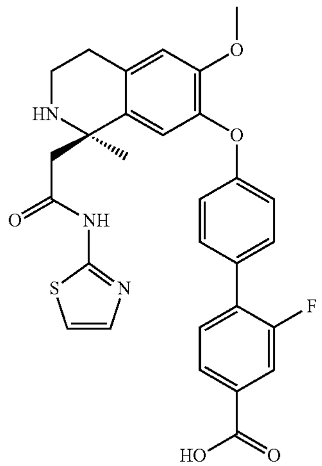 [SMILES: COc1cc2c(cc1Oc1ccc(-c3ccc(C(=O)O)cc3F)cc1)[C@@](C)(CC(=O)Nc1nccs1)NCC2] | (R)-2-fluoro-4'-((6-methoxy-1-methyl-1-(2-oxo-2-(thiazol-2-ylamino)ethyl)-1,2,3,4-tetrahydroisoquinolin-7-yl)oxy)-[1,1'-biphenyl]-4-carboxylic acid | 548.3 |
| 30 | 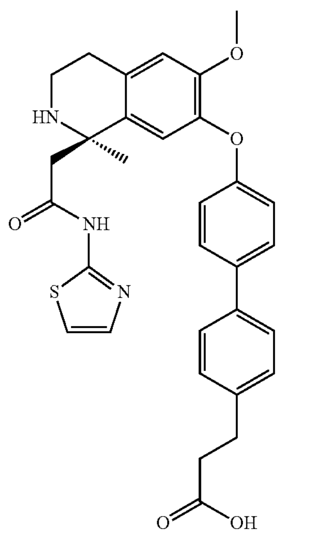 [SMILES: COc1cc2c(cc1Oc1ccc(-c3ccc(CCC(=O)O)cc3)cc1)[C@@](C)(CC(=O)Nc1nccs1)NCC2] | (R)-3-(4'-((6-methoxy-1-methyl-1-(2-oxo-2-(thiazol-2-ylamino)ethyl)-1,2,3,4-tetrahydroisoquinolin-7-yl)oxy)-[1,1'-biphenyl]-4-yl)propanoic acid | 558.29 |
| 31 | 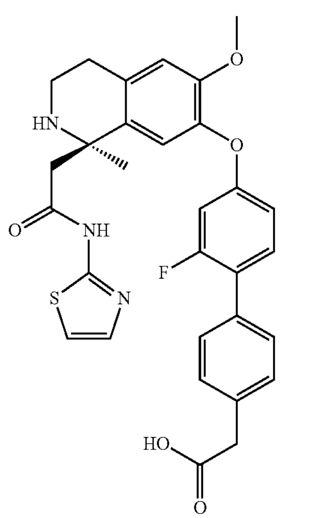 [SMILES: COc1cc2c(cc1Oc1ccc(-c3ccc(CC(=O)O)cc3)c(F)c1)[C@@](C)(CC(=O)Nc1nccs1)NCC2] | (R)-2-(2'-fluoro-4'-((6-methoxy-1-methyl-1-(2-oxo-2-(thiazol-2-ylamino)ethyl)-1,2,3,4-tetrahydroisoquinolin-7-yl)oxy)-[1,1'-biphenyl]-4-yl)acetic acid | 562.32 |

| EX. No. | Structure | Name | LC/MS [M + H]+ |
|---|---|---|---|
| 32 | 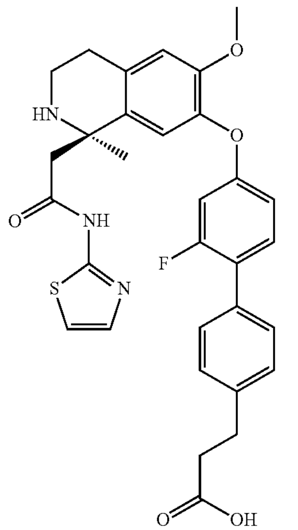 [SMILES: COc1cc2c(cc1Oc1ccc(-c3ccc(CCC(=O)O)cc3)c(F)c1)[C@@](C)(CC(=O)Nc1nccs1)NCC2] | (R)-3-(2'-fluoro-4'-((6-methoxy-1-methyl-1-(2-oxo-2-(thiazol-2-ylamino)ethyl)-1,2,3,4-tetrahydroisoquinolin-7-yl)oxy)-[1,1'-biphenyl]-4-yl)propanoic acid | 576.25 |
| 33 | 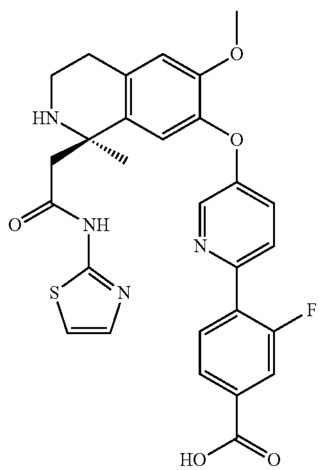 [SMILES: COc1cc2c(cc1Oc1ccc(-c3ccc(C(=O)O)cc3F)nc1)[C@@](C)(CC(=O)Nc1nccs1)NCC2] | (R)-3-fluoro-4-(5-((6-methoxy-1-methyl-1-(2-oxo-2-(thiazol-2-ylamino)ethyl)-1,2,3,4-tetrahydroisoquinolin-7-yl)oxy)pyridin-2-yl)benzoic acid | 549.27 |
| 34 | 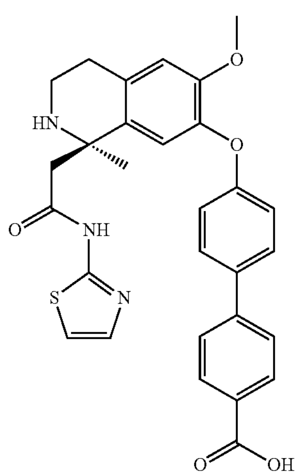 [SMILES: COc1cc2c(cc1Oc1ccc(-c3ccc(C(=O)O)cc3)cc1)[C@@](C)(CC(=O)Nc1nccs1)NCC2] | (R)-4'-((6-methoxy-1-methyl-1-(2-oxo-2-(thiazol-2-ylamino)ethyl)-1,2,3,4-tetrahydroisoquinolin-7-yl)oxy)-[1,1'-biphenyl]-4-carboxylic acid | 530.19 |

| EX. No. | Structure | Name | LC/MS [M + H]+ |
|---|---|---|---|
| 35 | 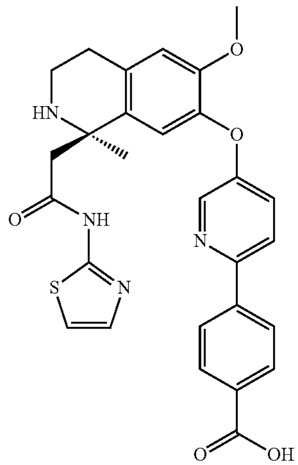 [SMILES: COc1cc2c(cc1Oc1ccc(-c3ccc(C(=O)O)cc3)nc1)[C@@](C)(CC(=O)Nc1nccs1)NCC2] | (R)-4-(5-((6-methoxy-1-methyl-1-(2-oxo-2-(thiazol-2-ylamino)ethyl)-1,2,3,4-tetrahydroisoquinolin-7-yl)oxy)pyridin-2-yl)benzoic acid | 531.21 |
| 36 | 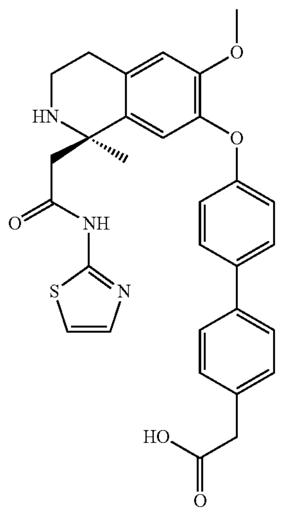 [SMILES: COc1cc2c(cc1Oc1ccc(-c3ccc(CC(=O)O)cc3)cc1)[C@@](C)(CC(=O)Nc1nccs1)NCC2] | (R)-2-(4'-((6-methoxy-1-methyl-1-(2-oxo-2-(thiazol-2-ylamino)ethyl)-1,2,3,4-tetrahydroisoquinolin-7-yl)oxy)-[1,1'-biphenyl]-4-yl)acetic acid | 544.28 |

Examples 37-56

Example 37: 4-(((1R)-6-(2-(4-(1-amino-2-hydroxy-ethyl)-1H-1,2,3-triazol-1-yl)ethoxy)-1-methyl-1-(2-oxo-2-(thiazol-2-ylamino)ethyl)-1,2,3,4-tetrahydroisoquinolin-7-yl)oxy)-2-fluorobenzoic acid

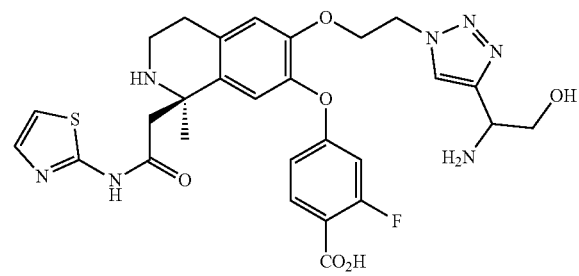 [SMILES: C[C@]1(CC(=O)Nc2nccs2)NCCc2cc(OCCn3cc(C(N)CO)nn3)c(Oc3ccc(C(=O)O)c(F)c3)cc21]

Example 37 was made according to general Scheme 6 below.

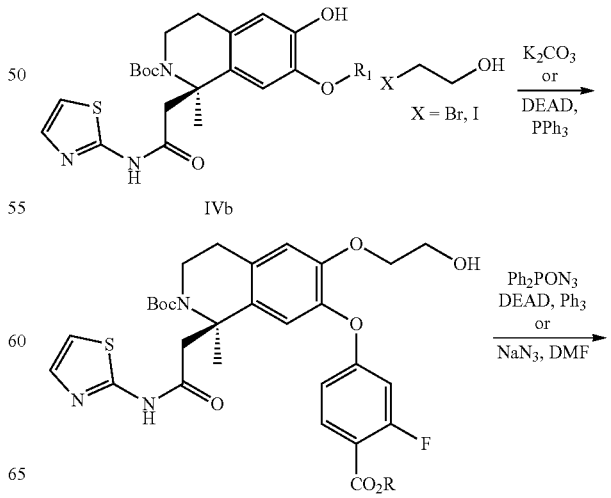

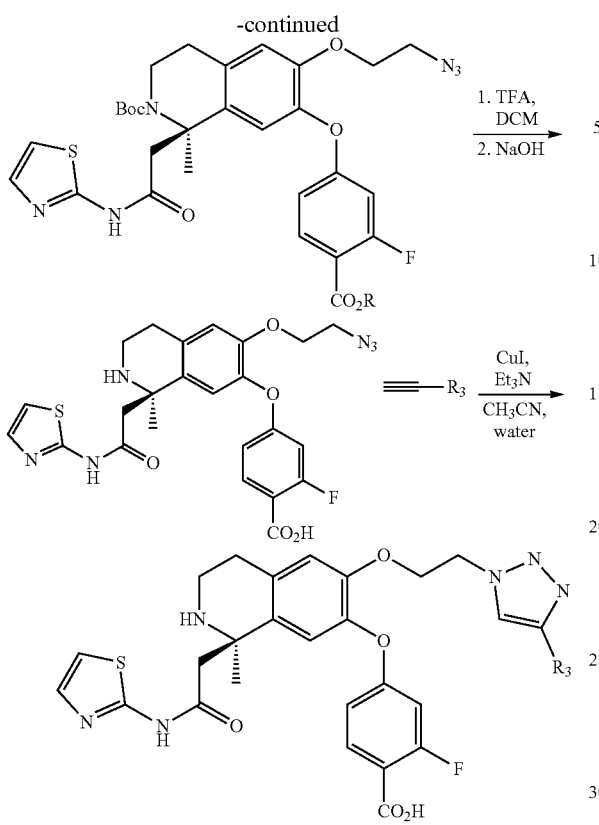

For amide-containing compounds, standard coupling reaction procedures such as Click Chemistry were utilized.

Step A: tert-butyl (R)-7-(4-(ethoxycarbonyl)-3-fluorophenoxy)-6-(2-hydroxyethoxy)-1-methyl-1-(2-oxo-2-(thiazol-2-ylamino)ethyl)-3,4-dihydroisoquinoline-2(1H)-carboxylate

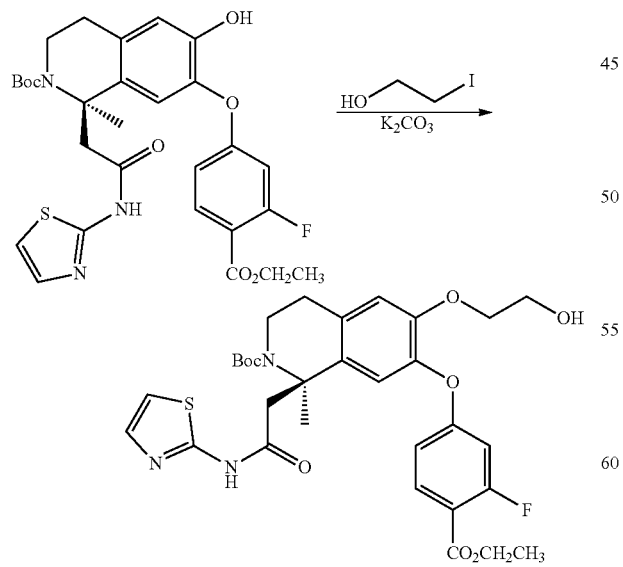

To a solution of tert-butyl (R)-7-(4-(ethoxycarbonyl)-3-fluorophenoxy)-6-hydroxy-1-methyl-1-(2-oxo-2-(thiazol-2-ylamino)ethyl)-3,4-dihydroisoquinoline-2(1H)-carboxylate (Int. IVb, 146 mg, 0.249 mmol) in acetone (997 μL) was added 2-iodomethanol (39.3 μl, 0.499 mmol) and potassium carbonate (138 mg, 0.997 mmol) at 0° C. The reaction mixture was heated to 40° C. After heating overnight the solvent was removed. The residue was purified by column chromatography on silica gel, eluting with EtOAc/isohexane to give the title compound: LCMS m/z 630.24 [M+H]⁺.

Step B: tert-butyl (R)-6-(2-azidoethoxy)-7-(4-(ethoxycarbonyl)-3-fluorophenoxy)-1-methyl-1-(2-oxo-2-(thiazol-2-ylamino)ethyl)-3,4-dihydroisoquinoline-2(1H)-carboxylate

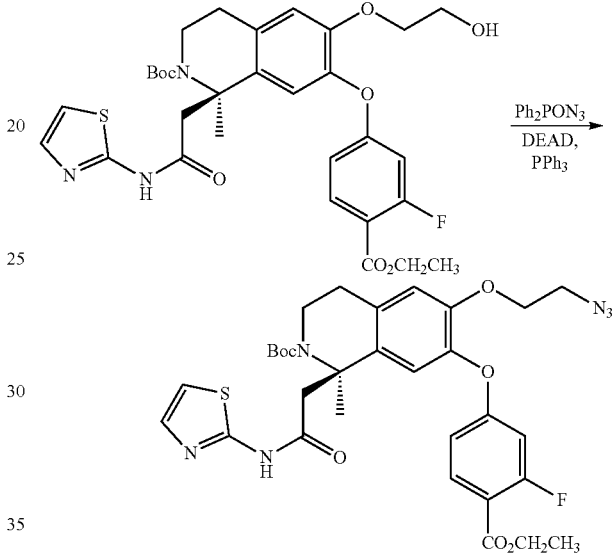

To a solution of the title compound from scheme 6, step A (60.0 mg, 0.095 mmol) in dichloromethane (2.38 mL) and tetrahydrofuran (2.32 mL) was added diphenylphosphinyl azide (92.0 μl, 0.476 mmol) followed by triphenylphosphine (125 mg, 0.476 mmol). A 40% solution of diethyl azodicarboxylate solution in toluene (75 μl, 0.476 mmol) was added dropwise at 0° C. and the reaction mixture was stirred at room temperature. After two hours the solvent was evaporated under reduced pressure. The residue was purified by column chromatography on silica gel, eluting with EtOAc/isohexane to give the title compound: LCMS m/z 655.3 [M+H]⁺.

Step C: ethyl (R)-4-((6-(2-azidoethoxy)-1-methyl-1-(2-oxo-2-(thiazol-2-ylamino)ethyl)-1,2,3,4-tetrahydroisoquinolin-7-yl)oxy)-2-fluorobenzoate

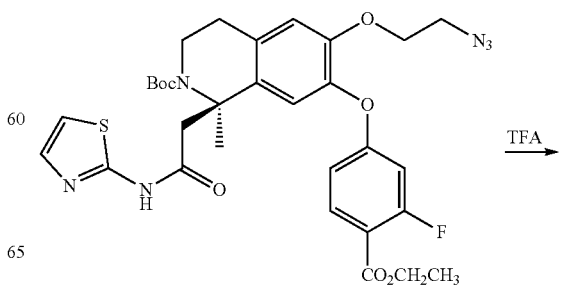

-continued

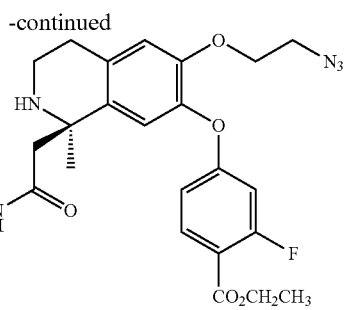

To a solution of the title compound in scheme 6, step B (60.0 mg, 0.092 mmol) in dichloromethane (458 μL) was added trifluoroacetic acid (500 μL, 6.49 mmol) dropwise at room temperature. After two hours the reaction was concentrated to afford the title compound which was used without purification: LCMS m/z 555.2 [M+H]$^+$.

Step D: (R)-4-((6-(2-azidoethoxy)-1-methyl-1-(2-oxo-2-(thiazol-2-ylamino)ethyl)-1,2,3,4-tetrahydroisoquinolin-7-yl)oxy)-2-fluorobenzoic acid

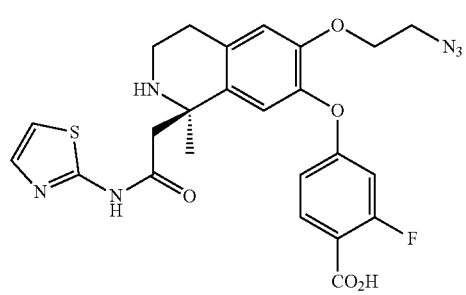

To a solution of the title compound from scheme 6, step C (40.0 mg, 0.072 mmol) in ethanol (361 μL) and water (361 μL) was added sodium hydroxide (57.7 mg, 1.44 mmol) at room temperature. After stirring at room temperature for 2 h the solvent was evaporated under reduced pressure. The residue was purified by preparative HPLC on a C18 reverse-phase column, eluting with acetonitrile/water+0.1% trifluoroacetic acid, to give the title compound: LCMS m/z 527.1 [M+H]$^+$.

Step E: 4-(((1R)-6-(2-(4-(1-amino-2-hydroxyethyl)-1H-1,2,3-triazol-1-yl)ethoxy)-1-methyl-1-(2-oxo-2-(thiazol-2-ylamino)ethyl)-1,2,3,4-tetrahydroisoquinolin-7-yl)oxy)-2-fluorobenzoic acid

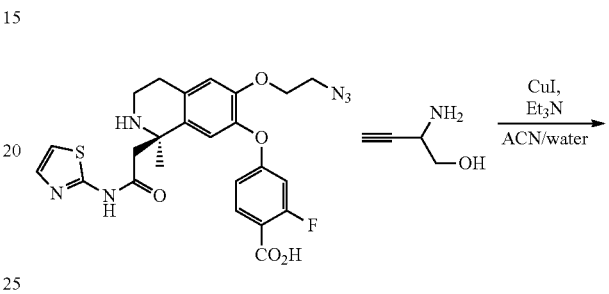

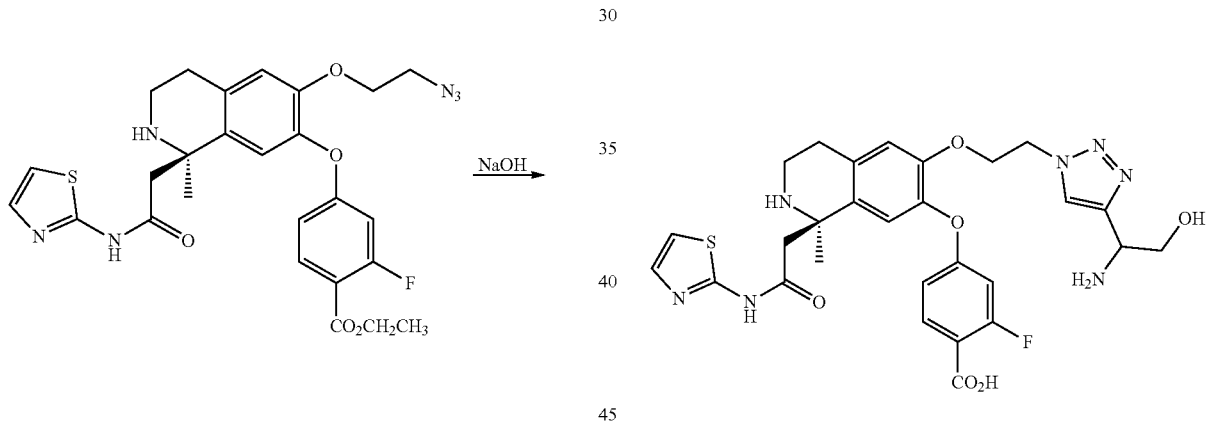

To a solution of the title compound from scheme 6, step D (20.0 mg, 0.038 mmol), 2-aminobut-3-yn-1-ol (6.93 mg, 0.057 mmol), and copper(I) iodide (0.723 mg, 3.80 μmol) in acetonitrile (0.500 mL) and water (1.00 mL) was added triethylamine (10.6 μL, 0.076 mmol) at room temperature. After stirring for an hour the mixture was filtered and the solvent was evaporated under reduced pressure. The residue was purified by preparative HPLC on a C18 reverse-phase column, eluting with acetonitrile:water+0.1% trifluoroacetic acid, to give the title compound: LCMS m/z 612.4 [M+H]$^+$ EXAMPLES 38-56 in the table below were prepared in an analogous fashion as described for EXAMPLE 37 and generally shown in Scheme 6, substituting the appropriate reactants and reagents that are prepared as described herein or that are commercially available,

| EX. No. | Structure | Name | LC/MS [M + H]+ |
|---|---|---|---|
| 38 | 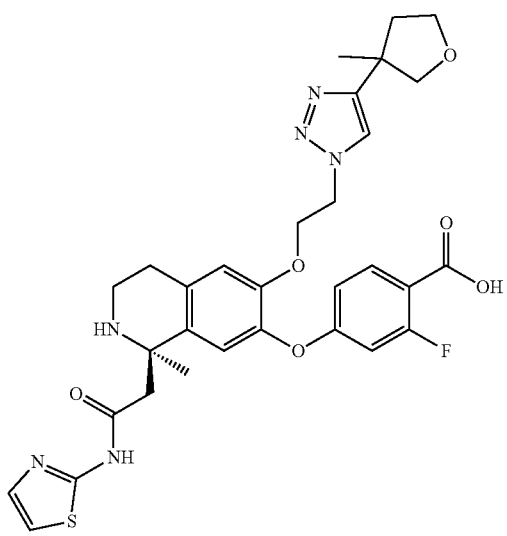 [SMILES: CC1(c2cn(CCOc3cc4c(cc3Oc3ccc(C(=O)O)c(F)c3)[C@@](C)(CC(=O)Nc3nccs3)NCC4)nn2)CCOC1] | 2-fluoro-4-(((1R)-1-methyl-6-(2-(4-(3-methyltetrahydrofuran-3-yl)-1H-1,2,3-triazol-1-yl)ethoxy)-1-(2-oxo-2-(thiazol-2-ylamino)ethyl)-1,2,3,4-tetrahydroisoquinolin-7-yl)oxy)benzoic acid | 637.52 |
| 39 | 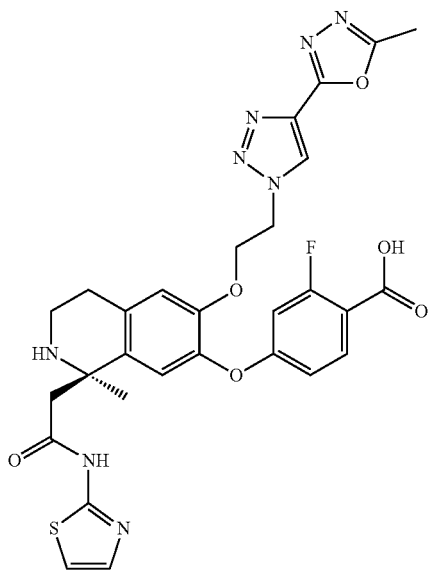 [SMILES: Cc1nnc(-c2cn(CCOc3cc4c(cc3Oc3ccc(C(=O)O)c(F)c3)[C@@](C)(CC(=O)Nc3nccs3)NCC4)nn2)o1] | (R)-2-fluoro-4-((1-methyl-6-(2-(4-(5-methyl-1,3,4-oxadiazol-2-yl)-1H-1,2,3-triazol-1-yl)ethoxy)-1-(2-oxo-2-(thiazol-2-ylamino)ethyl)-1,2,3,4-tetrahydroisoquinolin-7-yl)oxy)benzoic acid | 635.5 |

| EX. No. | Structure | Name | LC/MS [M + H]+ |
|---|---|---|---|
| 40 | 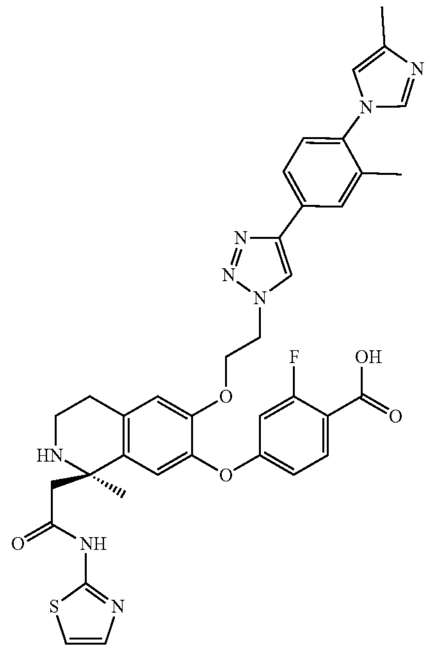 [SMILES: Cc1cn(-c2ccc(-c3cn(CCOc4cc5c(cc4Oc4ccc(C(=O)O)c(F)c4)[C@@](C)(CC(=O)Nc4nccs4)NCC5)nn3)cc2C)cn1] | (R)-2-fluoro-4-((1-methyl-6-(2-(4-(3-methyl-4-(4-methyl-1H-imidazol-1-yl)phenyl)-1H-1,2,3-triazol-1-yl)ethoxy)-1-(2-oxo-2-(thiazol-2-ylamino)ethyl)-1,2,3,4-tetrahydroisoquinolin-7-yl)oxy)benzoic acid | 723.51 |
| 41 | 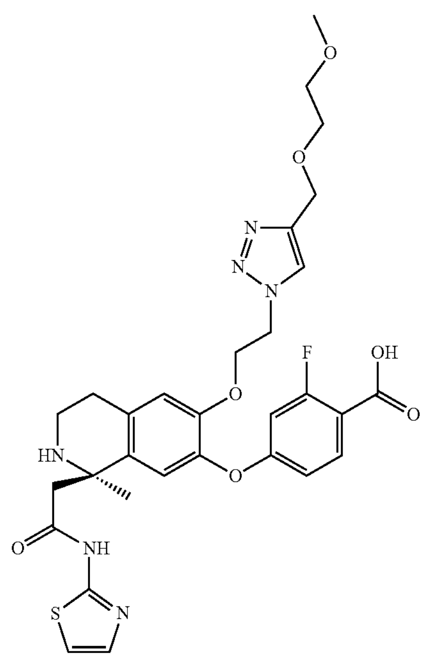 [SMILES: COCCOCc1cn(CCOc2cc3c(cc2Oc2ccc(C(=O)O)c(F)c2)[C@@](C)(CC(=O)Nc2nccs2)NCC3)nn1] | (R)-2-fluoro-4-((6-(2-(4-((2-methoxyethoxy)methyl)-1H-1,2,3-triazol-1-yl)ethoxy)-1-methyl-1-(2-oxo-2-(thiazol-2-ylamino)ethyl)-1,2,3,4-tetrahydroisoquinolin-7-yl)oxy)benzoic acid | 641.51 |

| EX. No. | Structure | Name | LC/MS [M + H]+ |
|---|---|---|---|
| 42 | 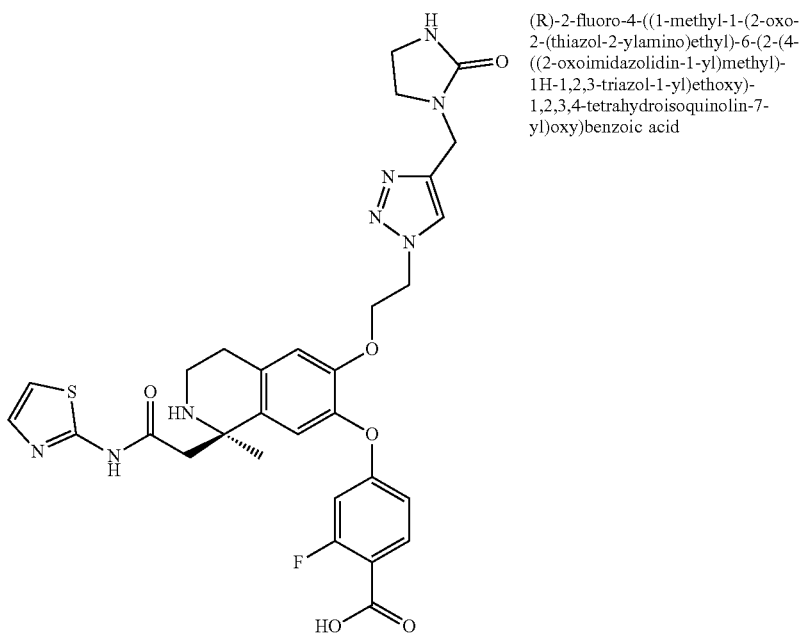 | (R)-2-fluoro-4-((1-methyl-1-(2-oxo-2-(thiazol-2-ylamino)ethyl)-6-(2-(4-((2-oxoimidazolidin-1-yl)methyl)-1H-1,2,3-triazol-1-yl)ethoxy)-1,2,3,4-tetrahydroisoquinolin-7-yl)oxy)benzoic acid | 651.48 |
| 43 | 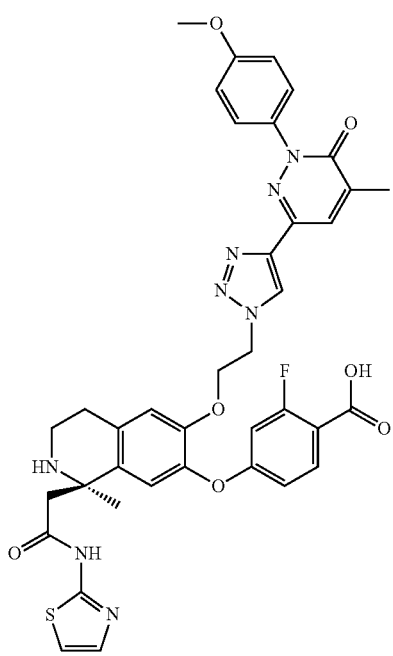 [SMILES: COc1ccc(-n2nc(-c3cn(CCOc4cc5c(cc4Oc4ccc(C(=O)O)c(F)c4)[C@@](C)(CC(=O)Nc4nccs4)NCC5)nn3)cc(C)c2=O)cc1] | (R)-2-fluoro-4-((6-(2-(4-(1-(4-methoxyphenyl)-5-methyl-6-oxo-1,6-dihydropyridazin-3-yl)-1H-1,2,3-triazol-1-yl)ethoxy)-1-methyl-1-(2-oxo-2-(thiazol-2-ylamino)ethyl)-1,2,3,4-tetrahydroisoquinolin-7-yl)oxy)benzoic acid | 767.55 |

-continued
| EX. No. | Structure | Name | LC/MS [M + H]+ |
|---|---|---|---|
| 44 | 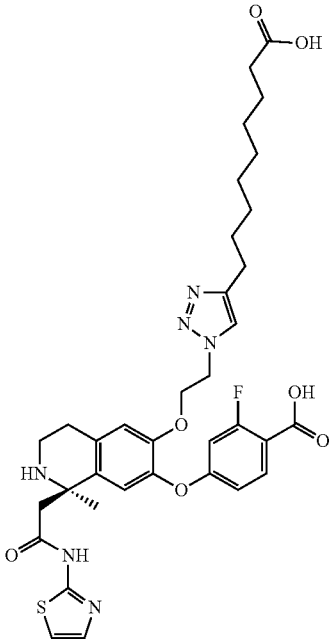 [SMILES: C[C@]1(CC(=O)Nc2nccs2)NCCc2cc(OCCn3cc(CCCCCCCCC(=O)O)nn3)c(Oc3ccc(C(=O)O)c(F)c3)cc21] | (R)-4-((6-(2-(4-(8-carboxyoctyl)-1H-1,2,3-triazol-1-yl)ethoxy)-1-methyl-1-(2-oxo-2-(thiazol-2-ylamino)ethyl)-1,2,3,4-tetrahydroisoquinolin-7-yl)oxy)-2-fluorobenzoic acid | 709.59 |
| 45 | 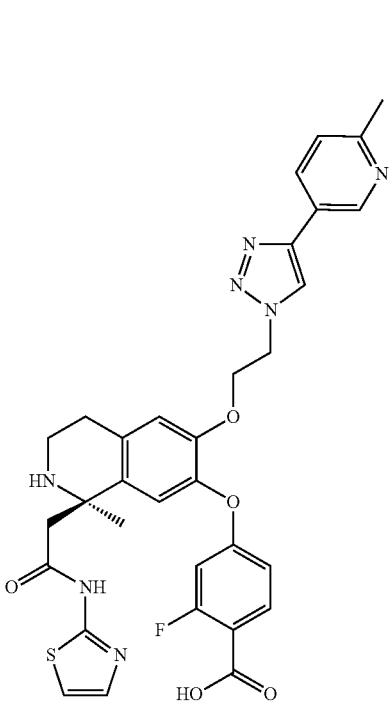 [SMILES: Cc1ccc(-c2cn(CCOc3cc4c(cc3Oc3ccc(C(=O)O)c(F)c3)[C@@](C)(CC(=O)Nc3nccs3)NCC4)nn2)cn1] | (R)-2-fluoro-4-((1-methyl-6-(2-(4-(6-methylpyridin-3-yl)-1H-1,2,3-triazol-1-yl)ethoxy)-1-(2-oxo-2-(thiazol-2-ylamino)ethyl)-1,2,3,4-tetrahydroisoquinolin-7-yl)oxy)benzoic acid | 644.46 |

-continued
| EX. No. | Structure | Name | LC/MS [M + H]+ |
|---|---|---|---|
| 46 | 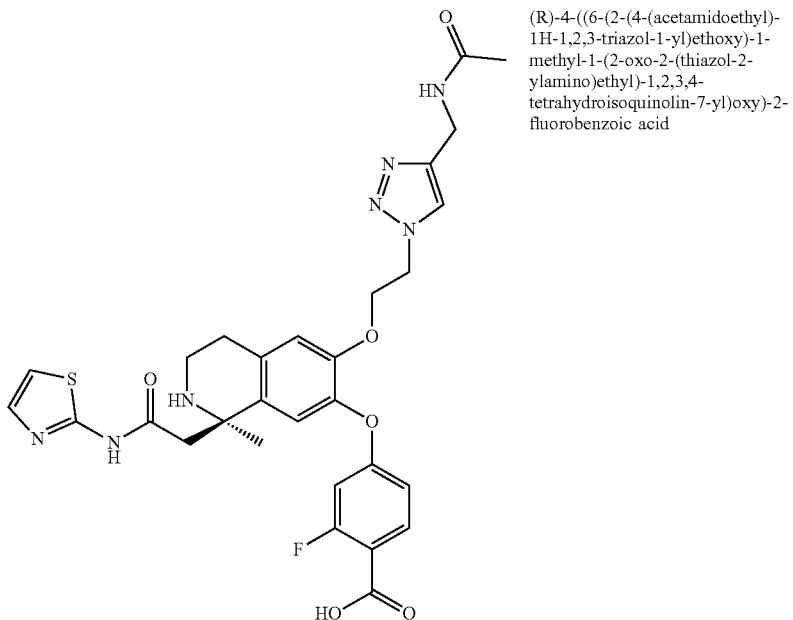 | (R)-4-((6-(2-(4-(acetamidoethyl)-1H-1,2,3-triazol-1-yl)ethoxy)-1-methyl-1-(2-oxo-2-(thiazol-2-ylamino)ethyl)-1,2,3,4-tetrahydroisoquinolin-7-yl)oxy)-2-fluorobenzoic acid | 624.46 |
| 47 | 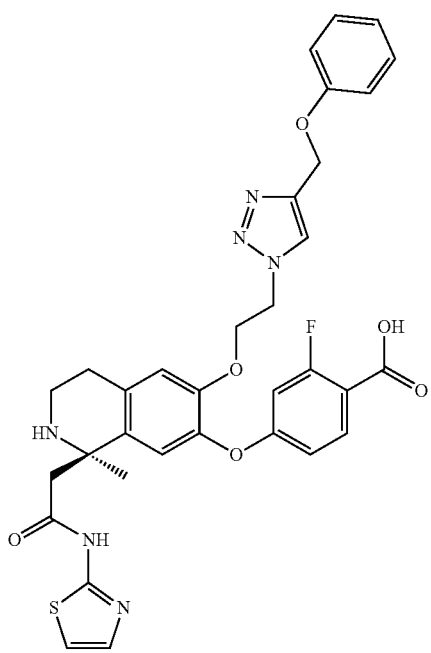 [SMILES: C[C@]1(CC(=O)Nc2nccs2)NCCc2cc(OCCn3cc(COc4ccccc4)nn3)c(Oc3ccc(C(=O)O)c(F)c3)cc21] | (R)-2-fluoro-4-((1-methyl-1-(2-oxo-2-(thiazol-2-ylamino)ethyl)-6-(2-(4-(phenoxymethyl)-1H-1,2,3-triazol-1-yl)ethoxy)-1,2,3,4-tetrahydroisoquinolin-7-yl)oxy)benzoic acid | 659.47 |

| EX. No. | Structure | Name | LC/MS [M + H]+ |
|---|---|---|---|
| 48 | 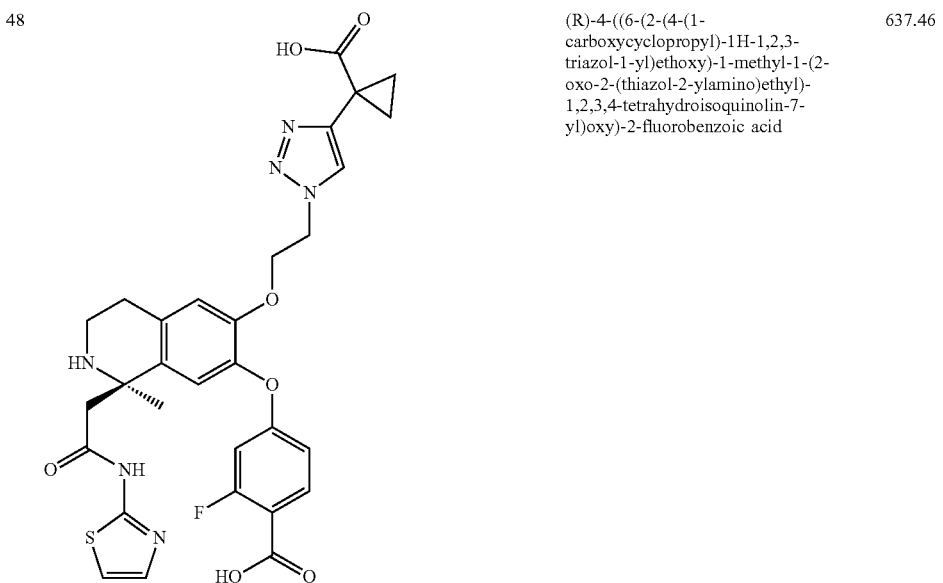 | (R)-4-((6-(2-(4-(1-carboxycyclopropyl)-1H-1,2,3-triazol-1-yl)ethoxy)-1-methyl-1-(2-oxo-2-(thiazol-2-ylamino)ethyl)-1,2,3,4-tetrahydroisoquinolin-7-yl)oxy)-2-fluorobenzoic acid | 637.46 |
| 49 | 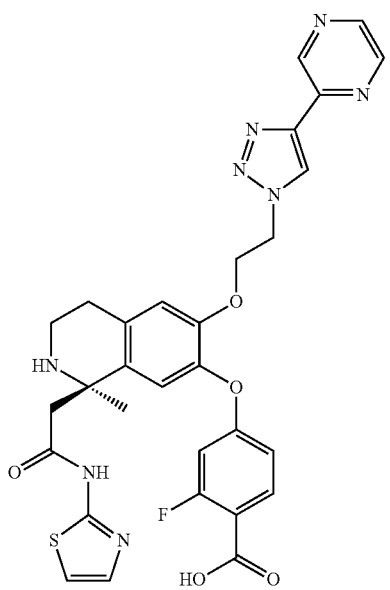 [SMILES: C[C@]1(CC(=O)Nc2nccs2)NCCc2cc(OCCn3cc(-c4cnccn4)nn3)c(Oc3ccc(C(=O)O)c(F)c3)cc21] | (R)-2-fluoro-4-((1-methyl-1-(2-oxo-2-(thiazol-2-ylamino)ethyl)-6-(2-(4-(pyrazin-2-yl)-1H-1,2,3-triazol-1-yl)ethoxy)-1,2,3,4-tetrahydroisoquinolin-7-yl)oxy)benzoic acid | 631.4 |

-continued
| EX. No. | Structure | Name | LC/MS [M + H]+ |
|---|---|---|---|
| 50 | 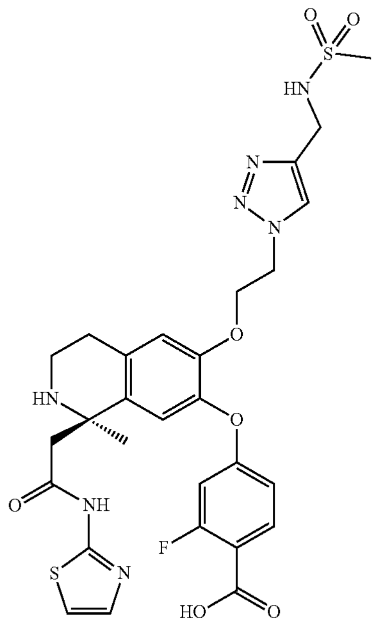 [SMILES: C[C@]1(CC(=O)Nc2nccs2)NCCc2cc(OCCn3cc(CNS(C)(=O)=O)nn3)c(Oc3ccc(C(=O)O)c(F)c3)cc21] | (R)-2-fluoro-4-((1-methyl-6-(2-(4-(methylsulfonamidomethyl)-1H-1,2,3-triazol-1-yl)ethoxy)-1-(2-oxo-2-(thiazol-2-ylamino)ethyl)-1,2,3,4-tetrahydroisoquinolin-7-yl)oxy)benzoic acid | 660.46 |
| 51 | 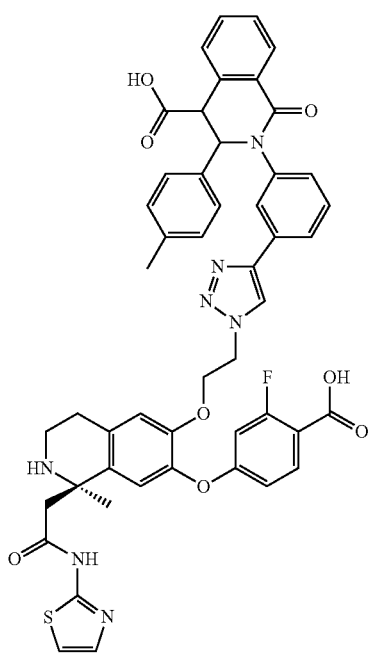 [SMILES: Cc1ccc(C2C(C(=O)O)c3ccccc3C(=O)N2c2cccc(-c3cn(CCOc4cc5c(cc4Oc4ccc(C(=O)O)c(F)c4)[C@@](C)(CC(=O)Nc4nccs4)NCC5)nn3)c2)cc1] | 2-(3-(1-(2-(((R)-7-(4-carboxy-3-fluorophenoxy)-1-methyl-1-(2-oxo-2-(thiazol-2-ylamino)ethyl)-1,2,3,4-tetrahydroisoquinolin-6-yl)oxy)ethyl)-1H-1,2,3-triazol-4-yl)phenyl)-1-oxo-3-(p-tolyl)-1,2,3,4-tetrahydroisoquinoline-4-carboxylic acid | 908.72 |

| EX. No. | Structure | Name | LC/MS [M + H]+ |
|---|---|---|---|
| 52 | 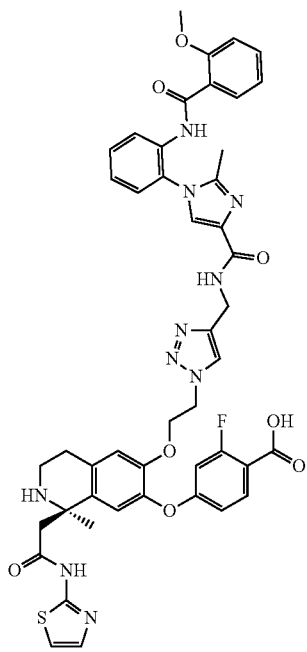 [SMILES: COc1ccccc1C(=O)Nc1ccccc1-n1cc(C(=O)NCc2cn(CCOc3cc4c(cc3Oc3ccc(C(=O)O)c(F)c3)[C@@](C)(CC(=O)Nc3nccs3)NCC4)nn2)nc1C] | (R)-2-fluoro-4-((6-(2-(4-((1-(2-(2-methoxybenzamido)phenyl)-2-methyl-1H-imidazole-4-carboxamido)methyl)-1H-1,2,3-triazol-1-yl)ethoxy)-1-methyl-1-(2-oxo-2-(thiazol-2-ylamino)ethyl)-1,2,3,4-tetrahydroisoquinolin-7-yl)oxy)benzoic acid | 915.81 |
| 53 | 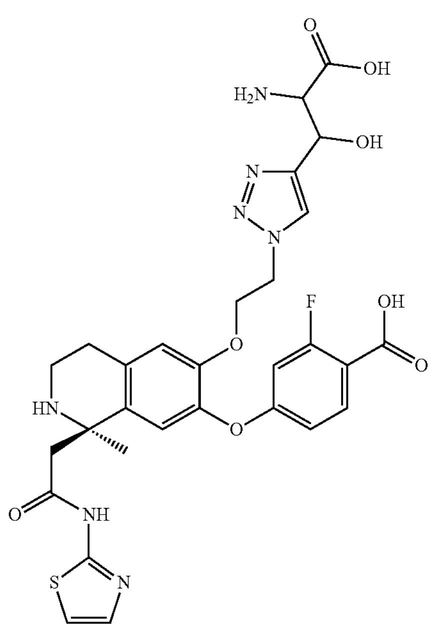 [SMILES: C[C@]1(CC(=O)Nc2nccs2)NCCc2cc(OCCn3cc(C(O)C(N)C(=O)O)nn3)c(Oc3ccc(C(=O)O)c(F)c3)cc21] | 4-(((1R)-6-(2-(4-(2-amino-2-carboxy-1-hydroxyethyl)-1H-1,2,3-triazol-1-yl)ethoxy)-1-methyl-1-(2-oxo-2-(thiazol-2-ylamino)ethyl)-1,2,3,4-tetrahydroisoquinolin-7-yl)oxy)-2-fluorobenzoic acid | 656.47 |
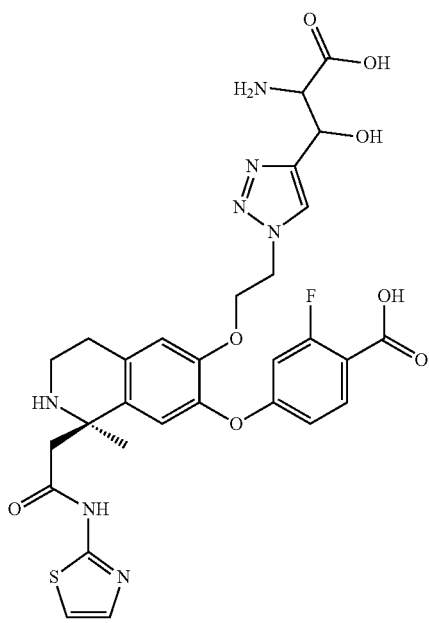

-continued
| EX. No. | Structure | Name | LC/MS [M + H]+ |
|---|---|---|---|
| 54 | 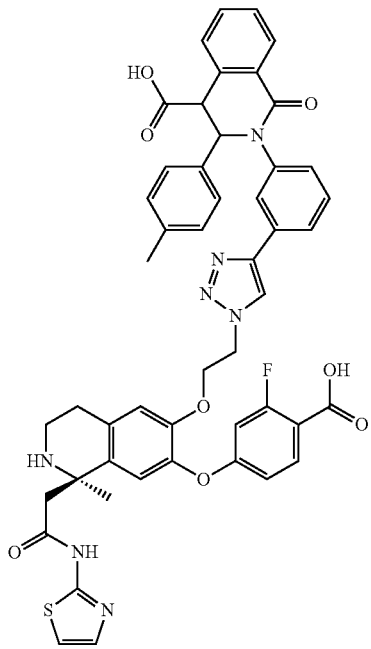 [SMILES: Cc1ccc(C2C(C(=O)O)c3ccccc3C(=O)N2c2cccc(-c3cn(CCOc4cc5c(cc4Oc4ccc(C(=O)O)c(F)c4)[C@@](C)(CC(=O)Nc4nccs4)NCC5)nn3)c2)cc1] | 2-(3-(1-(2-(((R)-7-(4-carboxy-3-fluorophenoxy)-1-methyl-1-(2-oxo-2-(thiazol-2-ylamino)ethyl)-1,2,3,4-tetrahydroisoquinolin-6-yl)oxy)ethyl)-1H-1,2,3-triazol-4-yl)phenyl)-1-oxo-3-(p-tolyl)-1,2,3,4-tetrahydroisoquinoline-4-carboxylic acid | 908.74 |
| 55 | 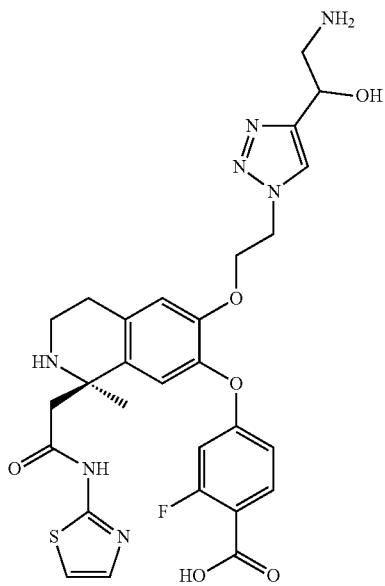 [SMILES: C[C@]1(CC(=O)Nc2nccs2)NCCc2cc(OCCn3cc(C(O)CN)nn3)c(Oc3ccc(C(=O)O)c(F)c3)cc21] | 4-(((1R)-6-(2-(4-(2-amino-1-hydroxyethyl)-1H-1,2,3-triazol-1-yl)ethoxy)-1-methyl-1-(2-oxo-2-(thiazol-2-ylamino)ethyl)-1,2,3,4-tetrahydroisoquinolin-7-yl)oxy)-2-fluorobenzoic acid | 612.41 |

| EX. No. | Structure | Name | LC/MS [M + H]+ |
|---|---|---|---|
| 56 | 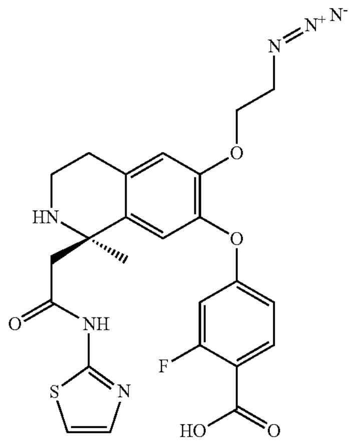 | (R)-2-(4'-((6-methoxy-1-methyl-1-(2-oxo-2-(thiazol-2-ylamino)ethyl)-1,2,3,4-tetrahydroisoquinolin-7-yl)oxy)-[1,1'-biphenyl]-4-yl)acetic acid | 527.1 |

Examples 57-61

Example 57: (R)-4-((6-(2-(2-(3-(5,5-difluoro-79-dimethyl-5H-4λ⁴,5λ⁴-dipyrrolo[1,2-c:2',1'-f][1,3,2]diazaborinin-3-yl)propanamido)ethoxyethoxy)-1-methyl-1-(2-oxo-2-(thiazol-2-ylamino)ethyl)-1,2,3,4-tetrahydroisoquinolin-7-yl)oxy)-2-fluorobenzoic acid

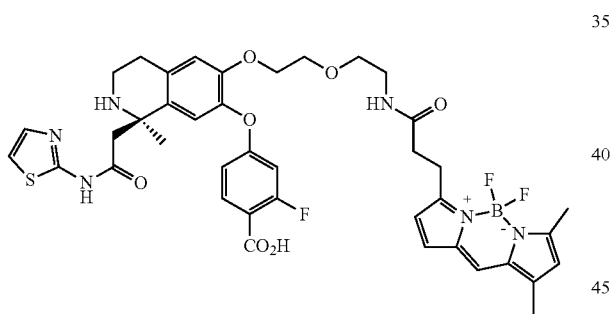

Example 57 was made according to general Scheme 7 below.

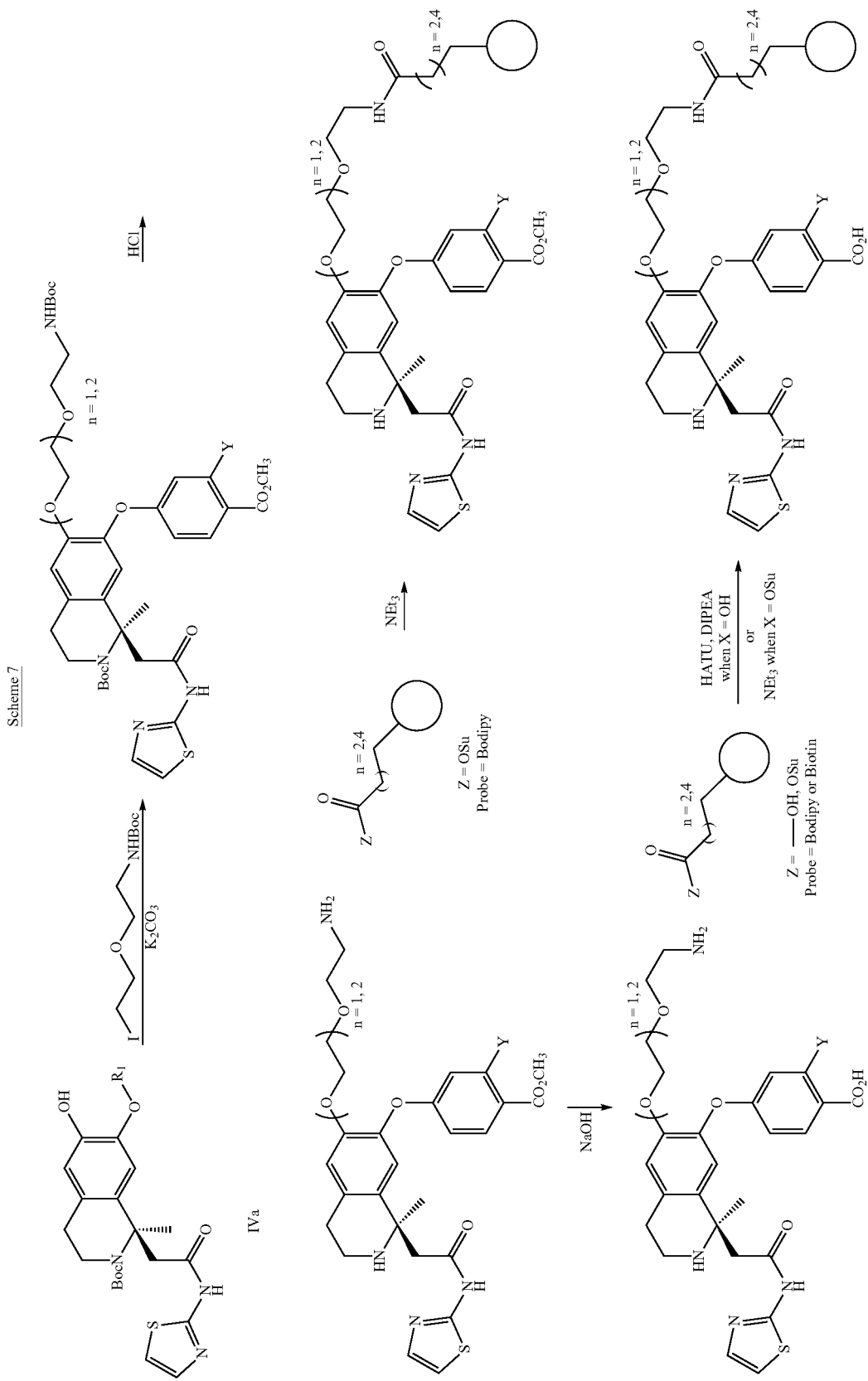

Step A: 2-(2 tert-butoxycarbonyl)amino)ethoxy)ethyl 4-methylbenzenesulfonate

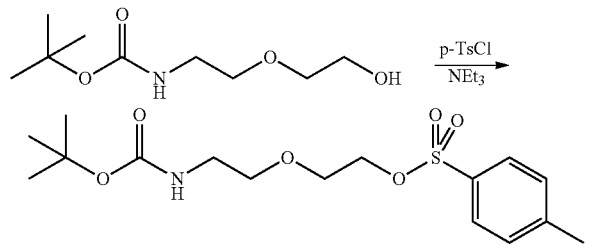

To a solution of tert-butyl (2-(2-hydroxyethoxy)ethyl)carbamate (300 mg, 1.462 mmol) in dichloromethane (14.6 mL) at 0° C. was added p-toluenesulfonyl chloride (697 mg, 3.65 mmol) followed by triethylamine (509 µl, 3.65 mmol). The reaction was warmed to room temperature where it was stirred for 16 hours overnight. The material was then concentrated to afford the title compound which was used without purification: LCMS m/z 360.7 [M+H]+.

Step B: tert-butyl (2-(2-iodoethoxy)ethyl)carbamate

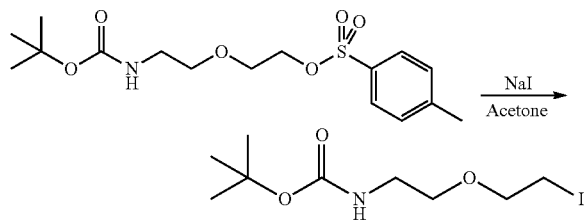

To a solution of the title compound from scheme 7, step A (525 mg, 1.461 mmol) in acetone (3.00 mL) was added sodium iodide (547 mg, 3.65 mmol). The reaction was heated to 65° C. The reaction was cooled to room temperature, filtered and then concentrated under reduced pressure. It was taken up in ethyl acetate then washed with 1% aqueous sodium thiosulfate and brine. The organics were dried over sodium sulfate, filtered and concentrated. The crude material was purified by column chromatography on silican gel, eluting with 0-60% ethyl acetate in hexanes to afford the title compound: LCMS m/z 315.8 [M+H]+.

Step C: tert-butyl (R)-6-(2-(2-(((tert-butoxycarbonyl)amino)ethoxy)ethoxy)-7-(3-fluoro-4-(methoxycarbonyl)phenoxy)-1-methyl-1-(2-oxo-2-(thiazol-2-ylamino)ethyl)-3,4-dihydroisoquinoline-2(1H)-carboxylate

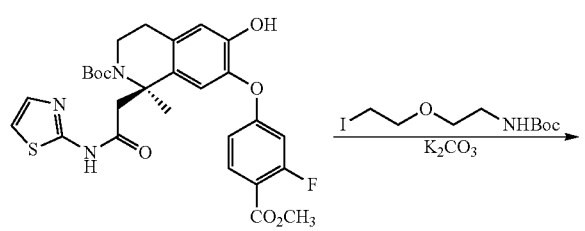

-continued

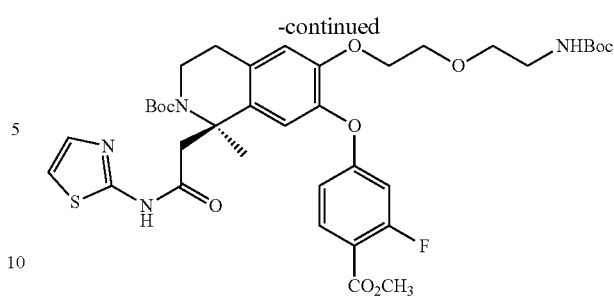

To a solution of Intermediate IVa, scheme 1, step L (85.0 mg, 0.149 mmol), the title compound from scheme 7, step B (46.9 mg, 0.149 mmol) and 18 crown 6 (98.0 mg, 0.372 mmol) in acetone (372 µL) was added potassium carbonate (25.7 mg, 0.186 mmol). The solution was heated to 65° C. for 18 hours overnight. It was then cooled to room temperature and concentrated. The crude material was purified by column chromatography on silica gel, eluting with 10-100% ethyl acetate in hexanes to afford the title compound: LCMS m/z 759.7 [M+H]+.

Step D: methyl (R)-4-((6-(2-(2-aminoethoxy)ethoxy)-1-methyl-1-(2-oxo-2-(thiazol-2-ylamino)ethyl)-1,2,3,4-tetrahydroisoquinolin-7-yl)oxy)-2-fluorobenzoate

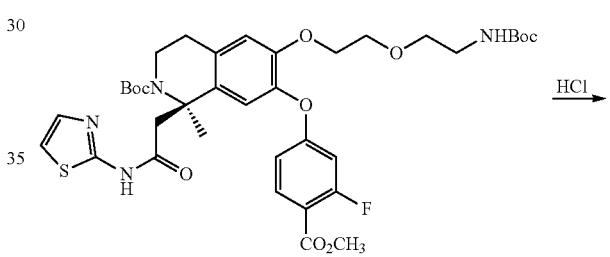

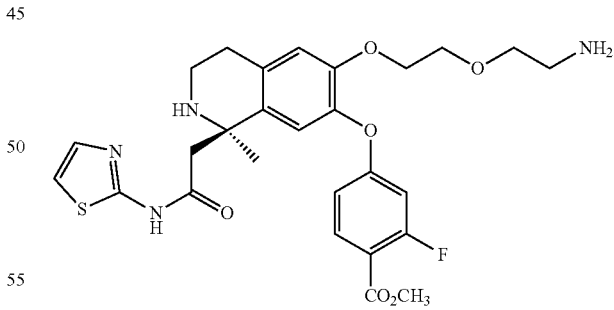

To solution of the title compound from scheme 7, step C (32.5 mg, 0.043 mmol) in dichloromethane (1.00 mL) was added trifluoroacetic acid (200 µL, 2.60 mmol). The solution was stirred at room temperature for an hour or until the Boc was completely removed. The solution was then concentrated and purified by preparative HPLC on a C18 reverse-phase column, eluting with 10-100% acetonitrile/water+ 0.05% trifluoroacetic acid. The fractions containing product were combined and lyophilized to give the title compound: LCMS m/z 558.96 [M+H]+.

167

Step E: (R)-4-((6-(2-(2-aminoethoxy)ethoxy)-1-methyl-1-(2-oxo-2-(thiazol-2-ylamino)ethyl)-1,2,3,4-tetrahydroisoquinolin-7-yl)oxy)-2-fluorobenzoic acid

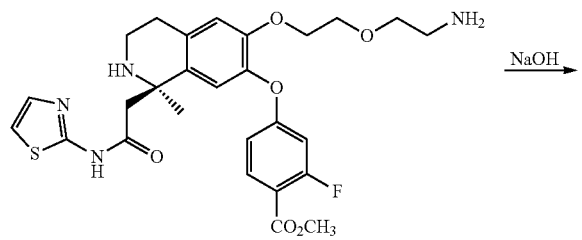

168 solution (500 µL, 0.500 mmol) was stirred at room temperature for about 3 hours or until complete conversion to the carboxylic acid. The solution was then acidified with a few drops of trifluoroacetic acid and passed through a syringe filter before being purified by preparative HPLC on a C18 reverse-phase column, eluting with 10-100% acetonitrile/water with 0.05% trifluoroacetic acid. The fractions containing product were combined and concentrated to afford the title compound: LCMS m/z 558.96 [M+H]$^+$.

Step F: (R)-4-((6-(2-(2-(3-(5,5-difluoro-7,9-dimethyl-5H-4l4,5l4-dipyrrolo[1,2-c:2',1'-f][1,3,2]diazaborinin-3-yl)propanamido)ethoxy)ethoxy)-1-methyl-1-(2-oxo-2-(thiazol-2-ylamino)ethyl)-1,2,3,4-tetrahydroisoquinolin-7-yl)oxy)-2-fluorobenzoic acid

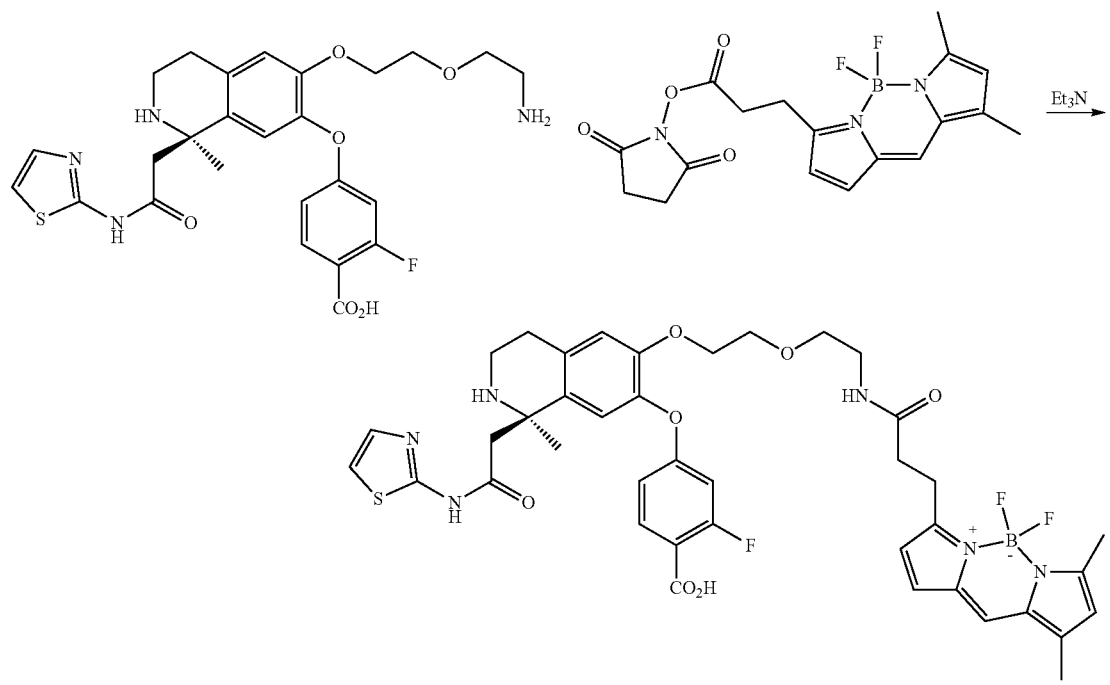

-continued

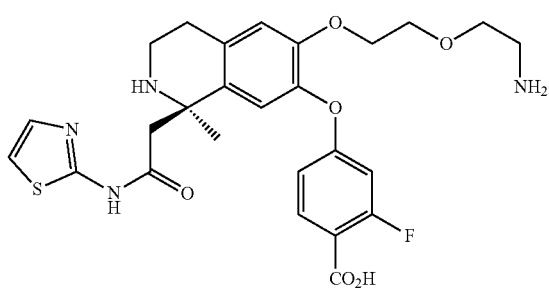

A solution of the title compound from scheme 7, step D (18.1 mg, 0.023 mmol) in sodium hydroxide, 1M aqueous A solution of the title compound from scheme 7, step E (7.50 mg, 0.014 mmol) in N,N-dimethylformamide (128 µL) was added to a vial containing 4,4-difluoro-5,7-dimethyl-4-bora-3a,4a-diaza-s-indacene-3-propionic acid, succinimidyl ester (BODIPY FL SE, 5.00 mg, 0.013 mmol). To this was added N,N-diisopropylethylamine (5.61 µL, 0.032 mmol) and the resulting reaction stirred at room temperature for 16 hours overnight. It was then neutralized using water containing 0.1% trifluoroacetic acid. The solution was passed through a syringe filter and purified by preparative HPLC on a C18 reverse-phase column, eluting with 0-60% acetonitrile/water+0.05% trifluoroacetic acid. The fractions were combined and lyophilized to afford the title compound: LCMS m/z 819.03 [M+H]$^+$.

EXAMPLES 58-61 in the table below were prepared in an analogous fashion as described for EXAMPLE 57 and generally shown in Scheme 7, substituting the appropriate reactants and reagents that are prepared as described herein or that are commercially available.

| EX. No. | Structure | Name | LC/MS [M + H]+ |
|---|---|---|---|
| 58 | 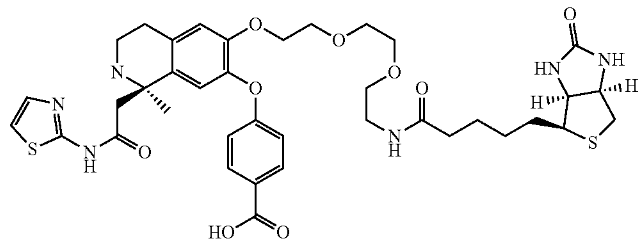 [SMILES: C[C@]1(CC(=O)Nc2nccs2)NCCc2cc(OCCOCCOCCNC(=O)CCCC[C@@H]3SC[C@@H]4NC(=O)N[C@@H]43)c(Oc3ccc(C(=O)O)cc3)cc21] | 4-(((R)-1-methyl-1-(2-oxo-2-(thiazol-2-ylamino)ethyl)-6-(2-(2-(2-(5-((3aS,4S,6aR)-2-oxohexahydro-1H-thieno[3,4-d]imidazol-4-yl)pentanamido)ethoxy)ethoxy)ethoxy)-1,2,3,4-tetrahydroisoquinolin-7-yl)oxy)benzoic acid | 797.74 |
| 59 | 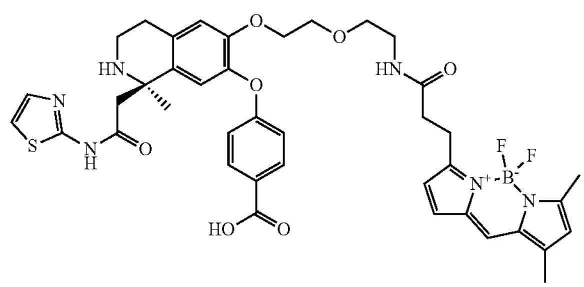 [SMILES: Cc1cc(C)n2c1C=C1C=CC(CCC(=O)NCCOCCOc3cc4c(cc3Oc3ccc(C(=O)O)cc3)[C@@](C)(CC(=O)Nc3nccs3)NCC4)=[N+]1[B-]2(F)F] | (R)-4-((6-(2-(2-(3-(5,5-difluoro-7,9-dimethyl-5H-4l4,5l4-dipyrrolo[1,2-c:2',1'-f][1,3,2]diazaborinin-3-yl)propanamido)ethoxy)ethoxy)-1-methyl-1-(2-oxo-2-(thiazol-2-ylamino)ethyl)-1,2,3,4-tetrahydroisoquinolin-7-yl)oxy)benzoic acid | 801.48 |
| 60 | 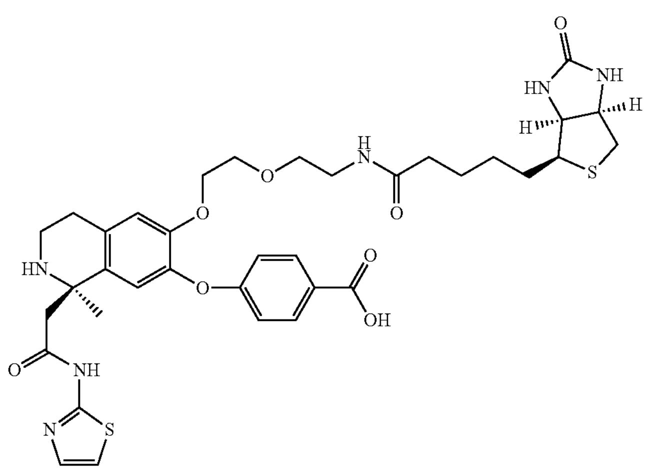 [SMILES: C[C@]1(CC(=O)Nc2nccs2)NCCc2cc(OCCOCCNC(=O)CCCC[C@@H]3SC[C@@H]4NC(=O)N[C@@H]43)c(Oc3ccc(C(=O)O)cc3)cc21] | 4-(((R)-1-methyl-1-(2-oxo-2-(thiazol-2-ylamino)ethyl)-6-(2-(2-(5-((3aS,4S,6aR)-2-oxohexahydro-1H-thieno[3,4-d]imidazol-4-yl)pentanamido)ethoxy)ethoxy)-1,2,3,4-tetrahydroisoquinolin-7-yl)oxy)benzoic acid | 753.35 |

| EX. No. | Structure | Name | LC/MS [M + H]+ |
|---|---|---|---|
| 61 | 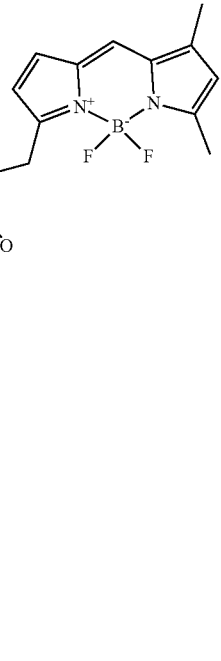 | methyl (R)-4-((6-(2-(2-(3-(5,5-difluoro-7,9-dimethyl-5H-4l4,5l4-dipyrrolo[1,2-c:2',1'-f][1,3,2]diazaborinin-3-yl)propanamido)ethoxy)ethoxy)-1-methyl-1-(2-oxo-2-(thiazol-2-ylamino)ethyl)-1,2,3,4-tetrahydroisoquinolin-7-yl)oxy)-2-fluorobenzoate | 833.11 |

Examples 62-72

Example 62: 2-fluoro-4-(((1R)-1-methyl-1-(2-oxo-2-(thiazol-2-ylamino)ethyl)-6-((tetrahydro-2H-pyran-2-yl)methoxy)-1,2,3,4-tetrahydroisoquinolin-7-yl)oxy)benzoic acid Example 62 was made according to general Scheme 8 below.

Scheme 8

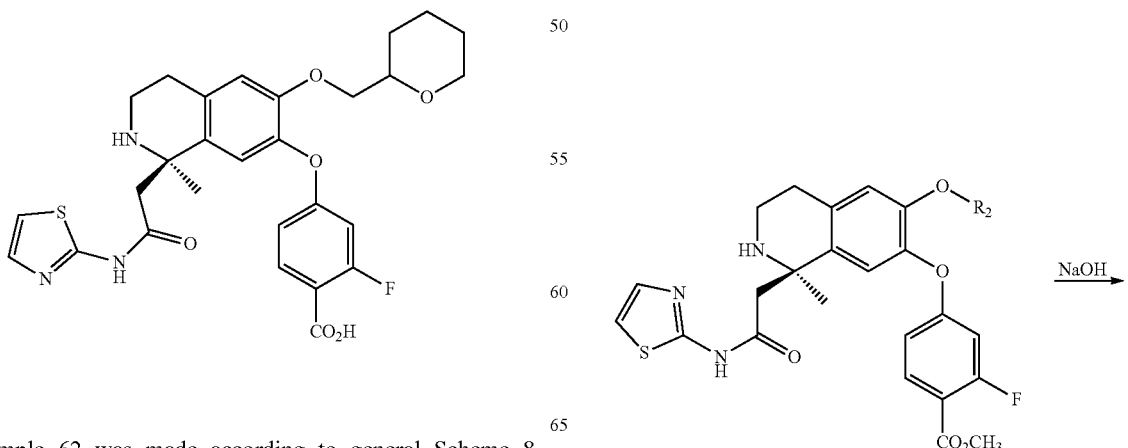

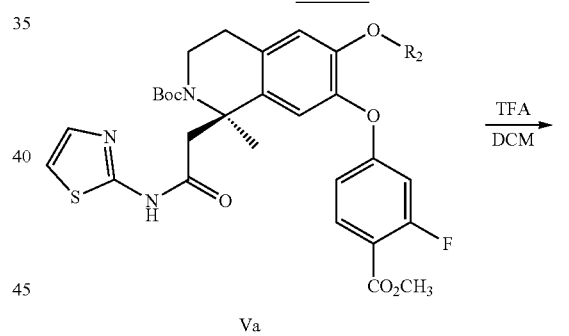

173

-continued

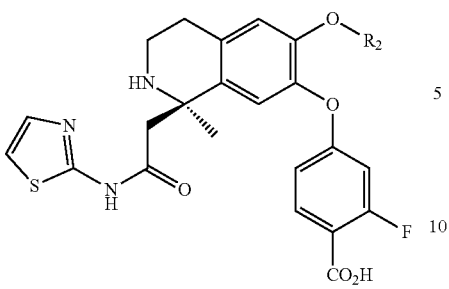

174

Step B: 2-fluoro-4-(((1R)-1-methyl-1-(2-oxo-2-(thiazol-2-ylamino)ethyl)-6-((tetrahydro-2H-pyran-2-yl)methoxy)-1,2,3,4-tetrahydroisoquinolin-7-yl)oxy)benzoic acid Step A: methyl 2-fluoro-4-(((1R)-1-methyl-1-(2-oxo-2-(thiazol-2-ylamino)ethyl)-6-((tetrahydro-2H-pyran-2-yl)methoxy)-1,2,3,4-tetrahydroisoquinolin-7-yl)oxy)benzoate

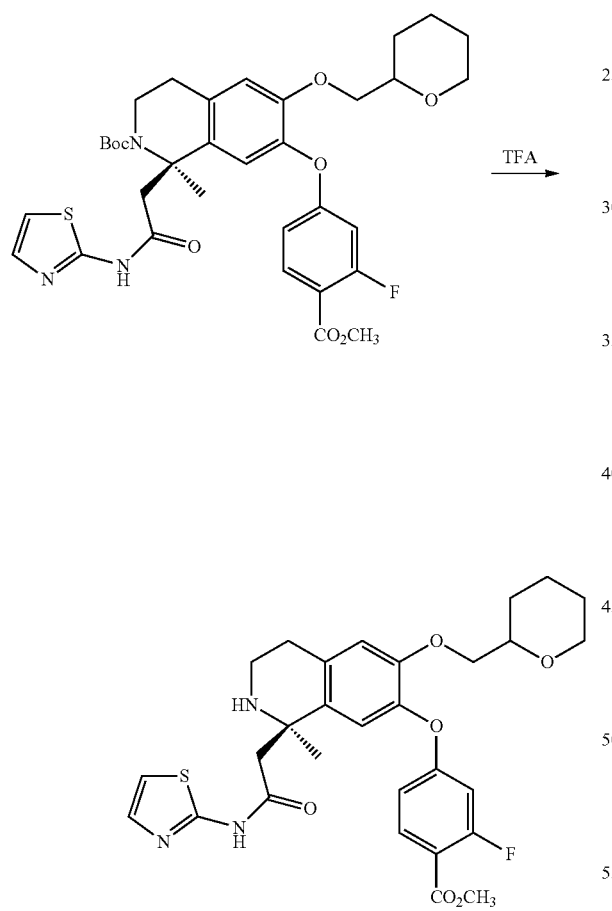

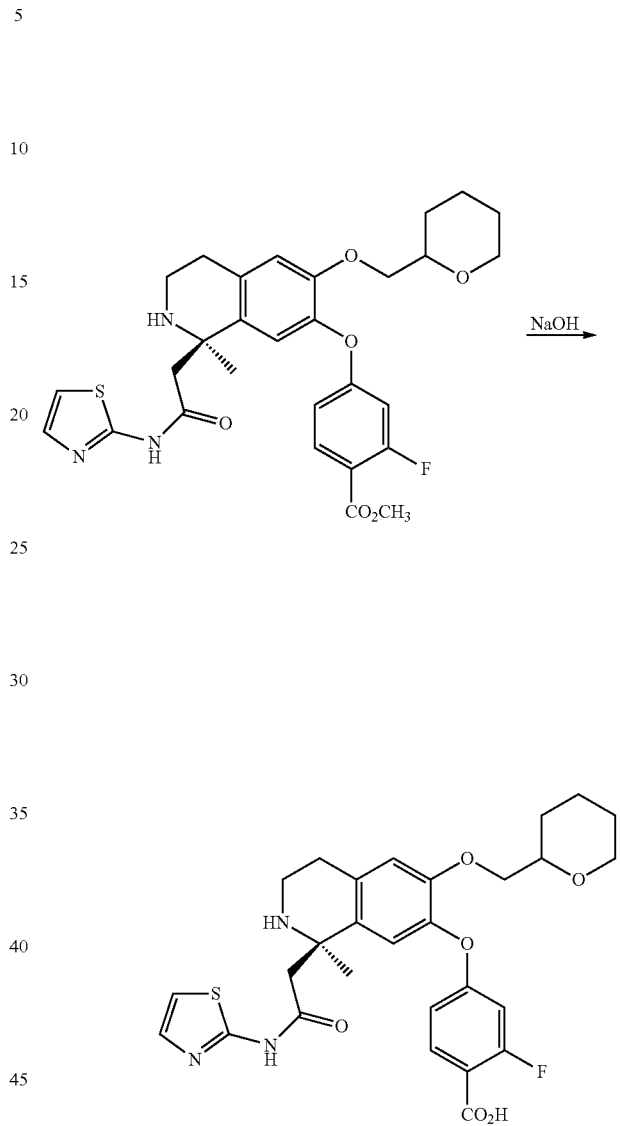

A solution of tert-butyl (1R)-7-(3-fluoro-4-(methoxycarbonyl)phenoxy)-1-methyl-1-(2-oxo-2-(thiazol-2-ylamino)ethyl)-6-((tetrahydro-2H-pyran-2-yl)methoxy)-3,4-dihydroisoquinoline-2(1H)-carboxylate (Int. Va, scheme 1, step N; 10.0 mg, 0.015 mmol) in 20% trifluoroacetic acid in dichloromethane (0.200 mL, 1.30 mmol) was stirred at room temperature for an hour. It was then concentrated to afford the title compound which was used without purification.

A solution of the title compound from scheme 8, step A (8.54 mg, 0.015 mmol) in sodium hydroxide, 1N aqueous solution (1.0 ml, 1.0 mmol) was stirred at room temperature for three hours. It was then acidified with 1N aqueous HCl until pH~4. The acidic solution was passed through a syringe filter. The residue was purified by HPLC on a reverse-phase column, eluting with 10-100% acetonitrile/water+0.05% TFA. The fractions containing product were combined and concentrated to afford the title compound: LCMS m/z 556.28 [M+H]$^+$.

EXAMPLES 63-72 in the table below were prepared in an analogous fashion as described for EXAMPLE 62 and generally shown in Scheme 8, substituting the appropriate reactants and reagents that are prepared as described herein or that are commercially available.

| EX. No. | Structure | Name | LC/MS [M + H]+ |
|---|---|---|---|
| 63 | 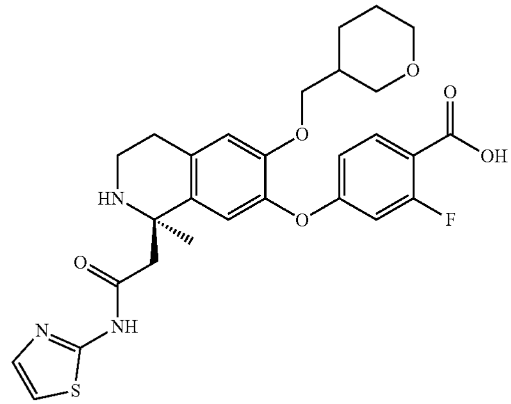 [SMILES: C[C@]1(CC(=O)Nc2nccs2)NCCc2cc(OCC3CCCOC3)c(Oc3ccc(C(=O)O)c(F)c3)cc21] | 2-fluoro-4-(((1R)-1-methyl-1-(2-oxo-2-(thiazol-2-ylamino)ethyl)-6-(((R or S)-tetrahydro-2H-pyran-2-yl)methoxy)-1,2,3,4-tetrahydroisoquinolin-7-yl)oxy)benzoic acid | 556.13 |
| 64 | 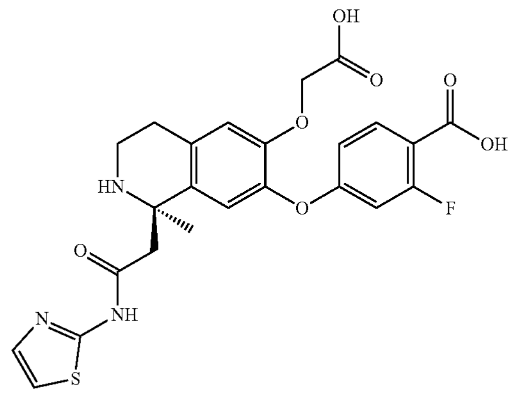 [SMILES: C[C@]1(CC(=O)Nc2nccs2)NCCc2cc(OCC(=O)O)c(Oc3ccc(C(=O)O)c(F)c3)cc21] | (R)-4-((6-(carboxymethoxy)-1-methyl-1-(2-oxo-2-(thiazol-2-ylamino)ethyl)-1,2,3,4-tetrahydroisoquinolin-7-yl)oxy)-2-fluorobenzoic acid | 516.21 |
| 65 | 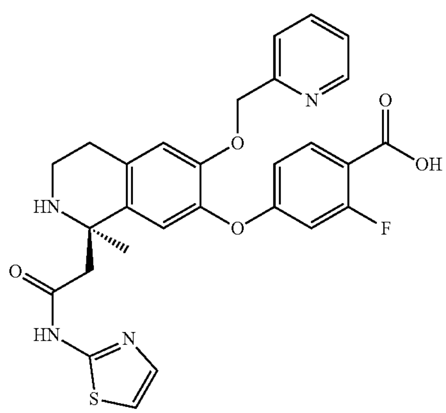 [SMILES: C[C@]1(CC(=O)Nc2nccs2)NCCc2cc(OCc3ccccn3)c(Oc3ccc(C(=O)O)c(F)c3)cc21] | (R)-2-fluoro-4-((1-methyl-1-(2-oxo-2-(thiazol-2-ylamino)ethyl)-6-(pyridin-2-ylmethoxy)-1,2,3,4-tetrahydroisoquinolin-7-yl)oxy)benzoic acid | 549.09 |
| 66 | 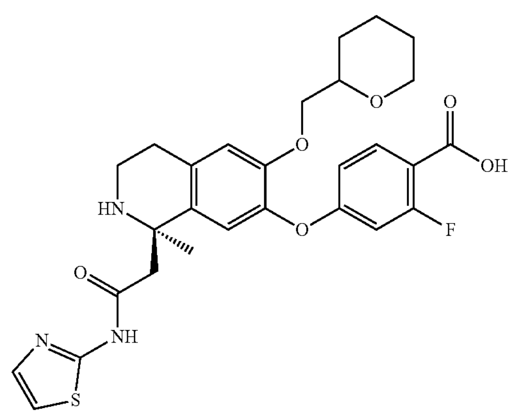 [SMILES: C[C@]1(CC(=O)Nc2nccs2)NCCc2cc(OCC3CCCCO3)c(Oc3ccc(C(=O)O)c(F)c3)cc21] | 2-fluoro-4-(((1R)-1-methyl-1-(2-oxo-2-(thiazol-2-ylamino)ethyl)-6-((tetrahydro-2H-pyran-2-yl)methoxy)-1,2,3,4-tetrahydroisoquinolin-7-yl)oxy)benzoic acid | 556.28 |

| EX. No. | Structure | Name | LC/MS [M + H]+ |
|---|---|---|---|
| 67 | 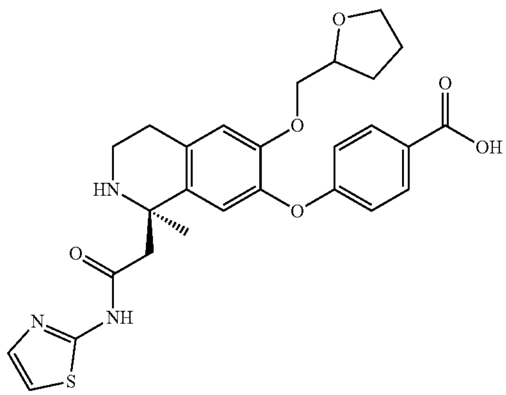 [SMILES: C[C@]1(CC(=O)Nc2nccs2)NCCc2cc(OCC3CCCO3)c(Oc3ccc(C(=O)O)cc3)cc21] | 4-(((1R)-1-methyl-1-(2-oxo-2-(thiazol-2-ylamino)ethyl)-6-((tetrahydrofuran-2-yl)methoxy)-1,2,3,4-tetrahydroisoquinolin-7-yl)oxy)benzoic acid | 524.23 |
| 68 | 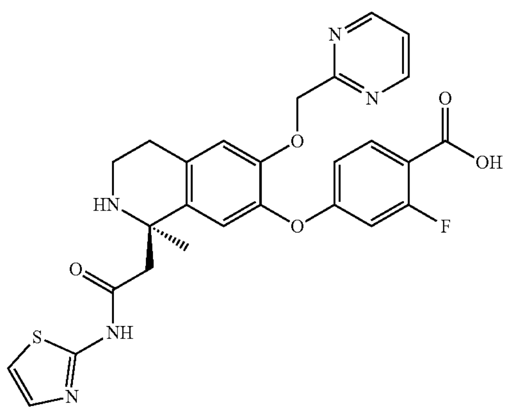 [SMILES: C[C@]1(CC(=O)Nc2nccs2)NCCc2cc(OCc3ncccn3)c(Oc3ccc(C(=O)O)c(F)c3)cc21] | (R)-2-fluoro-4-((1-methyl-1-(2-oxo-2-{thiazol-2-ylamino)ethyl)-6-(pyrimidin-2-ylmethoxy)-1,2,3,4-tetrahydroisoquinolin-7-yl)oxy)benzoic acid | 550.05 |
| 69 | 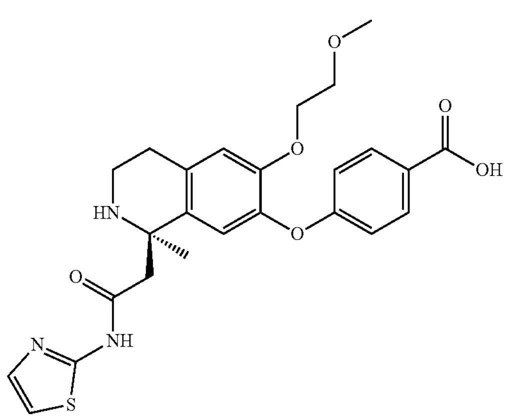 [SMILES: COCCOc1cc2c(cc1Oc1ccc(C(=O)O)cc1)[C@@](C)(CC(=O)Nc1nccs1)NCC2] | (R)-4-((6-(2-methoxyethoxy)-1-methyl-1-(2-oxo-2-(thiazol-2-ylamino)ethyl)-1,2,3,4-tetrahydroisoquinolin-7-yl)oxy)benzoic acid | 498.01 |

| EX. No. | Structure | Name | LC/MS [M + H]+ |
|---|---|---|---|
| 70 | 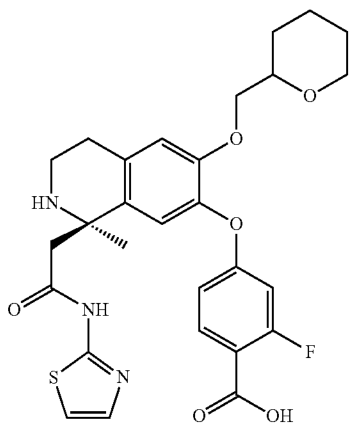 [SMILES: C[C@]1(CC(=O)Nc2nccs2)NCCc2cc(OCC3CCCCO3)c(Oc3ccc(C(=O)O)c(F)c3)cc21] | 2-fluoro-4-(((1R)-1-methyl-1-(2-oxo-2-(thiazol-2-ylamino)ethyl)-6-(((R or S)-tetrahydro-2H-pyran-2-yl)methoxy)-1,2,3,4-tetrahydroisoquinolin-7-yl)oxy)benzoic acid | 556.11 |
| 71 | 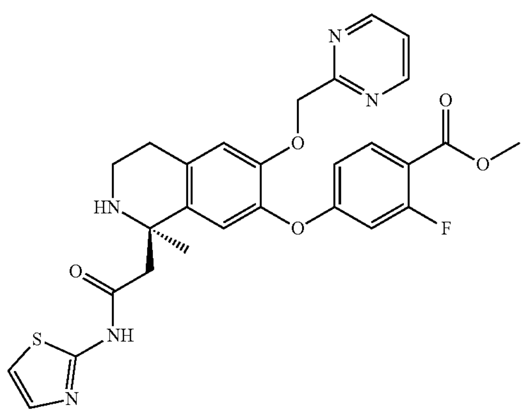 [SMILES: COC(=O)c1ccc(Oc2cc3c(cc2OCc2ncccn2)CCN[C@]3(C)CC(=O)Nc2nccs2)cc1F] | methyl (R)-2-fluoro-4-((1-methyl-1-(2-oxo-2-(thiazol-2-ylamino)ethyl)-6-(pyrimidin-2-ylmethoxy)-1,2,3,4-tetrahydroisoquinolin-7-yl)oxy)benzoate | 564.12 |
| 72 | 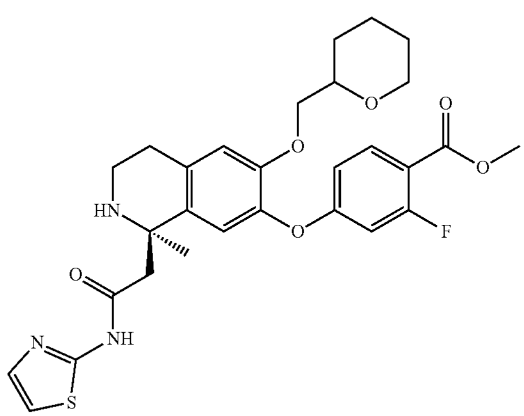 [SMILES: COC(=O)c1ccc(Oc2cc3c(cc2OCC2CCCCO2)CCN[C@]3(C)CC(=O)Nc2nccs2)cc1F] | methyl 2-fluoro-4-(((1R)-1-methyl-1-(2-oxo-2-(thiazol-2-ylamino)ethyl)-6-((tetrahydro-2H-pyran-2-yl)methoxy)-1,2,3,4-tetrahydroisoquinolin-7-yl)oxy)benzoate | 570.3 |

181

Examples 73-78

Example 73: 2-fluoro-4-(((1R)-1-methyl-1-(2-oxo-2-(thiazol-2-ylamino)ethyl)-6-((tetrahydro-2H-pyran-2-yl)methoxy)-1,2,3,4-tetrahydroisoquinolin-7-yl)oxy)-N-(1-methyl-1H-pyrazol-5-yl)benzamide

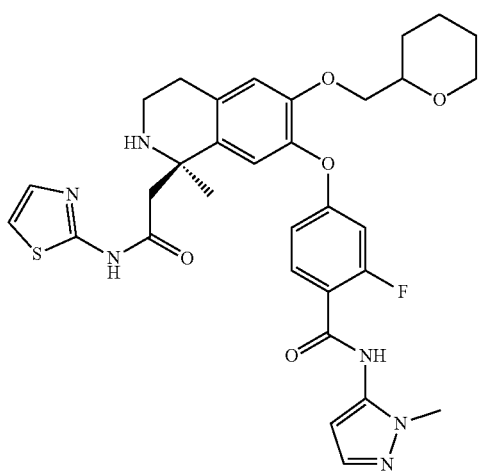 [SMILES: Cn1nccc1NC(=O)c1ccc(Oc2cc3c(cc2OCC2CCCCO2)CCN[C@]3(C)CC(=O)Nc2nccs2)cc1F]

Example 73 was made according to general Scheme 9 below.

Scheme 9

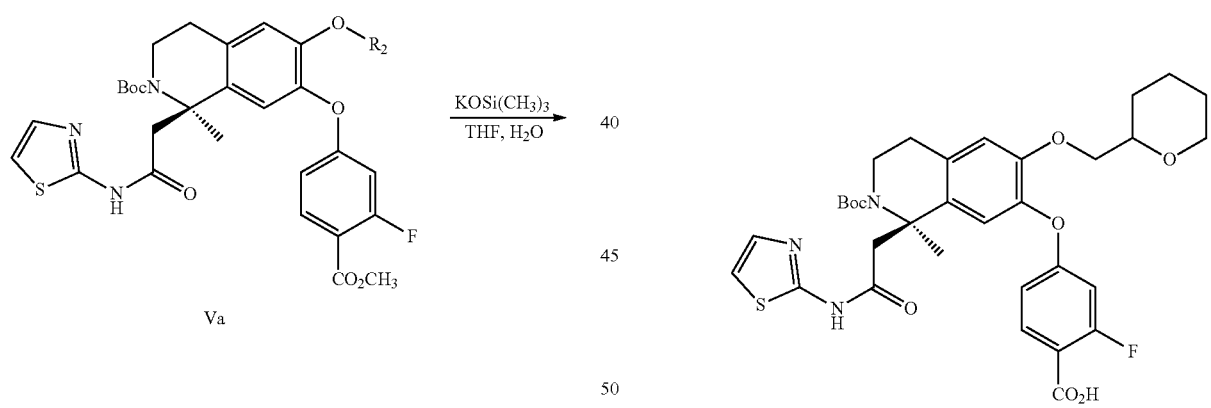

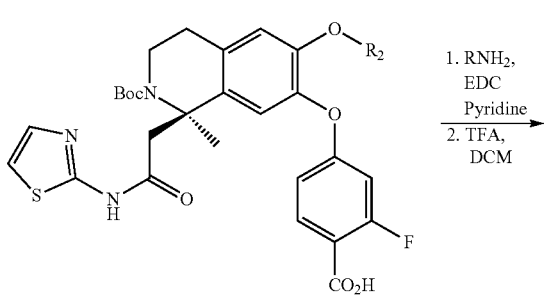

182

-continued

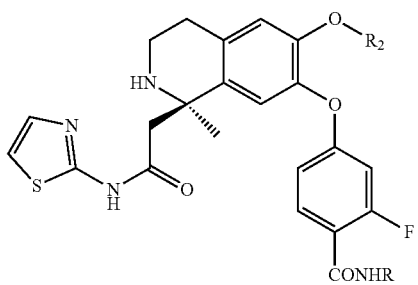

Step A: 4-(((1R)-2-(tert-butoxycarbonyl)-1-methyl-1-(2-oxo-2-(thiazol-2-ylamino)ethyl)-6-((tetrahydro-2H-pyran-2-yl)methoxy)-1,2,3,4-tetrahydroisoquinolin-7-yl)oxy)-2-fluorobenzoic acid

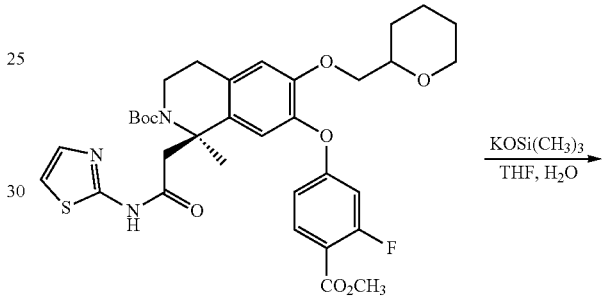

A solution of tert-butyl (1R)-7-(3-fluoro-4-(methoxycarbonyl)phenoxy)-1-methyl-1-(2-oxo-2-(thiazol-2-ylamino)ethyl)-6-((tetrahydro-2H-pyran-2-yl)methoxy)-3,4-dihydroisoquinoline-2(1H)-carboxylate (Int. Va, scheme 1, step N; 200 mg, 0.299 mmol) and potassium trimethylsilanolate (115 mg, 0.896 mmol) in tetrahydrofuran (30.0 mL) and water (6.00 mL) was heated to 50° C. overnight. The reaction was acidified with 1.00 mL glacial acetic acid dropwise with stirring. The solvent was removed in vacuo and the residue was purified by preparative HPLC on a C18 reverse-phase column eluting with 10-100% acetonitrile/water to afford the title compound: LCMS m/z 656.30 [M+H]$^+$.

Step B: 2-fluoro-4-(((1R)-1-methyl-1-(2-oxo-2-(thiazol-2-ylamino)ethyl)-6-((tetrahydro-2H-pyran-2-yl)methoxy)-1,2,3,4-tetrahydroisoquinolin-7-yl)oxy)-N-(1-methyl-H-pyrazol-5-yl)benzamide

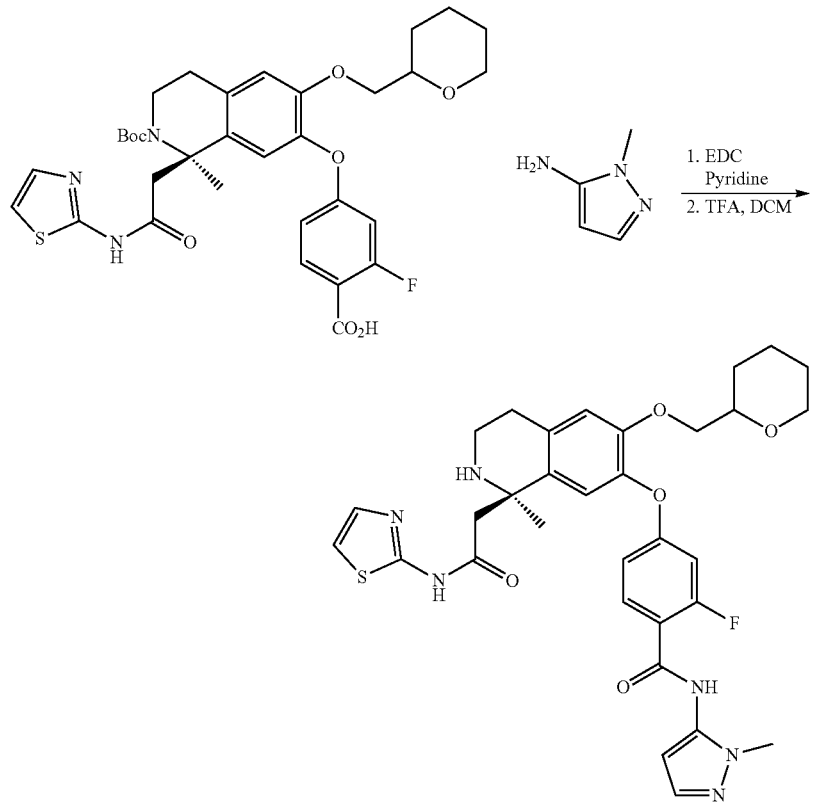

To the title compound from scheme 9, step A (25.0 mg, 0.038 mmol) in pyridine (2.00 mL) was added N-(3-dimethylaminopropyl)-N'-ethylcarbodiimide hydrochloride (21.9 mg, 0.114 mmol), followed by 1-methyl-1H-pyrazol-5-amine (11.1 mg, 0.114 mmol). The resulting mixture was stirred overnight at room temperature. The solvent was removed in vacuo at 35° C. and the residue was purified by preparative HPLC on a C18 reverse-phase column eluting with 10-100% acetonitrile/water. The BOC group was removed by treating with 6 mL TFA/DCM (1:1) for 3 hr. The solution was concentrated to afford the title compound: LCMS m/z 635.35 [M+H]+.

EXAMPLES 74-78 in the table below were prepared in an analogous fashion as described for EXAMPLE 73 and generally shown in Scheme 9, substituting the appropriate reactants and reagents that are prepared as described herein or that are commercially available.

| EX. No. | Structure | Name | LC/MS [M + H]+ |
|---|---|---|---|
| 74 | 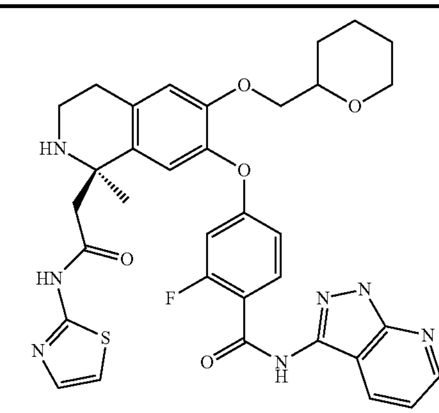 | 2-fluoro-4-(((1R)-1-methyl-1-(2-oxo-2-(thiazol-2-ylamino)ethyl)-6-((tetrahydro-2H-pyran-2-yl)methoxy)-1,2,3,4-tetrahydroisoquinolin-7-yl)oxy)-N-(1H-pyrazolo[3,4-b]pyridin-3-yl)benzamide | 672.21 |

-continued

| EX. No. | Structure | Name | LC/MS [M + H]+ |
|---|---|---|---|
| 75 | 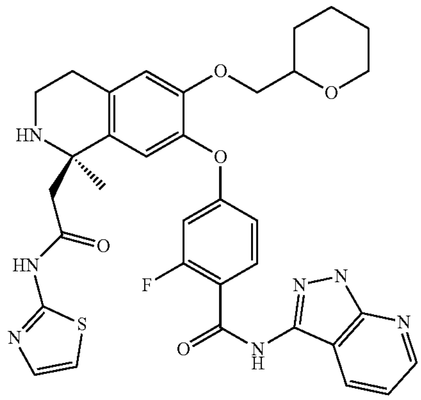 [SMILES: C[C@]1(CC(=O)Nc2nccs2)NCCc2cc(OCC3CCCCO3)c(Oc3ccc(C(=O)Nc4n[nH]c5ncccc45)c(F)c3)cc21] | 2-fluoro-4-(((R)-1-methyl-1-(2-oxo-2-(thiazol-2-ylamino)ethyl)-6-(((R or S)-tetrahydro-2H-pyran-2-yl)methoxy)-1,2,3,4-tetrahydroisoquinolin-7-yl)oxy)-N-(1H-pyrazolo[3,4-b]pyridin-3-yl)benzamide | 672.26 |
| 76 | 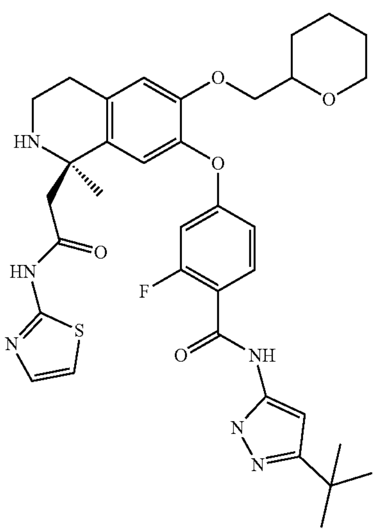 [SMILES: CC(C)(C)c1cc(NC(=O)c2ccc(Oc3cc4c(cc3OCC3CCCCO3)CCN[C@]4(C)CC(=O)Nc3nccs3)cc2F)[nH]n1] | N-(3-(tert-butyl)-1H-pyrazol-5-yl)-2-fluoro-4-(((1R)-1-methyl-1-(2-oxo-2-(thiazol-2-ylamino)ethyl)-6-((tetrahydro-2H-pyran-2-yl)methoxy)-1,2,3,4-tetrahydroisoquinolin-7-yl)oxy)benzamide | 677.27 |
| 77 | 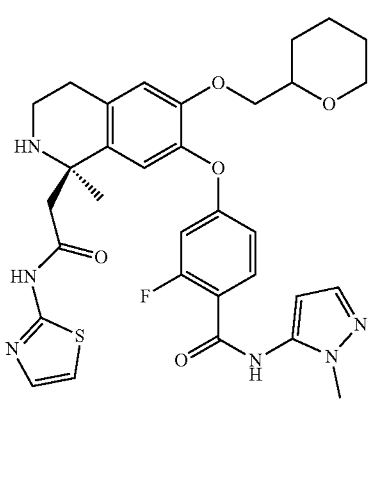 [SMILES: Cn1nccc1NC(=O)c1ccc(Oc2cc3c(cc2OCC2CCCCO2)CCN[C@]3(C)CC(=O)Nc2nccs2)cc1F] | 2-fluoro-4-(((R)-1-methyl-1-(2-oxo-2-(thiazol-2-ylamino)ethyl)-6-(((R or S)-tetrahydro-2H-pyran-2-yl)methoxy)-1,2,3,4-tetrahydroisoquinolin-7-yl)oxy)-N-(1-methyl-1H-pyrazol-5-yl)benzamide | 635.15 |

| EX. No. | Structure | Name | LC/MS [M + H]+ |
|---|---|---|---|
| 78 | 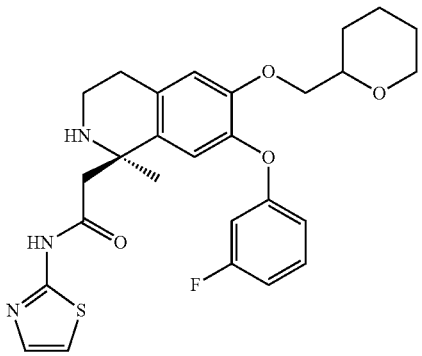 [SMILES: C[C@]1(CC(=O)Nc2nccs2)NCCc2cc(OCC3CCCCO3)c(Oc3cccc(F)c3)cc21] | 2-fluoro-4-(((1R)-1-methyl-1-(2-oxo-2-(thiazol-2-ylamino)ethyl)-6-((tetrahydro-2H-pyran-2-yl)methoxy)-1,2,3,4-tetrahydroisoquinolin-7-yl)oxy)-N-(1H-pyrazolo[3,4-b]pyridin-3-yl)benzamide | 672.37 |

Examples 79-84

Example 79: 2-((1R)-7-(3-fluorophenoxy)-1-methyl-6-((tetrahydro-2H-pyran-2-yl)methoxy)-1,2,3,4-tetrahydroisoquinolin-1-yl)-N-(thiazol-2-yl)acetamide

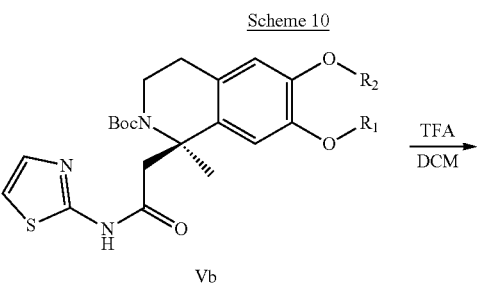

Example 79 was made according to general Scheme 10 below.

Scheme 10

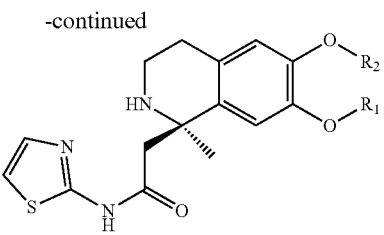

Step A: 2-((1R)-7-(3-fluorophenoxy)-1-methyl-6-((tetrahydro-2H-pyran-2-yl)methoxy)-1,2,3,4-tetrahydroisoquinolin-1-yl)-N-(thiazol-2-yl)acetamide

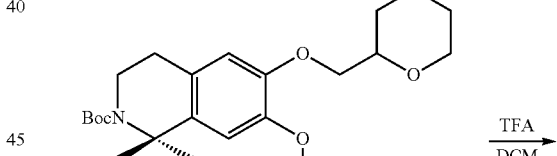
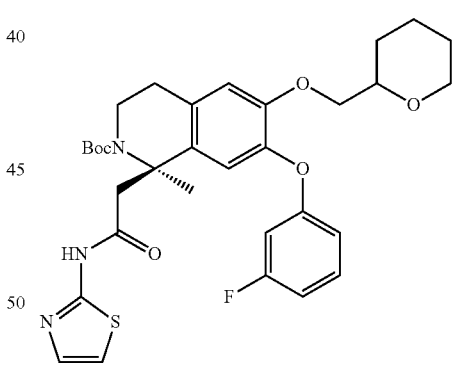

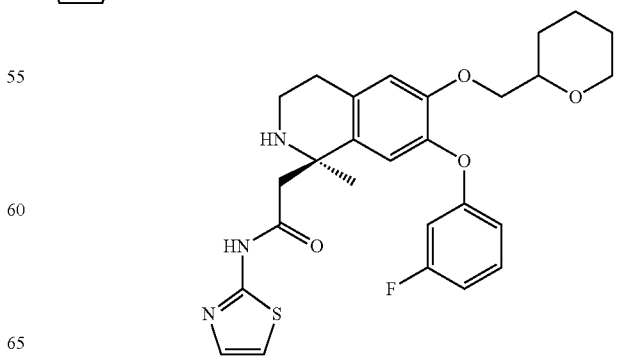

A solution of tert-butyl (1R)-7-(3-fluorophenoxy)-1-methyl-1-(2-oxo-2-(thiazol-2-ylamino)ethyl)-6-((tetrahydro-2H-pyran-2-yl)methoxy)-3,4-dihydroisoquinoline-2(1H)-carboxylate (Int. Vb, 23 mg, 0.039 mmol) in a 20° trifluoroacetic acid solution in dichloromethane (1.0 mL, 2.60 mmol) was stirred at room temperature for an hour. The solution was concentrated and then purified by preparative HPLC on a C18 reverse-phase column eluting with 10-100% acetonitrile in water with 0.1% TFA. The fractions containing product were combined and concentrated to afford the title compound: LCMS m/z 512.05[M+H]$^+$.

EXAMPLES 80-84 in the table below were prepared in an analogous fashion as described for EXAMPLE 79 and generally shown in Scheme 10, substituting the appropriate reactants and reagents that are prepared as described herein or that are commercially available.

| EX. No. | Structure | Name | LC/MS [M + H]$^+$ |
|---|---|---|---|
| 80 | 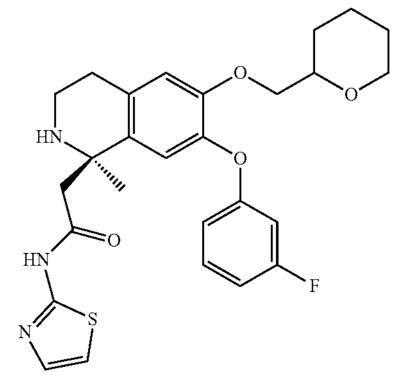 [SMILES: C[C@]1(CC(=O)Nc2nccs2)NCCc2cc(OCC3CCCCO3)c(Oc3cccc(F)c3)cc21] | 2-((1R)-7-(3-fluorophenoxy)-1-methyl-6-(((R or S)-tetrahydro-2H-pyran-2-yl)methoxy)-1,2,3,4-tetrahydroisoquinolin-1-yl)-N-(thiazol-2-yl)acetamide | 512.05 |
| 81 | 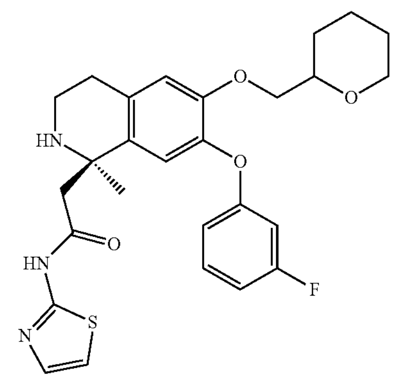 [SMILES: C[C@]1(CC(=O)Nc2nccs2)NCCc2cc(OCC3CCCCO3)c(Oc3cccc(F)c3)cc21] | 2-((1R)-7-(3-fluorophenoxy)-1-methyl-6-(((S or R)-tetrahydro-2H-pyran-2-yl)methoxy)-1,2,3,4-tetrahydroisoquinolin-1-yl)-N-(thiazol-2-yl)acetamide | 512.1 |
| 82 | 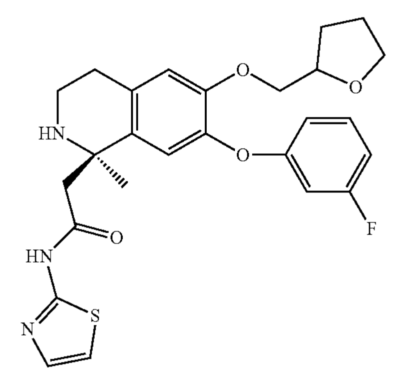 [SMILES: C[C@]1(CC(=O)Nc2nccs2)NCCc2cc(OCC3CCCO3)c(Oc3cccc(F)c3)cc21] | 2-((1R)-7-(3-fluorophenoxy)-1-methyl-6-((tetrahydrofuran-2-yl)methoxy)-1,2,3,4-tetrahydroisoquinolin-1-yl)-N-(thiazol-2-yl)acetamide | |

-continued

| EX. No. | Structure | Name | LC/MS [M + H]+ |
|---|---|---|---|
| 83 | 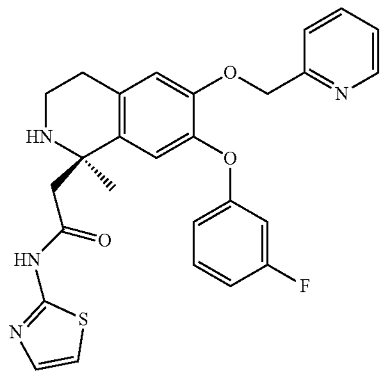 [SMILES: C[C@]1(CC(=O)Nc2nccs2)NCCc2cc(OCc3ccccn3)c(Oc3cccc(F)c3)cc21] | (R)-2-(7-(3-fluorophenoxy)-1-methyl-6-(pyridin-2-ylmethoxy)-1,2,3,4-tetrahydroisoquinolin-1-yl)-N-(thiazol-2-yl)acetamide | 505.16 |
| 84 | 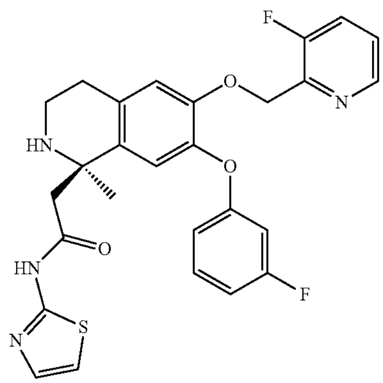 [SMILES: C[C@]1(CC(=O)Nc2nccs2)NCCc2cc(OCc3ncccc3F)c(Oc3cccc(F)c3)cc21] | (R)-2-(7-(3-fluorophenoxy)-6-((3-fluoropyridin-2-yl)methoxy)-1-methyl-1,2,3,4-tetrahydroisoquinolin-1-yl)-N-(thiazol-2-yl)acetamide | 523.22 |

Examples 85-92

Example 85: 2'-fluoro-4'-(((1R)-1-(2-((3-methoxyphenyl)amino-2-oxoethyl)-1-methyl-6-((tetrahydro-2H-pyran-2-yl)methoxy-1,2,3,4-tetrahydroisoquinolin-7-yl)oxy-[1,1'-biphenyl]-4-carboxylic acid

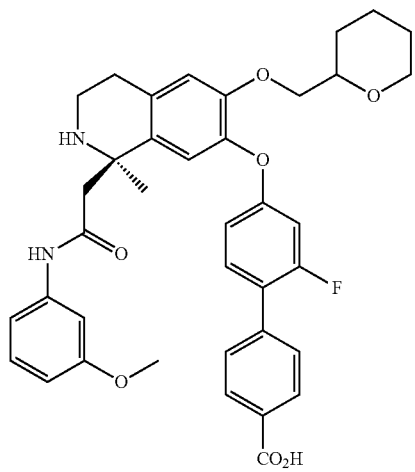 [SMILES: COc1cccc(NC(=O)C[C@@]2(C)NCCc3cc(OCC4CCCCO4)c(Oc4ccc(-c5ccc(C(=O)O)cc5)c(F)c4)cc32)c1]

Example 85 was made according to general Scheme 11 below.

Scheme 11

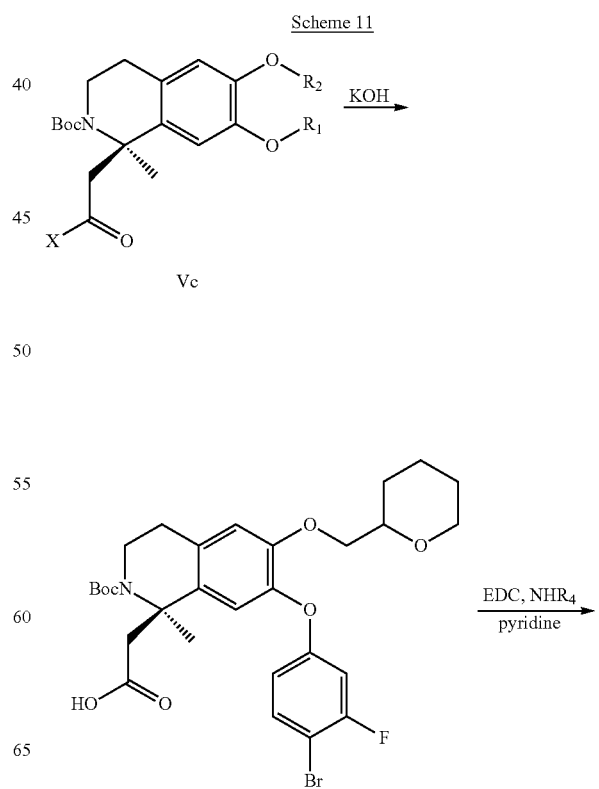

193
-continued

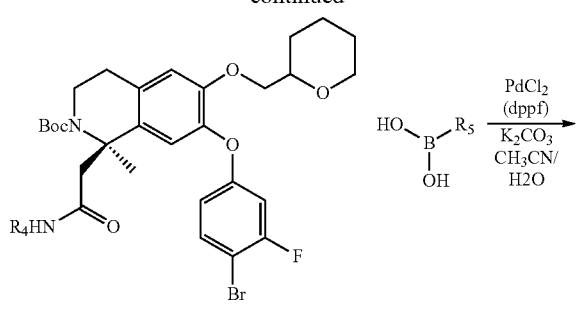

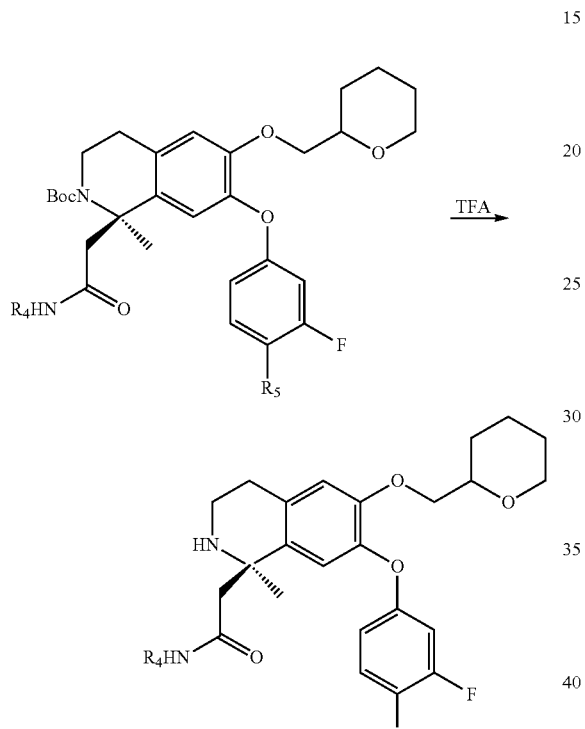

Step A: 2-((1R)-7-(4-bromo-3-fluorophenoxy)-2-tert-butoxycarbonyl)-1-methyl-6-((tetrahydro-2H-pyran-2-yl)methoxy)-1,2,3,4-tetrahydroisoquinolin-1-yl)acetic acid

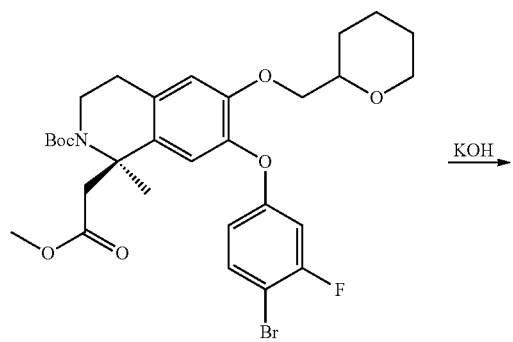

194
-continued

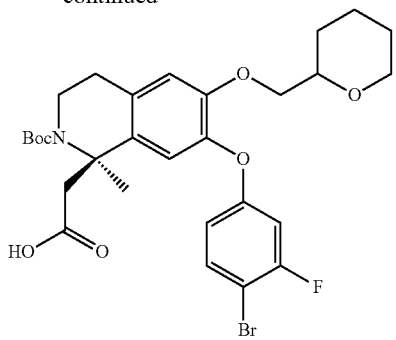

To a solution of tert-butyl (1R)-7-(4-bromo-3-fluorophenoxy)-1-(2-methoxy-2-oxoethyl)-1-methyl-6-((tetrahydro-2H-pyran-2-yl)methoxy)-3,4-dihydroisoquinoline-2(1H)-carboxylate (Int. Vc, 305 mg, 0.490 mmol) in methanol (1.00 mL), tetrahydrofuran (1.00 mL) and water (1.00 mL) was added potassium hydroxide (550 mg, 9.80 mmol). The reaction mixture was then heated to 80° C. for 3 hours. The reaction mixture was cooled to room temperature, acidified with 4N aq. HCl and then extracted three times with ethyl acetate. The combined organics were then washed with a saturated solution of NaCl, dried over anhydrous sodium sulfate, filtered and concentrated under reduced pressure to give the title compound: LCMS m/z 609.9 [M+H]$^+$.

Step B: tert-butyl (1R)-7-(4-bromo-3-fluorophenoxy)-1-(2-((3-methoxyphenyl)amino)-2-oxoethyl)-1-methyl-6-((tetrahydro-2H-pyran-2-yl)methoxy)-3,4-dihydroisoquinoline-2(1H)-carboxylate

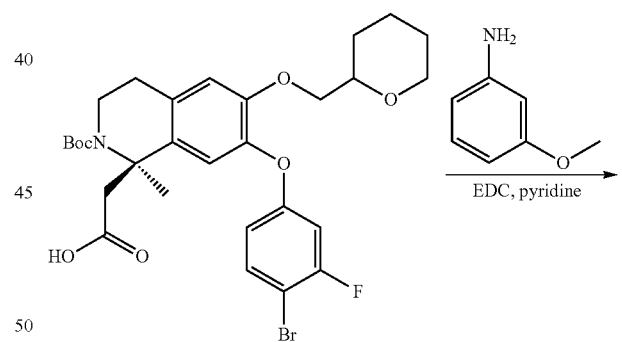

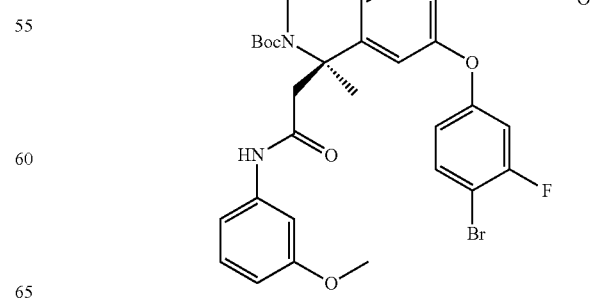

The title compound from scheme 11, step A (30 mg, 0.05 mmol) was stirred in pyridine (0.50 mL) and then N-(3-Dimethylaminopropyl)-N-ethylcarbodiimide hydrochloride (19 mg, 0.10 mmol) and 3-methoxyaniline (30 mg, 0.25 mmol) were added to the reaction mixture which was stirred for 72 hours at room temperature. The reaction mixture was diluted up in methanol and purified by preparative HPLC on a C18 reverse-phase column eluting with 20-100% acetonitrile/water with 0.05% trifluoroacetic acid to give the title compound: LCMS m/z 715.19 [M+H]$^+$.

Step C: tert-butyl (1R)-7-((2-fluoro-4'-(methoxycarbonyl)-[1,1'-biphenyl]-4-yl)oxy)-1-(2-((3-methoxyphenyl)amino)-2-oxoethyl)-1-methyl-6-((tetrahydro-2H-pyran-2-yl)methoxy-3,4-dihydroisoquinoline-2(1H)-carboxylate

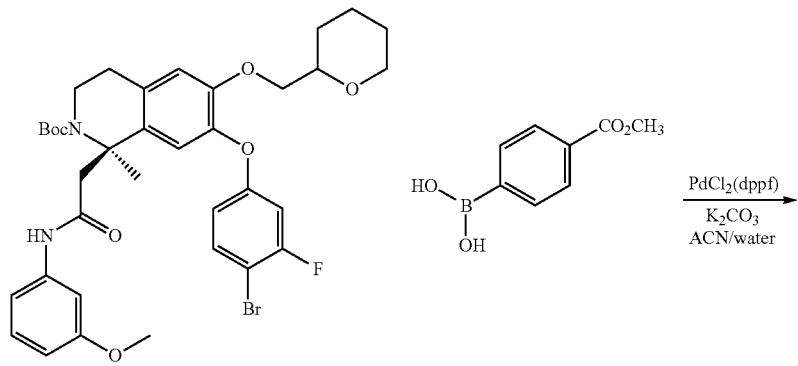

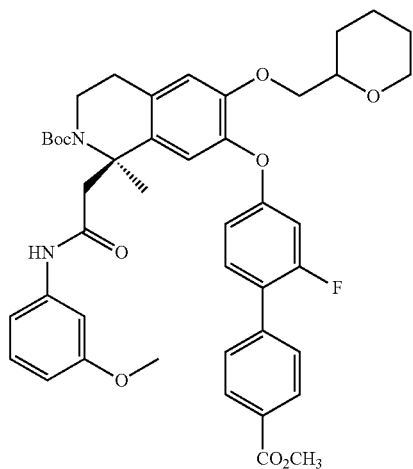

The title compound from scheme 11, step B (30 mg, 0.04 mmol) was dissolved in acetonitrile (1.5 mL) in a microwave vial and then 4-methoxycarbonylphenylboronic acid (11 mg, 0.06 mmol), potassium carbonate (12 mg, 0.08 mmol), PdCl$_2$(dppf) (3.1 mg, 4.2 µmol) and water (0.50 mL) were added to the reaction mixture. The mixture was heated in the microwave for 30 minutes at 100° C. The organic layer was decanted, filtered and purified by preparative HPLC on a C18 reverse-phase column eluting with 30-100% acetonitrile/water with 0.05% TFA to afford the title compound: LCMS m/z 769.44 [M+H]$^+$.

Step D: methyl 2'-fluoro-4'-(((1R)-1-(2-((3-methoxyphenyl)amino)-2-oxoethyl)-1-methyl-6-((tetrahydro-2H-pyran-2-yl)methoxy)-1,2,3,4-tetrahydroisoquinolin-7-yl)oxy)-[1,1'-biphenyl]-4-carboxylate Step E: 2'-fluoro-4'-(((1R)-1-(2-((3-methoxyphenyl)amino)-2-oxoethyl)-1-methyl-6-((tetrahydro-2H-pyran-2-yl)methoxy)-1,2,3,4-tetrahydroisoquinolin-7-yl)oxy)-[1,1'-biphenyl]-4-carboxylic acid

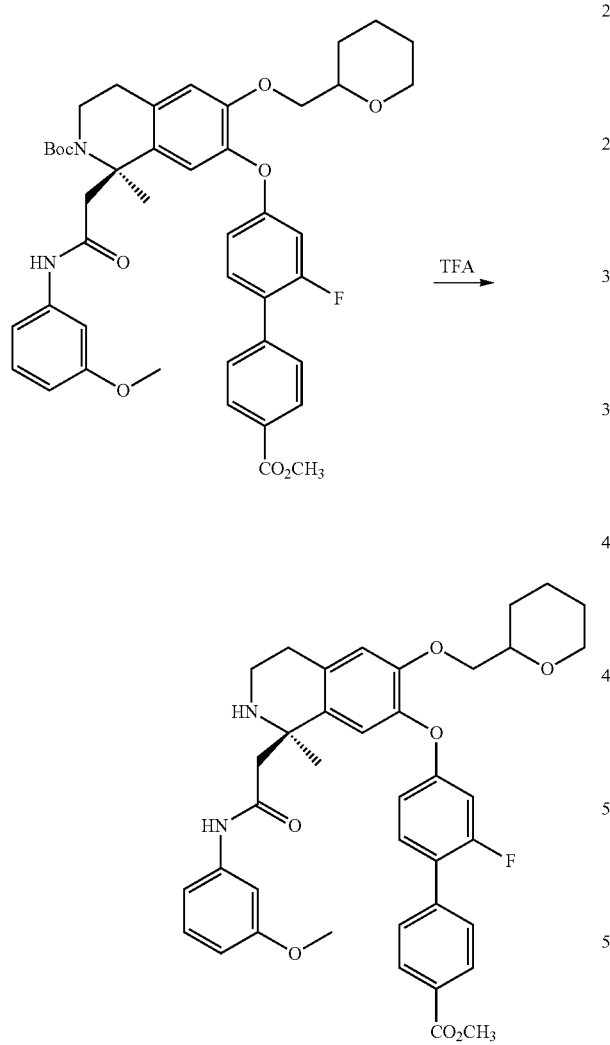

The title compound from scheme 11, step C (27.0 mg, 0.035 mmol) was dissolved in dichloromethane (1.00 mL) and then trifluoroacetic acid (2.7 µl, 0.04 mmol) was added at room temperature. After stirring for 1 hour at room temperature the solution was concentrated under reduced pressure to give the title compound: LCMS m/z 669.27 [M+H]$^+$.

The title compound from scheme 11, step D (5.0 mg, 6.0 µmol) was stirred in methanol (0.50 mL) and water (0.50 mL) before sodium hydroxide (0.26 mg, 6.4 µmol) was added at room temperature. The reaction mixture was stirred for 2 hours at room temperature and was then acidified with TFA and purified by preparative HPLC on a C18 reverse-phase column eluting with 10-100% acetonitrile/water with 0.05% TFA as an additive to give the title compound: LCMS m/z 655.35 [M+H]$^+$.

EXAMPLES 86-92 in the table below were prepared in an analogous fashion as described for EXAMPLE 85 and generally shown in Scheme 11, substituting the appropriate reactants and reagents that are prepared as described herein or that are commercially available.

| EX. No. | Structure | Name | LC/MS [M + H]+ |
|---|---|---|---|
| 86 | 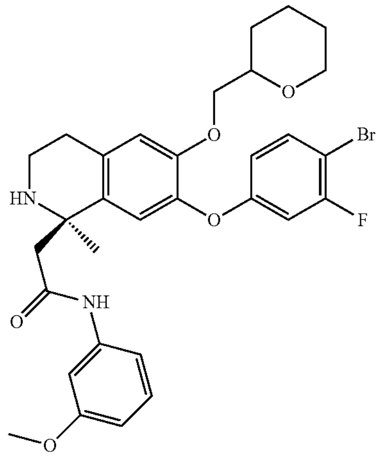 [SMILES: COc1cccc(NC(=O)C[C@@]2(C)NCCc3cc(OCC4CCCCO4)c(Oc4ccc(Br)c(F)c4)cc32)c1] | 2-((1R)-7-(4-bromo-3-fluorophenoxy)-1-methyl-6-((tetrahydro-2H-pyran-2-yl)methoxy)-1,2,3,4-tetrahydroisoquinolin-1-yl)-N-(3-methoxyphenyl)acetamide | 615.08 |
| 87 | 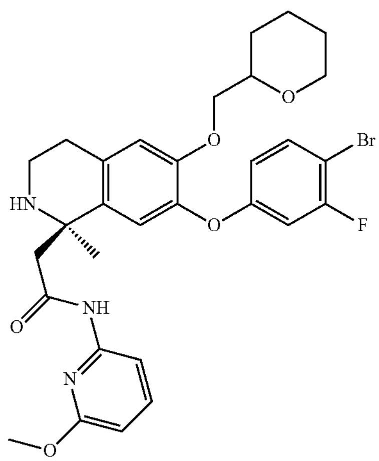 [SMILES: COc1cccc(NC(=O)C[C@@]2(C)NCCc3cc(OCC4CCCCO4)c(Oc4ccc(Br)c(F)c4)cc32)n1] | 2-((1R)-7-(4-bromo-3-fluorophenoxy)-1-methyl-6-((tetrahydro-2H-pyran-2-yl)methoxy)-1,2,3,4-tetrahydroisoquinolin-1-yl)-N-(6-methoxypyridin-2-yl)acetamide | 449.87 |
| 88 | 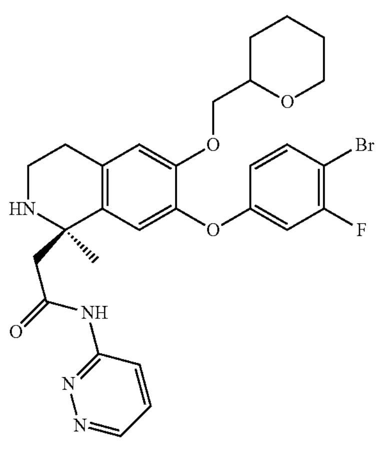 [SMILES: C[C@]1(CC(=O)Nc2cccnn2)NCCc2cc(OCC3CCCCO3)c(Oc3ccc(Br)c(F)c3)cc21] | 2-((1R)-7-(4-bromo-3-fluorophenoxy)-1-methyl-6-((tetrahydro-2H-pyran-2-yl)methoxy)-1,2,3,4-tetrahydroisoquinolin-1-yl)-N-(pyridazin-3-yl)acetamide | 586.93 |

| EX. No. | Structure | Name | LC/MS [M + H]⁺ |
|---|---|---|---|
| 89 | 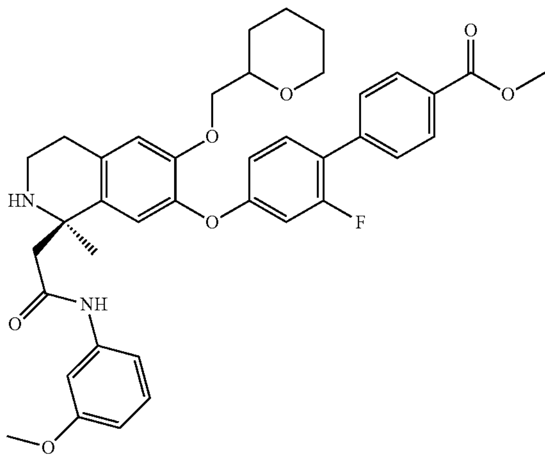 | methyl 2'-fluoro-4'-(((1R)-1-(2-((3-methoxyphenyl)amino)-2-oxoethyl)-1-methyl-6-((tetrahydro-2H-pyran-2-yl)methoxy)-1,2,3,4-tetrahydroisoquinolin-7-yl)oxy)-[1,1'-biphenyl]-4-carboxylate | 669.27 |
| 90 | 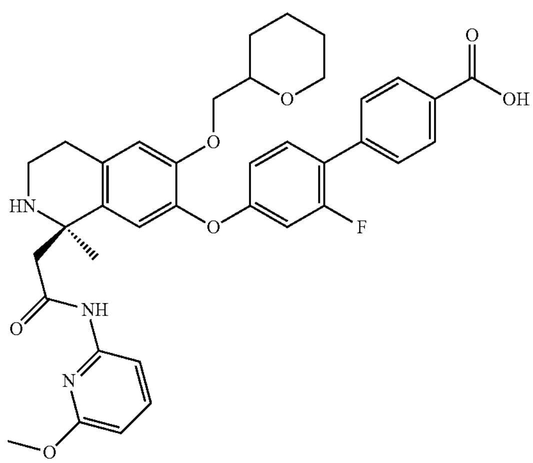 [SMILES: COc1cccc(NC(=O)C[C@@]2(C)NCCc3cc(OCC4CCCCO4)c(Oc4ccc(-c5ccc(C(=O)O)cc5)c(F)c4)cc32)n1] | 2'-fluoro-4'-(((1R)-1-(2-((6-methoxypyridin-2-yl)amino)-2-oxoethyl)-1-methyl-6-((tetrahydro-2H-pyran-2-yl)methoxy)-1,2,3,4-tetrahydroisoquinolin-7-yl)oxy)-[1,1'-biphenyl]-4-carboxylic acid | |
| 91 | 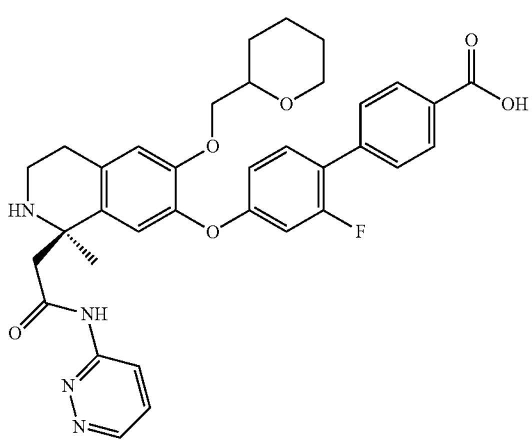 [SMILES: C[C@]1(CC(=O)Nc2cccnn2)NCCc2cc(OCC3CCCCO3)c(Oc3ccc(-c4ccc(C(=O)O)cc4)c(F)c3)cc21] | 2'-fluoro-4'-(((1R)-1-methyl-1-(2-oxo-2-(pyridazin-3-ylamino)ethyl)-6-((tetrahydro-2H-pyran-2-yl)methoxy)-1,2,3,4-tetrahydroisoquinolin-7-yl)oxy)-[1,1'-biphenyl]-4-carboxylic acid | 627.21 |

| EX. No. | Structure | Name | LC/MS [M + H]+ |
|---|---|---|---|
| 92 | 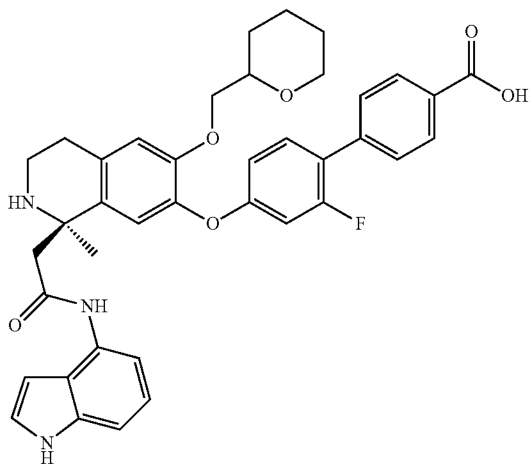 [SMILES: C[C@]1(CC(=O)Nc2cccc3[nH]ccc23)NCCc2cc(OCC3CCCCO3)c(Oc3ccc(-c4ccc(C(=O)O)cc4)c(F)c3)cc21] | 4'-(((1R)-1-(2-((1H-indol-4-yl)amino)-2-oxoethyl)-1-methyl-6-((tetrahydro-2H-pyran-2-yl)methoxy)-1,2,3,4-tetrahydroisoquinolin-7-yl)oxy)-2'-fluoro-[1,1'-biphenyl]-4-carboxylic acid | 664.26 |

Examples 93-108

Example 93: 2'-fluoro-4'-(((R)-6-(2-(2-(2-((S)-2-(4-isobutyl)phenyl)propanamido)ethoxy)ethoxy)ethoxy)-1-methyl-1-(2-oxo-2-(thiazol-2-ylamino)ethyl)-1,2,3,4-tetrahydroisoquinolin-7-yl)oxy)-[1,1'-biphenyl]-4-carboxylic acid

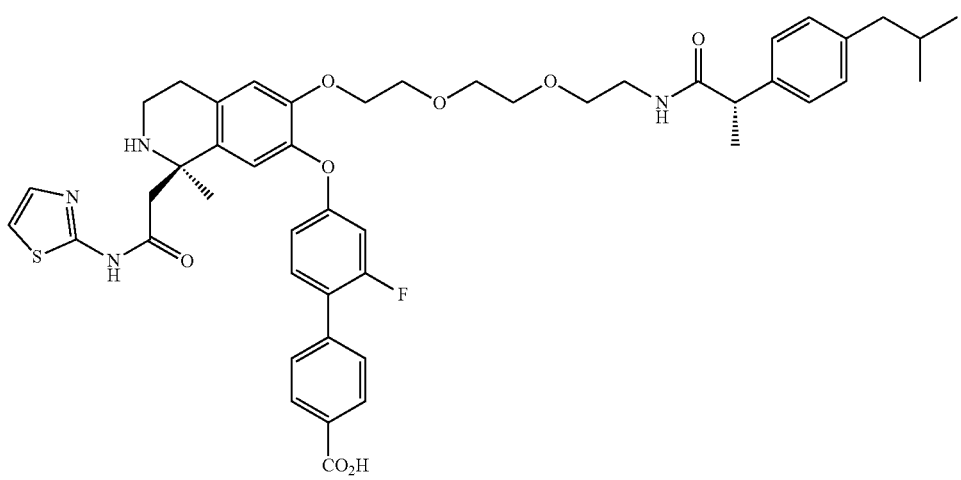 [SMILES: CC(C)Cc1ccc([C@H](C)C(=O)NCCOCCOCCOc2cc3c(cc2Oc2ccc(-c4ccc(C(=O)O)cc4)c(F)c2)[C@@](C)(CC(=O)Nc2nccs2)NCC3)cc1]

Example 93 was made according to general Scheme 12 below.

Scheme 12
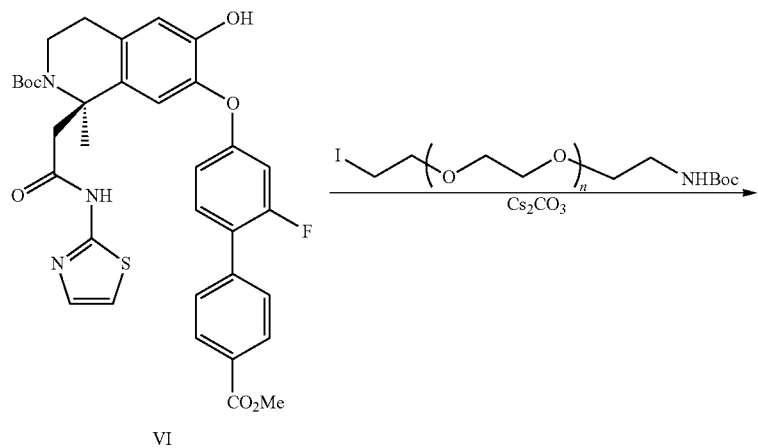
VI
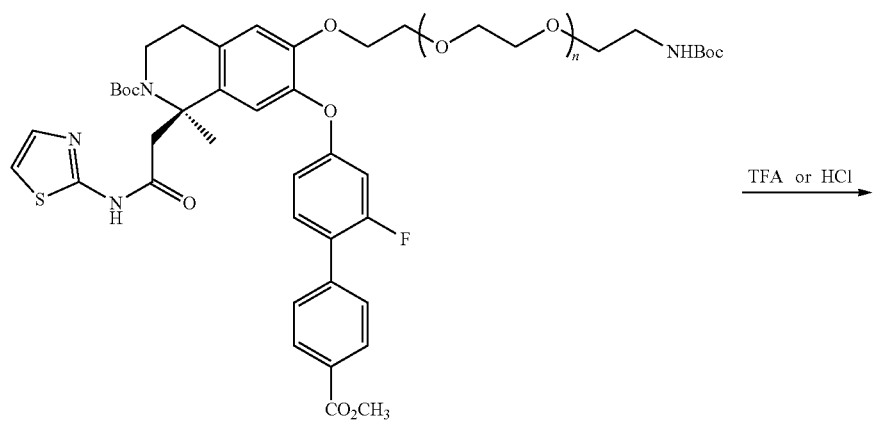
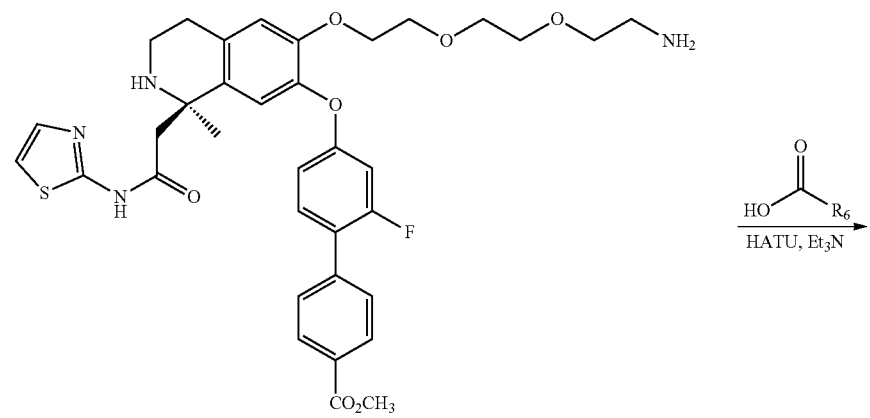

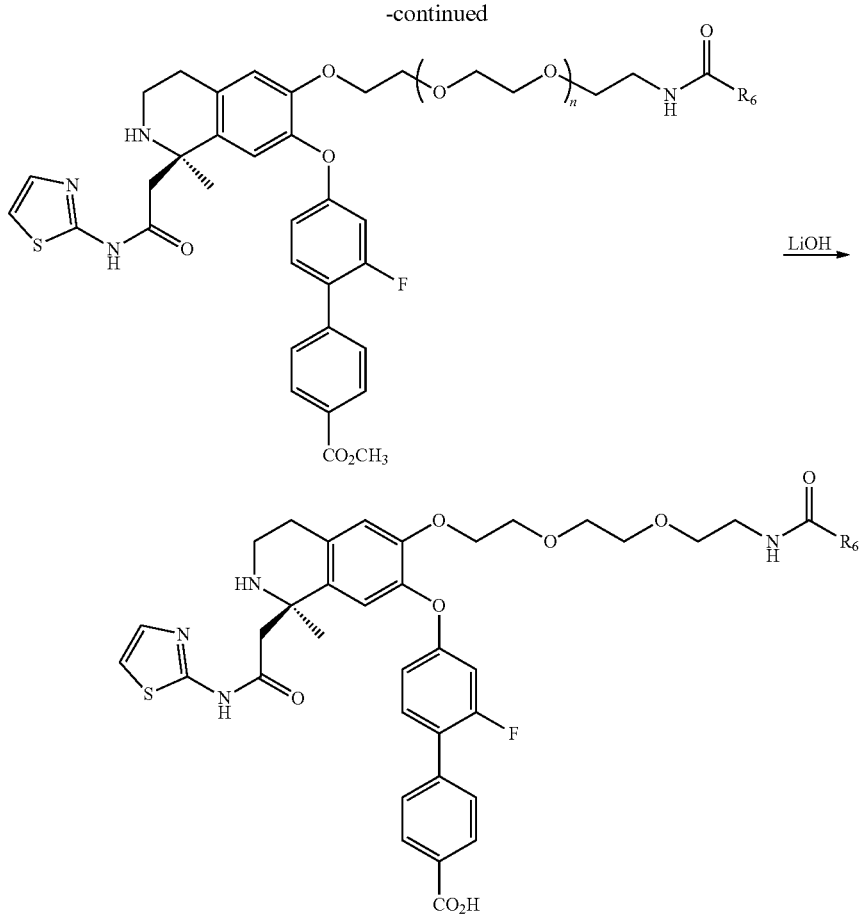

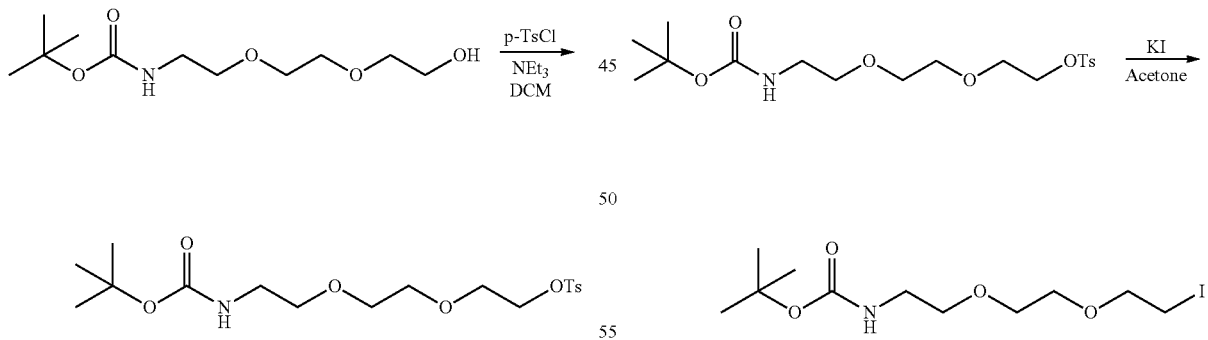

Step A: 2,2-dimethyl-4-oxo-3,8,11-trioxa-5-azatridecan-13-yl 4-methylbenzenesulfonate Step B: tert-butyl (2-(2-(2-iodoethoxy)ethoxy)ethyl)carbamate To a solution of tert-butyl (2-(2-(2-hydroxyethoxy)ethoxy)ethyl)carbamate (1.10 g, 4.41 mmol) in dichloromethane (15.0 mL) was added p-toluenesulfonyl chloride (1.26 g, 6.62 mmol) and triethylamine (1.23 mL, 8.82 mmol). The reaction was stirred for 24 h at room temperature. The solution was concentrated and then dichloromethane (3.00 mL) and hexane (3.00 mL) were added. The solid was filtered off and the filtrate was purified by column chromatography on silica gel eluting with 0 to 75% ethyl acetate/hexane to give the title compound: LCMS m/z 426.3 [M+Na]$^+$.

To a solution of the title compound from scheme 12, step A (1.69 g, 4.19 mmol) in acetone (25 mL) was added potassium iodide (1.39 g, 8.38 mmol). The reaction was heated to 65° C. for 18 h. The solution was concentrated and then ethyl acetate (20 mL) and water (5 mL) were added. The layers were separated and the organic layer was washed with sat aq $Na_2S_2O_3$ solution (3 mL) and brine (3 mL), dried (MgSO4), and purified by column chromatography on silica gel eluting with 0 to 70% ethyl acetate/hexane to give the title compound: LCMS m/z 360.2 [M+H]$^+$.

Step C: tert-butyl (R)-6-((2,2-dimethyl-4-oxo-3,8,11-trioxa-5-azatridecan-13-yl)oxy)-7-((2-fluoro-4'-(methoxycarbonyl)-[1,1'-biphenyl]-4-yl)oxy)-1-methyl-1-(2-oxo-2-(thiazol-2-ylamino)ethyl)-3,4-dihydroisoquinoline-2(1H)-carboxylate

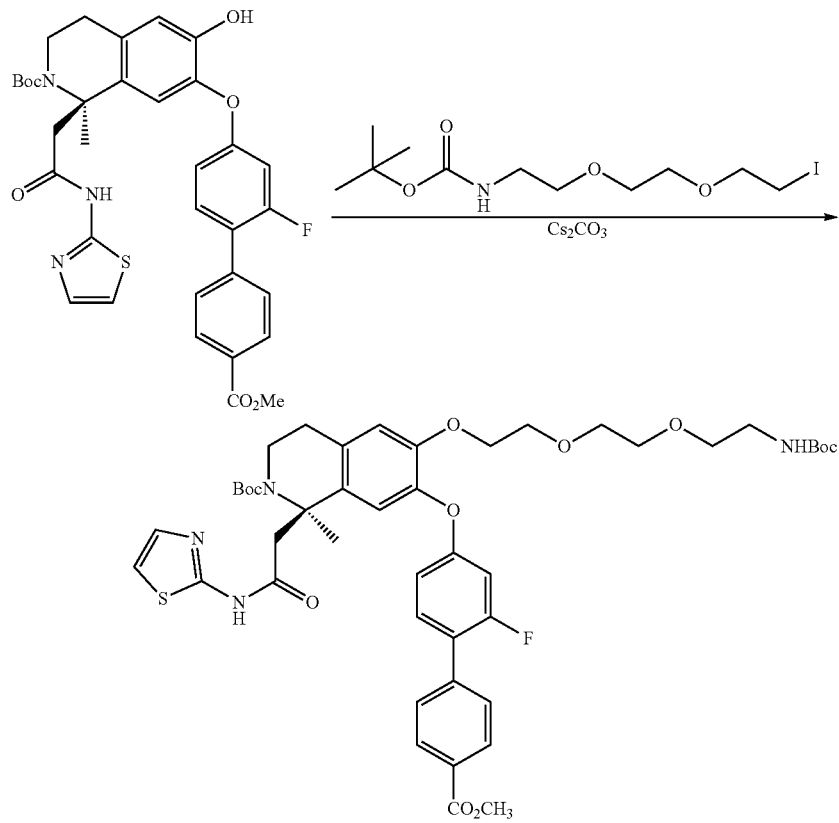

To a solution of Intermediate VI (scheme 5, step C, 125 mg, 0.193 mmol) in N,N-dimethylformamide (2.2 mL) at −10° C. was added cesium carbonate (82.0 mg, 0.251 mmol) and the title compound from Scheme 11, step B (97.0 mg, 0.270 mmol). It was slowly warmed to rt over 18 h. To the reaction was added saturated aqueous ammonium chloride solution (0.5 mL) and water (1 mL). The layers were separated and organic layer was washed with water (1 mL), brine (1 mL), dried over magnesium sulfate and concentrated. The resultant product was purified by column chromatography on silica gel eluting with 0 to 35 to 55% ethyl acetate/hexane to give the title compound: LCMS m/z 879.6 [M+H]⁺.

Step D: methyl (R)-4'-((6-(2-(2-(2-aminoethoxy)ethoxy)ethoxy)-1-methyl-1-(2-oxo-2-(thiazol-2-ylamino)ethyl)-1,2,3,4-tetrahydroisoquinolin-7-yl)oxy)-2'-fluoro-[1,1'-biphenyl]-4-carboxylate

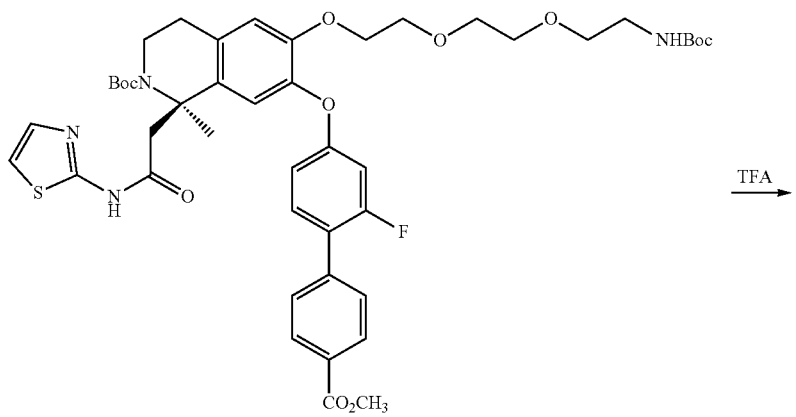

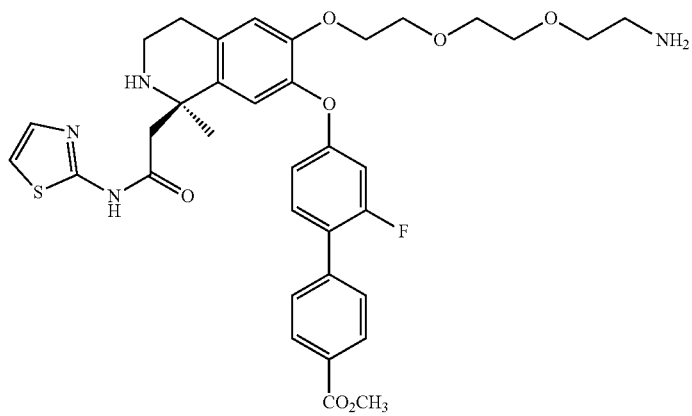

To a solution of the title compound from scheme 12, step C (69.0 mg, 0.078 mmol) in dichloromethane (1.00 mL) was added a solution of trifluoroacetic acid (0.121 mL, 1.57 mmol) in dichloromethane (200 μL) dropwise. After 3 h at room temperature, LCMS showed the completion of the reaction. It was concentrated and purified by reverse phase chromatography (C18 column, eluting with 0 to 60% acetonitrile/water both with 0.05% v/v trifluoroacetic acid) to give the title compound: LCMS m/z 679.5 [M+H]$^+$.

Step E: methyl 2'-fluoro-4'-(((R)-6-(2-(2-(2-((S)-2-(4-isobutylphenyl)propanamido)ethoxy)ethoxy)ethoxy)-1-methyl-1-(2-oxo-2-(thiazol-2-ylamino)ethyl)-1,2,3,4-tetrahydroisoquinolin-7-yl)oxy)-[1,1'-biphenyl]-4-carboxylate

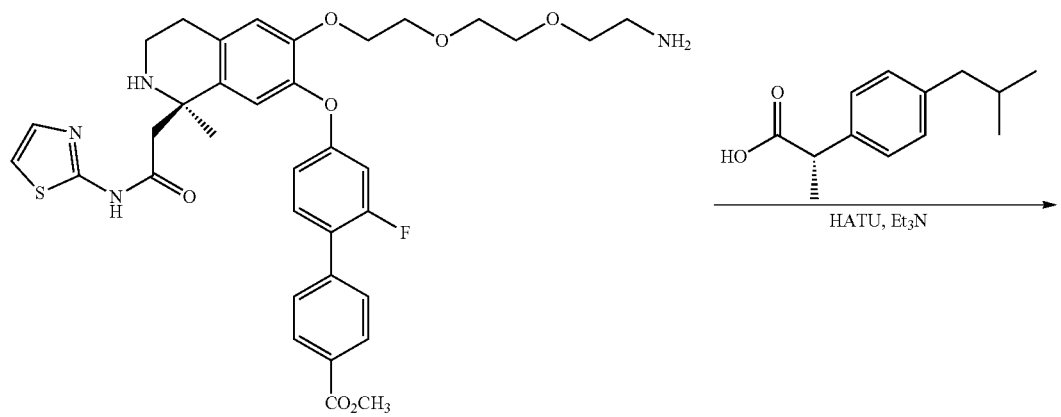

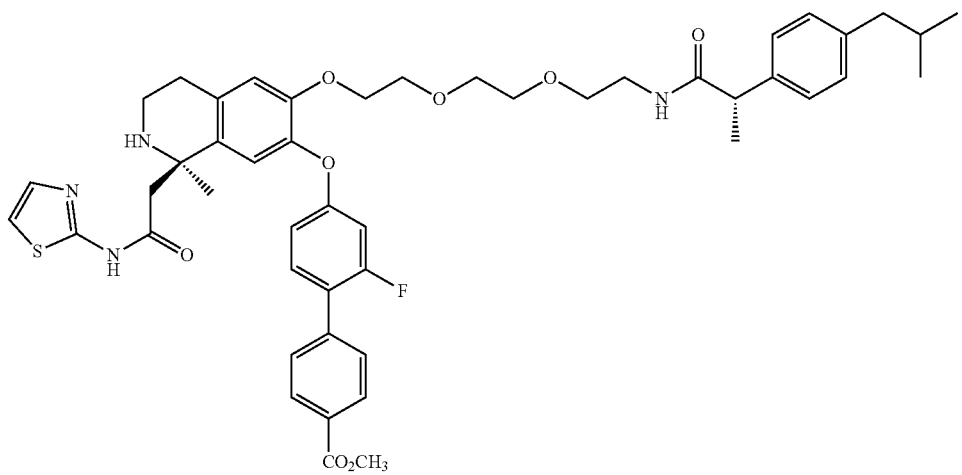

To a solution of the title compound in scheme 12, step D (9.00 mg, 0.013 mmol) and 1-[Bis(dimethylamino)methylene]-1H-1,2,3-triazolo[4,5-b]pyridinium 3-oxid hexafluorophosphate (5.04 mg, 0.013 mmol) in dichloromethane (1.50 mL) at rt was added triethylamine (1.85 μL, 0.013 mmol). After stirring for thirty minutes the reaction mixture was added to a solution of (S)-2-(4-isobutylphenyl)propanoic acid (2.74 mg, 0.013 mmol) in dichloromethane (1.5 mL) at 0° C. The activated ester solution was added dropwise. After 1 hr, LCMS showed completion of the reaction. Water (0.1 mL) was added and the mixture was stirred for half an hour. The organic layer was separated, concentrated and purified by column chromatography on silica gel (0 to 10% methanol in dichloromethane) to give the title compound: LCMS m/z 867.6 [M+H]$^+$.

Step F: 2'-fluoro-4'-(((R)-6-(2-(2-(2-((S)-2-(4-isobutylphenyl)propanamido)ethoxy)ethoxy)ethoxy)-1-methyl-1-(2-oxo-2-(thiazol-2-ylamino)ethyl)-1,2,3,4-tetrahydroisoquinolin-7-yl)oxy)-[1,1'-biphenyl]-4-carboxylic acid

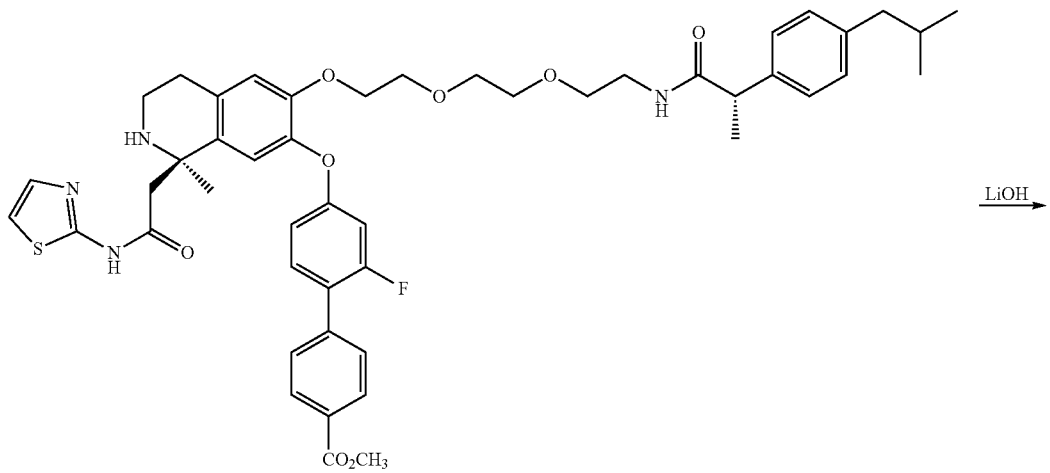

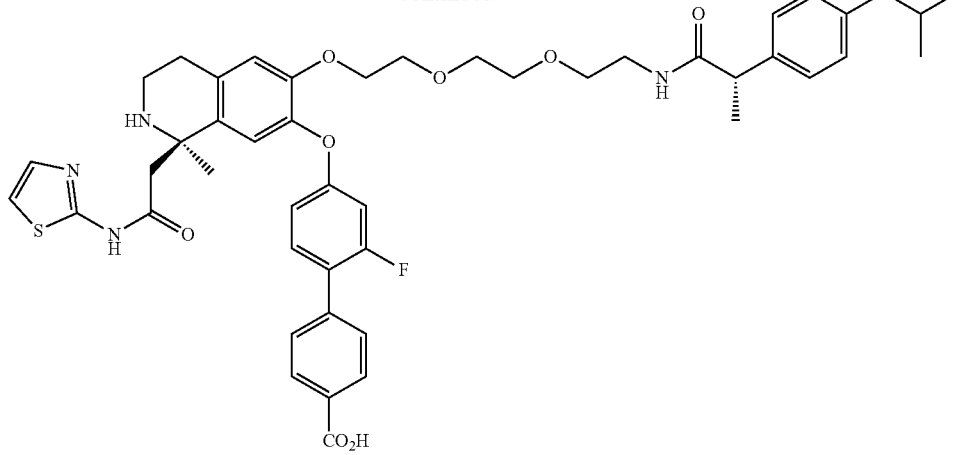

To a solution of the title compound from scheme 12, step E (6.90 mg, 7.96 μmol) in tetrahydrofuran (1 mL) was added lithium hydroxide (1M aqueous solution, 0.10 mL, 0.10 mmol). The reaction was heated to 45° C. for 20 hours. It was concentrated and purified by preparative HPLC (C18 column, 10 to 60% acetonitrile/water both 0.05%/0/v trifluoroacetic acid) to afford the title compound: LCMS m/z 853.6 [M+H]+.

EXAMPLES 94-108 in the table below were prepared in an analogous fashion as described for EXAMPLE 93 and generally shown in Scheme 12, substituting the appropriate reactants and reagents that are prepared as described herein or that are commercially available.

| EX. No. | Structure | Name | LC/MS [M + H]+ |
|---|---|---|---|
| 94 | 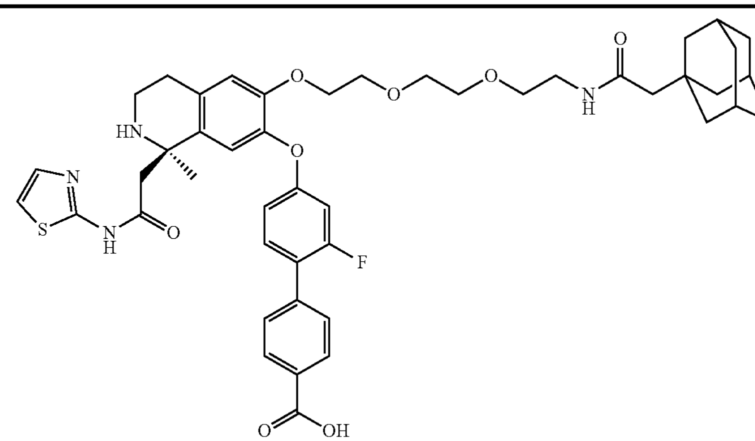 | 4-(((R)-6-(2-(2-(2-(2-((3r,5r,7r)-adamantan-1-yl)acetamido)ethoxy)ethoxy)ethoxy)-1-methyl-1-(2-oxo-2-(thiazol-2-ylamino)ethyl)-1,2,3,4-tetrahydroisoquinolin-7-yl)oxy)-2'-fluoro-[1,1'-biphenyl]-4-carboxylic acid | 841.5 |
| 95 | 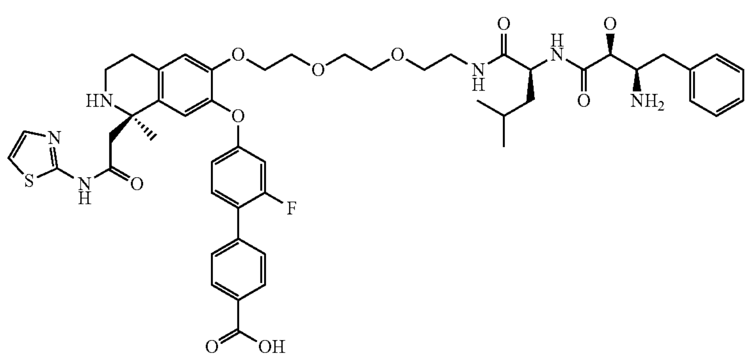 [SMILES: CC(C)C[C@H](NC(=O)[C@@H](O)[C@H](N)Cc1ccccc1)C(=O)NCCOCCOCCOc1cc2c(cc1Oc1ccc(-c3ccc(C(=O)O)cc3)c(F)c1)[C@@](C)(CC(=O)Nc1nccs1)NCC2] | 4'-(((R)-6-(((11S,14S,15R)-15-amino-14-hydroxy-11-isobutyl-10,13-dioxo-16-phenyl-3,6-dioxa-9,12-diazahexadecyl)oxy)-1-methyl-1-(2-oxo-2-(thiazol-2-ylamino)ethyl)-1,2,3,4-tetrahydroisoquinolin-7-yl)oxy)-2'-fluoro-[1,1'-biphenyl]-4-carboxylic acid | 955.7 |

| EX. No. | Structure | Name | LC/MS [M + H]+ |
|---|---|---|---|
| 96 | 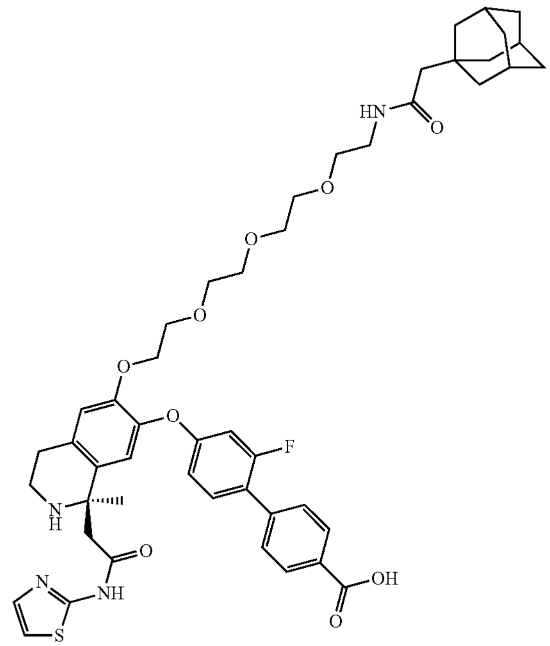 [SMILES: C[C@]1(CC(=O)Nc2nccs2)NCCc2cc(OCCOCCOCCOCCNC(=O)CC34CC5CC(CC(C5)C3)C4)c(Oc3ccc(-c4ccc(C(=O)O)cc4)c(F)c3)cc21] | 4'-(((1R)-6-((1-(1s,3s)-adamantan-1-yl)-2-oxo-6,9,12-trioxa-3-azatetradecan-14-yl)oxy)-1-methyl-1-(2-oxo-2-(thiazol-2-ylamino)ethyl)-1,2,3,4-tetrahydroisoquinolin-7-yl)oxy)-2'-fluoro-[1,1'-biphenyl]-4-carboxylic acid | 885.9 |
| 97 | 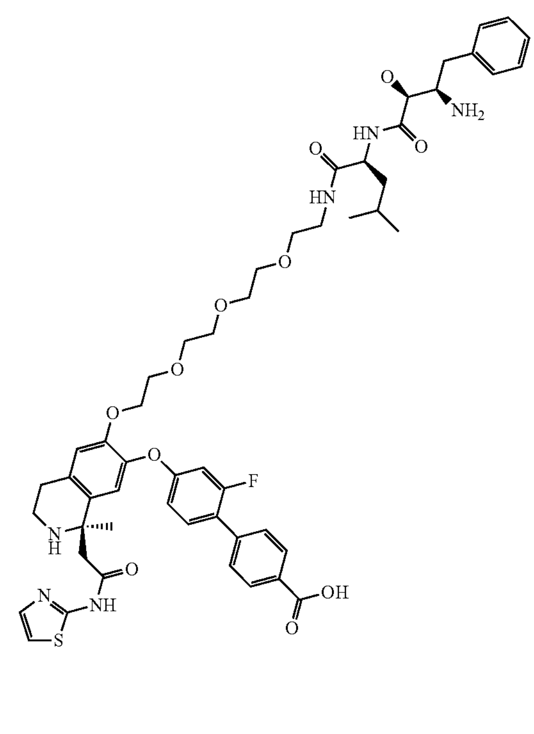 [SMILES: CC(C)C[C@H](NC(=O)[C@@H](O)[C@H](N)Cc1ccccc1)C(=O)NCCOCCOCCOCCOc1cc2c(cc1Oc1ccc(-c3ccc(C(=O)O)cc3)c(F)c1)[C@@](C)(CC(=O)Nc1nccs1)NCC2] | 4'-(((R)-6-(((14S,17S,18R)-18-amino-17-hydroxy-14-isobutyl-13,16-dioxo-19-phenyl-3,6,9-trioxa-12,15-diazanonadecyl)oxy)-1-methyl-1-(2-oxo-2-(thiazol-2-ylamino)ethyl)-1,2,3,4-tetrahydroisoquinolin-7-yl)oxy)-2'-fluoro-[1,1'-biphenyl]-4-carboxylic acid | 999.7 |

| EX. No. | Structure | Name | LC/MS [M + H]+ |
|---|---|---|---|
| 98 | 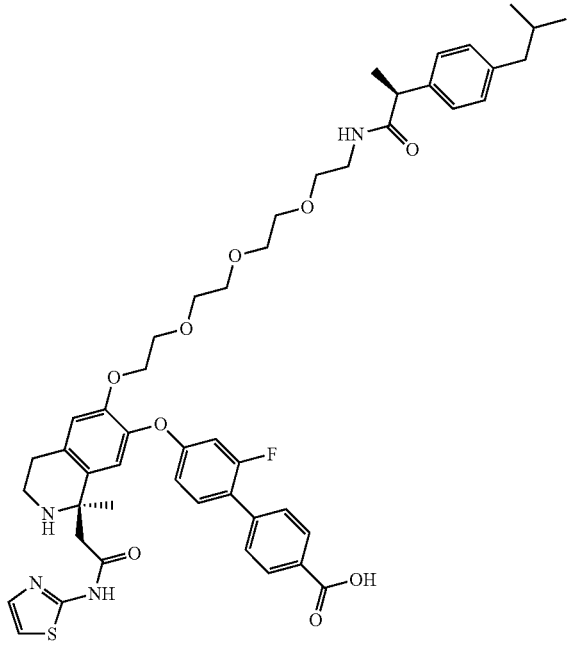 [SMILES: CC(C)Cc1ccc([C@H](C)C(=O)NCCOCCOCCOCCOc2cc3c(cc2Oc2ccc(-c4ccc(C(=O)O)cc4)c(F)c2)[C@@](C)(CC(=O)Nc2nccs2)NCC3)cc1] | 2'-fluoro-4'-(((R)-6-(((S)-14-(4-isobutylphenyl)-13-oxo-3,6,9-trioxa-12-azapentadecyl)oxy)-1-methyl-1-(2-oxo-2-(thiazol-2-ylamino)ethyl)-1,2,3,4-tetrahydroisoquinolin-7-yl)oxy)-[1,1'-biphenyl]-4-carboxylic acid | 898.0 |
| 99 | 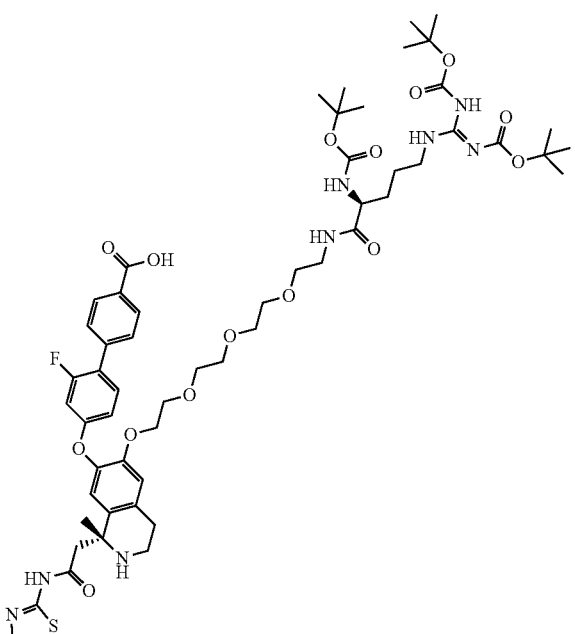 | 4'-(((R)-6-(((S,Z)-6,11-bis((tert-butoxycarbonyl)amino)-2,2-dimethyl-4,12-dioxo-3,16,19,22-tetraoxa-5,7,13-triazatetracos-5-en-24-yl)oxy)-1-methyl-1-(2-oxo-2-(thiazol-2-ylamino)ethyl)-1,2,3,4-tetrahydroisoquinolin-7-yl)oxy)-2'-fluoro-[1,1'-biphenyl]-4-carboxylic acid | 1165 |

-continued
| EX. No. | Structure | Name | LC/MS [M + H]+ |
|---|---|---|---|
| 100 | 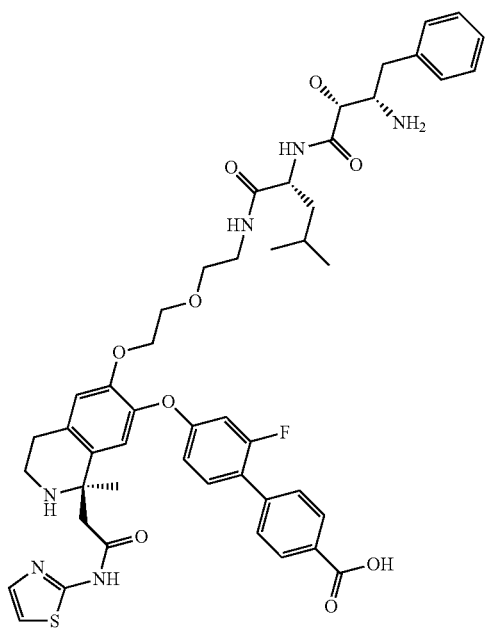 [SMILES: CC(C)C[C@@H](NC(=O)[C@H](O)[C@@H](N)Cc1ccccc1)C(=O)NCCOCCOc1cc2c(cc1Oc1ccc(-c3ccc(C(=O)O)cc3)c(F)c1)[C@@](C)(CC(=O)Nc1nccs1)NCC2] | 4'-(((R)-6-(2-(2-((R)-2-((2R,3S)-3-amino-2-hydroxy-4-phenylbutanamido)-4-methylpentanamido)ethoxy)ethoxy)-1-methyl-1-(2-oxo-2-(thiazol-2-ylamino)ethyl)-1,2,3,4-tetrahydroisoquinolin-7-yl)oxy)-2'-fluoro-[1,1'-biphenyl]-4-carboxylic acid | 911.6 |
| 101 | 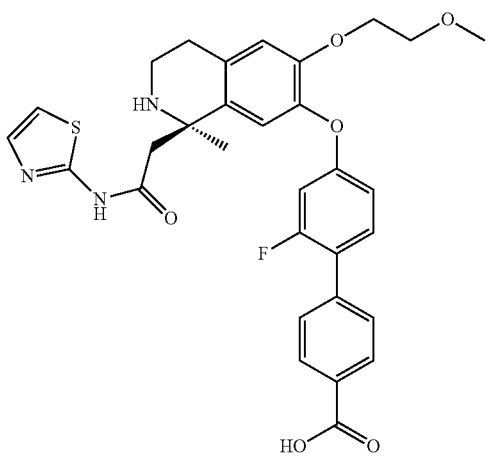 [SMILES: COCCOc1cc2c(cc1Oc1ccc(-c3ccc(C(=O)O)cc3)c(F)c1)[C@@](C)(CC(=O)Nc1nccs1)NCC2] | (R)-2'-fluoro-4'-((6-(2-methoxyethoxy)-1-methyl-1-(2-oxo-2-(thiazol-2-ylamino)ethyl)-1,2,3,4-tetrahydroisoquinolin-7-yl)oxy)-[1,1'-biphenyl]-4-carboxylic acid | 592.3 |

-continued

| EX. No. | Structure | Name | LC/MS [M + H]+ |
|---|---|---|---|
| 102 | 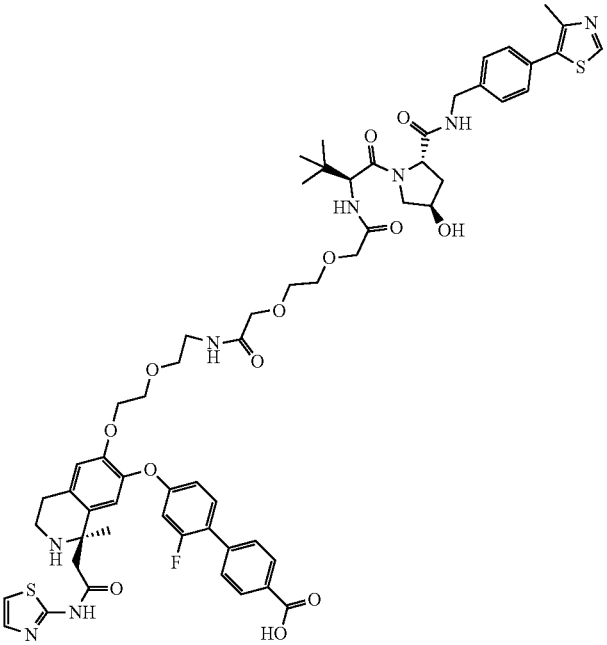 [SMILES: Cc1ncsc1-c1ccc(CNC(=O)[C@@H]2C[C@@H](O)CN2C(=O)[C@@H](NC(=O)COCCOCC(=O)NCCOCCOc2cc3c(cc2Oc2ccc(-c4ccc(C(=O)O)cc4)c(F)c2)[C@@](C)(CC(=O)Nc2nccs2)NCC3)C(C)(C)C)cc1] | 2'-fluoro-4'-(((R)-6-(((S)-16-((2S,4R)-4-hydroxy-2-((4-(4-methylthiazol-5-yl)benzyl)carbamoyl)pyrrolidine-1-carbonyl)-17,17-dimethyl-7,14-dioxo-3,9,12-trioxa-6,15-diazaoctadecyl)oxy)-1-methyl-1-(2-oxo-2-(thiazol-2-ylamino)ethyl)-1,2,3,4-tetrahydroisoquinolin-7-yl)oxy)-[1,1'-biphenyl]-4-carboxylic acid | 1193.7 |
| 103 | 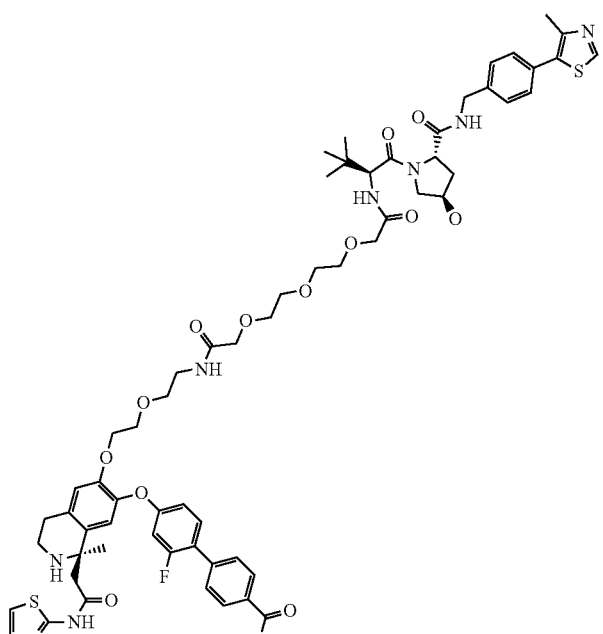 | 2'-fluoro-4'-(((R)-6-(((S)-19-((2S,4R)-4-hydroxy-2-((4-(4-methylthiazol-5-yl)benzyl)carbamoyl)pyrrolidine-1-carbonyl)-20,20-dimethyl-7,17-dioxo-3,9,12,15-tetraoxa-6,18-diazahenicosyl)oxy)-1-methyl-1-(2-oxo-2-(thiazol-2-ylamino)ethyl)-1,2,3,4-tetrahydroisoquinolin-7-yl)oxy)-[1,1'-biphenyl]-4-carboxylic acid | 1238.7 |

-continued

| EX. No. | Structure | Name | LC/MS [M + H]+ |
|---|---|---|---|
| 104 | 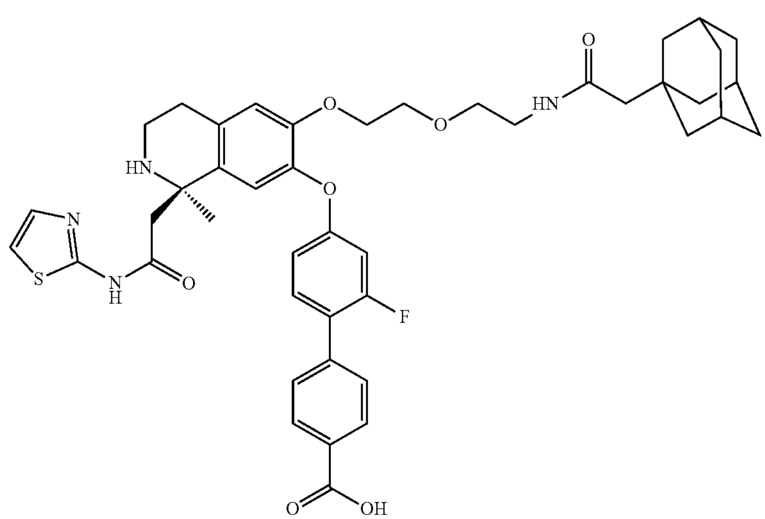 [SMILES: C[C@]1(CC(=O)Nc2nccs2)NCCc2cc(OCCOCCNC(=O)CC34CC5CC(CC(C5)C3)C4)c(Oc3ccc(-c4ccc(C(=O)O)cc4)c(F)c3)cc21] | 4'-(((R)-6-(2-(2-(2-((3r,5r,7r)-adamantan-1-yl)acetamido)ethoxy)ethoxy)-1-methyl-1-(2-oxo-2-(thiazol-2-ylamino)ethyl)-1,2,3,4-tetrahydroisoquinolin-7-yl)oxy)-2'-fluoro-[1,1'-biphenyl]-4-carboxylic acid | 797.4 |
| 105 | 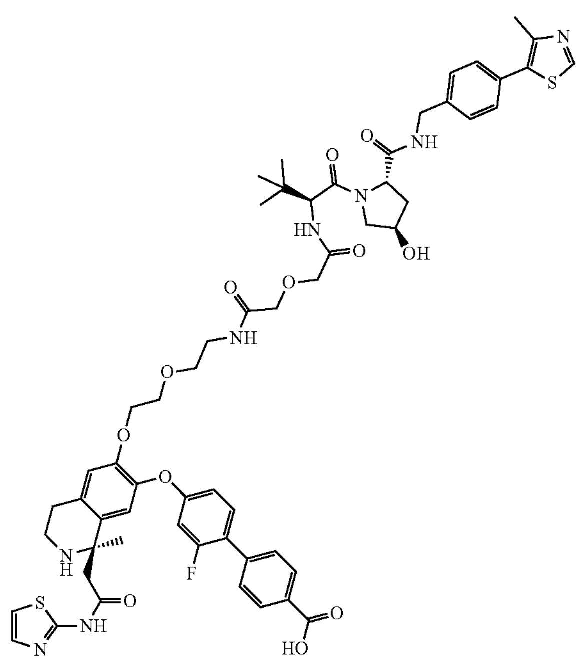 [SMILES: Cc1ncsc1-c1ccc(CNC(=O)[C@@H]2C[C@@H](O)CN2C(=O)[C@@H](NC(=O)COCC(=O)NCCOCCOc2cc3c(cc2Oc2ccc(-c4ccc(C(=O)O)cc4)c(F)c2)[C@@](C)(CC(=O)Nc2nccs2)NCC3)C(C)(C)C)cc1] | 2'-fluoro-4'-(((R)-6-(((S)-13-((2S,4R)-4-hydroxy-2-((4-(4-methylthiazol-5-yl)benzyl)carbamoyl)pyrrolidine-1-carbonyl)-14,14-dimethyl-7,11-dioxo-3,9-dioxa-6,12-diazapentadecyl)oxy)-1-methyl-1-(2-oxo-2-(thiazol-2-ylamino)ethyl)-1,2,3,4-tetrahydroisoquinolin-7-yl)oxy)-[1,1'-biphenyl]-4-carboxylic acid | 1150.4 |

-continued

| EX. No. | Structure | Name | LC/MS [M + H]+ |
|---|---|---|---|
| 106 | 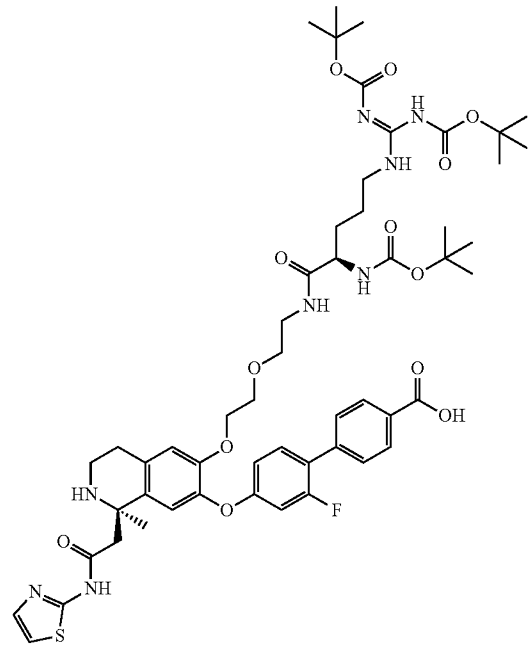 [SMILES: CC(C)(C)OC(=O)/N=C(/NCCC[C@@H](NC(=O)OC(C)(C)C)C(=O)NCCOCCOc1cc2c(cc1Oc1ccc(-c3ccc(C(=O)O)cc3)c(F)c1)[C@@](C)(CC(=O)Nc1nccs1)NCC2)NC(=O)OC(C)(C)C] | 4'-(((R)-6-(((R,Z)-6,11-bis((tert-butoxycarbonyl)amino)-2,2-dimethyl-4,12-dioxo-3,16-dioxa-5,7,13-triazaoctadec-5-en-18-yl)oxy)-1-methyl-1-(2-oxo-2-(thiazol-2-ylamino)ethyl)-1,2,3,4-tetrahydroisoquinolin-7-yl)oxy)-2'-fluoro-[1,1'-biphenyl]-4-carboxylic acid | 1077.38 |
| 107 | 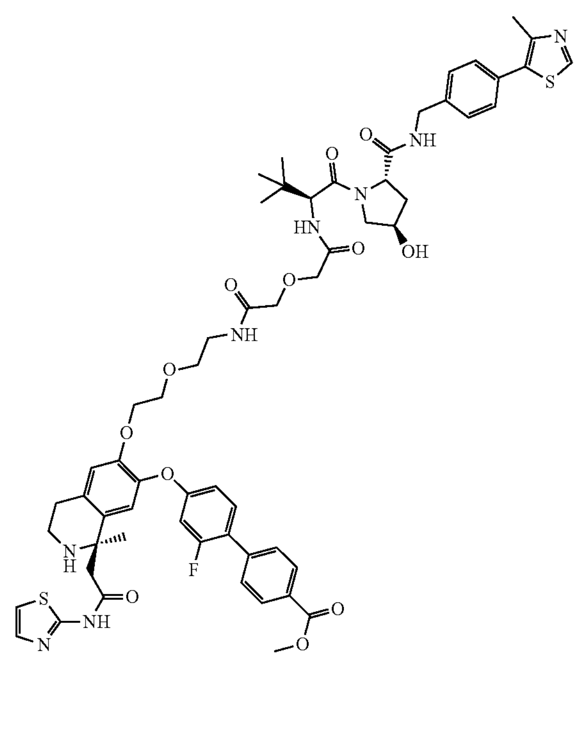 [SMILES: COC(=O)c1ccc(-c2ccc(Oc3cc4c(cc3OCCOCCNC(=O)COCC(=O)N[C@H](C(=O)N3C[C@H](O)C[C@H]3C(=O)NCc3ccc(-c5scnc5C)cc3)C(C)(C)C)CCN[C@]4(C)CC(=O)Nc3nccs3)cc2F)cc1] | methyl 2'-fluoro-4'-(((R)-6-(((S)-13-(((2S,4R)-4-hydroxy-2-((4-(4-methylthiazol-5-yl)benzyl)carbamoyl)pyrrolidine-1-carbonyl)-14,14-dimethyl-7,11-dioxo-3,9-dioxa-6,12-diazapentadecyl)oxy)-1-methyl-1-(2-oxo-2-(thiazol-2-ylamino)ethyl)-1,2,3,4-tetrahydroisoquinolin-7-yl)oxy)-[1,1'-biphenyl]-4-carboxylate | 1164.5 |

| EX. No. | Structure | Name | LC/MS [M + H]+ |
|---|---|---|---|
| 108 | 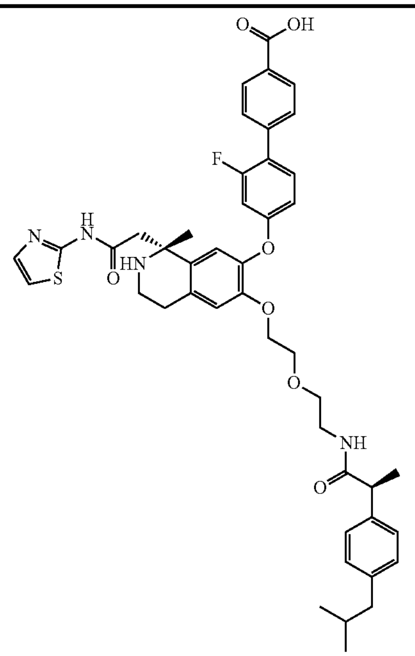 | 2'-fluoro-4'-(((R)-6-(2-(2-isobutylphenyl)propanamido)ethoxy)ethoxy)-1-methyl-1-(2-oxo-2-(thiazol-2-ylamino)ethyl)-1,2,3,4-tetrahydroisoquinolin-7-yl)oxy)-[1,1'-biphenyl]-4-carboxylic acid | 809.6 |

Example 109 methyl (R)-2-fluoro-5-(6-methoxy-1-methyl-1-(2-oxo-2-(thiazol-2-ylamino)ethyl)-1,2,3,4-tetrahydroisoquinolin-7-yl)benzoate

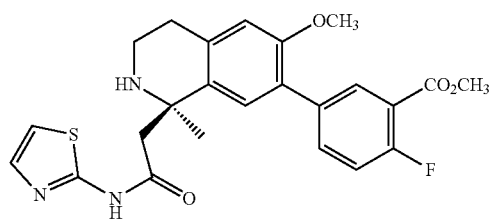 [SMILES: COC(=O)c1cc(-c2cc3c(cc2OC)CCN[C@]3(C)CC(=O)Nc2nccs2)ccc1F]

Example 109 was made according to general Scheme 13 below.

Scheme 13. Preparation of Intermediates VII and VIII

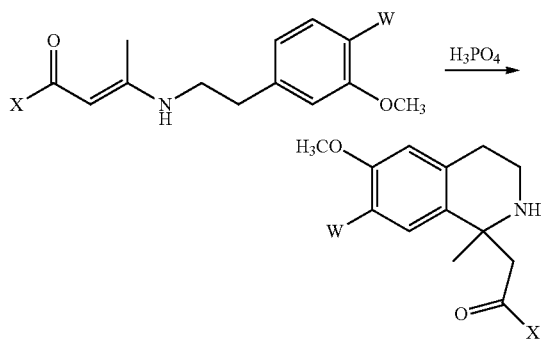

VII a and b
W = H, Br
X = -OEt or

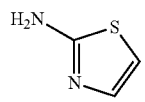

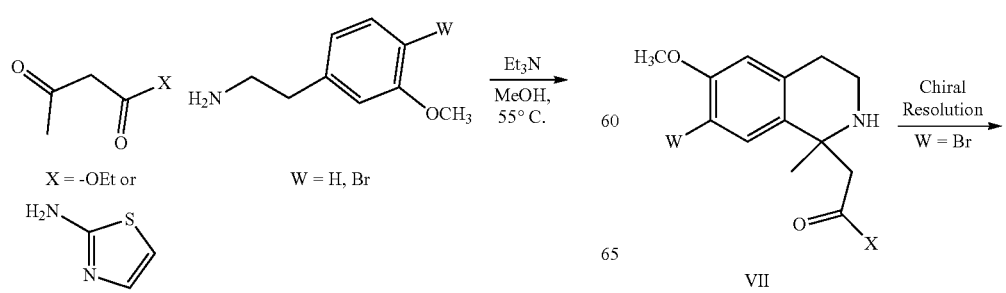

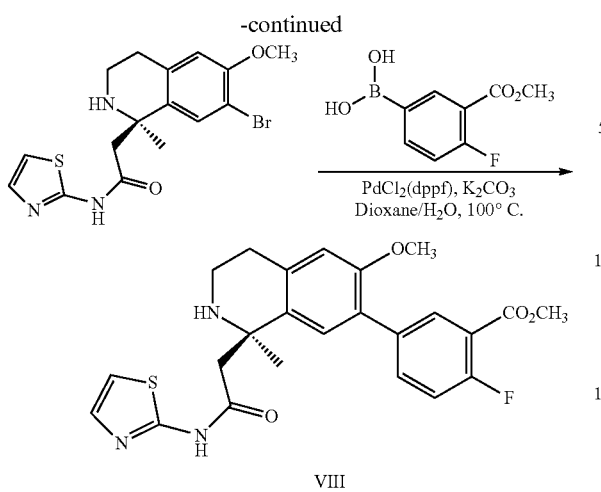

Step A: methyl 2'-fluoro-4'-(((R)-6-(2-(2-(2-((S)-2-(4-isobutylphenyl)propanamido)ethoxy)ethoxy)ethoxy)-1-methyl-1-(2-oxo-2-(thiazol-2-ylamino)ethyl)-1,2,3,4-tetrahydroisoquinolin-7-yl)oxy)-[1,1'-biphenyl]-4-carboxylate

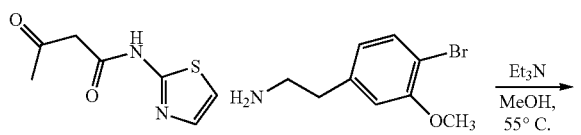

To a solution of 2-(3-methoxy-4-bromophenyl)ethylamine (1.00 g, 4.35 mmol) in methanol (8.69 mL) was added 3-oxo-N-(thiazol-2-yl)butanamide (0.801 g, 4.35 mmol) followed by the addition of triethylamine (1.51 mL, 10.9 mmol). The reaction mixture was heated to 55° C. Once the reaction was complete the solid was filtered off and dried under vacuum to afford the title compound: LCMS m/z 396.05 [M+H]⁺.

Step B: Preparation of Intermediate VIIa, Exemplified by 2-(7-bromo-6-methoxy-1-methyl-1,2,3,4-tetrahydroisoquinolin-1-yl)-N-(thiazol-2-yl)acetamide

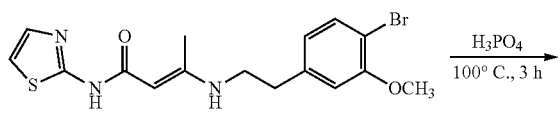

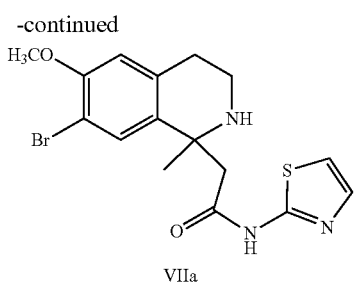

A vial of the title compound from scheme 13, step A (1.49 g, 3.77 mmol) and solid phosphoric acid (6.58 ml, 113 mmol) were placed in a vial. The reaction mixture was heated to 100° C. After heating; for 3 hours the reaction was cooled in an ice bath and then added to 10 mL of ice water with stirring. The acidic mixture was extracted with dichloromethane (3×5 mL). The aqueous layer was cooled in an ice bath and NH₄OH (aq) was added, with stirring, until a pH of 10 was obtained. The basic mixture was extracted with dichloromethane (3×10 mL). The organic layer was dried, filtered and concentrated. The residue was purified by column chromatography on silica gel, eluting with 0-10% EtOAc/MeOH/NH₃) to afford the title compound: LCMS m/z 398.05 [M+3H (Br)]⁺.

Intermediate VIIb in the table below was prepared in an analogous fashion as described for Intermediate VIIa substituting the appropriate reactants and reagents that are prepared as described herein or that are commercially available.

| EX. No. | Structure | Name | LC/MS [M + H]⁺ |
|---|---|---|---|
| VIIb | 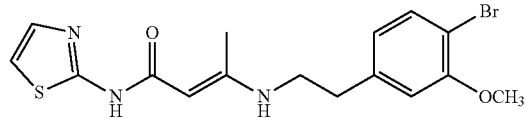 | ethyl 2-(6-methoxy-1-methyl-1,2,3,4-tetrahydroisoquinolin-1-yl)acetate | 264.23 [M + H]⁺ |

Step C: (R)-2-(7-bromo-6-methoxy-1-methyl-1,2,3,4-tetrahydroisoquinolin-1-yl)-N-(thiazol-2-yl)acetamide

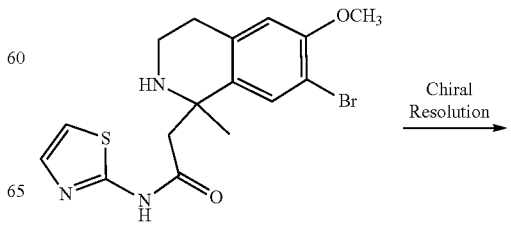

233
-continued

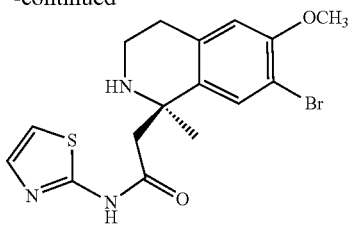

The racemic title compound was resolved by supercritical fluid chromatography on a chiral AD column, eluting with 40% ethanol:CO$_2$ (with 0.2% N,N-diisopropylethylamine). The fast eluting enantiomer A eluted at 3.7 minutes; the slow eluting enantiomer B eluted at 5.2 minutes. Data for the fast-eluting (R)-enantiomer: LCMS m/z 395.97 [M+H]$^+$. Data for the slower-eluting (S)-enantiomer: LCMS m/z 396.0 [M+H]$^+$. Enantiomer A was carried forward as the (R)-enantiomer.

Step D: Preparation of Intermediate VIII, Exemplified by Compound X (L-005028836-001K) methyl (R)-2-fluoro-5-(6-methoxy-1-methyl-1-(2-oxo-2-(thiazol-2-ylamino)ethyl)-1,2,3,4-tetrahydroisoquinolin-7-yl)benzoate

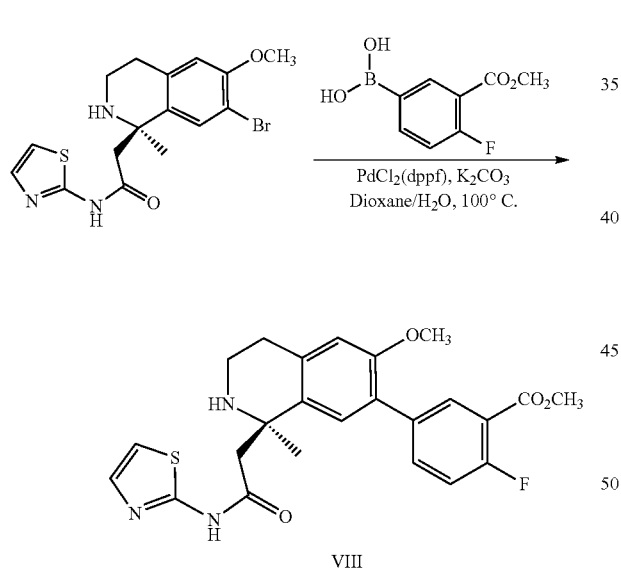

The title compound from scheme 13, step C (50 mg, 0.126 mmol) and (4-fluoro-3-(methoxycarbonyl)phenyl)boronic acid (31.2 mg, 0.158 mmol) were taken up in 1,4-dioxane (1.00 mL) and water (0.100 mL) and placed in a microwave tube. Potassium carbonate (69.7 mg, 0.505 mmol) and PdCl$_2$(dppf) (18.46 mg, 0.025 mmol) were added. The reaction was purged with nitrogen for 5 minutes and then heated in the microwave at 100° C. for 30 minutes. The layers were separated and then organic was concentrated to dryness. The resulting residue was purified by prep HPLC on a C18 reverse-phase column to afford the title compound: LCMS m/z 470.27 [M+H]$^+$.

234
Examples 110-111

Example 110: 2-fluoro-5-(1-methyl-1-(2-oxo-2-(thiazol-2-ylamino)ethyl)-6-((tetrahydro-2H-pyran-2-yl)methoxy)-1,2,3,4-tetrahydroisoquinolin-7-yl)benzoic acid

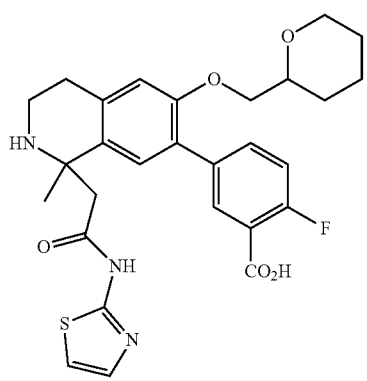 [SMILES: CC1(CC(=O)Nc2nccs2)NCCc2cc(OCC3CCCCO3)c(-c3ccc(F)c(C(=O)O)c3)cc21]

Example 110 was made according to general Scheme 14 below.

Scheme 14

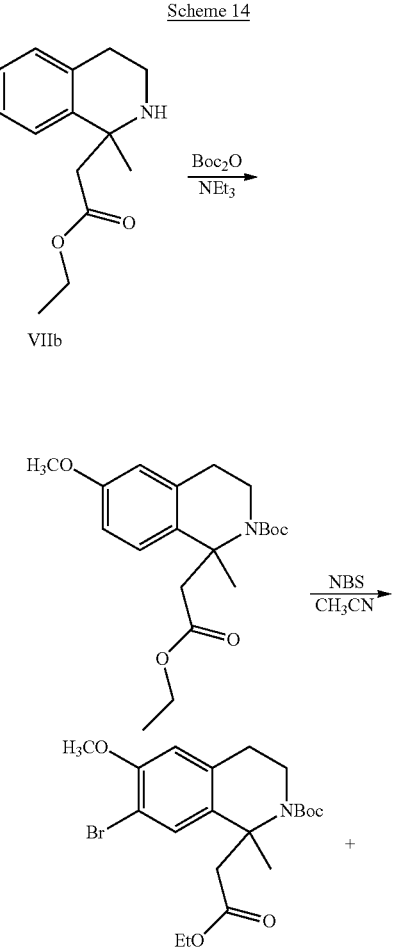

235
-continued

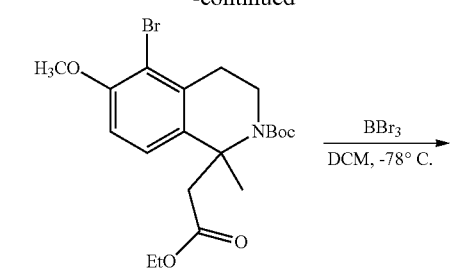

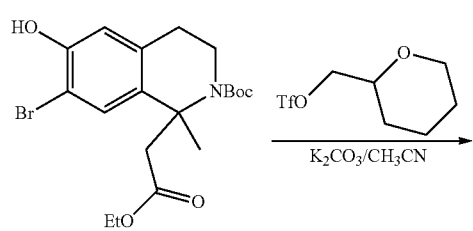

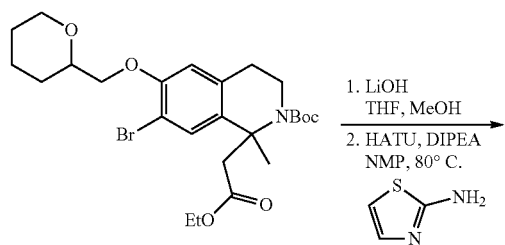

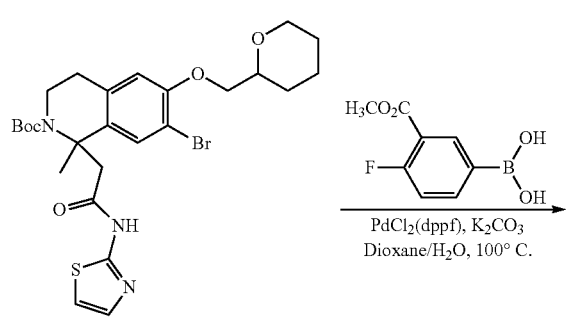

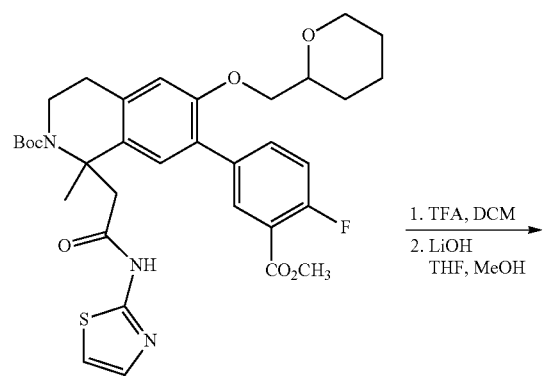

236
-continued

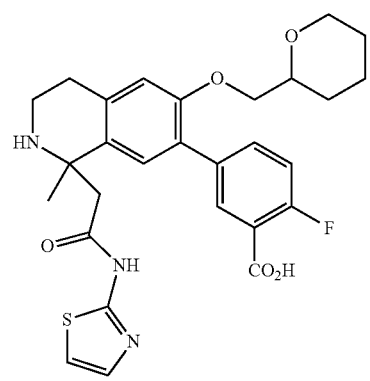

Step A: tert-butyl 7-bromo-1-(2-ethoxy-2-oxoethyl)-6-methoxy-1-methyl-3,4-dihydroisoquinoline-2(1H)-carboxylate

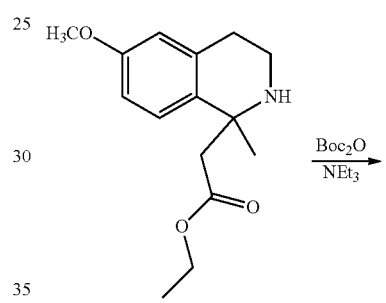

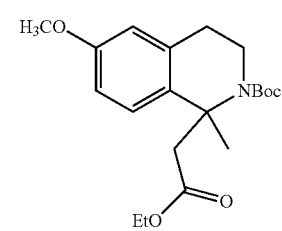

To a solution of ethyl 2-(6-methoxy-1-methyl-1,2,3,4-tetrahydroisoquinolin-1-yl)acetate (Intermediate VIIb) (24 g, 91 mmol) in 1,4-dioxane (50 mL) was added di-tert-butyl dicarbonate (29.8 g, 137 mmol) followed by triethylamine (31.8 mL, 228 mmol). The reaction mixture was heated to 80° C. for 2 h. The reaction was cooled to rt and poured into water and was then extracted with dichloromethane (2×). The organic layer was dried over sodium sulfate. The residue was purified by column chromatography on silica gel, eluting with 0-100% ethyl acetate/hexane to give the title compound: LCMS m/z 386.19 [M+H]⁺.

Step B: tert-butyl 7-bromo-1-(2-ethoxy-2-oxoethyl)-6-methoxy-1-methyl-3,4-dihydroisoquinoline-2(1H)-carboxylate

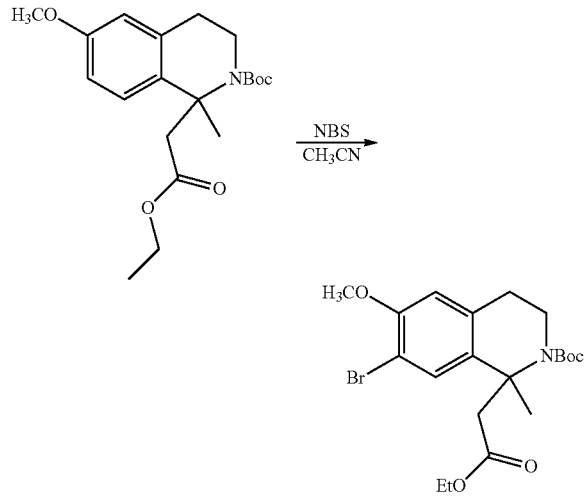

To a solution of the title compound from scheme 14, step A (7.5 g, 21 mmol) in acetonitrile (30 mL) was added a solution of NBS (4.77 g, 26.8 mmol) in acetonitrile (20 mL) dropwise via an additional funnel over 20 min. The mixture was stirred at rt for 1 h. The solvent was concentrated and the residue was purified by column chromatography on silica gel, eluting with 0-25% ethyl acetate/hexan. A mixture of about 1:1 monobrominated product was isolated. 7-bromo product is slightly more than 5-bromo product. It was carried forward as a mixture: LCMS m/z 344.0 [M+H]$^+$.

Step C: tert-butyl 7-bromo-1-(2-ethoxy-2-oxoethyl)-6-hydroxy-1-methyl-3,4-dihydroisoquinoline-2(1H)-carboxylate

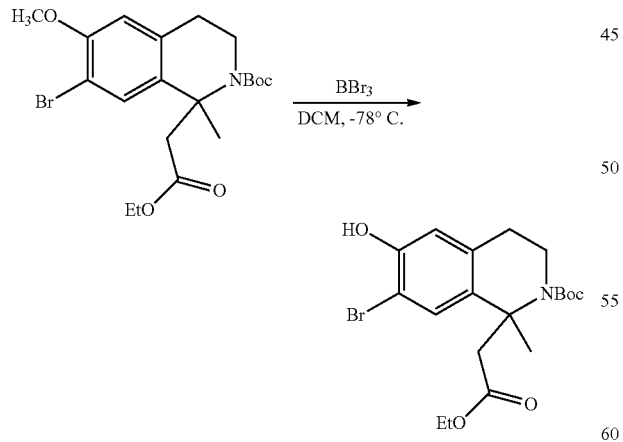

The mixture of bromo isomers from scheme 14, step B (7.20 g, 16.3 mmol) was dissolved in dichloromethane (50 mL) and cooled to −78° C. A solution of boron tribromide (1M in dichloromethane, 65.1 mL, 65.1 mmol) was added dropwise via an additional funnel. The mixture was allowed to warm up slowly to rt and stirred at rt for overnight. The reaction mixture was cooled back to −78° C. and anhydrous ethanol (50 mL) was added. The ice bath was removed and the reaction was stirred at rt for 30 min. It was then heated at 80° C. for 3 h with the top open. The reaction was concentrated to dryness and poured slowly to a saturated aqueous sodium bicarbonate solution. It was extracted with ethyl acetate (3×), dried over sodium sulfate, filtered and concentrated to dryness. The above intermediate was taken up in dioxane, and di-tert-butyldicarbonate (8.88 g, 40.7 mmol) was added, followed by triethylamine (6.81 ml, 48.8 mmol). The reaction mixture was heated at 80° C. for 3 h. The solvent was removed and the residue was purified by column chromatography on silica gel eluting with 0-30% EtOAc/Hexane. The di-Boc intermediate was taken up in methanol (100 mL), potassium carbonate (2.250 g, 16.28 mmol) was added and the reaction was heated to 50° C. for 1 h. The mixture was cooled to rt, slowly poured into 1N aqueous HCl and extracted with ethyl acetate (3×). The organics were dried over sodium sulfate, filtered and concentrated to dryness to afford the title compound (which was a mixture of bromo regioisomers): LCMS m/z 430.08 [M+H]$^+$.

Step D: (tetrahydro-2H-pyran-2-yl)methyl trifluoromethanesulfonate

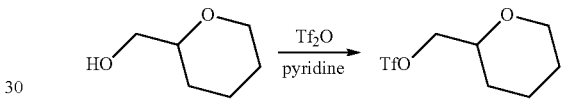

Tetrahydropyran-2-methanol (0.946 mL, 8.61 mmol) was taken up in dry dichloromethane (34.4 mL), under an inert atmosphere. The mixture was cooled to −5° C. before pyridine (1.18 mL, 14.64 mmol) was added to the reaction mixture, followed by the addition of trifluoromethanesulfonic anhydride (2.03 mL, 12.05 mmol). The reaction was allowed to stir at −5° C. for 20 minutes. The mixture was then passed through a silica plug. The fractions containing product were concentrated to afford the title compound.

Step E: tert-butyl 7-bromo-1-(2-ethoxy-2-oxoethyl)-1-methyl-6-((tetrahydro-2H-pyran-2-yl)methoxy)-3,4-dihydroisoquinoline-2(1H)-carboxylate

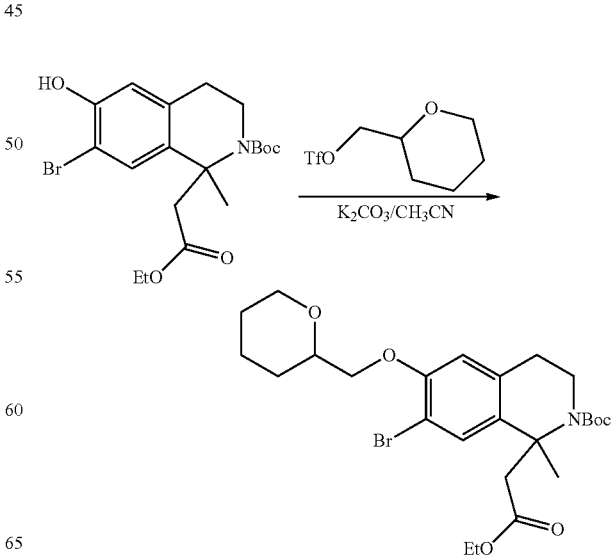

To a solution of the title compound from scheme 14, step C (1.01 g, 2.36 mmol) and the title compound from scheme 14, step D (1.46 g, 5.90 mmol) were taken up in acetone (23.6 mL). Potassium carbonate (0.815 g, 5.90 mmol) was added and the mixture was stirred overnight at room temperature. The mixture was filtered, to remove the potassium carbonate, and concentrated to dryness. The residue was purified by column chromatography on silica gel eluting with EtOAc/isohexane, 0-50-100%. The fractions containing product were concentrated to afford the title compound (which was still a mixture of two bromo regioisomers): LCMS m/z 526 [M+H, 79Br]+, 528 [M+H, 81Br]+.

Step F: 2-(7-bromo-2-(tert-butoxycarbonyl)-1-methyl-6-((tetrahydro-2H-pyran-2-yl)methoxy)-1,2,3,4-tetrahydroisoquinolin-1-yl)acetic acid

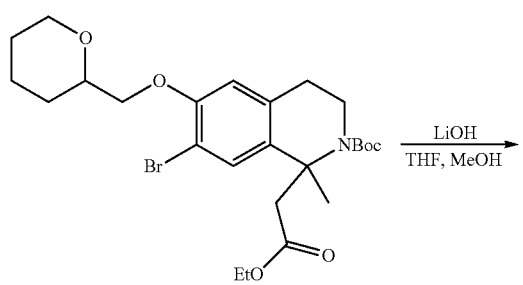

The crude mixture of the two regioisomer products from scheme 14, step E (1.24 g, 2.36 mmol) were taken up in tetrahydrofuran (10.0 mL) and methanol (10.0 mL). Lithium hydroxide (3M aqueous solution, 5.00 mL, 15.0 mmol) was added. The reaction was stirred overnight at room temperature. Additional lithium hydroxide (3M aqueous solution, 5.00 mL, 15.0 mmol) was added, and the reaction was heated to 50° C. After 4 hours of heating the reaction was complete. The mixture was neutralized with 2N aqueous HCl then 50 mL of water and 100 mL of ethyl acetate were added. It was extracted with ethyl acetate (3×100 ml), dried over sodium sulfate, filtered and concentrated to dryness to give the title compound (which was a mixture of bromine regioisomers): LCMS m/z=498 [M+H, 79Br]+, 500 [M+H, 81Br]+.

Step G: tert-butyl 7-bromo-1-methyl-1-(2-oxo-2-(thiazol-2-ylamino)ethyl)-6-((tetrahydro-2H-pyran-2-yl)methoxy)-3,4-dihydroisoquinoline-2(1H)-carboxylate

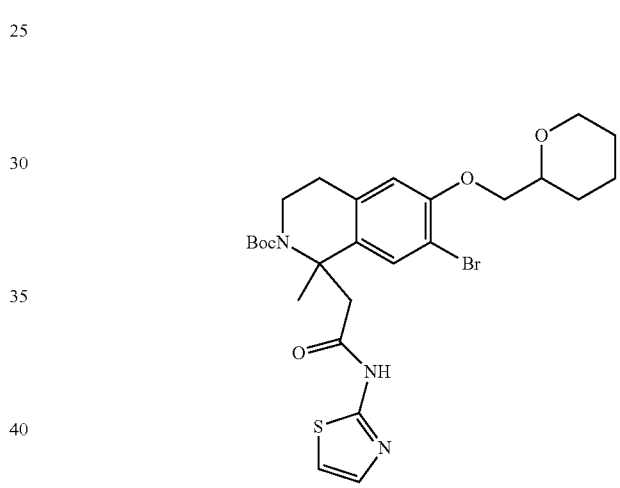

A mixture of the title compound from scheme 14, step F (1.175 g, 2.358 mmol), 1-[Bis(dimethylamino)methylene]-1H-1,2,3-triazolo[4,5-b]pyridinium 3-oxid hexafluorophosphate (2.69 g, 7.07 mmol) and N,N-diisopropylethylamine (1.235 ml, 7.07 mmol) in N-methylmorpholine (25 ml) was stirred at it for 1 hour. By LCMS there was complete consumption of the carboxylic acid. 2-aminothiazole (0.472 g, 4.72 mmol) was added and the reaction mixture was heated overnight at 80° C. The reaction was cooled to room temperature and then poured into 100 mL of brine. The product was extracted with ethyl acetate (3×200 mL). The organic layers were combined and washed with 1N aq. HCl (2×200 mL) and brine (1×200 mL). The organic layer was dried over sodium sulfate, filtered and concentrated to dryness. The residue was purified by column chromatography on silica gel eluting with 0-60%-90% EtOAc/isohexane. The two peaks, which correspond to the two regioisomers, separated well. Fractions were combined and concentrated to give the title compound: LCMS m/z 582.29 [M+H]+.

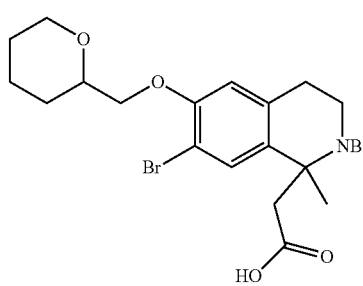

Step H: tert-butyl 7-(4-fluoro-3-(methoxycarbonyl)phenyl)-1-methyl-1-(2-oxo-2-(thiazol-2-ylaminHo)ethyl)-6-((tetrahydro-2H-pyran-2-yl)methoxy)-3,4-dihydroisoquinoline-2(1H)-carboxylate Step I: 2-fluoro-5-(1-methyl-1-(2-oxo-2-(thiazol-2-ylamino)ethyl)-6-((tetrahydro-2H-pyran-2-yl)methoxy)-1,2,3,4-tetrahydroisoquinolin-7-yl)benzoic acid

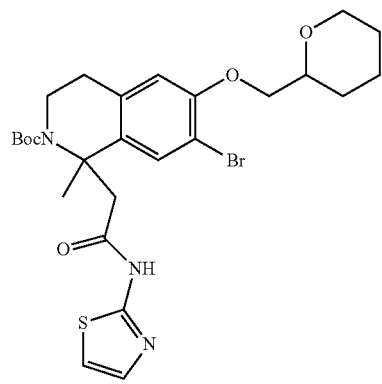

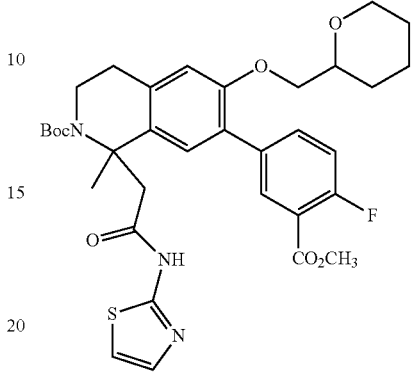

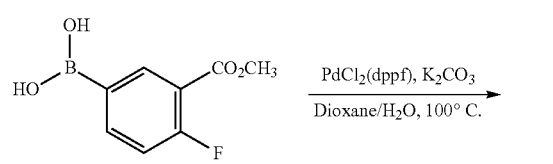

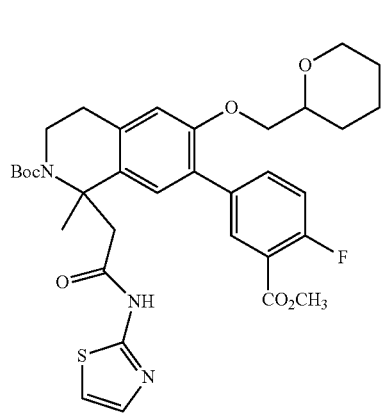

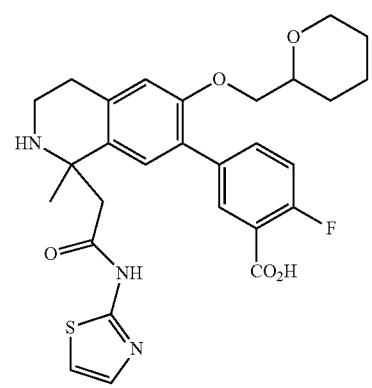

The title compound from scheme 14, step G (30 mg, 0.05 mmol), (4-fluoro-3-methoxycarbonylphenyl)boronic acid (15 mg, 0.08 mmol), PdCl2(dppf) (5.7 mg, 10 µmol) and potassium carbonate (29 mg, 0.21 mmol) were placed in a microwave tube and taken up in dioxane (3.0 mL) and water (0.30 mL). The reaction was purged with nitrogen before being sealed in a microwave vial and heated at 100° C. for 1 h. The organic layer was separated from the aqueous layer, and EtOAc was used as a wash solvent for the microwave tube in order to assure complete transfer of the product. The organics were concentrated to dryness. The residue was purified by column chromatography on silica gel eluting with 0-50% EtOAc/hexane. The like fractions were combined and concentrated to afford the title compound: LCMS m/z 654.42 [M+H]$^+$.

The title compound from scheme 14, step H (30.0 mg, 0.046 mmol) was taken up in tetrahydrofuran (2.00 mL) and methanol (2.00 mL). Lithium hydroxide (3M aqueous solution, 2.00 mL, 6.00 mmol) was added and the reaction was stirred overnight at room temperature. The reaction mixture was neutralized and acidified with trifluoroacetic acid. The solution was concentrated to dryness. The residue was taken up in 10 mL of water and 10 mL of ethyl acetate. It was then extracted with ethyl acetate (3×15 mL). The combined organics were dried over sodium sulfate, filtered and concentrated to dryness. The residue was purified by preparative HPLC using a reverse phase (C-18) column, eluting with 5-95% acetonitrile/water+0.05% trifluoroacetic acid. The fractions containing product were combined and concentrated to afford the title compound: LCMS m/z 540.07 [M+H]$^+$.

EXAMPLE 111 in the table below was prepared in an analogous fashion as described for EXAMPLE 110 and generally shown in Scheme 14, substituting the appropriate reactants and reagents that are prepared as described herein or that are commercially available.

| EX. No. | Structure | Name | LC/MS [M + H]⁺ |
|---|---|---|---|
| 111 | 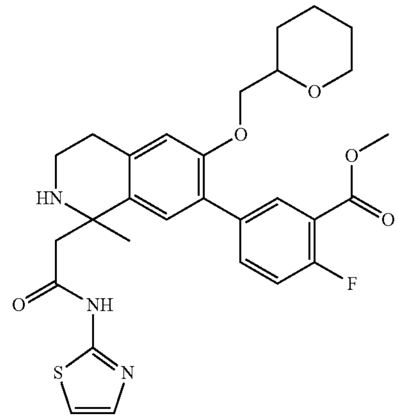 [SMILES: COC(=O)c1cc(-c2cc3c(cc2OCC2CCCCO2)CCNC3(C)CC(=O)Nc2nccs2)ccc1F] | methyl 2-fluoro-5-(1-methyl-1-(2-oxo-2-(thiazol-2-ylamino)ethyl)-6-((tetrahydro-2H-pyran-2-yl)methoxy)-1,2,3,4-tetrahydroisoquinolin-7-yl)benzoate | 554.32 |

Example 112

(R)-2-fluoro-5-(6-methoxy-1-methyl-1-(2-oxo-2-(thiazol-2-ylamino)ethyl)-1,2,3,4-tetrahydroisoquinolin-7-yl)benzoic acid

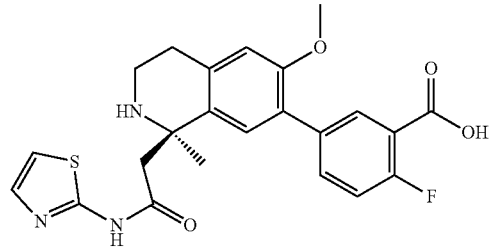 [SMILES: COc1cc2c(cc1-c1ccc(F)c(C(=O)O)c1)[C@@](C)(CC(=O)Nc1nccs1)NCC2]

Example 112 was made according to general Scheme 15 below.

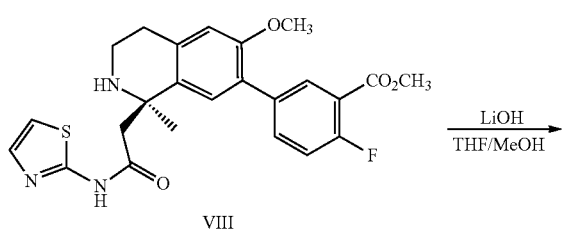

Step A: (R)-2-fluoro-5-(6-methoxy-1-methyl-1-(2-oxo-2-(thiazol-2-ylamino)ethyl)-1,2,3,4-tetrahydroisoquinolin-7-yl)benzoic acid

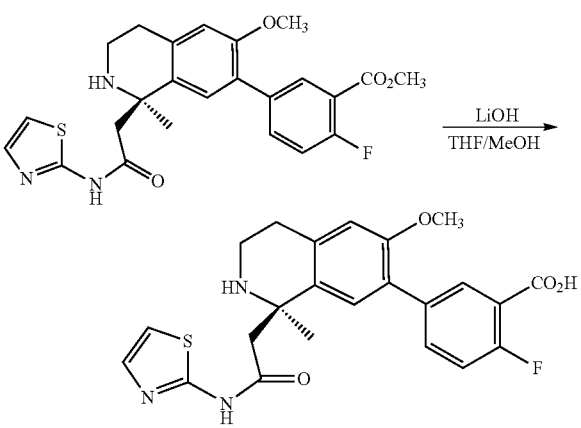

To a solution of Intermediate VIII (scheme 13, step D, 56.5 mg, 0.120 mmol) in a 1:1 solution of tetrahydrofuran (1.00 mL) and methanol (1.00 mL) was added lithium hydroxide (1.5M aqueous solution, 1.00 mL, 1.500 mmol). The reaction was stirred overnight at room temperature, neutralized with trifluoroacetic acid, and concentrated to dryness. The residue was purified via preparative HPLC to afford the title compound: LCMS m/z 456.25 [M+H]⁺.

BIOLOGICAL ASSAYS

Differential Scanning Calorimetry Assay

Differential scanning calorimetry (DSC) was used as a biophysical method to confirm direct binding to PCSK9. A solution containing 2 μM PCSK9 with or without 300 μM test compound in 25 mM HEPES (pH 7.5)/150 mM NaCl/1 mM CaCl$_2$/3.75% DMSO was transferred to the sample cell of the DSC instrument, while buffer alone was placed in the reference cell. Both cells were heated at a constant rate (200° C./hr) from 20-80° C. while recording the excess heat capacity of the sample cell relative to the reference cell. Each thermogram was analyzed to provide the melting temperature ($T_m$) of the protein. The difference $T_m$(with compound)−$T_m$(no compound)=ΔT was determined. ΔT>1° C. indicated compound-induced stabilization of PCSK9 assumed to result from productive binding, while ΔT<1° C. indicated that the compound either failed to bind PCSK9 or reduced protein thermostability through nonproductive binding.

Representative compounds of the present invention exhibit direct binding to PCSK9 in this assay. For example, the compounds of Examples 1-92 and 109-112 were tested in this assay and the majority of the compounds were found to have the ΔT values>1° C. as shown in Assay Table 1. The higher the temperature shift generally, the higher the affinity.

Agents capable of stabilizing PCSK9 may stabilize PCSK9 in an inactive conformation, a conformation that inhibits PCSK9's ability to bind to the low density lipoprotein (LDL) receptor. Inhibiting this function of PCSK9 could increase the cell surface function of the low density lipoprotein (LDL) receptor and accordingly reduce LDL cholesterol. Such agents may prove useful for the treatment and correction of the various dyslipidemias observed to be associated with the development and incidence of atherosclerosis and cardiovascular disease.

ASSAY TABLE 1

Stabilization of PCSK9 resulting from the binding of Examples 1-92 and 109-112 to PCSK9.

| Example No. | DSC ΔTm |
| --- | --- |
| 1 | 4.29 |
| 2 | 6.21 |
| 3 | 4.915 |
| 4 | 7.056 |
| 5 | 6.99 |
| 6 | 5.78 |
| 7 | 5.59 |
| 8 | 5.44 |
| 9 | 5.92 |
| 10 | 5.55 |
| 11 | 5.69 |
| 12 | −0.225 |
| 13 | 8.4 |
| 14 | 5.89 |
| 15 | 3.31 |
| 16 | 3.57 |
| 17 | 2.62 |
| 18 | 7.62 |
| 19 | 9.053 |
| 20 | 8.56 |
| 21 | 6.58 |
| 22 | 7.52 |
| 23 | 8.71 |
| 24 | 7.203 |
| 25 | 6.6 |
| 26 | 5.75 |
| 27 | 7.11 |
| 28 | 6.91 |
| 29 | 5.37 |
| 30 | 5.48 |
| 31 | 5.84 |
| 32 | 6.18 |
| 33 | 5.2 |
| 34 | 5.5 |
| 35 | 5.293 |
| 36 | 5.56 |
| 37 | 5.63 |
| 38 | 7 |
| 39 | 5.98 |
| 40 | 6.75 |
| 41 | 7.18 |
| 42 | 5.97 |
| 43 | 5.45 |
| 44 | 6.89 |

ASSAY TABLE 1-continued

Stabilization of PCSK9 resulting from the binding of Examples 1-92 and 109-112 to PCSK9.

| Example No. | DSC ΔTm |
| --- | --- |
| 45 | 6.96 |
| 46 | 6.48 |
| 47 | 6.27 |
| 48 | 6.02 |
| 49 | 6.293 |
| 50 | 6.74 |
| 51 | 6.87 |
| 52 | 5.583 |
| 53 | 6.96 |
| 54 | 5.98 |
| 55 | 5.823 |
| 56 | 5.723 |
| 57 | 6.15 |
| 58 | 5.88 |
| 59 | 5.153 |
| 60 | 6.423 |
| 61 | 2.87 |
| 62 | 6.03 |
| 63 | 8.383 |
| 64 | 7.83 |
| 65 | 7.313 |
| 66 | 9.14 |
| 67 | 7.307 |
| 68 | 7.563 |
| 69 | 7.65 |
| 70 | 7.983 |
| 71 | 6.363 |
| 72 | 6.15 |
| 73 | 6.66 |
| 74 | 7.08 |
| 75 | 6.18 |
| 76 | 7.92 |
| 77 | 6.665 |
| 78 | 6.67 |
| 79 | 6.76 |
| 80 | 6.095 |
| 81 | 6.585 |
| 82 | 7.47 |
| 83 | 5.2 |
| 84 | 6.32 |
| 85 | 9.623 |
| 86 | 6.18 |
| 87 | 6.57 |
| 88 | 5.51 |
| 89 | 5.98 |
| 90 | 8.593 |
| 91 | 7.193 |
| 92 | 7.283 |
| 109 | 6.02 |
| 110 | 6.7 |
| 111 | 6.27 |
| 112 | 6.805 |

Fluoresence Polarization Assay

Relative compound affinities were determined using a competition binding assay with a fluorescence polarization format. Solution (49 μL) containing 2 μM PCSK9 and 50 nM compound of Example 57 in 20 mM HEPES (pH 7.5)/150 mM NaCl/1 mM CaCl2/0.005% P-20 was dispensed to wells of a 384-well black non-binding microplate before the addition of 1 μL of test compound or DMSO. After mixing, the plate was centrifuged and sealed for overnight incubation in the dark. The anisotropy signal was read using a fluorescence polarization protocol on a Perkin-Elmer Envision plate reader. The % inhibition was determined relative to the window defined by the DMSO control wells and wells containing 50 nM probe in the absence of PCSK9.

Representative compounds of the present invention exhibit the ability to bind PCSK9 with high affinity. For example, the compounds of Examples 1-56, 62-111 were tested in this assay and the majority of the compounds were found to be high affinity binders to PCSK9 as shown in Assay Table 2.

Agents capable of binding to PCSK9 with high affinity may bind to PCSK9 in an inactive conformation, a conformation that inhibits PCSK9's ability to bind to the low density liproprotein (LDL) receptor. Inhibiting this function of PCSK9 could increase the cell surface function of the low density lipoprotein (LDL) receptor and accordingly reduce LDL cholesterol. Such agents may prove useful for the treatment and correction of the various dyslipidemias observed to be associated with the development and incidence of atherosclerosis and cardiovascular disease.

ASSAY TABLE 2

Affinity measurements based on fluorescence polarization

| Example No. | FP IC ($\mu$M) |
|---|---|
| 1 | 3.666 |
| 2 | 1.239 |
| 3 | 1.247 |
| 4 | 0.4874 |
| 5 | 0.5607 |
| 6 | 0.6482 |
| 7 | 0.6516 |
| 8 | 0.7527 |
| 9 | 0.8473 |
| 10 | 0.9018 |
| 11 | 0.756 |
| 12 | 0.7533 |
| 13 | 0.09931 |
| 14 | 2.37E-04 |
| 15 | 0.00376 |
| 16 | 0.004148 |
| 17 | 0.01147 |
| 18 | 0.09434 |
| 19 | 0.1618 |
| 20 | 0.1884 |
| 21 | 0.2003 |
| 22 | 0.2109 |
| 23 | 0.2284 |
| 24 | 0.2611 |
| 25 | 0.3016 |
| 26 | 0.386 |
| 27 | 0.3864 |
| 28 | 0.4073 |
| 29 | 0.4156 |
| 30 | 0.4504 |
| 31 | 0.5223 |
| 32 | 0.5318 |
| 33 | 0.5602 |
| 34 | 0.667 |
| 35 | 0.6808 |
| 36 | 0.7665 |
| 37 | 0.6152 |
| 38 | 0.2671 |
| 39 | 0.2917 |
| 40 | 0.302 |
| 41 | 0.3536 |
| 42 | 0.3886 |
| 43 | 0.4176 |
| 44 | 0.4259 |
| 45 | 0.5301 |
| 46 | 0.6023 |
| 47 | 0.6455 |
| 48 | 0.6781 |
| 49 | 0.6821 |
| 50 | 0.6828 |
| 51 | 0.705 |
| 52 | 0.7779 |
| 53 | 0.8233 |
| 54 | 0.8369 |
| 55 | 0.8775 |
| 56 | 0.9656 |
| 62 | 0.5289 |
| 63 | 0.1762 |
| 64 | 0.2941 |
| 65 | 0.2993 |
| 66 | 0.3949 |
| 67 | 0.4198 |
| 68 | 0.4771 |
| 69 | 0.5411 |
| 70 | 0.5505 |
| 71 | 0.6452 |
| 72 | 0.6803 |
| 73 | 0.6323 |
| 74 | 0.7901 |
| 75 | 0.41 |
| 76 | 0.5346 |
| 77 | 0.5912 |
| 78 | 0.6043 |
| 79 | 0.8229 |
| 80 | 0.5499 |
| 81 | 0.5504 |
| 82 | 0.721 |
| 83 | 0.8518 |
| 84 | 0.9428 |
| 85 | 0.1705 |
| 86 | 0.001169 |
| 87 | 0.001399 |
| 88 | 0.001596 |
| 89 | 0.002756 |
| 90 | 0.1086 |
| 91 | 0.86 |
| 92 | 0.9576 |
| 93 | 0.188 |
| 93 | 0.5782 |
| 94 | 0.0769 |
| 95 | 0.1071 |
| 96 | 0.1097 |
| 97 | 0.13 |
| 98 | 0.2603 |
| 99 | 0.7177 |
| 100 | 0.09637 |
| 101 | 0.1296 |
| 102 | 0.1617 |
| 103 | 0.162 |
| 104 | 0.2221 |
| 105 | 0.2251 |
| 106 | 0.6554 |
| 107 | 0.8306 |
| 108 | 0.578 |
| 109 | 0.6644 |
| 110 | 9.80E-04 |
| 111 | 0.001547 |

Protein Degradation Assay (Western Blot/Sally Sue Assay)

Samples were run on the Sally Simple Western system from ProteinSimple (San Jose, Calif.) using default assay conditions. Briefly, 5×104 HEK293 cells stably overexpressing PCSK9 were seeded into Collagen I coated 96 well plates and allowed to recover overnight at 37° C. with 5% $CO_2$. After 24 hrs of compound treatment in serum free DMEM cell culture medium, cells were washed with PBS and lysed in 100 ul RIPA buffer (Teknova) supplemented with protease inhibitors and subsequently mixed with fluorescent standards as per manufacturer's specifications, followed by denaturation at 95° C. for 5 minutes. Anti-PCSK9 mAb antibody (Abbomax, Cat. No. 601-650) was used for PCSK9 detection. The reported $DC_{50}$ values represent the effective concentration of compound to lower PCSK9 protein levels, pro and mature, by 50%.

Select compounds of the present invention exhibit the ability to lower steady state concentrations of both the pro and mature forms of PCSK9. For example, the compounds of Examples 93-104 and 106-108 were tested in this assay and a number of the compounds were found to degrade PCSK9 levels, with $DC_{50}$ values in the low micromolar range as shown in Assay Table 3. Agents capable of decreasing PCSK9 levels may increase the cell surface expression of the low density lipoprotein (LDL) receptor and accordingly reduce LDL cholesterol; see. e.g., E. M. Roth, et al., A phase III randomized trial evaluating alirocumab 300 mg every 4 weeks as monotherapy or add-on to statin: ODYSSEY CHOICE 1, Atherosclerosis (2016), http://dx.doi.org/10.1016/j.atherosclerosis.2016.08.043, where anti-PCSK9 antibodies which inhibit the functioning of PCSK9 resulted in significant LDL-C reductions from baseline. Such agents may prove useful for the treatment and correction of the various dyslipidemias observed to be associated with the development and incidence of atherosclerosis and cardiovascular disease.

ASSAY TABLE 3

Effective concentration of compound to lower PCSK9 protein levels pro and mature by 50%.

| Example No. | PCSK9 $DC_{50}$ (Pro) μM | PCSK9 $DC_{50}$ (Mature) μM |
| --- | --- | --- |
| 93 | 6.18 | 4.24 |
| 94 | 1.36 | 8.52 |
| 95 | Inactive | inactive |
| 96 | 6.55 | 1.05 |
| 97 | Inactive | inactive |
| 98 | 6.08 | 5.07 |
| 99 | 1.37 | 9.00 |
| 100 | Inactive | inactive |
| 101 | Inactive | inactive |
| 102 | Inactive | inactive |
| 103 | Inactive | inactive |
| 104 | 1.53 | 7.52 |
| 106 | 4.82 | 3.42 |
| 107 | Inactive | inactive |
| 108 | Inactive | inactive |

What is claimed:
1. A compound of Formula I

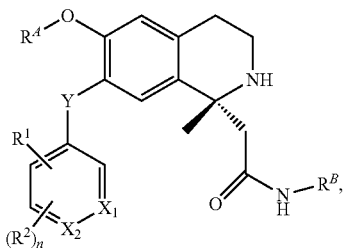

(I)

or a pharmaceutically acceptable salt thereof,
wherein:
$R^A$ is —$C_1$-$C_6$alkyl, —[$OCH_2CH_2$]$_m$$NR^aC(O)R^C$, —($CH_2$)$_n$-AryA1, —($CH_2$)$_n$-HetA1 or —$C_1$-$C_3$alkylN$_3$; wherein the —$C_1$-$C_6$alkyl or —$C_1$-$C_3$alkylN$_3$ is optionally substituted with 1, 2, or 3 substituents independently selected from the group consisting of halogen, —$C_1$-$C_6$alkoxy, —$C_1$-$C_6$haloalkoxy, —C(O)OR$^a$, —NR$^a$R$^b$ and —OH;
AryA1 is a 5-6 membered aromatic monocyclic ring with 0, 1, 2 or 3 heteroatom ring atoms independently selected from the group consisting of N and O, optionally substituted with 1, 2, or 3 substituents independently selected from the group consisting of halogen, —$C_1$-$C_6$alkyl, —$C_1$-$C_6$haloalkyl, —$C_1$-$C_6$alkoxy, —$C_1$-$C_6$haloalkoxy, —CN, —$CH_2$OH, —C(O)NR$^a$R$^b$, —SC$_1$-$C_6$alkyl, —SO$_2$R$^a$, —SO$_2$NR$^a$R$^b$, —C(O)OR$^a$, —CH(OH)C(NH$_2$)C(O)OR$^a$, —$CH_2OCH_2CH_2$CH, AryA2, —($CH_2$)$_n$-HetA1, —NR$^a$ and —OH; wherein the —$C_1$-$C_6$alkyl is optionally substituted with 1 or 2 substituents independently selected from the group consisting of —OR$^a$, —NR$^a$R$^b$, —COOR$^a$, —$C_3$-$C_6$cycloalkyl, —$C_1$-$C_4$alkylCOOR$^a$, —NR$^a$C(O)R$^b$, —NR$^a$S(O)$_2$R$^b$, —($CH_2$)$_n$-AryA2, —OAryA2 and —NR$^a$C(O)-AryA2,
each occurrence of AryA2 is individually a 5-6 membered aromatic monocyclic ring with 0, 1, 2 or 3 heteroatom ring atoms independently selected from the group consisting of N and O, optionally substituted with 1, 2, or 3 substituents independently selected from the group consisting of halogen, —$C_1$-$C_6$alkyl, —$C_1$-$C_6$haloalkyl-$C_1$-$C_6$alkoxy, —$C_1$-$C_6$haloalkoxy, —COOR$^a$, —CN, —$CH_2$OH, —C(O)NR$^a$R$^b$, —SC$_1$-$C_6$alkyl, —SO$_2$R$^a$, —SO$_2$NR$^a$R$^b$, —OR$^a$, —NR$^a$R$^b$, AryA3 and oxo;
HetA1 is a 5-6-membered saturated monocyclic ring with 1 or 2 heteroatom ring atoms independently selected from the group consisting of N and O, wherein the ring is optionally substituted with 1 or 2 substituents independently selected from the group consisting of —$C_1$-$C_6$alkyl, —$CH_2$OH, —C(O)NR$^a$R$^b$, —SC$_1$-$C_6$alkyl, —SO$_2$R$^a$, —SO$_2$NR$^a$R$^b$, —OR$^a$, —NR$^a$R$^b$, —CN and oxo;
$X_1$ and $X_2$ are independently selected from the group consisting of N and CH;
wherein if $X_1$ is CH, $X_1$ is optionally linked to $R^B$ through an —O$C_6$-$C_7$alkylene or an —O$C_6$-$C_7$alkenylene, wherein the O of the —O$C_6$-$C_7$alkylene or —O$C_6$-$C_7$alkenylene is bound at the $X_1$ position;
or alternatively $X_1$ and $X_2$ together with the ring atoms to which they are attached form a 5-6 membered aromatic monocyclic ring with 0, 1 or 2 heteroatom ring atoms independently selected from the group consisting of N and O, wherein said monocyclic ring is fused to the ring having $X_1$ and $X_2$, further wherein said monocyclic ring is optionally substituted with 1, 2, or 3 substituents independently selected from the group consisting of halogen, —$C_1$-$C_6$alkyl and —$C_1$-$C_6$haloalkyl;
Y is O or a bond;
$R^1$ is:
 1) hydrogen,
 2) halogen,
 3) —$C_1$-$C_6$alkyl,
 4) —$C_1$-$C_6$haloalkyl,
 5) —$C_1$-$C_6$alkoxy,
 6) —$C_1$-$C_6$haloalkoxy,
 7) —C(O)OR$^a$,
 8) —C(O)NR$^a$R$^b$,
 9) —CN,
 10) —$CH_2$OH,
 11) —SC$_1$-$C_6$alkyl,
 12) —SO$_2$R$^a$,
 13) —SO$_2$NR$^a$R$^b$,
 14) —OR$^a$,
 15) —NR$^a$R$^b$,
 16) —C(O)NR$^a$AryA3, or
 17) -AryA3;
AryA3 is an aromatic 5-6 membered monocyclic ring or an 8-10 membered bicyclic ring with 0, 1, 2, or 3 heteroatom ring atoms independently selected from the group consisting of N and O, wherein the 5-6 membered monocyclic ring or the 8-10 membered bicyclic ring are optionally substituted with 1, 2 or 3 substituents independently selected from the group consisting of halogen, —$C_1$-$C_6$alkyl, —$C_1$-$C_6$alkenyl, —$C_1$-$C_6$haloalkyl, —$C_1$-$C_6$alkoxy, —$C_1$-$C_6$haloalkoxy, —CN, —$CH_2OH$, —$SC_1$-$C_6$alkyl, —$SO_2R^a$, —$SO_2NR^aR^b$, —$OR^a$, —$C(O)OR^a$, —$C(O)NR^aR^b$, —$C(O)NR^a$AryA4, —$NR^aC(O)$AryA4, AryA4, —$NR^aR^b$, oxo and —OH wherein the —$C_1$-$C_6$alkyl or the —$C_1$-$C_6$alkenyl are optionally substituted with 1 or 2 substituents independently selected from the group consisting of —$C_1$-$C_6$cycloalkyl, —$C(O)OR^a$ and —$C(O)NR^aR^b$;

AryA4 is a 5-6 membered aromatic monocyclic ring with 0, 1, 2 or 3 heteroatom ring atoms independently selected from the group consisting of N and O, optionally substituted with 1, 2, or 3 substituents independently selected from the group consisting of halogen, —$C_1$-$C_6$alkyl, —$C_1$-$C_6$haloalkyl, —$C_1$-$C_6$alkoxy, —$C_1$-$C_6$haloalkoxy, —CN, —$CH_2OH$, —$C(O)NR^aR^b$, —$SC_1$-$C_6$alkyl, —$SO_2R^a$, —$SO_2NR^aR^b$, —$OR^a$ and —$NR^aR^b$;

each $R^2$ is independently halogen, —$C_1$-$C_6$alkyl, —$C_1$-$C_6$haloalkyl, —$C_1$-$C_6$alkoxy, —$C_1$-$C_6$haloalkoxy, —CN, —$CH_2OH$, —$C(O)NR^aR^b$, —$SC_1$-$C_6$alkyl, —$SO_2R^a$, —$SO_2NR^aR^b$, —$OR^a$ or —$NR^aR^b$;

$R^B$ is -AryA5; wherein if $X_1$ is CH, $R^B$ is optionally linked to $X_1$ through an —$OC_6$-$C_7$alkylene or an —$OC_6$-$C_7$alkenylene, wherein the O of the —$OC_6$-$C_7$alkylene or —$OC_6$-$C_7$alkenylene is bound at the $X_1$ position;

AryA5 is an aromatic 5-6 membered monocyclic ring or an 8-10 membered bicyclic ring with 0, 1, 2, or 3 heteroatom ring atoms independently selected from the group consisting of N, O and S, optionally substituted with 1, 2 or 3 substituents independently selected from the group consisting of halogen, —$C_1$-$C_6$alkyl, —$C_1$-$C_6$haloalkyl, —$C_1$-$C_6$alkoxy, —$C_1$-$C_6$haloalkoxy, —$NR^aR^b$, —CN, —$CH_2OH$, —$C(O)NR^aR^b$, —$SC_1$-$C_6$alkyl, —$SO_2R^a$, —$SO_2NR^aR^b$, and —$OR^a$;

$R^C$ is —$(CH_2)_p$-adamantane, —$(CH_2)_m$-5,5-difluoro-1,3-dimethyl-5H-5$\lambda^4$,6$\lambda^4$-dipyrrolo[1,2-c:2',1'-f][1,3,2]diazaborinine, —$(CH_2)_m$-(3aR,6aS)-tetrahydro-1H-thieno[3,4-d]imidazol-2(3H)-one, —$C_1$-$C_6$alkyl and —$C_1$-$C_2$alkylene[$OC_1$-$C_2$alkylene]$_o$C(O)NR$^a$C$_1$-C$_6$alkyl;

wherein the —$C_1$-$C_6$alkyl is optionally substituted with 1 or 2 substituents independently selected from the group consisting of —$NR^aC(O)C_1$-$C_6$alkyl, —$NR^aC(O)OC_1$-$C_6$alkyl, —$NR^aC(=NC(O)OR^b)(NR^aC(O)OR^b)$, —[$OC_1$-$C_2$alkylene]$_o$C(O)NR$^a$C$_1$-C$_6$alkyl and AryB1;

wherein the —$NR^aC(O)C_1$-$C_6$alkyl is optionally substituted with 1, 2 or 3 substituents independently selected from the group consisting of —$OR^a$, —$NR^aR^b$ and AryB1;

wherein the —$C_1$-$C_2$alkylene[$OC_1$-$C_2$alkylene]$_o$C(O)NR$^a$C$_1$-$C_6$alkyl is optionally substituted with a substituent selected from the group consisting of -HetB1 and —C(O)HetB1;

HetB1 is a 5-membered saturated monocyclic ring with 1 N atom, optionally substituted with 1 or 2 substituents independently selected from the group consisting of —$C(O)NR^a(CH_2)_n$-AryB1 and —$OR^a$;

AryB1 is a 5-6 membered aromatic monocyclic ring with 0 or 1 N ring atoms, optionally substituted with 1, 2, or 3 substituents independently selected from the group consisting of AryB2, halogen, —$C_1$-$C_6$alkyl, —$C_1$-$C_6$haloalkyl, —$C_1$-$C_6$alkoxy, —$C_1$-$C_6$haloalkoxy, —$C(O)OR^a$, —$NR^aR^b$ and —OH;

AryB2 is a 5-6 membered aromatic monocyclic ring with 0, 1, 2 or 3 heteroatom ring atoms independently selected from the group consisting of N, O and S, optionally substituted with 1, 2, or 3 substituents independently selected from the group consisting of halogen, —$C_1$-$C_6$alkyl, —$C_1$-$C_6$haloalkyl, —$C_1$-$C_6$alkoxy, —$C_1$-$C_6$haloalkoxy, and —$OR^a$;

$R^a$ and $R^b$ are independently H or $C_1$-$C_6$ alkyl;

or alternatively $R^a$ and $R^b$, if bound to the same atom, can together with the atom to which they are both attached form a —$C_1$-$C_6$cycloalkyl;

each n is independently 0, 1 or 2;

each m is independently 1, 2, 3 or 4;

each o is independently 1, 2 or 3; and each p is independently 1, 2, 3 or 4.

2. The compound of claim 1, or a pharmaceutically acceptable salt thereof, wherein $X^1$ and $X^2$ are CH.

3. The compound of claim 1, or a pharmaceutically acceptable salt thereof, wherein $X^1$ is CH.

4. The compound of claim 3, or a pharmaceutically acceptable salt thereof, wherein $R^B$ is -AryA5 linked to $X^1$ through an —$OC_6$-$C_7$alkylene or an —$OC_6$-$C_7$alkenylene, wherein the O of the —$OC_6$-$C_7$alkylene or —$OC_6$-$C_7$alkenylene is bound at the $X_1$ position.

5. The compound of claim 1, or a pharmaceutically acceptable salt thereof, wherein Y is O.

6. The compound of claim 1, or a pharmaceutically acceptable salt thereof, wherein $R^B$ is thiazolyl.

7. The compound of claim 1, or a pharmaceutically acceptable salt thereof, wherein $R^A$ is —[$OCH_2CH_2$]$_m$NR$^a$C(O)R$^C$; each m is 2, 3 or 4, and $R^C$ is selected from the group consisting of:

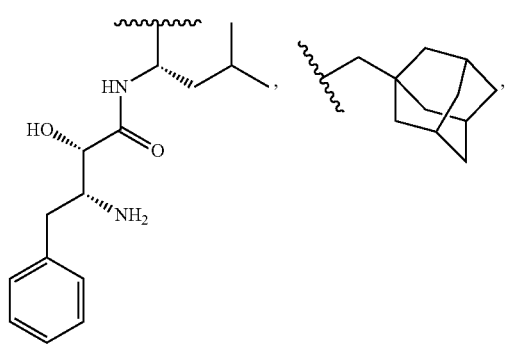

-continued

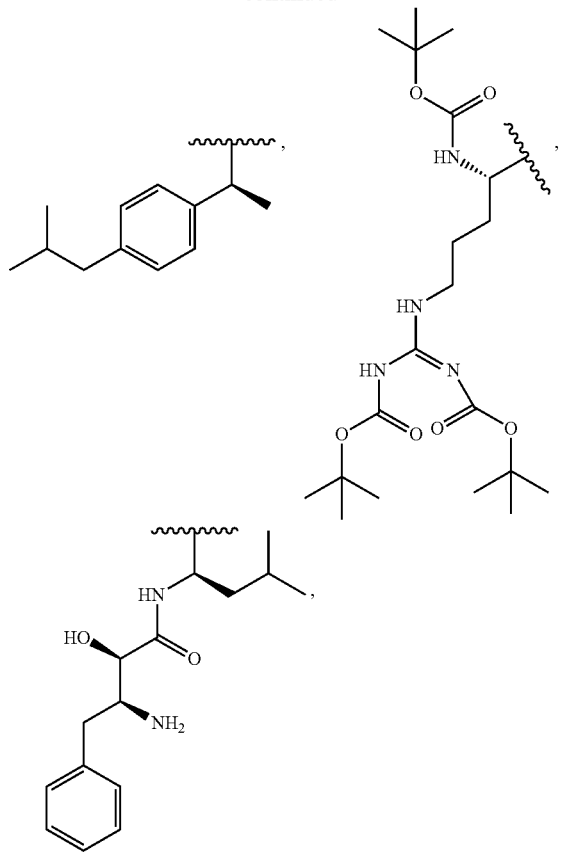

-continued

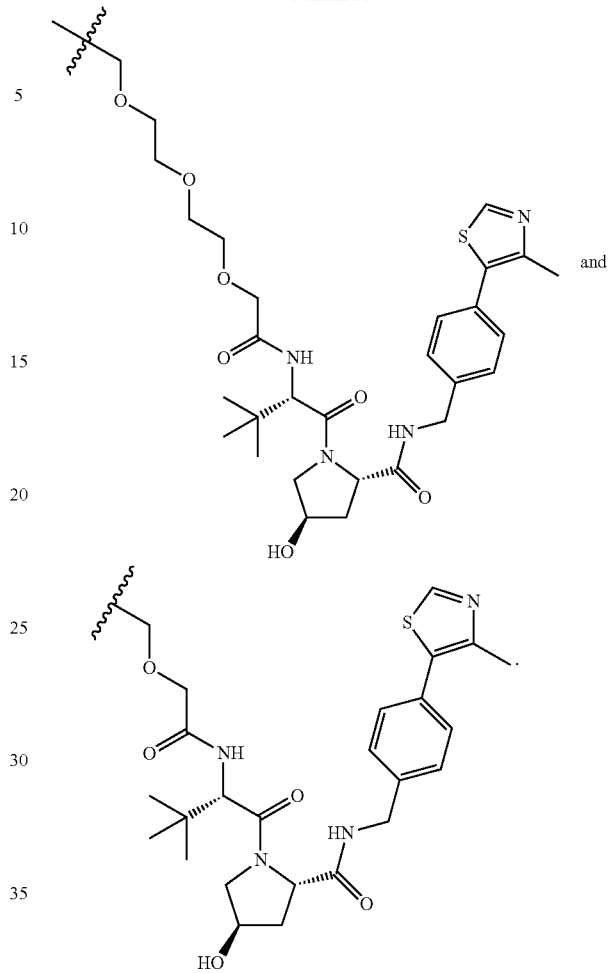

8. The compound of claim 1, or a pharmaceutically acceptable salt thereof, wherein $R^A$ is —$[OCH_2CH_2]_mNR^aC(O)R^C$; each m is 2, 3 or 4, and $R^C$ is a BODIPY group which is:

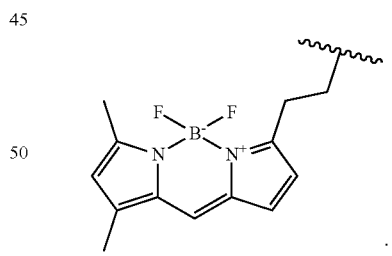

9. A pharmaceutical composition which comprises a compound according to claim 1, or a pharmaceutically acceptable salt thereof, and a pharmaceutically acceptable carrier.

10. A method for the in vitro labeling, detection and/or quantification of PCSK9 in a biological sample, which comprises the steps of: (i) incubating the sample with a compound or pharmaceutically acceptable salt of claim 8 for a time sufficient for the compound or salt to bind to PCSK9 present in the sample, (ii) activating or irradiating the detectable marker of step (i), and (iii) visualizing a fluorescent signal conferred by the BODIPY group of the compound or pharmaceutically acceptable salt of step (i).

11. A method for inducing PCSK9 protein degradation in a subject which comprises administering to the subject (i) an effective amount of a compound according to claim 7 or a pharmaceutically acceptable salt thereof or (ii) a pharmaceutical composition comprising a compound according to claim 7 or a pharmaceutically acceptable salt thereof, and a pharmaceutically acceptable carrier.

12. The method of claim 11 wherein the compound is selected from the group consisting of:

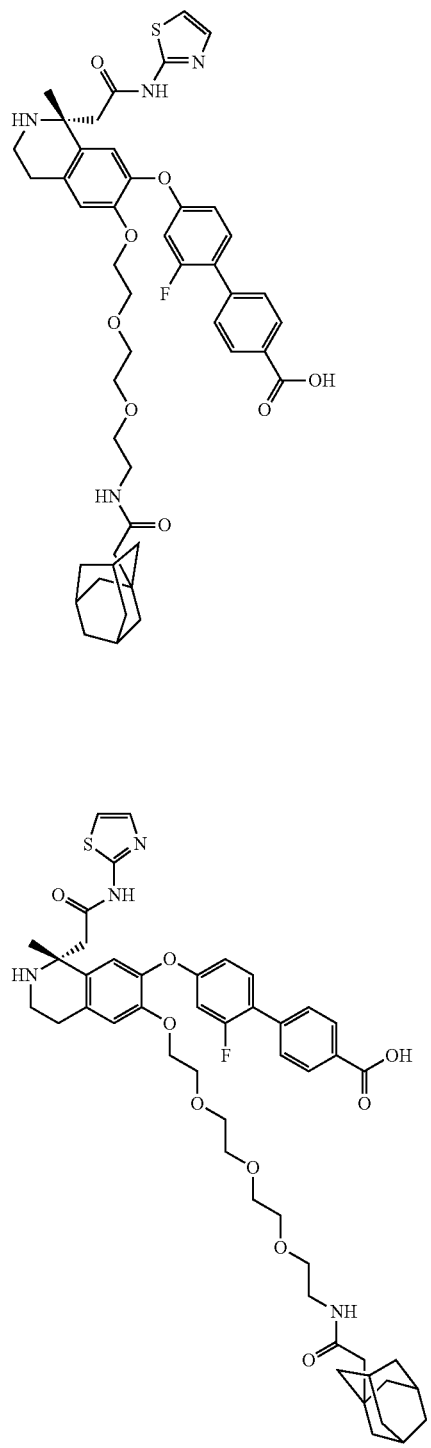

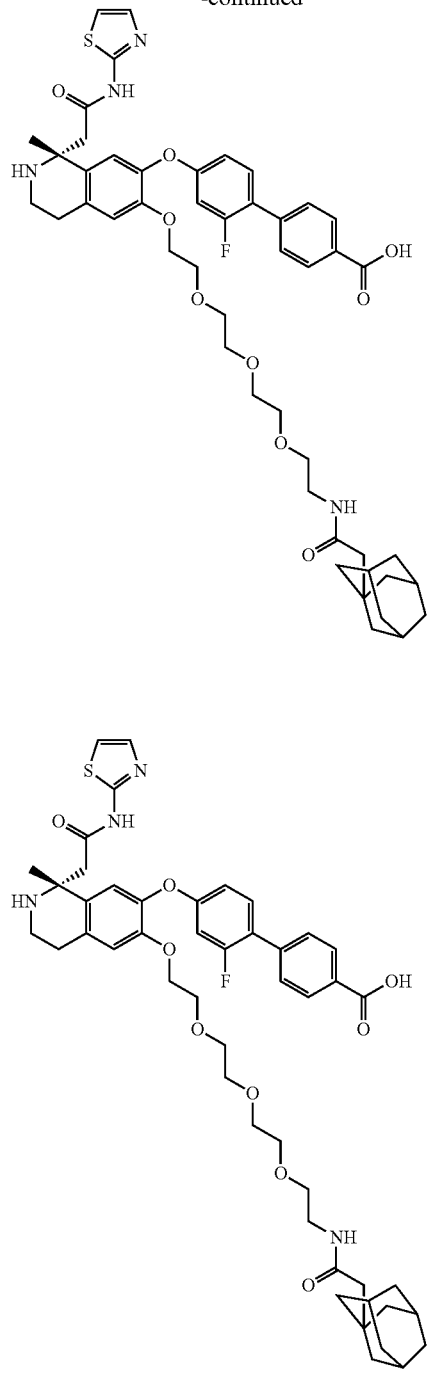

or a pharmaceutically acceptable salt thereof.

13. A method for treating atherosclerosis, hypercholesterolemia, coronary heart disease, metabolic syndrome, acute coronary syndrome, or related cardiovascular disease and cardiometabolic conditions which comprises administering to a subject in need of such treatment (i) a therapeutically effective amount of a compound according to claim 7, or a pharmaceutically acceptable salt thereof or (ii) a pharmaceutical composition comprising a compound according to claim 7 or a pharmaceutically acceptable salt thereof, and a pharmaceutically acceptable carrier.

14. The method of claim 13 wherein the compound is selected from the group consisting of:

257
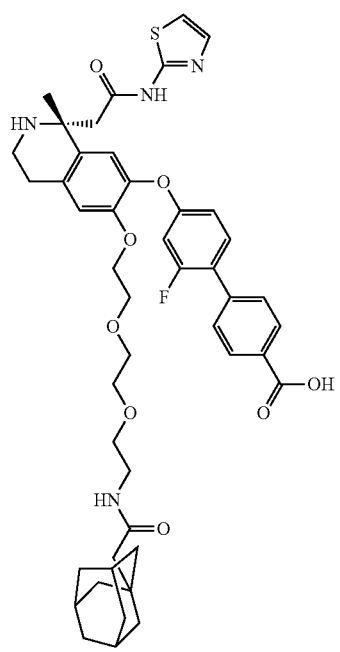
258
-continued
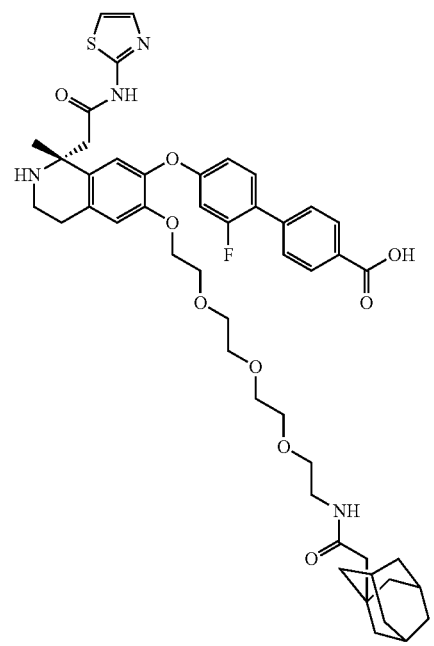
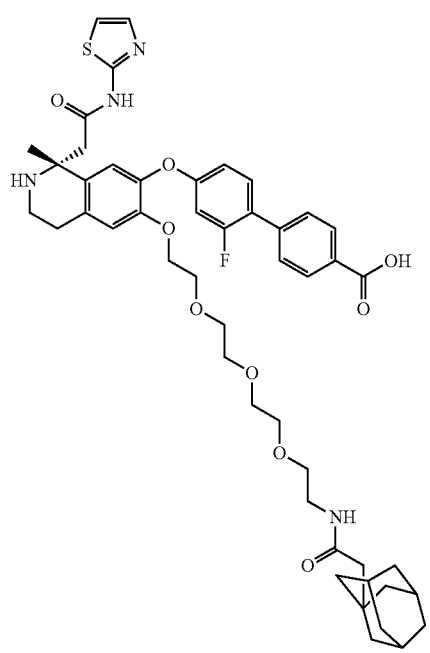
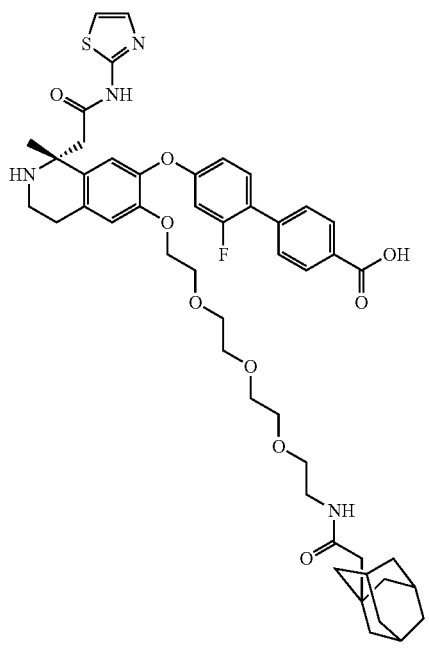 [SMILES: C[C@]1(CC(=O)Nc2nccs2)NCCc2cc(OCCOCCOCCOCCNC(=O)CC34CC5CC(CC(C5)C3)C4)c(Oc3ccc(-c4ccc(C(=O)O)cc4)c(F)c3)cc21]

259
-continued
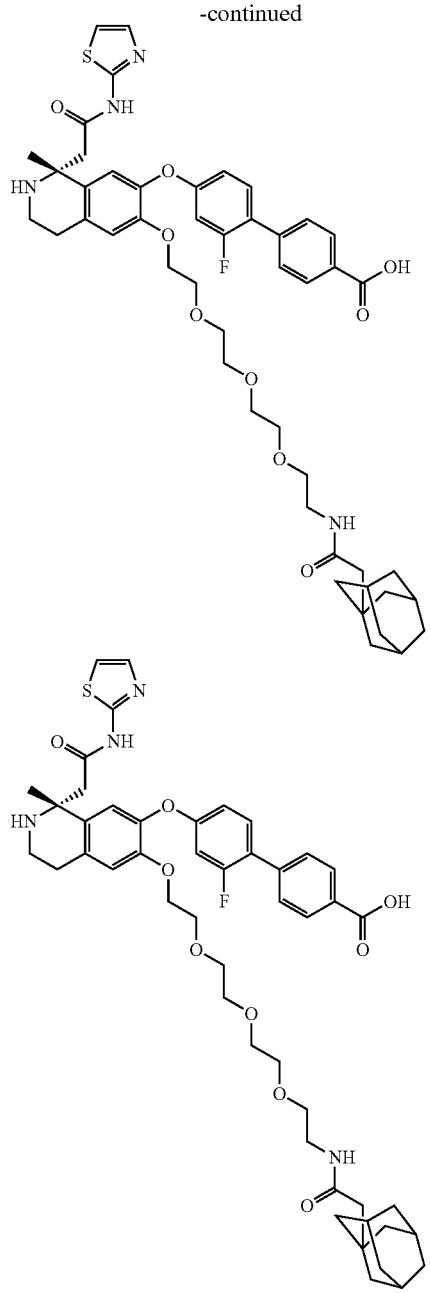
, and
260
-continued
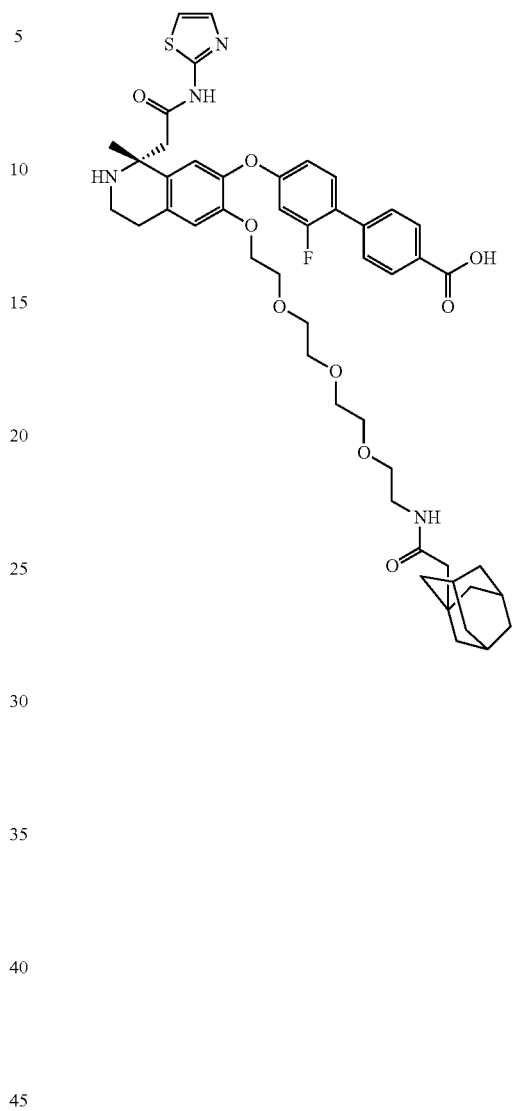
or a pharmaceutically acceptable salt thereof.
* * * * *